United States Patent
Boveja et al.

(10) Patent No.: US 12,303,203 B1
(45) Date of Patent: May 20, 2025

(54) METHODS AND SYSTEM FOR ATRIAL FIBRILLATION ABLATION USING BALLOON BASED CATHETERS AND UTILIZING MEDICAL IMAGES (CT OR MRI IN SEGMENTS) BASED CARDIAC MAPPING AND/OR UTILIZING VIRTUAL REALITY (VR), AND/OR AUGMENTED REALITY (AR), AND/OR MIXED REALITY (MR) FOR AIDING IN CARDIAC PROCEDURES

(71) Applicants: Birinder R. Boveja, Milwaukee, WI (US); Angely Widhany, Greenfield, WI (US)

(72) Inventors: Birinder R. Boveja, Milwaukee, WI (US); Angely Widhany, Greenfield, WI (US)

(73) Assignee: Birider Boveja, Milwaukee, WI (US)

( * ) Notice: Subject to any disclaimer, the term of this patent is extended or adjusted under 35 U.S.C. 154(b) by 1155 days.

(21) Appl. No.: 17/156,556

(22) Filed: Jan. 23, 2021

Related U.S. Application Data

(63) Continuation-in-part of application No. 16/560,873, filed on Sep. 4, 2019, now Pat. No. 11,039,883, which
(Continued)

(51) Int. Cl.
*A61B 18/02* (2006.01)
*A61B 17/12* (2006.01)
(Continued)

(52) U.S. Cl.
CPC ........ *A61B 34/10* (2016.02); *A61B 17/12122* (2013.01); *A61B 18/02* (2013.01);
(Continued)

(58) Field of Classification Search
CPC ... A61B 34/10; A61B 34/20; A61B 17/12122; A61B 18/02; A61B 18/1492;
(Continued)

(56) References Cited

U.S. PATENT DOCUMENTS

| 7,991,509 B2 | 8/2011 | Lipow |
| 10,286,179 B2 | 3/2019 | Giap et al. |

(Continued)

*Primary Examiner* — George Manuel

(57) ABSTRACT

Methods and system for atrial fibrillation ablations and other cardiac procedures utilizes a cardiac mapping system for navigation and guidance, and includes an additional virtual reality (VR) system and an augmented reality (AR) or mixed reality (MR) system. The Cardiac mapping system utilizes medical images and patient's electrical signals. The virtual reality (VR) system is utilized pre-procedure for visualization and pre-procedure planning. The augmented reality (AR) or mixed reality (MR) system is utilized pre-procedure or intra-procedure. Methods and system are disclosed utilizing pre-built virtual device models which interact with 3D volume rendered structures from patient's CT or MRI of the region of interest (ROI) for the different type of cardiac procedure. With virtual reality (VR) the operator utilizes hand-held sensors. With augmented reality (AR) or mixed reality (MR) a combination of hand gestures and an X-box controller is used to manipulate virtual devices, anatomical structures in the Hologram.

22 Claims, 68 Drawing Sheets

Related U.S. Application Data is a continuation-in-part of application No. 15/817,664, filed on Nov. 20, 2017, now Pat. No. 10,413,185, which is a continuation-in-part of application No. 15/209,265, filed on Jul. 13, 2016, now Pat. No. 9,820,802, which is a continuation-in-part of application No. 14/709,445, filed on May 11, 2015, now Pat. No. 9,393,071, which is a continuation-in-part of application No. 13/718,284, filed on Dec. 18, 2012, now Pat. No. 9,033,968.

(60) Provisional application No. 63/045,679, filed on Jun. 29, 2020, provisional application No. 62/965,609, filed on Jan. 24, 2020, provisional application No. 61/630,771, filed on Dec. 19, 2011.

(51) Int. Cl.
| *A61B 18/14* | (2006.01) |
| *A61B 34/10* | (2016.01) |
| *A61B 34/20* | (2016.01) |
| *A61F 2/24* | (2006.01) |
| *A63F 13/24* | (2014.01) |
| *G06F 3/01* | (2006.01) |
| *G06T 15/08* | (2011.01) |
| *A61B 18/00* | (2006.01) |
| *A61B 90/00* | (2016.01) |

(52) U.S. Cl.
CPC .......... *A61B 18/1492* (2013.01); *A61B 34/20* (2016.02); *A61F 2/2433* (2013.01); *A63F 13/24* (2014.09); *G06F 3/011* (2013.01); *G06F 3/017* (2013.01); *G06T 15/08* (2013.01); *A61B 2018/0022* (2013.01); *A61B 2018/00375* (2013.01); *A61B 2018/00577* (2013.01); *A61B 2018/00821* (2013.01); *A61B 2018/0212* (2013.01); *A61B 2034/105* (2016.02); *A61B 2090/365* (2016.02); *A61B 2090/374* (2016.02); *A61B 2090/376* (2016.02); *A61B 2090/3762* (2016.02); *A61B 2090/378* (2016.02); *A63F 2300/8082* (2013.01); *G06T 2210/41* (2013.01)

(58) Field of Classification Search
CPC ........ A61B 2034/105; A61B 2090/365; A61B 2090/474; A61B 2090/37632; A61B 2090/378; A61B 2018/0022; A61B 2018/00375; A61B 2018/00577; A61B 2018/00212; A63F 13/24; A63F 2300/8082; A61F 2/2433; G06F 3/011; G06F 3/017; G06T 15/08; G06T 2210/41
See application file for complete search history.

(56) References Cited

U.S. PATENT DOCUMENTS

| 10,603,113 | B2 | | 3/2020 | Lang | |
| 10,672,288 | B2 | | 6/2020 | Ribeira et al. | |
| 10,813,619 | B2 | | 10/2020 | Samee et al. | |
| 10,945,807 | B2 | | 3/2021 | Gibby et al. | |
| 10,969,583 | B2 | * | 4/2021 | Hresko | A61N 1/0484 |
| 2018/0165854 | A1 | * | 6/2018 | Du | G06F 16/00 |
| 2018/0310907 | A1 | * | 11/2018 | Zhang | G06F 3/0346 |
| 2019/0069955 | A1 | * | 3/2019 | Popovic | A61B 34/20 |

* cited by examiner

Live and Recorded Images in high resolution

FIG. 19  629  2nd Recorded "dye" injection
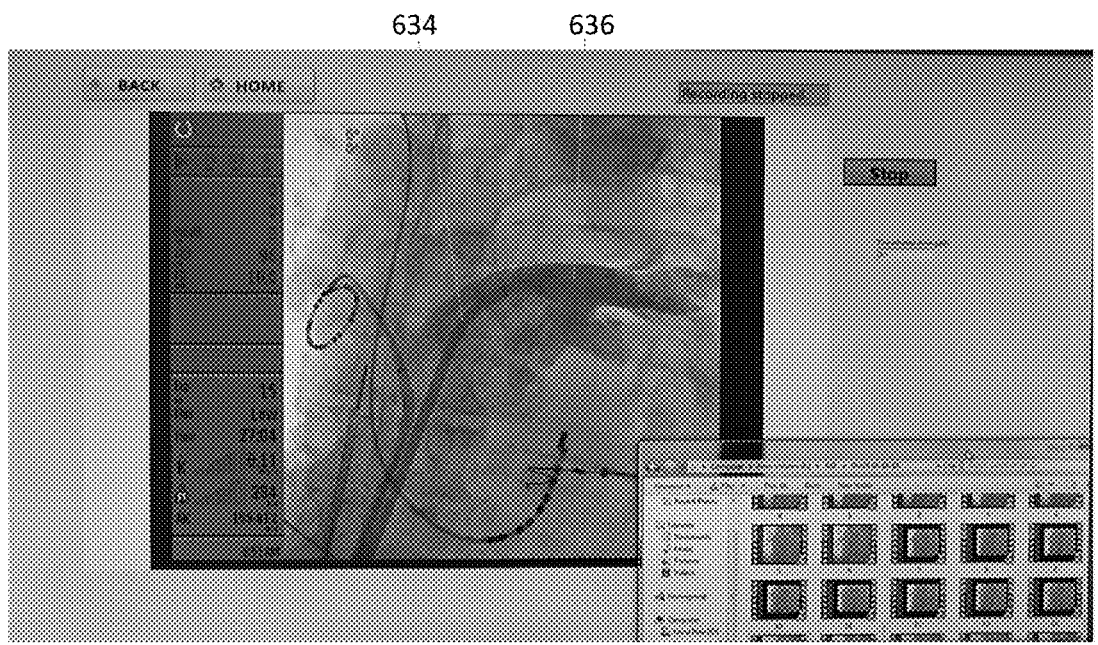
FIG. 20  Recorded "dye" injection  638

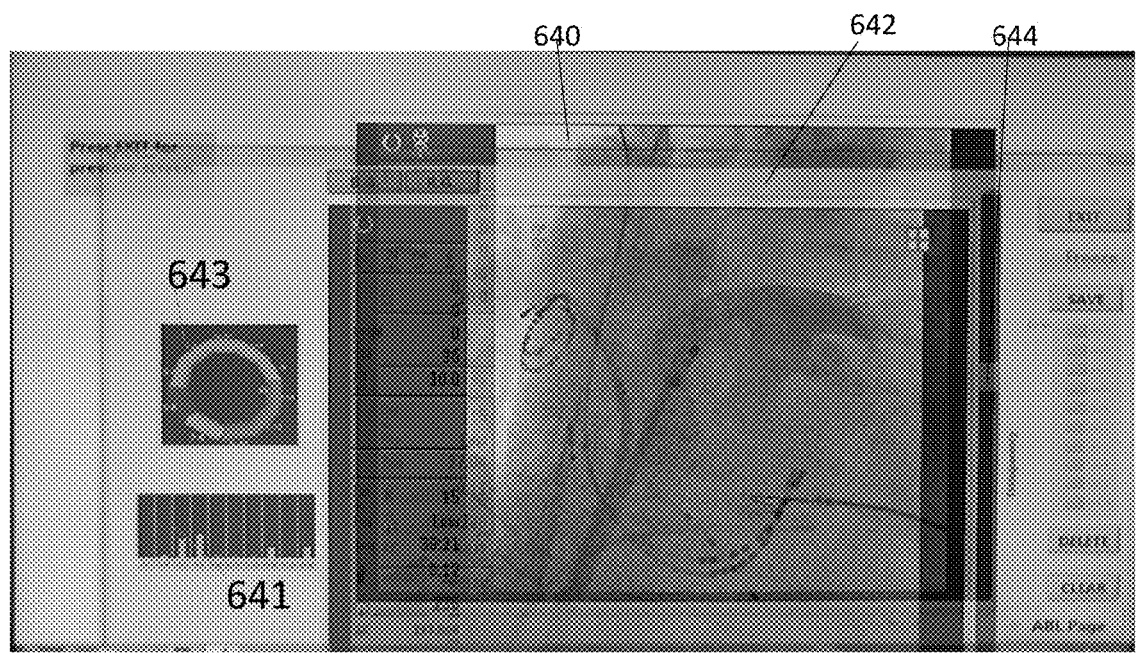
Live fluoroscopy overlaid on recorded dye injection image with signals from circular catheter
FIG 21
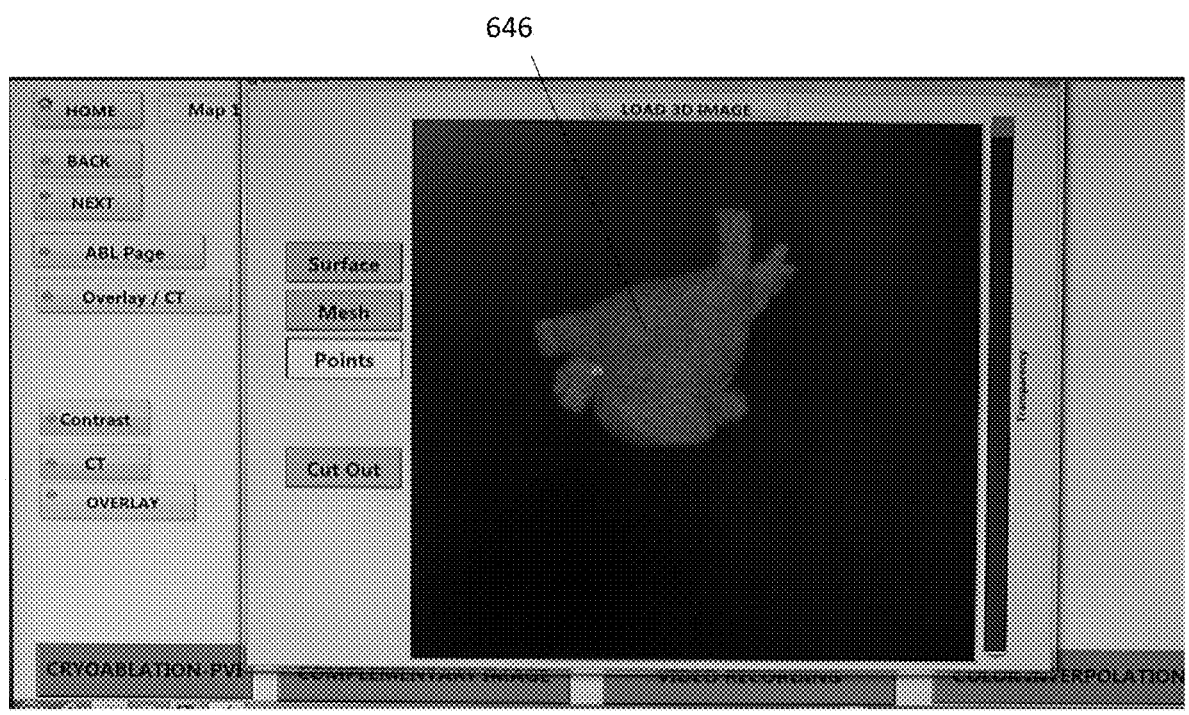
FIG 22 — Patient's CT CT overlaid on contrast image CT overlaid on contrast image with live fluoro overlayed and signals from circ. Catheter (contrast + CT+ live fluoro + signals)

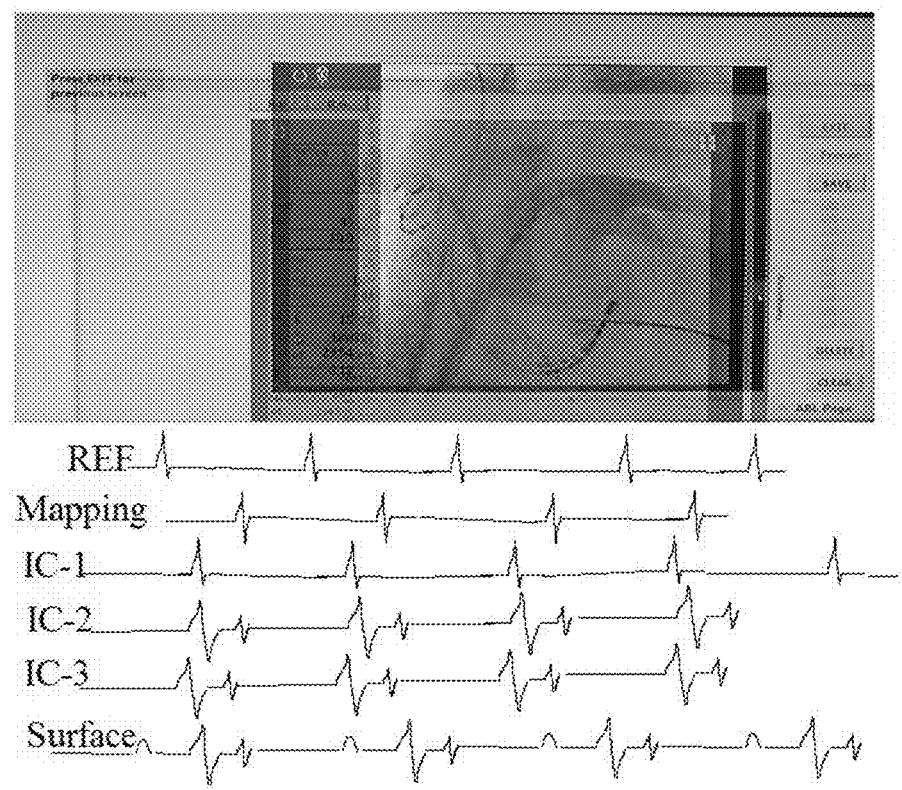
FIG. 54
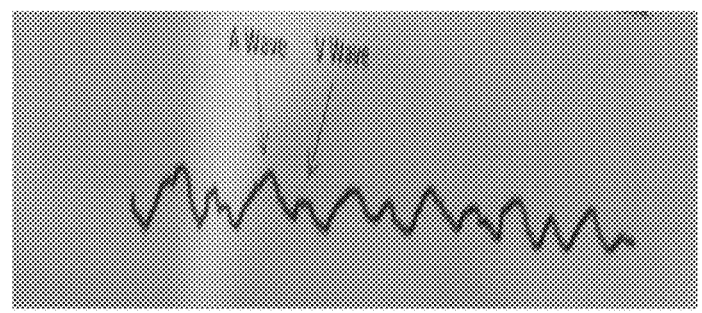
Before the balloon is advanced to the pulmonary vein OS
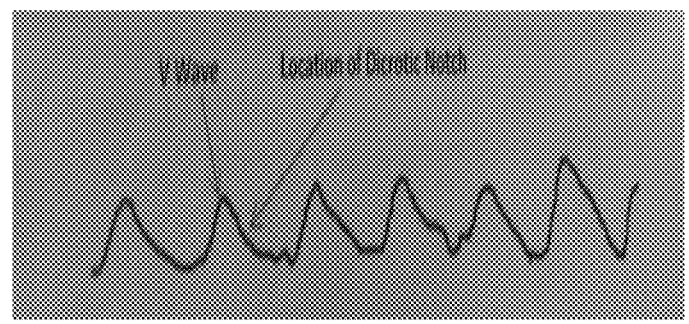
Making a good seal against the pulmonary vein OS
FIG 55

Bottom of the figure further shows examples of tracing when there is no occlusion, when there is incomplete occlusion and when there is complete occlusion.

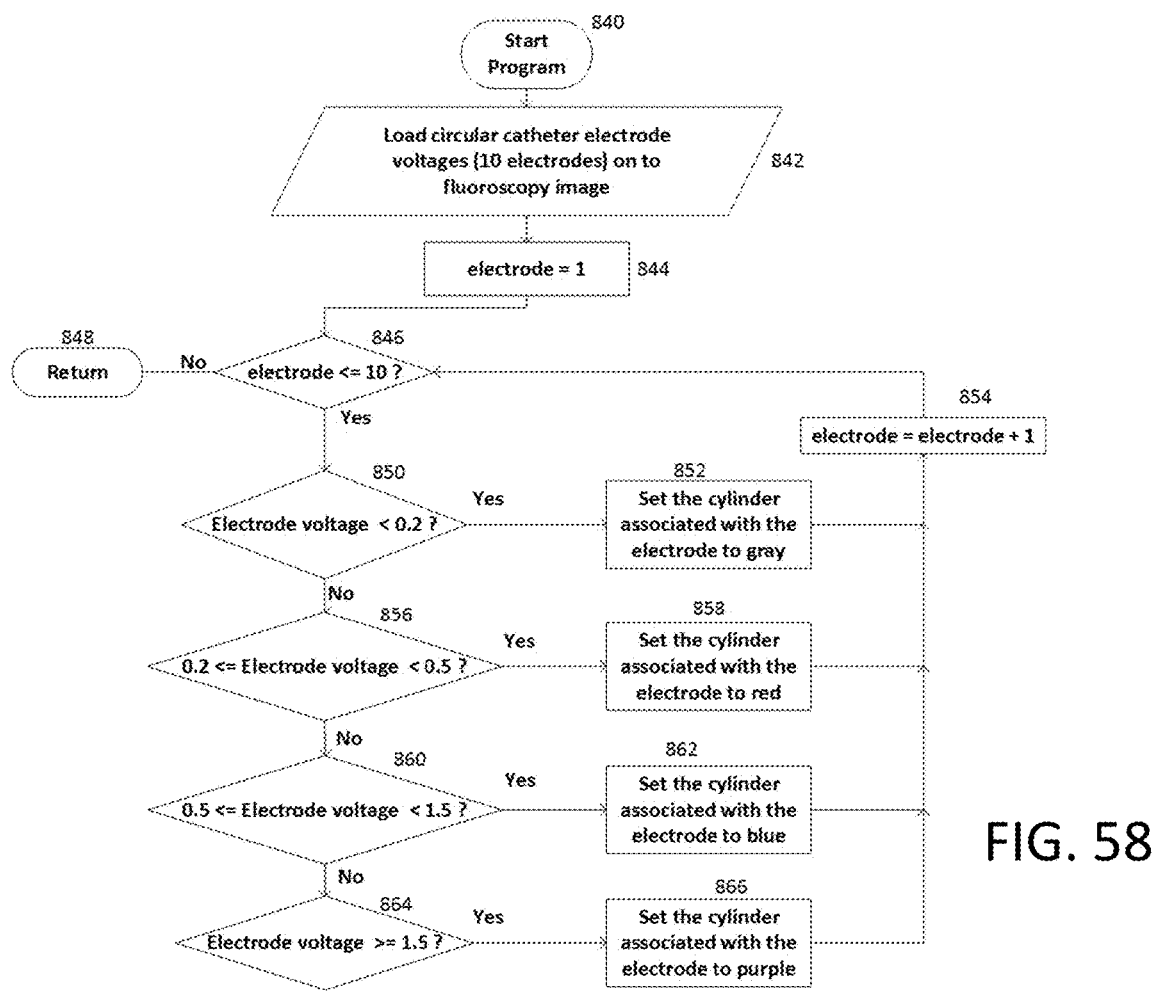
FIG. 58
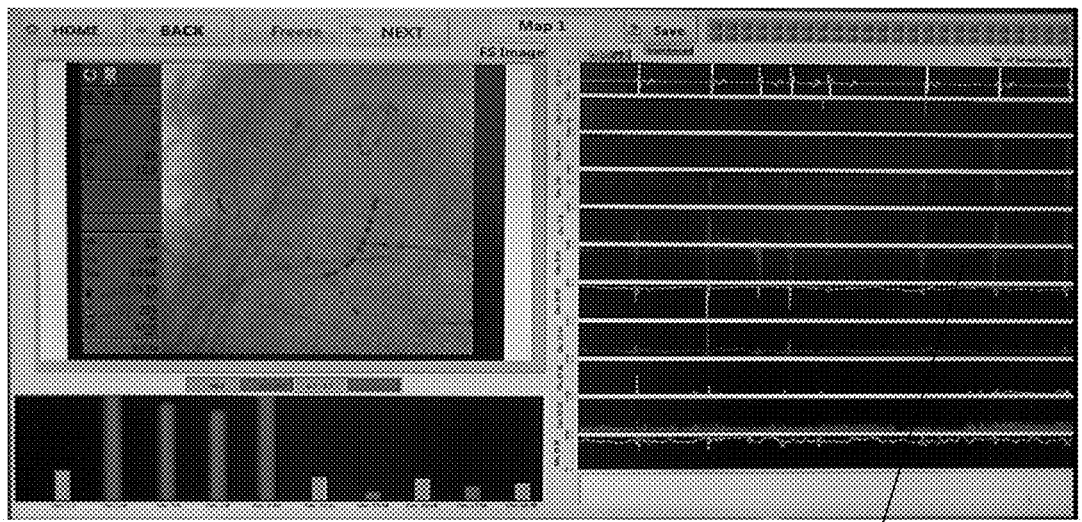
FIG 59    Time Domain signals

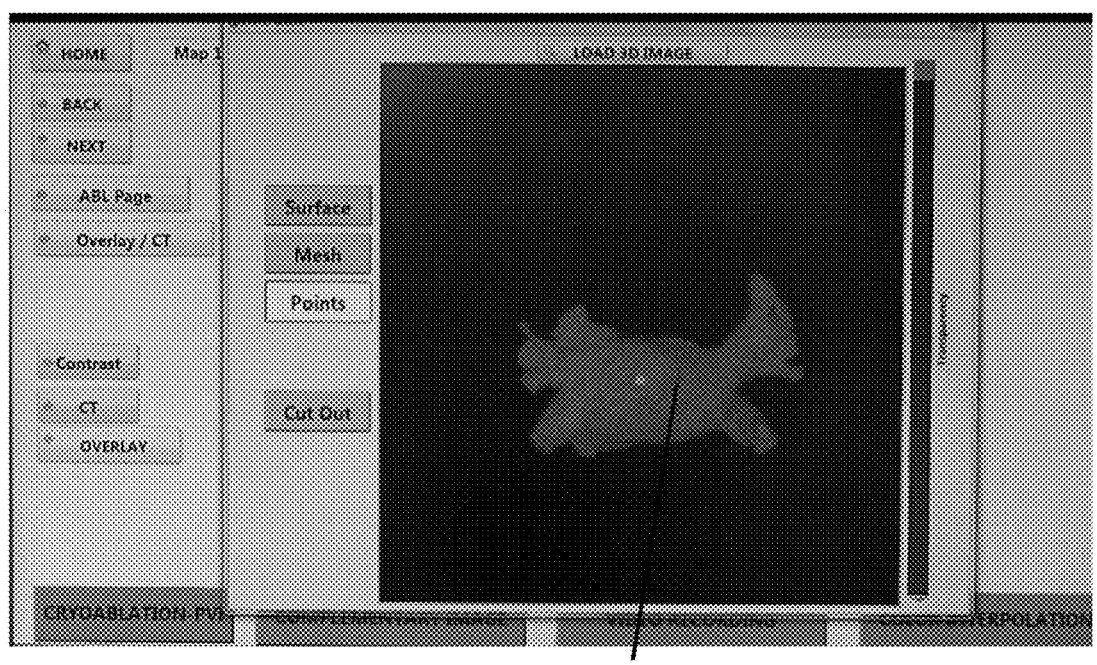
Computed tomography (CT) image
FIG 60
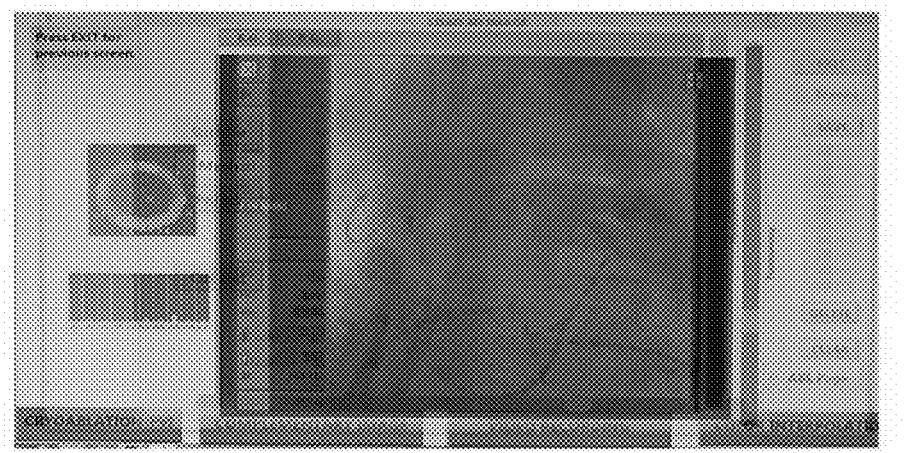
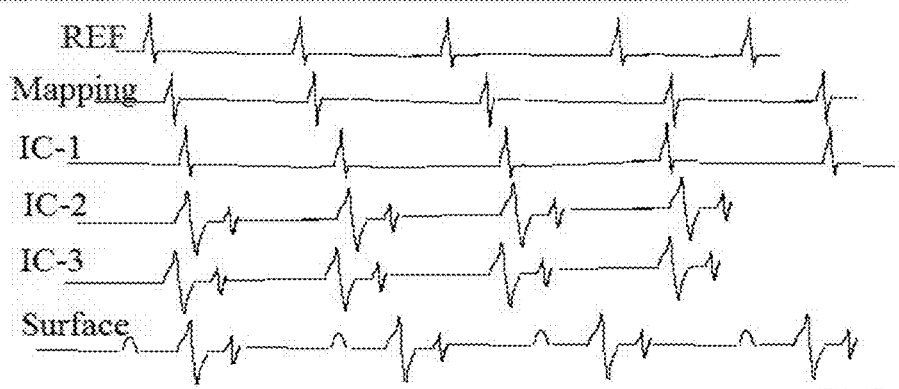
FIG. 61

VR system ⟶ Load LAA region of interest ⟶
Start program ⟶ Choose patient

MR system ⟶ Load program on Hololens 2 ⟶
Change object to LAA of the patient via WiFi or internet

FIG. 69A

VR system ⟶ Load LA and PV region of interest ⟶
Start program ⟶ Choose patient

MR system ⟶ Load program on Hololens 2 ⟶
Change object to LA and PV region of the patient via WiFi or internet

FIG. 69B

VR system ⟶ Load Aortic root region of interest ⟶
Start program ⟶ Choose patient MR system ⟶ Load program on Hololens 2 ⟶
Change object to Aortic root of the patient via WiFi or internet

FIG. 69C

| Example File Formats | |
|---|---|
| 3d Manufacturing Format | Open Game Engineer Exchange |
| 3DMF | PLY |
| 3DML | PRC |
| 3DXML | STL |
| Additive Manufacturing File Format | Universal 3D |
| Alembic (computer graphics) | VRML |
| COLLADA | Wavefront . Obj file |
| FBX | X3D |
| Generative Modelling Language | XVL |
| GITF | OBJ | i)

1020

1018   1016

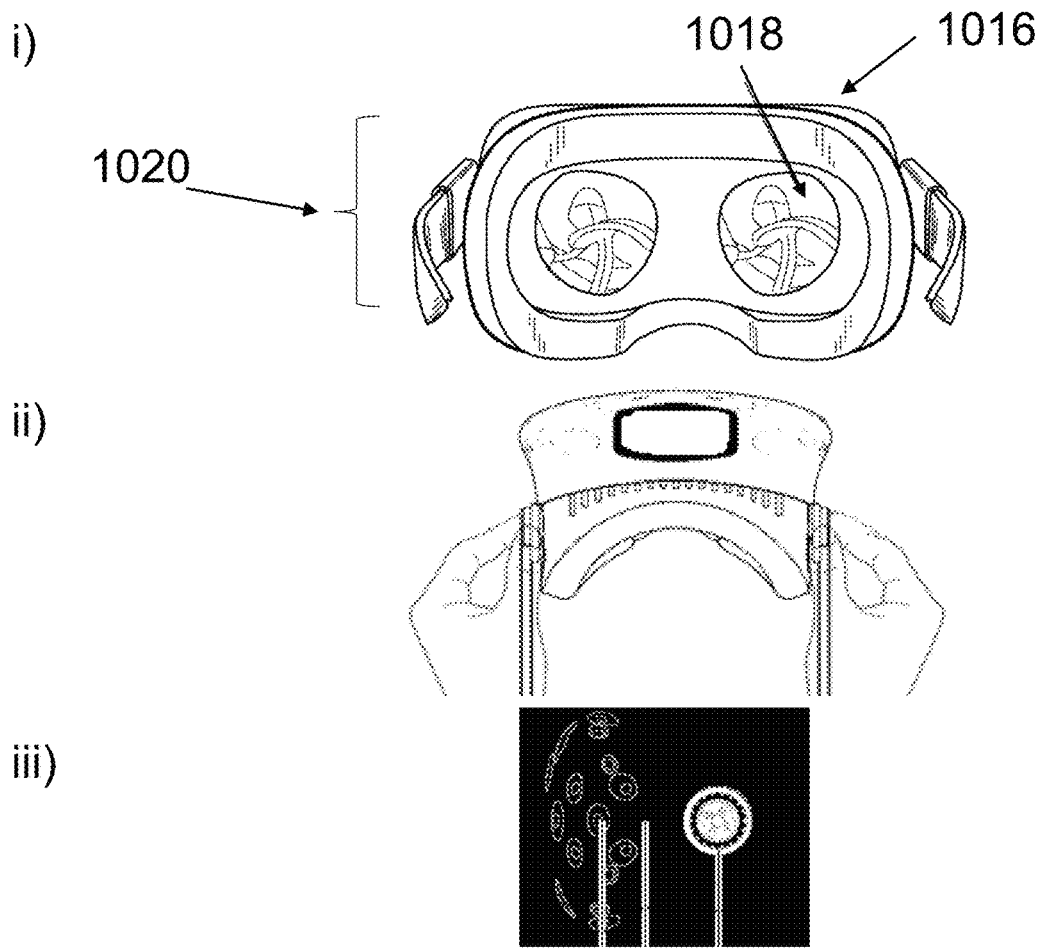

ii)

iii)

FIG. 72

| Components of Device | (Not all elements are needed in one implementation/ embodiment of the device) |
|---|---|
| Processor and device | This includes the software/hardware that runs the application and produces the visualization to the lenes |
| headset | The headset fits on the user's head and includes the lenses that are used to project and visualize the interface and virtual objects. |
| Sensors | Infrared sensors for position |
|  | spatial sensors |
|  | Bluetooth |
|  | internet connectivity |
| External Controllers | Remotes(Oculus, Xbox..) |

FIG. 73

| Examples of combinations | | | |
|---|---|---|---|
| Example Game Engines | Example programming languages and scripting | Platform | Example devices |
| 4A Engine | C++ | Windows | Oculus Rift |
| A-Frame (VR) | JavaScript | OS X | HTC Vive |
| Adventure Game Interpreter | C# | Linux | Gear VR |
| Adventure Game Studio | C | PlayStation(s) | |
| Alamo | Assembler | Xbox(s) | |
| Aleph One | FFL | Cross-Platform | |
| Antiryad Gx | BASIC | DOS | |
| Anura | Java | Mac OS | |
| Arivi | LabVIEW | Android | |
| AppGameKit | Pythin | AmigaOS | |
| Ardor3D | Objective-C | AROS | |
| Aurora toolset | Lua | OS X | |
| BigWorld | ActionScript | HTML 5 | |
| Blend4Web | ActionScript 3 | Raspberry Pi | |
| Blender | GML | WebGL | |
| Bork3D Game Engine | Lang | Solaris | |
| BRender | Asssembly | iOS | |
| Build engine | Pascal | DOS | |
| Buildbox | AMPL | Adobe Flash | |
| C4 Engine | Clipper | Nintendo | |
| Cafu Engine | Linux | WebGL | |
| Chrome Engine | HTML | TV Platforms | |
| ClanLib | HTML 5 | | |
| Clausewitz | FreeBASIC | | |
| Clickteam Fusion | NScripter | | |
| Cocos2d, Cocos2d-x, Cocos2d-html5 | Haxe | | |
| Codea | Visual Basic | | |
| Coldstone | Type Script | | |
| Construct | .NET | | |
| CopperCube | | | |
| CPAL3D | | | |
| Creation Engine | | | |
| CryEngine | | | |
| Crystal Tools | | | |
| Crystal Space | | | |
| Cube | | | |
| Cube 2: Sauerbraten | | | |
| Dagor Engine | | | |
| Dark Engine | | | |
| Decima | | | |
| Defold | | | |
| Delta3D | | | |
| Dim3 | | | |
| DimensioneX Multiplayer Engine | | | |
| DX Studio | | | |
| Dunia Engine | | | |
| ego | | | |

| Example Game Engines |
|---|
| Electron toolset |
| Enforce |
| Enigma Engine |
| Essence Engine |
| Euphoria |
| Exult |
| Flare3D |
| Flixel |
| Forgelight Engine |
| Fox Engine |
| Freescape |
| Frostbite |
| Future Pinball |
| Gamebryo |
| Game Editor |
| GameMaker Studio |
| GameSalad |
| Gamestudio |
| Gamvas |
| GDevelop |
| Godot |
| Gold Box |
| GoldSrc |
| HeroEngine |
| Horde3D |
| HPL Engine |
| id Tech 1 (Doom) |
| id Tech 2 (Quake) |
| id Tech 2 (Quake II) |
| id Tech 3 |
| id Tech 4 |
| id Tech 5 |
| id Tech 6 |
| id Tech 7 |
| IMUSE |
| Infinity Engine |
| Irrlicht |
| Ioquake3 |
| Iron Engine |
| IW engine |
| Jade |
| Jake2 |
| Java 3D |
| Jedi |
| MonkeyEngine |
| Kinetica |
| Kivy (framework) |
| LavaAir |
| Leadwerks |
| LibGDX |
| LithTech |
| Lumberyard |
| PlayCanvas |
| PlayN |
| Pyrogenesis |
| Q |
| Qfusion |
| Real Virtuality |
| REDengine |
| Ren'Py |
| RenderWare |

| Example Game Engines |
|---|
| Rockstar Advanced Game Engine (RAGE) |
| RPG Maker |
| SAGE |
| SCUMM |
| Shark 3D |
| ShiVa |
| Sierra's Creative Interpreter (SCI) |
| Silent Storm engine |
| Snowdrop |
| Solar2D |
| Source |
| Source 2 |
| Spring |
| Starling Framework |
| Stencyl |
| Autodesk Stingray (Bitsquid) |
| StepMania |
| Stratagus |
| Stride |
| Three.js |
| TOSHI |
| Truevision3D |
| Torque3D |
| Turbulenz |
| UbiArt Framework |
| Unigine |
| Unity |
| Unreal Engine |
| V-Play Game Engine |
| Vengeance Engine |
| Vicarious Visions |
| Alchemy |
| Vicious Engine |
| Virtools |
| Vision |
| Visual3D Game Engine |
| Visual Pinball |
| VRAGE |
| Wintermute Engine |
| World Builder |
| WorldForge |
| XnGine |
| Zillions of Games |

FIG. 76

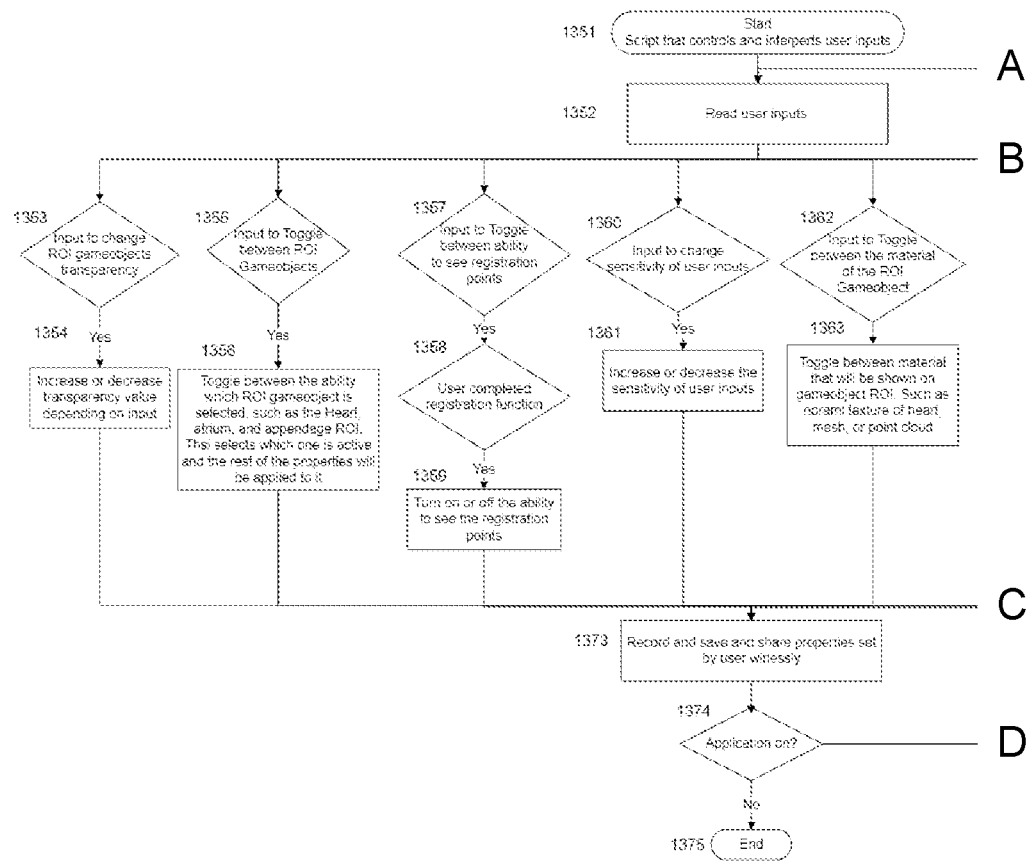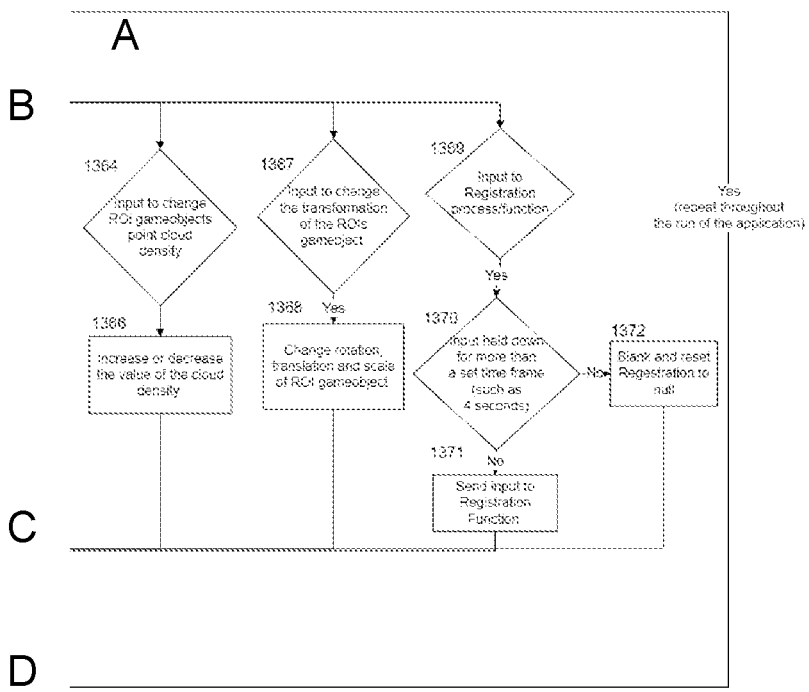
FIG. 98

METHODS AND SYSTEM FOR ATRIAL FIBRILLATION ABLATION USING BALLOON BASED CATHETERS AND UTILIZING MEDICAL IMAGES (CT OR MRI IN SEGMENTS) BASED CARDIAC MAPPING AND/OR UTILIZING VIRTUAL REALITY (VR), AND/OR AUGMENTED REALITY (AR), AND/OR MIXED REALITY (MR) FOR AIDING IN CARDIAC PROCEDURES

This application is a Continuation-In-Part (CIP) of U.S. application Ser. No. 16/560,873 filed on Sep. 4, 2019. which is a Continuation-In-Part (CIP) of U.S. application Ser. No. 15/817,664 filed Nov. 20, 2017 now U.S. Pat. No. 10,413,185, which is a Continuation-In-Part (CIP) of U.S. application Ser. No. 15/209,265 filed Jul. 13, 2016 now U.S. Pat. No. 9,820,802, which is a Continuation-In-Part (CIP) of U.S. application Ser. No. 14/709,445 filed May 11, 2015 now U.S. Pat. No. 9,393,071, which is a Continuation-In-Part (CIP) of U.S. application Ser. No. 13/718,284 now U.S. Pat. No. 9,033,968.

This application also claims priority to two provisional patent applications, 1) patent application No. 62/965,609 filed on Jan. 24, 2020 entitled "Methods and system of utilizing virtual reality (VR), augmented reality (AR), and/or mixed reality (MR) for guidance in cardiac procedures", and 2) provisional U.S. patent application No. 63/045,679 filed on Jun. 29, 2020, entitled "Methods and system of visualization for navigation for atrial fibrillation ablations utilizing virtual reality (VR), augmented reality (AR), and/or mixed reality (MR)".

FIELD OF DISCLOSURE

The present disclosure relates to methods and system of navigation and/or guidance for medical procedures, more specifically methods and system for cardiac navigation and guidance and utilizing virtual reality (VR), augmented reality (AR) or mixed reality (MR) or any combinations thereof for cardiac ablations and other medical procedures.

REFERENCES USED

EP 2 921 938
U.S. Pat. No. 9,681,925
Virtual Reality: Recent Advances in Virtual Rehabilitation system design-Wendy Powell, Albert Rizzo, Paul Sharkey, and Joav Merrick-Chapter 2
U.S. Pat. No. 9,681,925
Virtual Reality: Advances in Research and Applications-Zachary Hill-Chapter 3

BACKGROUND

Background—Overview of Cardiac Mapping Systems and Visualization Devices

Cardiac mapping systems to guide various cardiac procedures exist in the market. These cardiac mapping systems utilize different sensor technologies for creating chamber geometries, such as impedance, magnetic, ultrasound etc. This disclosure builds upon our previous cardiac mapping system for atrial fibrillation ablation procedures utilizing balloon based catheters. Novel methods and system disclosed include a virtual reality (VR) system and mixed reality (MR) system for aiding in various cardiac procedures, such as atrial fibrillation ablations, transcutaneous aortic valve replacement (TAVR), and left atrial appendage (LAA) device closure procedures. Generally, the virtual reality (VR) system is utilized for visualization and pre-procedure planning, and the mixed reality system is utilized intra-procedure. But, the mixed reality system may be utilized either for pre-procedure or intra-procedure, for aiding in the procedure.

In the method and system of this disclosure, as shown in conjunction with FIG. 1A, the cardiac mapping system, the virtual reality (VR) system and the mixed reality (MR) system may be utilized separately or in combination with each other. If the three systems are utilized together, they may be utilized in any combination. As an example, the virtual reality (VR) system may be utilized for immersive visualization and pre-procedure planning for atrial fibrillation ablation procedures, transcutaneous aortic valve replacement (TAVR), and left atrial appendage (LAA) device closure procedures. The mixed reality (MR) system may be utilized intra-procedure for atrial fibrillation ablation procedures, transcutaneous aortic valve replacement (TAVR), and left atrial appendage (LAA) device closure procedures.

Immersive visualization utilizing virtual reality (VR) and mixed reality (MR) offers advantages over conventional visualization as to the extent of detailed visualization of the important 3D structures. Further realistic virtual models of devices for various cardiac procedures are pre-built and are utilized for aiding in various procedures (such as atrial fibrillation ablations, transcutaneous aortic valve replacement (TAVR), and left atrial appendage (LAA) device closure procedures) by placing the virtual device models in the 3D volume rendered patient's anatomy from the patient's CT or MRI. This involves application programming utilizing a game engine and object oriented programming, as detailed later in this disclosure.

Background of Transcutaneous Aortic Valve Replacement (TAVR), Left Atrial Appendage (LAA) Device Closure Procedures, and Atrial Fibrillation Ablations

Background—TAVR

Aortic valve (which is a semilunar valve) is one of the four valves of the heart. With aging, over time the leaflets of the aortic valve become calcified and the valves do not function properly. Transcatheter aortic valve replacement (TAVR), is a procedure in which the replacement of the aortic valve of the heart is through the blood vessels (as opposed to valve replacement by open heart surgery). The replacement valve is generally delivered via one of several access methods: transfemoral (in the upper leg), transapical (through the wall of the heart), subclavian (beneath the collar bone), direct aortic (through a minimally invasive surgical incision into the aorta), and transcaval (from a temporary hole in the aorta near the belly button through a vein in the upper leg).

Severe symptomatic aortic stenosis generally carries a poor prognosis. Currently no medical cure exists today, making the timing of aortic valve replacement the most important decision to make for these patients. Until recently, surgical aortic valve replacement was the standard of care in adults with severe symptomatic aortic stenosis. However, the risks associated with surgical aortic valve replacement are increased in elderly patients and those with concomitant severe systolic heart failure or coronary artery disease, as well as in people with comorbidities such as cerebrovascular and peripheral arterial disease, chronic kidney disease, and chronic respiratory dysfunction.

Patients with symptomatic severe aortic stenosis have a mortality rate of approximately 50% at 2 years without intervention. Patients who are deemed too high risk for open heart surgery, TAVR significantly reduces the rates of death and cardiac symptoms. TAVR is increasingly being offered to intermediate risk patients, based on recent studies showing it to be non-inferior to surgical aortic valve replacement.

The TAVR devices are effective in improving functioning in the patients with severe aortic stenosis, and these devices are currently manufactured by various companies in the US. These are Medtronic's CoreValve Transcatheter Aortic Valve which is constructed of a self-expanding Nitinol frame and delivered through the femoral artery, Boston Scientific's Lotus Valve system which was has been designed to minimize regurgitation. St Jude Medical's Portico Transcatheter aortic valve is designed to be repositionable before release to ensure accurate placement helping to improve patient outcomes. Edwards' Sapien aortic valve is made from bovine pericardial tissue and is implanted via a catheter-based delivery system.

These devices are implanted without open heart surgery. The valve delivery system is inserted in the body, the valve is positioned and then implanted inside the diseased aortic valve, and then the delivery system is removed. The catheter based delivery system can be inserted into the body from one of several sites.

The transfemoral approach requires the catheter and valve to be inserted via the femoral artery. Similar to coronary artery stenting procedures, this is accessed via a small incision in the groin, through which the delivery system is slowly fed along the artery to the correct position at the aortic valve. A larger incision in the groin may be required in some circumstances. The transapical approach sees the catheter and valve inserted through the tip of the heart and into the left ventricle. Under general anesthesia, a small surgical incision is made between the ribs, followed by a small puncture of the heart. The delivery system is then fed slowly to the correct position at the aortic valve. The puncture in the heart is then sutured shut.

The transaortic approach sees the catheter and valve inserted through the top of the right chest. Under general anesthesia, a small surgical incision is made alongside the right upper breastbone, followed by a small puncture of the aorta. The delivery system is then fed slowly to the correct position at the aortic valve. The hole in the aorta is then sutured shut. In the subclavian approach, an incision is made under the collar bone under general anesthesia, and the delivery system is advanced into the correct position in the aortic valve. The delivery system is then removed and the incision is sutured closed.

Background—Left Atrial Appendage (LAA) Device Closure Procedures

Left atrial appendage occlusion (LAAO), also referred to as Left atrial appendage closure (LAAC) is a treatment strategy to reduce the risk of left atrial appendage blood clots from entering the bloodstream and causing a stroke in patients with non-valvular atrial fibrillation (AF). Over 90% of stroke-causing clots that come from the heart are formed in the left atrial appendage. The most common treatment for AF stroke risk is treatment with blood-thinning medications, also called (oral anticoagulants), which reduce the chance for blood clots to form. These medications (which include warfarin, and other newer approved blood thinners) are very effective in lowering the risk of stroke in AF patients. Most patients can safely take these medications for years (and even decades) without serious side effects.

However, some patients find that blood thinning medications can be difficult to tolerate or are risky. Because they prevent blood clots by thinning the blood, blood thinners can increase the risk of bleeding problems. In select patients, physicians determine that an alternative to blood thinners is needed to reduce AF stroke risk. Approximately 45% of patients who are eligible for warfarin are not being treated, due to tolerance or adherence issues. This applies particularly to the elderly patient's.

Left atrial appendage closure is an implant-based alternative to blood thinners. Like blood thinning medications, an LAAC implant does not cure AF. A stroke can be due to factors not related to a clot traveling to the brain from the left atrium. Other causes of stroke can include high blood pressure and narrowing of the blood vessels to the brain. An LAAC implant will not prevent these other causes of stroke.

Occlusion of the left atrial appendage can be achieved from an inside (endovascular) blood exposed device such as the Watchman device available from Boston Scientific. The WATCHMAN Implant is a one-time implant typically performed under general anesthesia with Transesophageal echo guidance (TEE). Similar to a stent procedure, the device is guided into the heart through a flexible tube (catheter) inserted through the femoral vein in the upper leg. The implant is introduced into the right atrium and is then passed into the left atrium through a puncture hole. These small iatrogenic atrial septal defects usually disappear within six months. Once the position is confirmed, the implant is released and is left permanently fixed in the heart. The implant does not require open heart surgery and does not need to be replaced. Recovery typically takes twenty-four hours.

The main adverse events related to this procedure are pericardial effusion, incomplete LAA closure, dislodgement of the device, blood clot formation on the device requiring prolonged oral anticoagulation, and the general risks of catheter-based techniques (such as air embolism). The left atrium anatomy can also preclude use of the device in some patients.

Background—Atrial Fibrillation Ablation Procedures

Atrial fibrillation (AF) is the most prevalent cardiac arrhythmia. It affects 1% to 2% of the general population with an important increase in incidence with age. In the United States it is estimated that over 5 million people have atrial fibrillation, and because of our aging population the prevalence of this arrhythmia will increase significantly over the next decade.

Atrial fibrillation is associated with increased morbidity and mortality, and in particular, a general decrease in quality of life for those afflicted with atrial fibrillation. AF can also cause tachycardia mediated cardiomyopathy or worsening of pre-existing heart failure. Moreover, AF is known to increase the mortality risk 1.5-2 fold with the risk for stroke increasing five-fold. Patients are at an increased risk of stroke unless they are treated adequately with anticoagulants. Anticoagulant treatment however, increases the patient's risk of bleeding, which carries with it is own set of dangers. Medications currently available for treating atrial fibrillation have proven to be only moderately effective in decreasing the incidence of recurrent atrial fibrillation, and these medications do not decrease the patient's risk of having a stroke.

One method of treating atrial fibrillation has been to perform ablation of selected areas of the left atrium. There is strong evidence to suggest that ablating these areas of the left atrium serves to cure or prevent further incidences of atrial fibrillation, which thereby has shown to reduce the risk of stroke and reduce the necessity of anticoagulant therapy. Typically, ablation of this type is carried out via an intravascular catheter using radiofrequency or microwave energy to cause thermal changes to the selected parts of the left atrial tissue.

Besides having a good safety profile, catheter ablation therapy for AF has proved effective in establishing and maintaining sinus rhythm. Ablation for atrial fibrillation is now the most commonly performed procedure in most laboratories.

It is well known that pulmonary vein isolation (PVI) is an accepted treatment modality for paroxysmal atrial fibrillation. Since pulmonary veins are the dominant initiating source of atrial fibrillation, the source of atrial fibrillation can be abolished by pulmonary vein isolation (PVI). Pulmonary vein isolation (PVI) involves rendering the tissue between pulmonary veins and the left atrium (LA) to be electrically inactive by an ablation procedure, for all the pulmonary veins. There are normally four pulmonary veins (PV), but many times there are variations in the pulmonary vein anatomy. Generally, the aim is to electrically isolate all the pulmonary veins (i.e. create bidirectional block) such that any triggers arising in the pulmonary veins are not conducted to the left atrium (LA).

Frequently these ablation procedures are performed using balloon based catheters. There are various types of balloon based catheters such as laser balloons, cryoballoons and other types of balloon based catheters for arial fibrillation ablations. Cryo ablations are performed utilizing a cryoballoon catheter, such as one available from Medtronic Inc. The ultimate purpose of cryoablation is to freeze tissue in a discrete and focused fashion to destroy cells in a precisely targeted area. Generally in cryo ablations tissue hypothermia causes cardiomyocytes to become less fluidic as metabolism slows, the ion pumps to lose transport capabilities, and the intracellular pH to become more acidic.

In addition to cryoballoon catheters, other balloon based catheters are also utilized. In one type of balloon based catheter, a laser energy is delivered from inside the balloon for point-by-point pulmonary vein isolation. In another type of balloon catheter, heating is applied for pulmonary vein isolation instead of freezing as with the Arctic Front® cryoballoon catheter.

In the method and system of this disclosure, any of these balloon based catheter may be used for atrial fibrillation ablation utilizing a fluoroscopy and/or medical images based cardiac mapping system of the current invention.

Other forms of ablation energy are also sometimes used, though currently they are not as common. These include, microwave energy ablations, laser ablation, and high frequency ultrasound (HIFU) ablations among others, and their us is within the scope of this disclosure. Even though the cardiac image mapping system disclosed here is described in conjunction with cyroablations, it can be used for other energy forms of ablation, such as RF, Microwave, high intensity focused ultrasound (HIFU), hot balloon and laser ablations.

For RF ablations, a contact force catheter is frequently utilized. Also, for RF ablations a non-fluoroscopic mapping system is frequently utilized. Generally, non-fluoroscopic mapping systems may be impedance based such as St Jude's Navix/Velocity system, or magnetic based such as Biosense Webster Carto mapping system.

For a non-fluoroscopic 3-D mapping system to have utility, the catheters must have sensors which communicate with and which can be registered with the image generated by the mapping system, especially the ablation catheters.

Cryoaballoon ablations is one type of ablation procedure whose popularity is increasing rapidly due to many advantages that it offers over RF ablations. One big advantage of cryoballoon ablations is that the whole pulmonary vein is ablated at once, instead of point by point ablations when performed with RF energy catheters.

Cryoballoon catheters do not have sensors for registering to impedance or magnetic based 3D mapping system.

A cryoballoon catheter generally consists of a hollow shaft with a closed distal end containing a cooling electrode tip, integrated thermocouple deice and three proximal ring electrodes for recording and pacing. A console that contains the cryorefrigerant fluid. The cooling liquid travels through the inner delivery lumen to the catheter tip, where the cryorefrigerant is pressurized and released. This accelerated liquid-to-gas phase results in rapid cooling of the distal tip. The gas is then conducted away from the catheter tip through a second coaxial return lumen maintained under vacuum and evacuated in the hospital medical gas disposal system.

The console allows the operator two different modes of operation. The first is the cryomapping mode in which the tip is cooled to a temperature not lower than −30 C for a maximum of 80 seconds so as to prevent irreversible tissue damage. The second mode is cryoablation, which results in cooling of the catheter tip to at least −50 C for a programmable period (nominally 4 minutes), producing the permanent lesion. The cryomapping mode can be used for an indefinite number of times before cryoablation. Cryoablation may be initiated at any time during a cryomapping application or, from the onset, if the operator wishes to forego the cryomapping function.

Advantages of Cryo Ablations Include:

Catheter stability-Hyperthermia generated at the distal cooling electrode, the trial catheter adheres to tissue affording greater catheter stability. The operator may let go of the catheter once it is adhered onto the endocardial surface. The programmed electrical stimulation may be performed during cryoablation without concern for catheter dislodgement. Moreover brushing effects that occurred during beat-to-beat rocketing heart motions and with respiratory variations are eliminated Minimal risk of thromboembolism—To compare the propensity for RF and cryo ablation to produce hot thrombus on the surface of the ablation lesion, a randomize preclinical study was conducted involving 197 ablation lesions in 22 dogs at right atrial, right front, left ventricular sites RF energy was five times more thermogenic than cryoablation, as confirmed by results of historical morphometric analysis seven days after ablation moreover, thrombus volume was significantly greater with RF compared with cryoablation. Interestingly, the extent of IPO thermic injury was positively correlated with thrombus spoke. This was unlike bioenergy, in which lesion that mentions are not predictive of thrombus ice.

Moreover, cryothermal ablation lesions are associated with a lesser degree of platelet and coagulation cascade activation when compared with RF ablation.

Minimal risk to vascular structures—Concerns have been raised regarding RF ablation adjacent to or within coronary venous system or TVs, with venous injury (including acute perforation and Tampanode, and/or delayed fibrosis/stenosis), acute or sub acute and/or luminal venous thrombosis, and collateral damage to the esophagus and/or adjacent coronary arteries being reported. Perforation, or not, and coronary artery stenosis are potential complications. The circumflex and/or coronary artery may course in close proximity to the arrhythmia substrate. Moreover, the AV nodal artery passes near the mouth of the coronary sinus, the ablation may conceivably damage this vessel. Preclinical studies suggest a lower incidence of coronary artery stenosis following cryoablation compared with RF ablation.

Painless ablation—RF ablation may be painful to the patient under conscious sedation through direct stimulation of cardiac sensory nerves or pericardial or collateral Whisler visceral irritation, particularly when ablating your thin-walled or venous structures such as posterior left atrium, coronary sinus, or posterior cable tricuspid Isthmus. In contrast to our FCA, several studies have noted that again perception, as assessed by standard Likert scale, is significantly less with cryoablation. This first select procedures associated with substantial patient discomfort, the use of cryoablation may theoretically result in lower anesthetic and analgesic requirements. This is especially relevant for electrophysiology laboratories that do not use general anesthesia. However, it should be noted that in the case of AF ablation, a rare incidence of transient ice cream headache has been described during ablation.

Visualization by ultrasound—The ability to visualize formation of ice ball by ultrasonic means was likewise demonstrated in preclinical transcatheter cryoablation studies. This feature of cryoablation has proved helpful in defining optimal freezing parameters.

Background—Virtual Reality (VR) and Mixed Reality (MR)

Virtual reality (VR) is a computer-simulated environment that can simulate a user's physical presence in real or imaginary environments. This perception of being physically present in a non-physical world is called immersion. A virtual reality environment typically includes visual images displayed either on a computer screen or through stereoscopic (e.g., 3D) head mounted displays (or referred to as a headset). A head mounted display is a device worn on the user's head, resembling such as a helmet or glasses for an example, in which a small display optic is in front of at least one eye. Recent virtual reality head mounted displays may rely on "lighthouses" or cameras to track the user's head position and movement and translate such in the virtual feedback such as in versions of the HTC vive or Oculus for an example. Others may rely on internal sensors (such as inertial measurement units), or a combination of both to properly communicate real world user movements to that visually presented in the virtual environment. The virtual reality environment may also include sound provided through speakers or headphones and force feedback via, for example, a vibrating controller or joystick. Applications of virtual reality include medical, gaming, and military environments. Virtual reality environments involving users typically consist of individuals controlling virtual representations of themselves in the virtual environment. For example, users may be sitting or standing near the operating computer and move within the virtual space through the use of a keyboard, mouse, joystick, or other input devices. The virtual environment may be affected by either the actual or relative physical locations of the user between the physical and virtual world using sensory inputs to relate the two. Further, users may interact with the virtual environment, such as picking up virtual objects or caring out virtual tasks (such as throwing such ball).

Augmented reality (AR), also commonly referred to as augmented vision or augmented reality vision, augments an observer's view of the real world by superimposing computer generated graphical information. This information may be as simple as a text label attached to an object in the scene, or as complex as a 3D model of a patient's brain derived from an MRI scan and aligned to the real view of the person's head. The observer may observe a real scene directly with his or her eyes, with the additional graphical information being blended therewith via a semi-transparent display located between the observer and the real scene. Such a display device can be, for example, a see-through head mounted display. The display can also be opaque, like a computer screen or a non-see-through head mounted display. Such a display then presents to the observer the complete augmented view, i.e., a combination of the real-world view and the graphics overlay. A video camera may take the place of the real-world observer to capture the real world-view. It is desirable to "anchor" the graphics to a real-world object. To do this, the position and orientation of the camera with respect to the object, as well as the orientation of the object, are known. That is, the relationship between two coordinate systems, one corresponding to the camera and the other corresponding to virtual object are used to realistically view the virtual object within the real word. This also allows for user interaction with the virtual object.

The use of a virtual reality, augmented reality, or combination of such (mixed reality) via a head mounted display will hence forth be known as immersive visualization devices. Visualization of the virtual environment occurs when users visually experience virtual components of the virtual reality, for an example using the immersive visualization devices to inspect a virtual model. These devices typically interact with a sensor(s) within the head mounted display itself to detect user movement, or supplementary via remotes to further gather user gestures and garner user interactivity. These sensors act as the bridge between the virtual environment and the physical world via user movement and input.

Background—Use of VR and AR in Surgery

With a rapidly increasing global population and a widening gap between demand for high quality healthcare and the resources available to support this, there is a pressing need for additional tools to support the delivery of clinical excellence. Recent years have seen a trend towards the use of virtual reality (VR) technologies for rehabilitation and disability support. This is partly driven by the decreasing cost and improved accessibility to the technology, but also by the growth in expertise of virtual rehabilitation researchers and practitioners.

Recent advances in virtual reality (VR) and augmented reality (AR) technologies have provided a tremendous boost to the field of virtual preprocedural planning. Two main drivers have contributed to the recent surge in VR/AR popularity and increased awareness in these technologies: availability of affordable VR/AR hardware and availability of software development tools. Both of these factors also have a large impact on Virtual Rehabilitation applications.

Largely driven by the entertainment industry, prices for VR/AR head-mounted displays (HMDs) and tracking devices have become more affordable and accessible for consumers. Instead of spending tens of thousands of dollars for sophisticated HMDs, researchers, clinicians and educators can now purchase immersive VR/AR systems affordably. Tracking solutions such as head, hand and body-tracking as well as a wide range of display methods have become available since the first Oculus Rift Prototype was released in March 2013.

Immersive visualization devices, specifically augmented reality visualization, can guide a user in manual mechanical tasks. For machine repair and maintenance scenarios, it has been suggested to augment the view with graphical pointers that show, e.g., which button to press or which screw to turn. Augmented reality visualization is also being suggested for medical applications where, e.g., biopsy needles have to be inserted into a target tumor without harming nearby nerves or where screws have to be inserted into bones at a precise location and in a precise direction.

The current surgical planning procedure includes computed tomography and magnetic resonance imaging study. This method can help the surgeons to get the rough image of the inner pathology that they may encounter beforehand. However, this method is unreliable and depend on the experience of the surgeons. Using a patient-specific virtual reality system, the surgeons can do the surgery virtually based on the model created from patients' imaging before doing the same operation on the actual patients. The surgeon can get the benefit from this system as they will face the same anatomical variation of the particular patients. This method will minimize the surgical error. The patients will also get the benefit as the surgical failure rate will decrease.

Surgery for the patient has an aim's for perfection. Any untoward errors, intend or not intend, are not acceptable. Unlike the practice on non-human, this can be done with the freedom of perfection. The surgeon usually needs to pass certain amounts of practices on non-human models or cadavers to ensure that their skills are close to perfect and ready to practice on the patients. Before practice on the patients, the pre-operative planning is the most important step. The planning can be briefly done by the attending surgeon for most uncomplicated case. In some cases, the planning need to be conducted as a group discussion from multi-disciplinary alliance for the higher success rate of the operation and the better prognosis of the patients. In the area of otolaryngology, imaging has until recently been of poor quality and could only be interpreted by a small number of highly experienced radiologists. Historically, most of the surgical otolaryngology procedure, the rhinoscopy otoscopy and laryngoscopy were the only reliable tool for the surgeons. The plain film x-ray may undertake as an optional pre-operative measure without much valuable information. The introduction of high-resolution computed tomography scanning in the 1980s, has allowed superb pre-operative imaging of anatomy, some evidence of the extent of the disease and a screen for asymptomatic complications. It was not until 1990s that the high-resolution imaging modalities have gained the popularization as an essential aid to surgical planning. However, due to the cost of the imaging in that era, most of the surgeons preserved the high resolution imaging modalities as for selected cases such as the case with complications Computer-aided surgical planning is a technique using the computer combined with the surgical imaging to help the surgeons for pre-surgical planning. Many computer-aided systems were developed to improve the safety and accuracy of the operations. In these systems, the users can manipulate the anatomical model derived from the patient's images on the screen freely e.g., rotation, zooming, measurement, etc. The computer-aid surgical planning system has offered more benefits over the conventional planning through computer-aided design (CAD) and computer-aided manufacturing (CAM) techniques. The system gives more precise preoperative planning and a decreased necessity for intraoperative trials and errors. Applications include preoperative planning through virtual surgery, fabrication of cutting guides and bone models using stereolithography techniques, and surgical navigation systems to aid in the placement of implants and to guide bone cuts. The CAD-CAM technology has been present for decades but never been introduced to the medical fields. The technological developments have made the possibility to integrate the new technology into the medical field including otolaryngology surgery. Improvement in resolution and quality of images as well as decreased slice thickness obtained from CT scans allow generation of more accurate 3D models for surgical planning and manipulation. Advanced surgical simulation tools allow manipulation of the 3D model with 6 degrees of freedom, therefore allowing visualization of simulated surgical approaches from different angles. Advances in rapid prototyping technology allow fabrication of more accurate 3D models with detailed internal contours through stereolithography (3D printing) techniques as well as demonstration of surgical approaches after preoperative virtual surgery. However, there are increased costs related to computer-aided surgical planning in some procedures that are not offset by the savings in valuable surgical time.

In maxillofacial surgery, volumetric analyses of anatomical structures have been utilized for the design of standardized anatomic implants for orbital reconstruction and custom patient-specific implants for complex orbital and midfacial defects. These advances have allowed for improved efficiency, accuracy, and safety in the surgical management of orbital pathology.

SUMMARY OF THE DISCLOSURE

The present invention and exemplary embodiments of the invention as described herein are generally directed to a method and system for use of visualization devices for procedural planning and use for transcutaneous aortic valve replacement (TAVR), or left atrial appendage (LAA) closure device procedure, or atrial fibrillation ablation procedures.

In an aspect of the invention, the method is visualization for pre-procedural planning for LAA closure device, TAVR, or atrial fibrillation ablation procedures. This method comprises the steps of providing a computer based hardware and a software configured with a virtual reality headset and sensors. Wherein, the software is adapted to be used with a gaming engine and object oriented programming. A medical image of the patients anatomy is provided, wherein this image may be from a computed tomography (CT) or medical resonance imaging (MRI) and converted to a 3 dimensional format about a specific region of interest for the procedure of the patient's anatomy using segmenting and volume rendering. The computer based hardware and software is programmed with an application, wherein said application can read the 3 dimensional region of interest created and in conjunction with the hardware and software, the user can visualize said 3 dimensional region of interest and virtual models of the devices used for the procedure with the virtual reality device and sensors. The visualization is for use in preprocedural planning of left atrial appendage (LAA) closure device, TAVR, or atrial fibrillation ablation procedures.

In another aspect of the invention, the virtual reality headset and sensors are independent of the manufacturer.

In another aspect of the invention, the virtual device models have the ability to be resized and/or placed within the virtual anatomic models of the region of interest for the procedure utilizing sensors.

In another aspect of the invention, measurements or marking are displayed within the virtual anatomic structure of the region of interest.

In another embodiment of the invention, the method of utilizing augmented and/or mixed reality (AR/MR) for TAVR, LAA closure device, or atrial fibrillation procedures is disclosed. An AR/MR device is provided, comprising of the headset, an application programmed to said AR/MR device, and a means to control. A medical image of the patients anatomy is provided, wherein this image may be from a computed tomography (CT) or medical resonance imaging (MRI) and converted to a 3 dimensional format about a specific region of interest for the procedure of the patient's anatomy using segmenting and volume rendering and adapted to be readable by the application utilized by the AR/MR device. At least one said 3D region of interest is loaded into the AR/MR device with the application, wherein the application is configured and programmed with gaming engine and object oriented programming and adapted for TAVR, LAA closure device, and atrial fibrillation procedures. Holograms displaying the 3d volume rendered images as previously described are utilized for intra-procedure use during TAVR, LAA closure device, or atrial fibrillation procedures.

In another aspect of the invention, the AR/MR device used is independent of the manufacturer.

In another aspect of the invention, the holgorams are controlled via hand gestures and/or an xbox controller.

In another aspect of the invention, the holograms are displayed next to fluoroscopy and/or ultrasound images.

In another aspect of the invention, the holograms are overlayed or registered to fluoroscopy and/or ultrasound images.

In another aspect of the invention, the application is configured and programmed such that measurements are displayed in or around the hologram.

In another aspect of the invention, previously created device model(s) and 3D anatomical models are loaded into the said AR/MR device for programming as holograms.

In another embodiment of the invention, the system is for visualization for pre-procedural planning for LAA closure device, TAVR, or atrial fibrillation ablation procedures utilizing virtual reality (VR). This system comprises a computer-based system with hardware and a software adapted to work with a VR headset and sensors wherein the software is adapted to be used with a gaming engine and object-oriented programming. The system incorporates a medical image of the patients anatomy, wherein this image may be from a computed tomography (CT) or medical resonance imaging (MRI) and converted to a 3 dimensional format about a specific region of interest for the TAVR, LAA closure device, or atrial fibrillation procedure of the patient's anatomy with volume rendering capabilities. The computer-based hardware and software are configured with an application with the ability to create a virtual device model and/or interact with the region of interest utilizing game engine and object oriented programming, in which the virtual device model and the region of interest may interact with each other to aid in TAVR, LAA closure device, or atrial fibrillation procedures utilizing the VR headset and sensors.

In another aspect of the invention, the virtual device models have the ability to be resized and/or placed within the virtual anatomic models of the region of interest.

In another aspect of the invention, measurements or markings are displayed within virtual anatomic structure, which is the region of interest, utilizing sensors.

In another embodiment of the invention, the system is for utilizing AR/MR for LAA closure device, TAVR, or atrial fibrillation ablation procedures. This comprises an AR/MR devise that comprises a MR/AR headset, an application programmed to said AR/MR device, and a means to control. The system incorporates a medical image of the patients anatomy, wherein this image may be from a computed tomography (CT) or medical resonance imaging (MRI) and converted to a 3 dimensional format about a specific region of interest for the TAVR, LAA closure device, or atrial fibrillation procedure of the patient's anatomy with volume rendering capabilities. The application is configured with the capability to load the region of interest in the AR/MR device, wherein the application is configured and programmed for aiding in TAVR, LAA closure device, or atrial fibrillation procedures. The AR/R device is capable of displaying holograms of at least one region of interest capable of free floating or being using with a fluoroscopy and/or ultrasound image(s).

In another aspect of the invention, the holograms are controlled via hand gestures and/or a Xbox controller In another aspect of the invention, the hologram is overlayed or registered to fluoroscopy images and/or ultrasound images.

In another aspect of the invention, the application is configured and programmed such that measurements are displayed in the hologram or around the hologram.

In another aspect of the invention, previously created models are placed with the hologram, or within the hologram.

In another aspect of the invention, the Microsoft's Hololens-2 or a higher version of MICROSOFT™ HOLOLENS™ is utilized for said augmented reality (AR) or mixed reality (MR) device.

In another aspect of the invention, the AR/MR device is independent of the manufacturer.

BRIEF DESCRIPTION OF THE DRAWINGS

For the purpose of illustrating this disclosure, there are shown in accompanying drawing forms which are presently preferred, it being understood that the disclosure is not intended to be limited to the precise arrangement and instrumentalities shown.

FIG. 12 is a block diagram depicting CT images overlaid on top of recorded fluoroscopy images and live fluoroscopy overlaid on top of that.

FIG. 16 is a block diagram depicting MRI imaging overlaid on recorded fluoroscopy, and live fluoroscopy overlaid on top of that.

FIG. 19 is a diagram showing a recording of fluoroscopy with contrast medium ("dye") injection.

FIG. 20 is a diagram showing a recording of fluoroscopy with contrast medium ("dye") injection close to left superior vein.

FIG. 21 is a diagram showing an example of one implementation where live fluoroscopy and recorded are overlaid on top of each other and the transparency between the two images has been adjusted. Further, electrical signals are also displayed on the top image.

FIG. 22 is a diagram showing an example of a CT image with volume rendering which can be combined with fluoroscopy and/or other types of medical images.

FIG. 54 shows and implementation of the recorded images and live images overlaid on top of each other.

FIG. 55 shows pressure tracing from a cryoballoon catheter which are used in the proper placement of the catheter.

FIG. 58 is a flow diagram showing implementation of putting graphical and color coded 3D signals on fluoroscopy image.

FIG. 59 shows the ablation screen in one implementation with time domain signals.

FIG. 60 shows volume rendered CT image which can be rotated in 3D.

FIG. 61 shows one example of implementation where a CT image is sandwiched between recorded and live fluoroscopy, and graphical display of electrical signals from a circular catheter is shown along with time domain signals.

FIG. 69A-69C depicts the setup/process for LAA closure device, atrial fibrillation, and TAVR procedures.

FIG. 72 demonstrates a generic virtual reality device from different views.

FIG. 73 is a table with a nonexclusive list of possible components in a VR, MR, or AR device.

FIG. 76 is a table with a nonexclusive list of example game engines, programming languages/scripting, platforms, and devices.

FIG. 98 is a flow diagram for the script that controls and interprets user inputs used by the intra-procedural application as in FIG. 94.

DETAILED DESCRIPTION OF THE DISCLOSURE

Figure 1A:
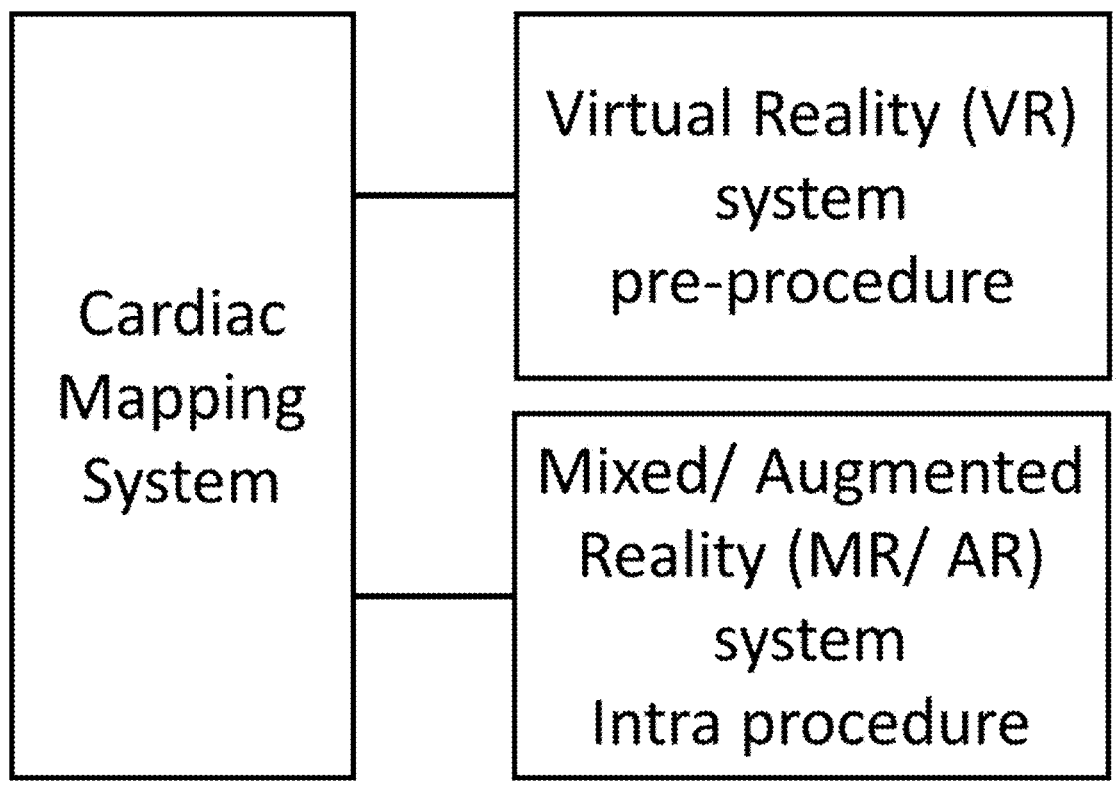
FIG. 1A is a block diagram showing the overall relationship between the concept of a cardiac mapping system and a virtual reality system for preprocedural planning and mixed/augmented reality systems for intra-procedure use.
Figure 1B:
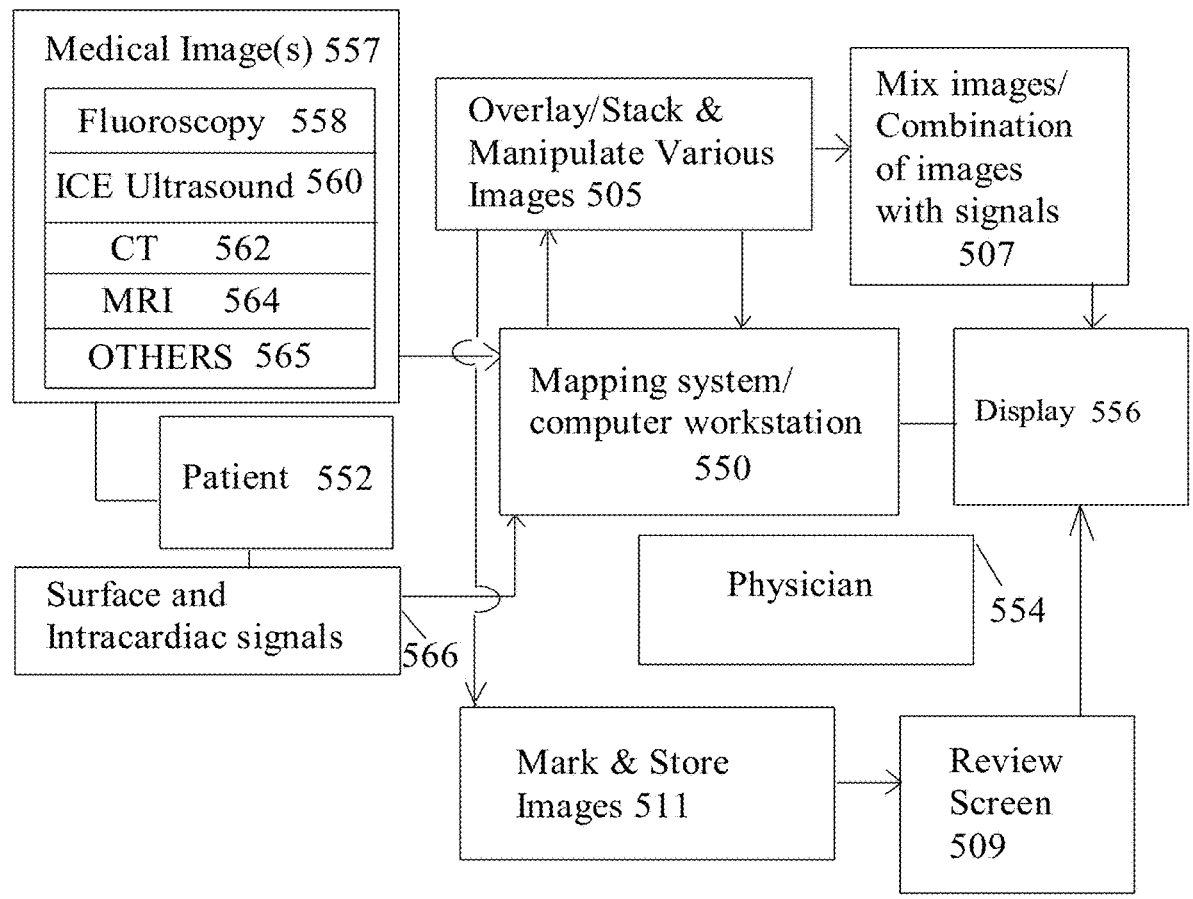
FIG. 1B is a block diagram showing the concept of the mapping system including overlaying/stacking of various images and marking and storing images.

The following description is of the best mode presently contemplated for carrying out the disclosure. This description is not to be taken in a limiting sense, but is made merely for the purpose of describing the general principles of the disclosure.

In the methods and system of this disclosure, medical images based cardiac mapping/electrophysiology tools is disclosed for cardiac ablations for arrhythmias. The methods and system of this disclosure can be employed with a methodology for monitoring esophageal temperature. In another embodiment, the mapping system and mapping methodology can also be used without the use of temperature monitoring.

Definitions

Basics for the idea:
Computed tomography (CT): as used in this application is standard CT as used in medical procedures.
Magnetic resonance imaging (MRI): as used in this application is standard MRI as used in medical procedures.
Gaming Engine: A software application used to create, render, and/or run programmed applications.
Object oriented programming: Refers to coding languages formatted. Specifically, it is a programming paradigm based on the concept of "objects", which can contain data and code: data in the form of fields, and code, in the form of procedures. A feature of objects is that an object's own procedures can access and often modify the data fields of itself.
Fluoroscopy: 2D image. As used in this application is image from fluoroscopy system being used in the procedure
Ultrasound: 2D image. As used in this application is image from an ultrasound based modality such as ICE (intra-cardiac echo) or TEE (trans esophageal echo).
For the device:
Virtual reality (VR): Virtual reality is a computer-simulated environment that can simulate a user's physical presence in real or imaginary environments. A virtual reality environment typically includes visual images displayed either on a computer screen or through stereoscopic (e.g., 3D) head mounted displays (or referred to as a headset)
Augmented reality (AR) or Mixed reality (MR) device: These terms may be used interchangeably to describe devices that augment an observer's view of the real world by superimposing computer generated graphical information. The observer may observe a real scene directly with his or her eyes, with the additional graphical information being blended therewith via a semi-transparent display located between the observer and the real scene. Such a display device can be, for example, a see-through head mounted display. The display can also be opaque, like a computer screen or a non-see-through head mounted display. Such a display then presents to the observer the complete augmented view, i.e., a combination of the real-world view and the graphics overlay. A video camera may take the place of the real-world observer to capture the real worldview. These devices often have sensors to distinguish the spatial representation of the real world about the users, sensors to record a user's position, rotation, and translation.

Related to these Vocab words are:
Headset: This can include a helmet, googles, or any VR, AR or MR device that is wearable on the face. These devices display optics in front of at least one eye.
Sensors: For virtual reality this may include lighthouses (IR) or cameras to track users positions and represent such in the virtual visual input. Sensors may further include internal sensors for position, rotation, and translation. Further sensors may include controller for user inputs, microphone for voice control, etc.
Computer based hardware: Laptops and desktops, or possibly an "computer" meeting the minimum specifications.
Minimum specs of computers: Minimum CPU, GPU, Processors, Memory, etc (refer to Table 2).
Software: This includes any game driven software to run the devices and/or the application, such as those suggested to be run with the devices, and backend executables needed to run such. Examples: Oculus, Vive, steam, backend executable (refer to Table 3).
Adapted to be readable: The 3D volume rendering/method to make the anatomical structures 3D are in a format that is accessible and useable by the application and the resulting device. Application: The executable collection of codes and builds created that run the application to load, manipulate, visualize, and interact with the ROI virtually within the VR and or AR devices. Virtual and/or CAD Model of device used in LAA, TAVR, or Afib procedure (Models): Models here refers to the ablation devices and those used for the LAA. Below is the list of examples.
CAD:
Holograms: a 3D representation of an object augmented in the real world via AR/MR.
The Descriptors:
Holograms free floating: Where the 3D augmented visualization of the heart is located in the real-world space without a specific spatial anchor.
Region of interest (ROI): Isolating parts of the volume rendering specific to the procedure. This will become the virtual object/visualization used with the application in the VR and/or AR device.
Means to control: Means to interact with the application within the VR and/or AR device. Listed are some definitions.
Voice: Using speech such as keywords or voice commands to control and interact with application.
Hand gestures: Using hand movement and gestures to control and interact with application.
Controller: Using an external controller, such as the Xbox controller, to control and interact with application.

Processes:
- Visualization: The ability to look through the VR, AR, or MR devices at the 3D model. Preplanning procedure: Prior to the procedure. May include examining the anatomical structure, planning surgical steps, taking measurements, or noting unexpected features.
- Intraprocedural: use of device during procedure for enhancement or in conjunction with other modalities
- Left atrial appendage (LAA) closure device procedure: are procedures where a device is implanted in the left atrial appendage to prevent strokes.
- Atrial fibrillation ablation procedure: are procedures where an ablation procedure is performed to treat atrial fibrillation.
- TAVR: Transcutaneous aortic valve replacement is a procedure where the aortic valve is replaced without performing open heart surgery.
- Segmenting and volume rendering: is a process where a patient's CT is utilized for defining a region of interest and performing a 3D volume rendering of that region of interest.
- Automatically registered: Choosing points on the patients/or the virtual ROI, choosing points in space to correspond to those landmarks to the location in the real world. Scaling rotating and translating the model to relocate the ROI to those points with minimum error between the final position of landmarks between the ROI and real world.
- Manually registered: The user changes the transformation (rotation, translation, scale) of the virtual ROI manually to align with real world features based on landmarks of the anatomy.

Cardiac mapping systems are navigation and/or guidance systems used during a cardiac ablation procedure which includes making maps, guiding physicians to the optimal placement of the catheters. Cardiac mapping systems may utilize various types of medical images or a combination of medical images, or overlays of different types of medical images. They may also make a computer model of the geometry based on electrical or magnetic sensors. Cardiac mapping also utilizes the patients electrical signals derived both from surface EKG and various electrode pairs of the intracardiac catheters. Frequently in cardiac mapping a patients electrical activity is superimposed on medical images (or combination of medical images) or a derived computer model of the geometry of the heart.

3D volumetric tags in this disclosure are defined as tags which have a predefined shape and volume. The tags can be resized. The tags may be such shapes as a ring with volume, sphere shaped, shaped like a pear, or any other shape with volume.

Anatomical segment(s) in this disclosure are one or more region(s) or an organ or part thereof on a patient's CT/MRI image identified as an area of interest, wherein each such area is 3D volume rendered and is stored in a separate digital file.

In this disclosure, turning ON a segment means displaying the segment, and turning OFF a segment means removing the segment from the display.

The methods and system of this disclosure is also used for atrial fibrillation (AF) ablations or pulmonary vain isolation (PVI). The method and system of the current disclosure is particularly useful for any balloon based catheter used in ablation for atrial fibrillation. This disclosure can be employed for any balloon based catheter, including cryoballoon catheter, laser balloon catheter, hot balloon catheter, radio frequency (RF) catheters or circular diagnostic catheters, as well as other balloon catheters that are currently being developed and will be in the market soon for atrial fibrillation ablation techniques/methodologies.

As will be obvious to one skilled in the art, that the CT or MRI overlay in anatomic segments over fluoroscopy for navigation and guidance applies to any of type balloon based catheter. The navigation method and system is agnostic to the type of balloon catheter.

Mapping systems are used for navigation and guidance, and sometimes are used interchangeably.

The temperature probe may comprise a single or multiple thermisters. The multiple thermister probe may comprise any number of thermisters. In one preferred embodiment, the temperature probe may have ten thermistors. In other embodiments the probe the probe may have any number of thermisters. The goal is to cover the whole esophageal region, which could correspond to the left atrium. Another goal is that the coverage is large enough so the physician shouldn't have to move the esophageal probe during the procedure.

Cardiac Mapping Systems

Cardiac mapping systems are known in the art and are generally used during cardiac ablation procedure in atrial fibrillation procedures where temperature monitoring is needed.

The role of these mapping systems has been to keep a log of and make manageable and interpretable the vast amount of information obtained during an electrophysiology study. These systems have made possible the extensive intracardiac mapping that can now be performed and applied during electrophysiologic procedures. This enhanced mapping capability has been especially useful in the treatment of complex arrhythmias that require extensive ablation in the cardiac chambers, e.g., atrial fibrillation and ventricular arrhythmias.

The two of the commonly used mapping systems are CARTO (Biosense Webster) and NavX EnSite (St. Jude Medical, Inc.). CARTO uses a low-level magnetic field measured by a catheter location sensor, whereas NavX registers electrode impedance sensor in relation to skin patches that apply a low-level electrical current.

Electromagnetic Based Mapping System

Systems such as CARTO (Biosense Webster, Diamond Bar, Calif.) use the electromagnetic position of the catheter tip relative to an electromagnetic locator pad which is placed below the patient, and a reference catheter at a fixed external (usually posterior) location. The CARTO system provides electroanatomic mapping based upon the premise that an electrical current is generated when a metallic coil is placed in a magnetic field. The magnitude of the current depends on the strength of the magnetic field and the orientation of the coil in the field. The CARTO system consists of,
- a magnetic field emitter mounted under the patient; the external magnetic field emitter has 3 coils that generate ultra-low-intensity magnetic fields (between $5 \times 10-6$ and $5 \times 10-5$ T) that code the surrounding space with spatial information sensed by the field sensor at the tip of the mapping catheter
- a location sensor inside the mapping and ablation catheter tips, and
- a data processing unit and graphical display unit to generate and display the 3D model of the cardiac chamber of interest.

Data on the amplitude, frequency, and phase of the magnetic field are gathered and analyzed by the processing unit and displayed on the display unit. The CARTO mapping system uses a triangulation algorithm in which a sensor in the catheter tip allows the determination of its distance from each coil. In addition to the x, y, and z coordinates of the catheter tip, the CARTO mapping system can determine three orientation determinants—roll, pitch, and yaw. The position and orientation of the catheter tip can be seen on the screen and monitored in real-time as it moves within the electroanatomic model of the chamber being mapped.

Since the CARTO mapping system is not an imaging technique, fluoroscopy is initially used to establish orientation by using generally known anatomic locations in the heart as references for the later creation of the model of the mapped chamber. An electromagnetic anatomical reference patch is placed on the back of the patient and is used to track the mapping and ablation catheter. For activation mapping, an electrical reference such as an ECG signal or an intracardiac recording is used. For intracardiac recordings, coronary sinus recordings are often selected because they are usually stable. For activation, points taken by the catheter are color-coded red, orange, yellow, green, blue and purple for progressively-delayed activation areas. Similarly, the voltage map is also color-coded and superimposed on the anatomic model. Using these techniques, both the mechanism of the arrhythmia and the 3D anatomy can be created. However, creation of an electroanatomic map may be a lengthy process involving the tagging of many points, depending upon the spatial details needed to analyze a given arrhythmia. Lack of accurate ECG and respiration gating and non-real-time data are other limitations of this technique. Furthermore, the catheters used are very expensive and fluoroscopy is always used as a backup to identify the location of catheters.

Electrical Impedance Electroanatomic Mapping

The concept underlying the use of electrical impedance to calculate a spatial locations is based on the following: A very low-voltage alternating current of a particular localization frequency is applied across a patient's body using two skin electrodes confers a relatively linear voltage gradient across the tissues in the axis of the electrodes. The voltage can be detected by a sensing electrode and can then be converted to the axial location of the sensor. Three such orthogonal electric currents applied separately and detected by a sensor can thus be used to triangulate the 3-dimensional (3D) location of the sensor.

Mapping using this concept requires fulfillment of the following 4 conditions: 1) 3 orthogonal currents with the heart at the center need to be used to allow triangulation in 3-dimensional space; 2) the externally applied electric current should be easily detectable but benign to the patient and not interfere with the recorded electrograms; 3) the voltage gradient need to be calibrated to interpret recorded voltages for localization; and 4) spatial variations associated with the cardiac and respiratory cycles need to be accounted for. Thus stabilization of the whole localization apparatus throughout the mapping and ablation procedure is important to limit inaccuracies.

The EnSite NavX (St. Jude Medical, Inc. St. Paul, Minnesota) was first described for electroanatomic mapping and navigation in atrial flutter ablation in 2004. A low electric current at 5.68 KHz is multiplexed with each of these pairs of electrodes to create the navigational electric field across the heart. A fixed intracardiac catheter (e.g., in the coronary sinus) or a surface electrode serves as the reference. The electrode position is averaged over 1 to 2 cardiac cycles to reduce cyclic cardiac variation. However, because of the long excursion of the respiratory cycle, eliminating respiratory variations by averaging becomes impossible without compromising the real-time localization and display.

Fluoroscopy Based Mapping System

In the method and system of fluoroscopy based mapping system, a cardiac mapping system has been disclosed where existing cardiac image or multiple images are utilized, and electrical parameter(s) information is/are superimposed on them to provide an "electro-anatomical" map. The existing cardiac image(s) may be a fluoroscope image or combined images such as a 3D computed tomography (CT) image overlaid or registered on a fluoroscope image, or other images as described later. This may also be referred to as a "sensor-less" cardiac mapping system, as the prior art systems comprise sensors that are impedance based or electromagnetic based, and the current disclosure describes a method and system that can perform electro-anatomical cardiac mapping without the impedance or electromagnetic based sensors.

In the concept of this disclosure, a computer 68 is configured to receive multiple channels of electrical signals including 12-lead EKG and various intracardiac signals, shown in a simplified form in conjunction with FIG. 22. A computer, is generally a desktop workstation 68 (or a laptop 66—not shown) is configured to receive fluoroscopy 72 and/or other images into the computer 68. Additionally, there may be an output from the computer for feedback control of various things, for example interrupting energy delivery in certain situations. The interruption of energy delivery may be based on electrical signals and/or other parameters. One example would be interrupting energy delivery for AVNRT ablation based on timing relationships of the acquired atrial and ventricular signals. Another example would be interrupting ablation energy delivery based on esophageal temperature monitoring.

Ablation Stopping Box

Use with Cryoablations and Other Balloon Based Catheters

It will be clear to one skilled in the art, that the esophageal temperature monitoring system may be used for all types of atrial fibrillation ablations including radiofrequency (RF) ablations and cryoablations. In RF ablations the concern is injury due to heating. In cryoablation, the concern is injury due to cooling. In Cryoablations with cryoballoons, the temperatures are typically brought to −40° C. Potentially, the injury due to freezing could be carried over to the esophagus. In this embodiment, the alarm(s) and/or interrupt are due to reaching the limit of the decrease in temperature as opposed to increase in temperature in RF ablation. In either case, the intent is to avoid or minimize the injury to the esophagus.

Cryotheraphy or use of cold temperatures to elicit a specific tissue response, has a history of effective medical use and cryoablation systems utilizing cryoballoons are also used routinely for atrial fibrillation ablations. The ultimate purpose of cryoablation is to freeze tissue in a discrete and focused fashion to destroy cells in a precisely targeted area. The application of cryothermal energy results in the formation of an ice ball. Cooling first occurs at the distal catheter tip in contact with endocardial tissue. Freezing then extends radially into the tissue, establishing a temperature gradient. The lowest temperature and fastest freezing rate are generated at the point of contact, with slower tissue cooling rates at the peripheral regions. The mechanism of tissue damage are complex and still debated, but involve freezing and thawing, hemorrhage and inflammation, replacement fibrosis, and apoptosis.

Generally in cryoablations tissue hypothermia causes cardiomyocytes to become less fluidic as metabolism slows, the ion pumps to lose transport capabilities, and the intracellular pH to become more acidic. These effects may be transient, depending on the interplay between temperature and duration. The shorter the exposure to a hypothermic insult and/or the warmer the temperature, the faster the cells recover. As a clinical correlate, this characteristic feature of cryoenergy permits functional assessment of putative ablation sites (i.e., cryomapping) without cellular destruction.

By contrast, the hallmark of permanent tissue injury induced by hypothermia is formation of ice crystal. As cells are rapidly cooled to freezing temperatures, ice crystals are first formed within the extracellular matrix, and then formed intracellularly. The size of ice crystals and their density are dependent on the combination of the following proximity to the cryoenergy source, the local tissue temperature achieved, and the rate of freezing, initially, ice crystals are formed exclusively in the extracellular space as the tissue temperature drops below −150 C. Progressive cooling to below −400 C results in the formation of intracellular ice crystals in the extracellular space results in it becoming relative hypertonic. In an attempt to reestablish osmotic equilibrium, there is a compensatory egress of water from the intracellular to the extracellular space, with subsequent cellular shrinkage, resulting in intracellular desiccation Further, the newly established osmotic gradient precipitates a diffusion gradient between extracellular and intracellular spaces, resulting in the net movement of H+ ions out of the cell, and the migration of solute ions into the cell. Concomitant increase in the intracellular saline concentration with a reduction in intracellular pH results in cellular protein damage, enzyme system impairment, and adverse effects on lipoprotein components of the plasma membrane. Of all the cytoplasmic components, the mitochondria are particularly sensitive and are the first structures to suffer irreversible damage.

Upon completion of the freezing phase, the tissue passively returns to body temperature resulting in a thawing effect. This second phase induces cellular damage through a combination of two mechanisms. First, recrystallization and coalescence of intracellular and extracellular ice crystals increase the osmotic damage and generate shear forces, which further disrupt tissue architecture. Second, restoration of microcirculatory function is associated with a hyperemic vascular response characterized by hemorrhage and inflammation (coagulation necrosis). Specifically, blood vessel walls become porous leading to increased capillary permeability and subsequent interstitial edema. This vascular congestion, combined with endothelial injury induces platelet aggregation and microthrombi formation, and culminates in vascular obliteration and ischemic cellular necrosis. As such, while the central region subjected to the coldest freezing temperature undergoes direct cellular damage, the surrounding microvascular injury results in the extension of tissue destruction.

The final phase of cryoinjury begins concurrent to thawing and is characterized by reactive inflammation, followed by tissue repair and replacement fibrosis. Over the subsequent weeks, these processes culminate in the generation of a mature lesion, which has a distinct, well-circumscribed central region of dense fibrosis surrounded by a narrow border zone of viable cellular death (due to microvacular injury and apoptosis).

Generally, a cryocatheter consists of a hollow shaft with a closed distal end containing a cooling electrode tip, integrated thermocouple deice and three proximal ring electrodes for recording and pacing. A console that contains the cryorefrigerant fluid. The cooling liquid travels through the inner delivery lumen to the catheter tip, where the cryorefrigerant is pressurized and released. This accelerated liquid-to-gas phase change results in rapid cooling of the distal tip. The gas is then conducted away from the catheter tip through a second coaxial return lumen maintained under vacuum and evacuated in the hospital medical gas disposal system.

The console allows the operator two different modes of operation. The first is the cryomapping mode in which the tip is cooled to a temperature not lower than −300 C for a maximum of 80 seconds so as to prevent irreversible tissue damage. The second mode is cryoablation, which results in cooling of the catheter tip to at least −75° C. for a programmable period (nominally 4 minutes), producing the permanent lesion. The cryomapping mode can be used for an indefinite number of times before cryoablation. Cryoablation may be initiated at any time during a cryomapping application or, from the onset, if the operator wishes to forego the cryomapping function.

One of the most exciting and truly remarkable characteristics of cryothermal energy is the ability to dynamically and prospectively assess the ability to safety and efficacy of a potential ablation lesion site, because a period of reversible electrophysiologic tissue inhibition obligatorily precedes permanent tissue destruction (a process that that can be dynamically manipulated by varying the temperature and/or time of application). While extreme freezing (i.e., tissue temperature colder than −50° C.) results in near instantaneous permanent tissue injury, a functional effect may be obtained at some lethal temperatures (i.e., −10° C. to −25° C.), but complete recovery of all electrophysiologic properties and no histologically identifiable damage. Prior mapping is not theoretically possible, but the broad temperature/time window between reversible and irreversible effects renders this feature readily clinically applicable. This by identifying the desired substrate before definitive ablation, the appropriate catheter placement site may be confirm to be efficacious (i.e., efficacy cryo mapping) and/or safe i.e., safety cyro mapping). Reversible cyro mapping may be of particular importance when ablating with myogenic substrates located near critical sites such as the AV node, where images target lesion may have major consequences. Reversibility observed with cryotherapy oh energy contrasts starkly with RF energy. With RF ablations, hydrothermal tissue energy leading to reversible loss of excitability occurs at a median tissue temperature of 48° C., as reversible tissue destruction occurs at tissue temperatures greater than 50° C. The reversibility window is, therefore, too narrow for safe clinical applications.

Even though the disclosure is described primarily with cryoballoon catheter for atrial fibrillation, such as the Arctic Front® available from Medtronic. It will be clear to one skilled in the art, that other balloon catheters are also available or will soon be available. The method and system also applies to any balloon catheter for pulmonary vein isolation and/or ablation for atrial fibrillation.

One such catheter is a balloon catheter where laser energy is applied from inside the balloon, for ablating the pulmonary vein in a point-by-point type of ablation.

Another catheter being tested in clinical trials, also applies energy though the balloon for "single shot" pulmonary vein isolation, but heats up the tissue instead of freezing the tissue as with cryoballoon catheter.

The method and system described in this disclosure can also be used for any balloon based catheter utilized for atrial fibrillation ablations, and is considered within the scope of this invention.

Medical Images (Including 3-D Images) Based Mapping System for Balloon Based Catheter Ablations In the mapping system of this disclosure, various medical images and various cardiac signals are brought into the mapping system.

Figure 2:
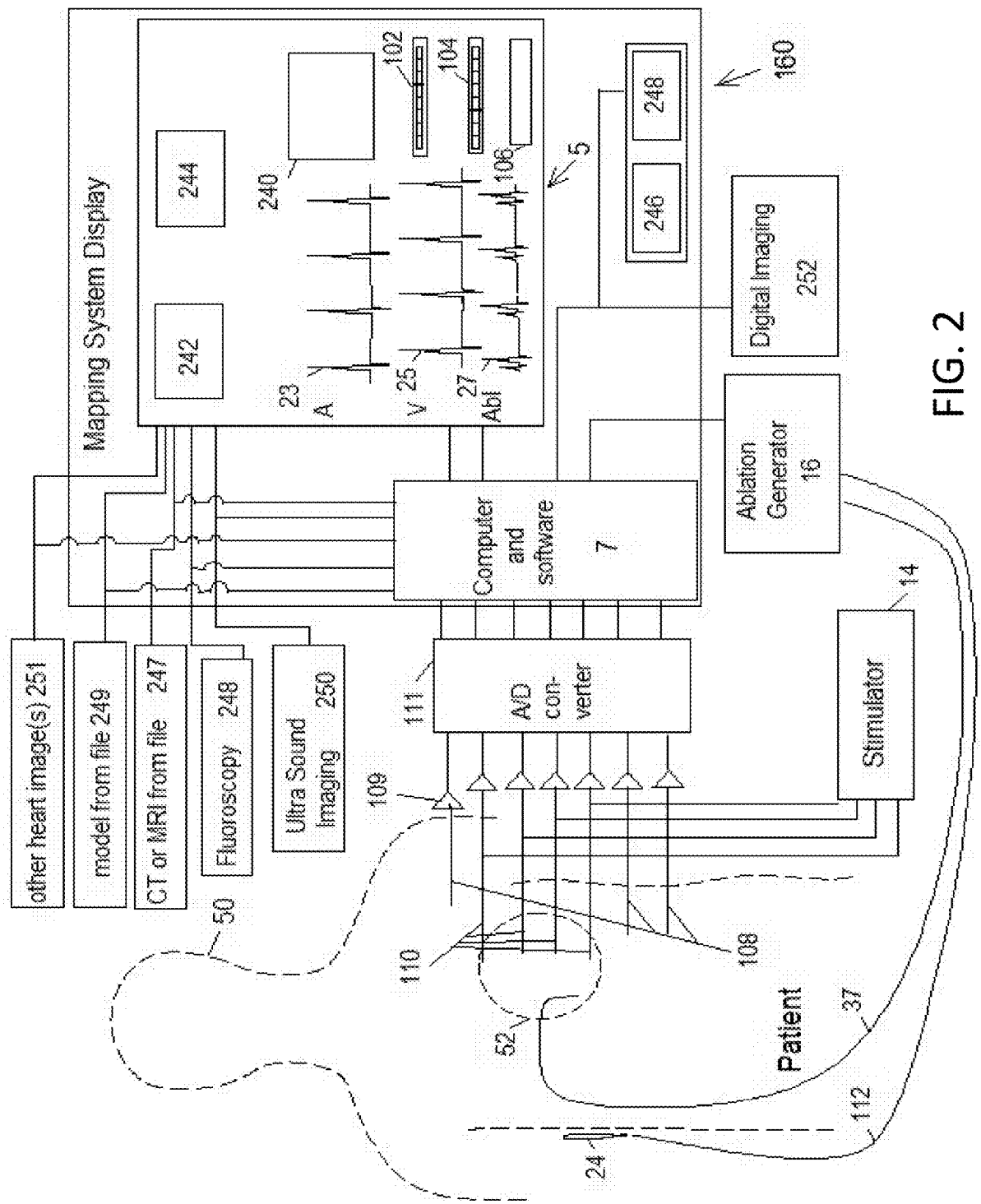
FIG. 2 is a schematic diagram showing acquiring intracardiac signals and medical images from a patient.

The signals acquisition and system setup is summarized and shown in conjunction with FIG. 2. It will be clear to one skilled in the art that the computer 7 can be a desktop computer, a server, a laptop computer, or a tablet such as an I-Pad. It could also be a mobile device that has sufficient computing power.

In one aspect of the disclosure, one or more imaging display(s) may be added to the display of the mapping system display. As shown in FIG. 2, examples of these displays without limitation includes ultrasound imaging of the heart 250, 2D ICE 250 (4D ICE not shown), fluoroscopic image 248 of the heart, detailed digital image of the heart such as CT 247 or MRI. Having one or more image modalities of the heart in addition to the electrical signals is advantageous, since detailed anatomical position in addition to electrical activation or timing information is useful for making decision about the ablation site. It will be clear to one skilled in the art that detailed anatomical imaging information such as available from GE Corporation, Siemens, Philips, Toshiba or Hitachi can be brought in the mapping system display, as an aid for selecting the site for ablation. The acquiring of images into mapping system 160 involves different types of input devices. The images brought in include real-time images and stored images. Real-time images like fluoroscopy can be brought into the mapping system utilizing boards configured for bring in medical images. These boards are available from several vendors and are well known to one skilled in the art. Real-time ICE images may also be brought into the mapping system via the output ports of the original ICE equipment. Stored images, for example CT image is generally on compact disk (CD) or DVD. Therefore the CT image is brought into the mapping system 160 via a digital file. Other images such as fluoroscopy may be brought into the mapping system 160, as an analog signal or brought in digitally.

It will be clear to one skilled in the art that various different software programs may be used to code these algorithm(s)/program(s), of this disclosure. Program code can be written using one of several commercially available software packages. The software that can be used for this purpose includes, but is not limited to Lab Windows/CVI, LabView (National Instruments Corp.), C, Microsoft Visual C++, Dot Net framework, MATLAB, and Microsoft Visual Basic, Phython among others. Use of these or other functional languages for this purpose that are available now or developed in the future, is considered within the scope of the disclosure. Testing of applicant's prototype and various aspects have been performed utilizing Microsoft visual C++, LabView and MATLAB.

In coding and configuring the software, the electrical signal reference timing can be taken (T=0) from the point of signal detection in the CS and ABL catheter. Signal detection can be from simple threshold detection to more sophisticated peak detection algorithms, as long as it consistent to both CS (or HRA) and ABL signals. The formulas for line coding in C++ or VI's in Labview are well known to one of ordinary skill in the art.

In the method and system of this disclosure, medical images instead of computer models are utilized for "electro anatomical mapping" and guide for ablation. Among the images utilized, without limitation, include,

- Two dimensional (2D) intracardiac echo (ICE) images
- Three dimensional (3D) intracardiac echo (ICE) images
- Four dimensional (4D) intracardiac echo (ICE) images
- Fluoroscopy images
- Fluoroscopy images that are overlaid
- CT (computed tomography) image(s)
- Fluoroscopy and CT based images, which may be overlaid or be side-by-side,
- ICE and fluoroscopy based images
- MRI (magnetic resonance imaging)

In one aspect of this disclosure, Intacardiac Echo images are utilized for mapping and ablation. In the methodology, ICE images are brought into the mapping system computer workstation, along with the intracardiac electrical signals and surface EKG electrical signals. The software is configured and programmed such that the mapping and ablation tags are placed on the ICE (intracardiac echo) images. The ICE images may be brought into the mapping system computer (workstation) via specialized boards installed in the workstation. One such board is available from Bitflow corporation. Alternatively, the ICE images may also be configured and brought into the workstation via the output ports of the ICE machine. In this case, the input into the workstation may be via USB ports.

It will be clear to one skilled in the art that the electrical signal sources 94 may be body surface signals such as 12-lead EKG, and/or intracardiac signals and/or other sensor signals, for example temperature. For the purposes of this disclosure, the image(s) source may be one or any combination of image sources shown in conjunction with FIG. 3.

Figure 3:
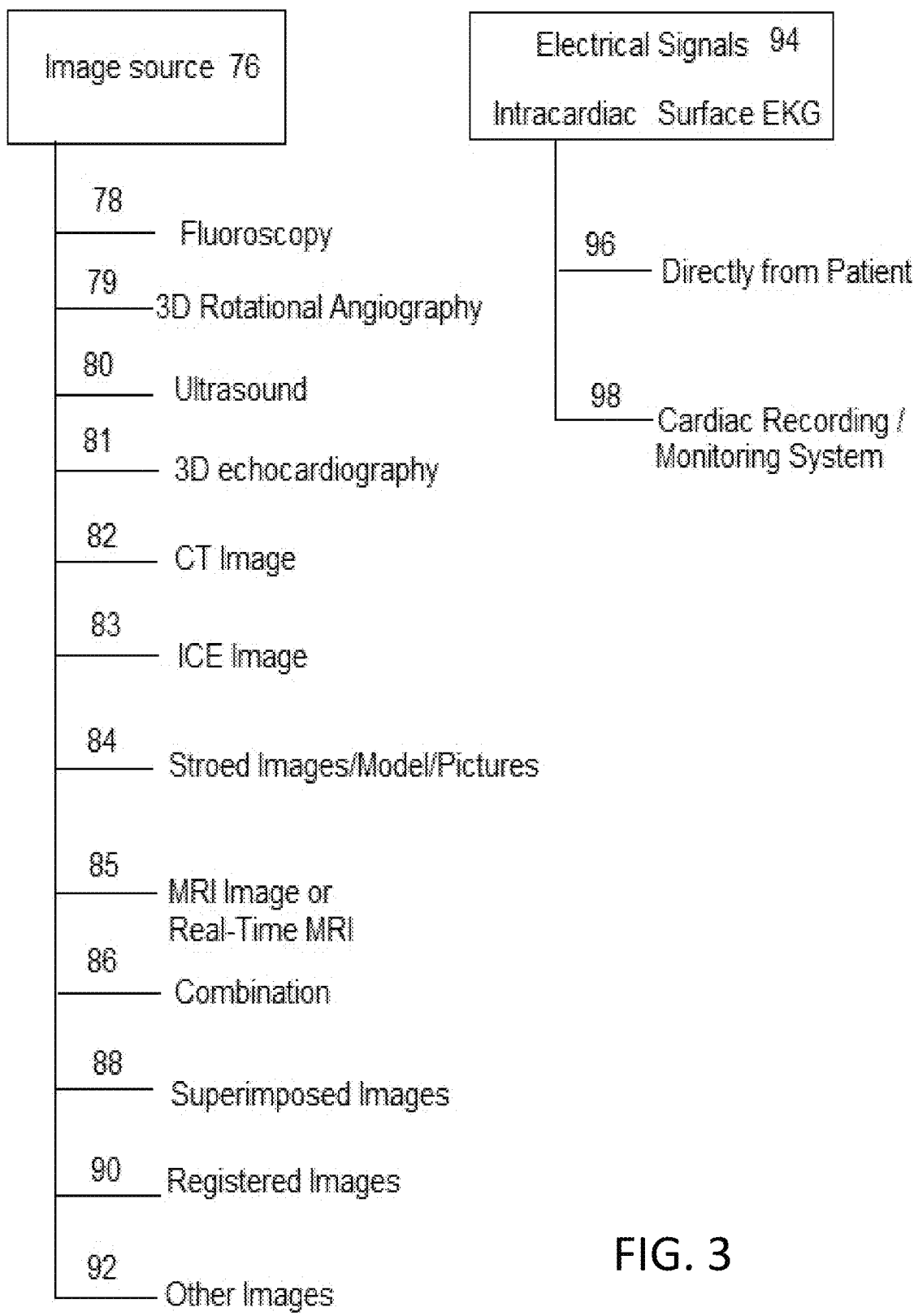
FIG. 3 is a diagram showing different type of images that are acquired for mapping, as well as, electrical signals acquired from a patient.

As shown in FIG. 3, medical imaging signals can be obtained from a variety of sources and imaging modalities, and can be combined with an overlap or side-by-side.

Also shown in conjunction with FIG. 3, in one preferred aspect of the disclosure, the image source(s) 76 may be fluoroscopy 78. Conventional fluoroscopy is the main imaging technology used for intracardiac device manipulation in a variety of interventional cardiovascular procedures, including electrophysiological (EP) studies. X-ray fluoroscopy is a continuous or dynamic imaging technique, where moving images of the patient can be seen in real time. An X-Ray beam is passed through the body, and the image is transmitted to a monitor so the movement of a body part can be seen in detail. The acquisition of digital fluoroscopic images can be combined with injection of contrast material to give an enhanced image. Fluoroscopy has major clinical advantages, such as its wide-scope in cardiology applications (catheter manipulation, cardiac motion, and an in-plane resolution similar to ultrasound). However, as in X-Ray modalities, Fluoroscopy is invasive due to its X-ray radiation, and injecting contrast materials could increase radiation. Therefore, reducing the procedural time is highly desired.

X-Ray modalities such as fluoroscopy and computed tomography (CT) rely on X-rays to penetrate objects. Objects with higher densities attenuate X-rays in different manners, and these cast an X-ray shadow of the radiopaque tissues (such as bone) on a fluorescent screen. In its original development, fluoroscopic images were seen with film. Now, electronic sensors convert X-Ray energy into electrical signals, which are then stored digitally. Within the computer receiver, multiple sequential fluoroscopic images produce real-time fluoroscope videos.

X-ray fluoroscopy can be combined with 3D mapping systems to aid in catheter manipulation. Electromagnetic fields are typically used to place the catheter in 3D space. The 3D position and orientation of the catheter tip is transferred to the fluoroscopy system and visualized in a virtual view projected on cine loops recorded at the beginning of the procedure. The cine loops play continuously and are ECG-gated to ensure that the movement of the virtual catheter tip and the previously recorded cine loop remain synchronized.

For the purposes of this disclosure, the fluoroscopy may be single plane or biplane fluoroscopy. Biplane fluoroscopy has the additional advantage to present another additional orthogonal view. Biplane fluoroscopy is similar to X-ray tomography in that it provides more views, and the multiple views showing rea-time cardiac movements aid in catheter placement and localizing structures in the heart.

In one aspect, the image source may be 3D rotational angiography 79. Rotational angiography is one of the latest angiographic modalities to map various cardiac chambers and the coronary venous tree anatomy. Without compromising the clinical utility of images, it requires both less contrast agent and less radiation dose. Rotational angiography produces CT-like 3D volumes during catheter intervention using a fixed C-Arm. The C-Arm rotates around the patient and acquires a series of X-ray images that are then reconstructed through software algorithms into a 3D image. Rotation takes between 5-20 seconds, acquiring hundreds of 2D images, and 3D reconstruction then follows. Contrast agents are sometimes administered to enhance certain structures or to reflect pulmonary transition time. Image integration is optionally done between 3D reconstructions and fluoroscopic videos during ablation. The benefit of rotational angiography to produce the 3D image overlays is that these are performed intraprocedural, removing the need for image registration which could lead to millimetric mis-registrations. Additionally, rotational angiography can be integrated with electroanatomical mappings to improve outcome relative to MRI 3D reconstruction integration to such maps.

In one aspect, the image source may be ultrasound 80. Ultrasound imaging uses sound waves and frequency-encoding to produce high-resolution and non-invasive images. The central principle of ultrasound imaging is that sound waves that are not absorbed by the body are reflected back. The ultrasound transducer that emits ultrasound waves also detects returning waves. The time between emission and detection encode distance. Generally, higher frequencies (shorter wavelengths) allow improved resolution of small structures, whereas lower frequencies allow for improved detection of deeper structures. In the field of cardiology, echocardiograms are able to produce 2D, 3D, and Doppler ultrasound images. Other echocardiographic modalities may include real-time 3-D echocardiography (3D echo), four dimensional (4D) echocardiography, strain and strain rate imaging, as well as speckle tracking. The use of ultrasound in cardiology has greatly expanded the understanding of patient specific anatomy, physiology and assessment of therapeutic interventions such as ablative procedures and cardiac resynchronization therapy (CRT).

The most common echo imaging in cardiology is real-time 2D imaging. The most common cross-sectional views—parasternal long axis, parasternal short axis, and the apical view—along with real-time imaging, allow for detecting abnormal anatomy or abnormal movement of structures. Generally, echocardiography provides improved accuracy and reproducibility over 2-D map thirds for left ventricular (LV) volume and function and detail cardiac structures. Tagging and/or tracking the LV surface in real-time may provide new approaches to quantifying myocardial mechanics, such as regional shape and strain. Color-flow mapping (CFM) uses Doppler technology and allows for the measurements of blood flow velocity and direction which is then color-coded and superimposed on a section of a 2D image. In this technique, blood flow changes the frequency of the emitted ultrasound wave. This information, along with the timing, can encode for distance and direction of flow, which is color-coded on the flow map.

In one aspect, the image source may be 3D echocardiography 81 which allows imaging and analysis of cardiovascular structures as they move in time and space, thus creating possibility for creation of four-dimensional (4D) data sets (i.e., 3D and real time). Advances in computer and transducer technologies, especially the fully-sampled matrix array transducer, have permitted real-time 3D image acquisition and display. Generally, real-time 3-D TEE-rendered visualization of the left atrium (LA) and pulmonary veins (TVs) provides unparalleled anatomic and functional information that will find additional application in clinical and surgical decision-making. The application of real-time 3-D echo in CRT, stress echocardiography, myocardial perfusion imaging and write hard evaluation are all evolving rapidly and are potential for tall grounds for translational research. The novel technology of 3-D speckle tracking, which makes possible the extension of robust strain-derived information to 3-D, has application in a variety of conditions. Real-time 3-D echo also opens exciting avenues by allowing custom-made 4D applications, which added dimension of time to existing 3-D data sets. 3D echo has great potential and will compliment and likely compare favorably with the quantitative ability of cardiac MRI (discussed later). The superior temporal resolution of echocardiography offers unique advantages for this purpose. Combining the greater temporal resolution of 3-D echo with the excellent spatial resolution of MRI (or CT) may yield imaging data set with unsurpassed anatomic and physiological information, an approach called "fusion imaging".

In one aspect of this disclosure, intracardiac echocardiography (ICE) images are utilized for mapping and ablation. The physics of ICE are similar than those used for ultrasound applications: sound wave reflect and refract differently according to the properties of tissue boundaries, and their timing and frequency information can be encoded into B and M-mode, and Doppler images. In this modality, a catheter is the source of the ultrasound waves, and the cardiologist is able to control the positioning and orientation, rather than a sonographer in transesophageal echo. This approach can also be maneuvered within the heart, allowing for visualization of cardiac structures and blood flow, and close-up views. The accurate imaging of the particular pathology, its anatomic features, and relative spatial relation to the surrounding structures aids in catheter and wire positioning, and the application can be done without anesthesia or radiation. Main interventional procedures performed with ICE systems include transseptal puncture, interarterial defect closure, percutaneous valvular implantation, lead extraction, and ablation of complex arrhythmias.

In ablating complex arrhythmias, ICE has had a major impact on identifying and targeting arrhythmic substrates, and can be augmented by using other imaging techniques such as electroanatomical mapping. The unique feature of ICE in ablation is that it provides information about the contact between the mapping/ablating catheter and the myocardial tissue. It can also guide the catheters in complex anatomic settings, especially when accessing the LA through transseptally. Real-time information can also be obtained, providing precise visualization of the mapping/ablating catheter position relative to the particular structures.

In the methodology of this disclosure, ICE images are brought into the mapping system computer workstation, along with the intracardiac electrical signals and surface EKG electrical signals. The software is configured and programmed such that the mapping and ablation tags are placed on the ICE (intracardiac echo) images. The ICE images may be brought into the mapping system computer (workstation) via specialized boards installed in the workstation. One such board is available from Bitflow corporation. Alternatively, the ICE images may also be configured and brought into the workstation via the output ports of the ICE machine. In this case, the input into the workstation may be via USB ports.

In one aspect, the image source may be 2D intracardiac echocardiography (ICE) 83. Generally, the new integration software module emerge from the marriage of the phased array intracardiac echo cardiac graffiti catheter (AcuNav diagnostic ultrasound catheter, at least on Siemens, Mountain View California, USA) with a special sensor of electromagnetic field that is used in the catheters for electroanatomical mapping. It enables semi-automatic tracing of the current contours of the chamber of interest in different planes, and subsequent addition of these contour points into the 3-D electro-anatomical map. In this way, a 3-D electro-anatomical map of the LA or the left ventricle (LV) could be constructed from a series of images obtained with intracardiac echocardiography catheter within the right atrium or right ventricle or even within the LA through a transeptal puncture, without increasing complications or procedural duration. This enables fluoroscopy exposure and mapping times to be reduced. This technique has also been used to identify LV scar and border zones during ablations of VT. Generally, the echocardiography images are gated to the atrial electrogram on the reference catheter.

In one aspect of this disclosure, the image source may be 3D intracardiac echocardiography (ICE) 81. 2D ICE only provides a slice through an individual pulmonary vein ostium, which makes it difficult to assess true anatomic extent in 3D space, and obtaining 3D ICE anatomical images could reduce procedure time. 3D ICE has been used in imaging the esophagus as a complementary tool to 2D ICE during ablation procedures. The Sequoia ultrasound system (Siemens Medical Solutions) is equipped with SoundStar® 3D diagnostic ultrasound catheter. Similar to 2D procedures, the catheter is inserted into the femoral vein and advanced into the right atrium. ICE imaging assists transseptal catheterization and positioning of the mapping/ablation catheter at the pulmonary vein ostia. This system also measures ostial blood flow before and after ablating lesions. 3D ICE provides complemental information to 2D ICE in that it can include additional anatomical detail and accurate spatial location of the lumen anterior and posterior wall (LAPW), which can aid in locating structures such as the esophagus. 2D ICE can also provide this information; however it requires 3D reconstruction, adding time to the procedure.

There are three strategies of 3D reconstruction in ICE. As described above, one of them marries the phase-array Ice catheter with a special sensor of electromagnetic field that is used in catheters for electroanatomical mapping. In this way, 3D electroanatomical map reconstruction can be achieved from a series of images obtained with ICE catheter. Reconstructions vary as a function of manual tracings with the ICE catheter, but merging these reconstructions with CT or MR angiography could improve construction. Another strategy mediates the aforementioned problem by using a special pull-back device that uses a stepping motor to move the Ice catheter linearly in the cranio-caudal direction. A third approach uses a motor to obtain a 3D reconstruction during rotational scanning using a conventional based-array ICE catheter. The latter two use cardiac gating and electroanatomical data can be overlaid on these images as well.

In one aspect of this disclosure, the image source may be 4D ICE. This is also known as real-time 3D ICE. Cardiac resynchronization therapy is an application that typically indicates 4D ICE. In this approach, 3D anatomy is imaged in time, allowing for complex imaging showing complex wall motion pattern. 4D ICE can offer the potential to identify dyssynchrony, in addition to the optimum placing site that would result in resynchronization. Real-time 3D ICE is accomplished using transducers with a matrix array that generates a pyramidal burst of ultrasound (some consisting of more than 3,600 transducers). An advantage of this method over 2D ICE is avoiding any assumption of ventricular mass and volume, in addition to rapid acquisition time compared to other imaging modalities. In ablation procedures, 4D ICE can aid in placement, relying on the advantages of 3D ICE in addition to characterizing the pattern of atrial flutter based on real-time motion.

In one aspect of this disclosure, the image source may be 5D ICE. In this implementation, real-time, 3-dimensional images are combined with intracardial electrical signal sources, producing an information-rich display of cardiac. It will be clear to one skilled in the art that the electrical signal sources 94 may be body surface signals such as 12-lead EKG, and/or intracardiac signals and/or other sensor signals, for example temperature. For the purposes of this disclosure, the image(s) source may be one or any combination of image sources shown in conjunction with FIG. 3.

In one aspect, the image source may be cardiac tomography (CT) 82. Because of its high resolution and fast acquisition, CT plays a great role in interventional electrophysiology. Generally, it is commonly used in patients undergoing AF ablations, contrast enhanced CT images provide accurate visual isolation of the LA, pulmonary veins and surrounding structures. This allows for pre procedure assessment of important anatomic variants, such as ectopic or anomalous veins, as well as the relationship of the esophagus to the posterior LA. Post procedure monitoring for complications of AF ablation, namely pulmonary vein stenosis, is mainly done with CT. A major disadvantage of CT is exposure to ionizing radiation. Another limitation in general is that the images are not usually acquired at the same time as the procedure. This limitation is circumvented, however, by using intraoperative/intraprocedural combined CT and rotational angiography.

In one aspect, the image may be cardiac computed tomography (CCT). CCT provides similar diagnostic accuracy to direct angiography. Generally, the role of multi-slice CT in mapping and ablation of cardiac arrhythmias is well-established and it is the most commonly used modality that is integrated with electro-anatomical map (EAM). CCT is quite useful for pre-procedure evaluation of left atrium (LA) and pulmonary vein (PV) anatomy; it provides a 3-D endocardial view of intracardiac structures with accurate measurement of target areas such as LA and PV. The current system provides a navigator view. CCT also provides assessment of myocardial mass, LV volume, coronary and pulmonary arteries and epicardial views. CCT can also be integrated with fluoroscopy. Both EAM and CCT are useful in detecting scar tissue. CT is able to re-create a real cardiac chamber in a short amount of time with great detail, such as LA and PVs. Recent advances in multi-detector technology have led to improvement in spatial and temporal resolution, allowing coronary artery imaging and gated Cine imaging to evaluate ventricular function.

In one aspect, the image source may be Magnetic resonance imaging (MRI) 85. The role of MRI is rapidly expanding in interventional electrophysiology in a similar fashion to CT. Because of its high resolution, the anatomic detail is superior with MRI. One of the advantages is the lack of ionizing radiation or iodinated contrast agent. Its main role is the range integration for AF ablation. Additionally, MRI plays an increasing role in the perioperative assessment of LA ablation lesion contiguity and transmurality, as well as in the ablation of structural heart-disease related VT. Pre-procedural imaging in a small group of patients with non-ischemic cardiomyopathy has shown strong correlation both quantitatively and qualitatively between MRI-identified myocardial scar and electro-anatomical definitions of scar. This pre-procedure data is used to help plan ablation strategies, such as a primary epicardial approach in selected patients with non-ischemic LV cardiomyopathy. The main limitation of MRI is in cardiac patients with pacemakers or defibrillators.

MR images are produced noninvasively using strong magnetic fields that align hydrogen protons to the main magnetic field axis. These protons precess about the main magnetic field at a frequency proportional to the field. Radio-frequency pulses set to that frequency tips the protons to a transverse plane. The rate at which the proton spins return to the main magnetic field direction is a function of the tissue properties and that time is measured using radio-frequency coils. MR images have similar spatial resolution to CT; however, the soft-tissue contrast in MRI is superior to that in CT. A technical drawback to MRI is the length of time required to create 3D images.

In one aspect of the disclosure, real-time MRI systems for the use during electrophysiology studies may be used. A real-time MRI system will allow visual isolation and remote navigation of catheters within the heart and potentially enable imaging of ablation lesions while they are being generated. This method provides excellent soft tissue characterization in a true 3D anatomical and temporal model, allowing for lesion development during ablation procedures. Additionally, real-time MRI can identify gaps in ablation lines, improving procedure outcome. The method could enhance fluoroscopy images, or even eliminate the use, thereby reducing the amount of ionizing radiation to the patient. Similar to fluoroscopy and rotational angiography, real-time MRI can be gated to the cardiac cycle, thus allowing for electroanatomical mappings.

In one aspect, the image may be Positron emission tomography. Ablation strategies for non-idiopathic VT are increasingly based on anatomic information of the scar and its border zone. The current "gold standard" for voltage mapping is limited by its inability to accurately describe complex 3-D scar morphology, it's in perfect spatial resolution and prolonged procedure times. Positron emission tomography (PET) generally plays a pivotal role in overcoming these limitations. Originally developed as an assessment of myocardial viability, hybrid scanning with F-fluorodeoxyglucose PET and CT allows for the display of a single image set with both detailed anatomic and metabolic information. These images can be integrated with the electro-anatomical maps (EAM) during ablation of VT, in a similar manner to traditional CT or MRI. PET-CT is also capable of imaging surviving regions within ventricular scar in patients with structural heart disease and VT. These regions often serve as critical isthmuses for scar related VT. The detection of critical components of the reentrant substrate prior to LV mapping may allow for more efficient substrate-based ablation.

It will be clear to one skilled in the art that the medical image or images utilized for the practice of current disclosure may also be stored images or models or pictures 84, certain image combinations 86, superimposed images 88, registered images 90, or other images 92. Any combination of image sources may be used for the practice of this disclosure. Many forms of above image technology alone or in combination is used.

In one embodiment of this disclosure, a mapping system is disclosed which bypasses the need for an electrical impedance and/or magnetic sensor for creating geometry and wherein electrical parameter information (both measured and calculated) is/are superimposed and displayed on the existing medical images. Superimposition of electrical parameter information may also be displayed on images that are overlain on top of each other or on fused images. One example of such superimposition of electrical information is shown on fluoroscope image information by way of example. It is to be made clear that such superimposition of electrical information may be on a 3D rendering such as rotational angiography or CT scan which can be rotated around any axis. It may also be on a combination of images that are registered and overlaid on top of each other, which is considered within the scope of the invention. In one aspect, such superimposition of information is on structure that can be rotated around any axis.

A fluoroscopy and/or medical images based system for cryoballoon ablations has been disclosed in Applicant's provisional application No. 62/346,539 having a filing date of Jun. 6, 2016 entitled "FLUOROSCOPY AND CARDIAC IMAGE(S) BASED MAPPING SYSTEM FOR GUIDING CRYOBALLOON ABLATIONS FOR ATRIAL FIBRILLATION WITH AUTOMATIC FLUOROSCOPIC RECORDING MECHANISM". The disclosure of the provisional application is also summarized below for convenience.

The mapping system of the current disclosure is designed to facilitate the balloon based catheter ablation procedure by providing an actual patient's cardiac image based mapping system, as opposed to sensor based geometry on a computer model. These medical images may include any combination of images including Fluoroscopy, Ultrasound, Intra-cardiac Echo (ICE), Computed Tomography (CT), Magnetic Resonance Image (MRI) or any other type of medical images. A combination of medical images may also be used for example a combination of fluoroscopy and ICE may be used, or any other combination of medical images may be used. The general concept of the mapping system is shown in conjunction with FIG. 4.

In one aspect of the system and method, live fluoroscopy 558 images are brought into the computer workstation of the Mapping System 550. Several computer boards are available for this purpose and are well known in the art.

Figure 4:
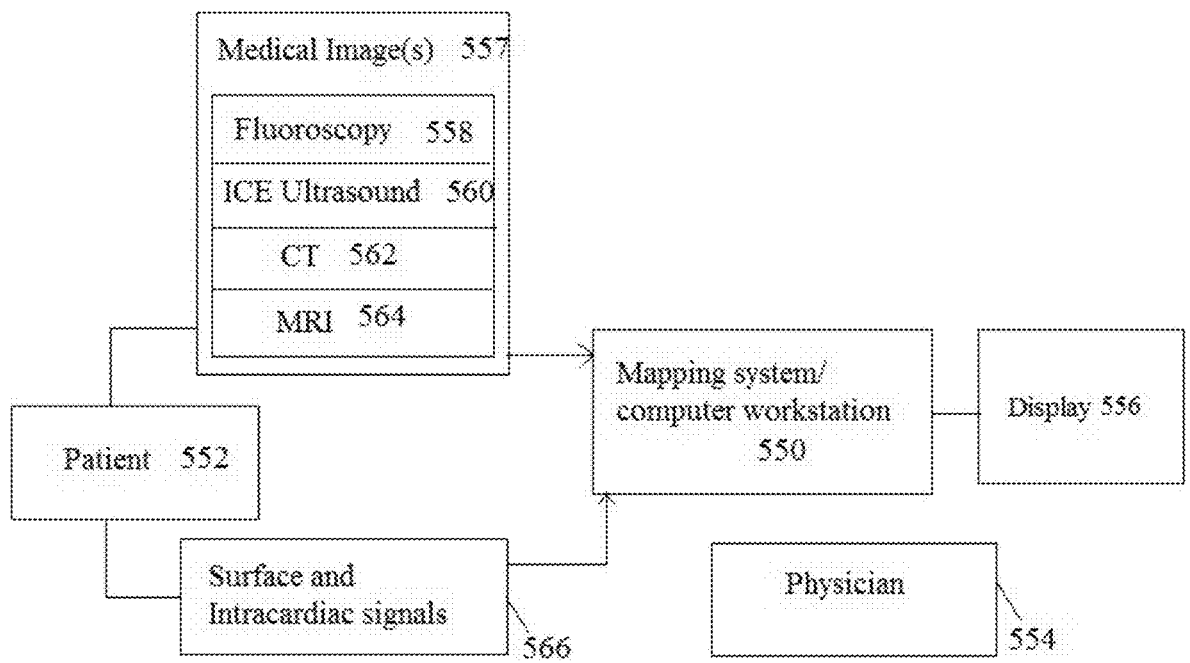
FIG. 4 is a generalized block diagram showing fluoroscopy or medical images based cardiac mapping system for cryoballoon ablations or for radiofrequency (RF) ablations.

As shown in FIG. 4, Intracardiac Echo (ICE) 560, computed tomography (CT) 562, Magnetic Resonance Imaging (MRI) 564 may also be used. Additionally, a combination of images may be used. For example, cryoballoon (or any other balloon catheter for atrial fibrillation procedures) may be localized both on fluoroscopic 558 and ultrasound (ICE) 560 images. Further, the fluoroscope and ICE images may be registered to each other in method and system of the current disclosure.

Figure 5:
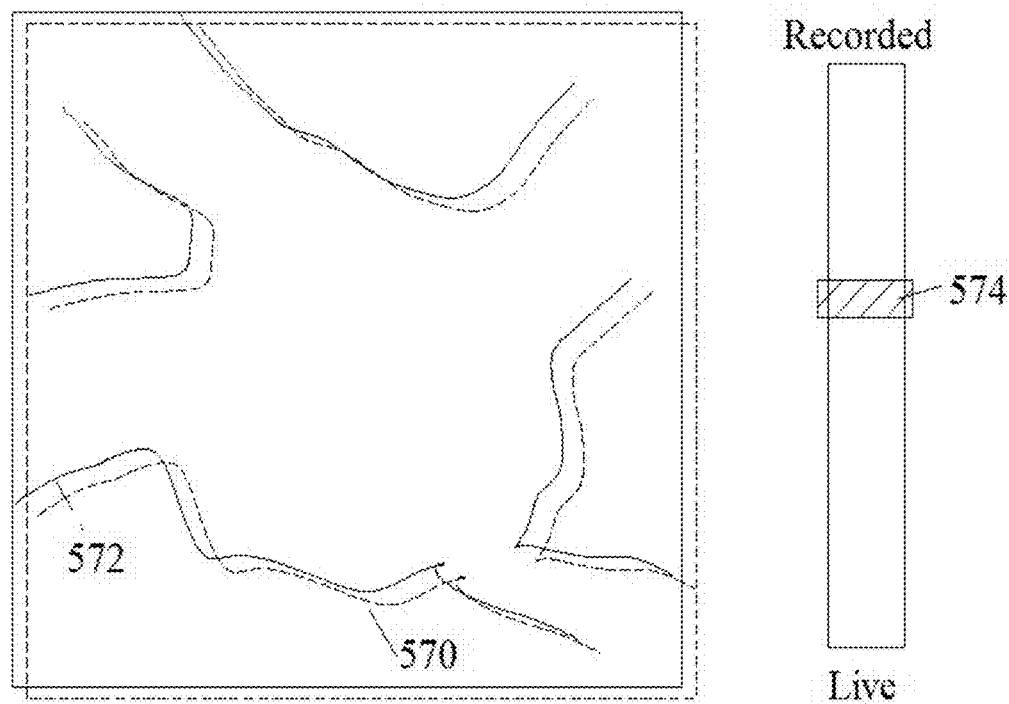
FIG. 5 depicts a live image and recorded image superimposed on each other with a way to adjust the transparency factor between the live and recorded image.
Figure 6:
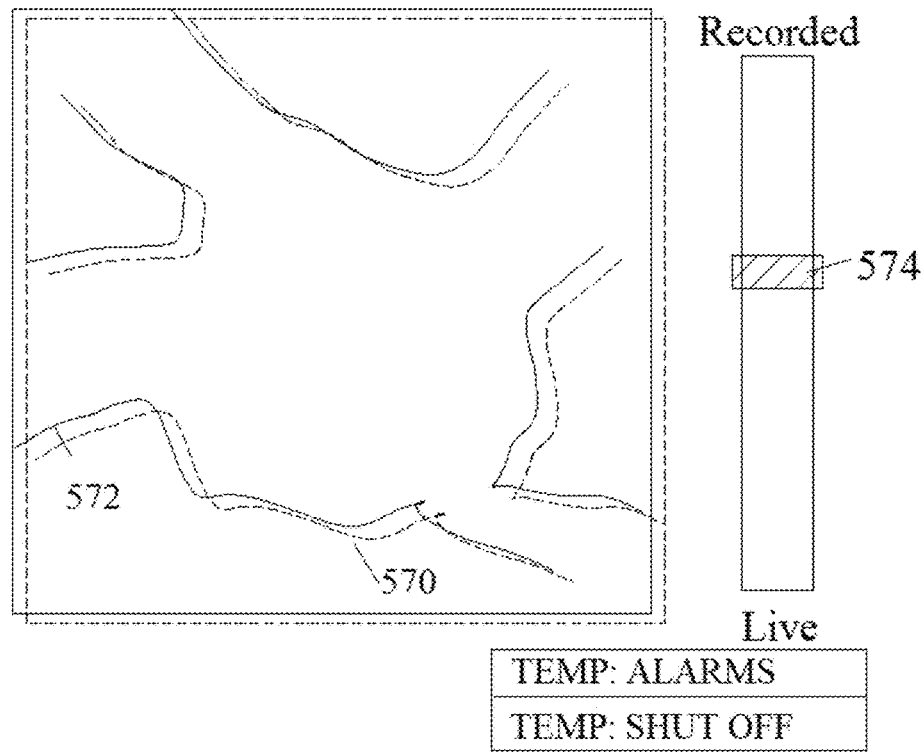
FIG. 6 depicts a live image and recorded image superimposed on each other with a way to adjust the transparency factor between the live and recorded image with temperature module interface.

In one preferred embodiment, shown in conjunction with FIGS. 5 and 6, a high resolution, high clarity image, i.e. with contrast medium or "dye" injection is recorded. These images will generally be recorded with a rotation of the fluoroscope. The advantage of rotation is that it provides 3-dimensional (3D) information. Additional recordings without rotation may also be recorded in one view such as an AP view or any other view.

Generally, in fluoroscopy high image quality is obtained by increasing radiation dose level. In the typical workflow of the method, highest resolution setting (Cine loop—30 frames/sec) is used for the recording. In addition, a contrast medium or "dye" is injected for the recording. The combination of highest exposure and contrast medium injection provides a high quality image which clearly delineates the left atrium (LA) and pulmonary vein(s) anatomy. The high resolution recording will generally be very brief so the patient is exposed to the high radiation level for only less than 10 seconds, more typically 5 seconds or less. For the purposes of injecting contrast medium or "dye" injection, a pump is preferably utilized but is not essential, as the injection may also be done by hand. In another aspect, less than the highest radiation level may also be utilized, based on the discretion of the physician and is within the scope of this disclosure.

Figure 7:
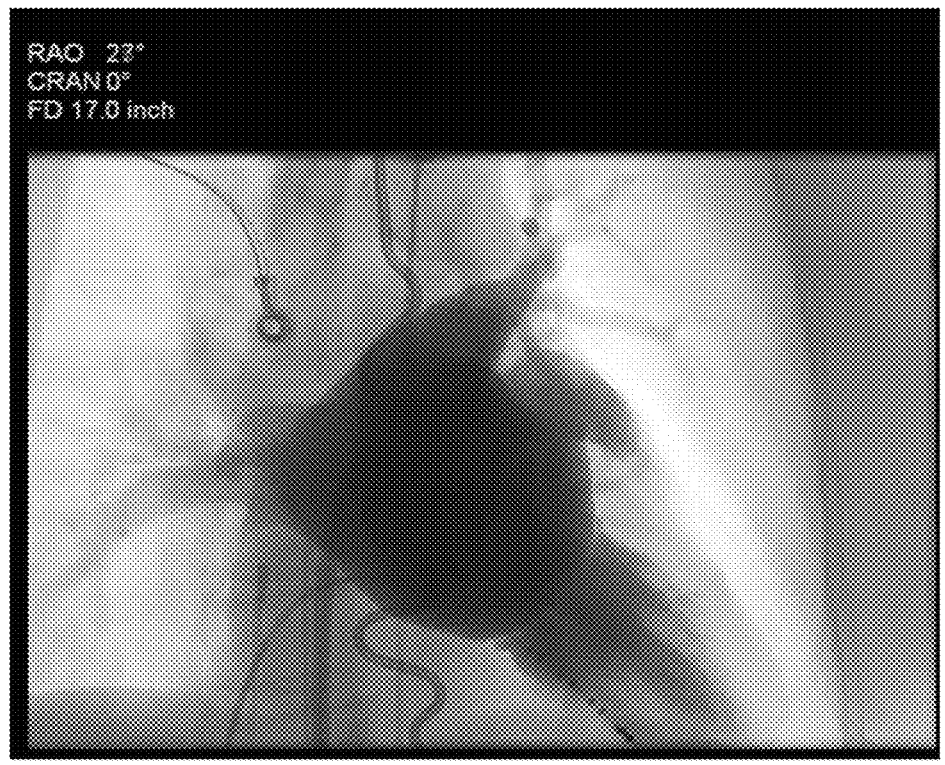
FIG. 7 shows an example of a recorded high resolution image of the left atrium recorded with "dye" injection.

Therefore in the first step, at the maximum 30 frames/sec (cine loop) resolution, a "dye" injection is performed and a rotation is recorded in the mapping system. This rotation will generally show a clear outline of the left atrium and the pulmonary veins at different angles. One example of a high resolution image is shown in FIG. 7.

There is a general need for a method and system to automatically record a procedure which utilizing fluoroscopy and with a computer based system, for the recording to occur only when the physician pushes the pedal and the fluoroscope (or radiation) is ON. Further, automatically stopping the recording when the physician takes the foot off the pedal, and the fluoroscope is turned OFF.

This is true for any situations where it is desirable to record the fluoroscopy from a procedure. This has application for any cases that require fluoroscopy in the fields of cardiac electrophysiology, interventional cardiology, or any fields of medicine that require fluoroscopy for a medical procedure. One application of this is in the current application, but the method and system can be used for any application or procedure requiring fluoroscopy.

In the method and system of this disclosure, for the current application more than one recording is generally made from the fluoroscope in the beginning part of the procedure. In one aspect of this disclosure, the software is configured and programmed such that the recordings from the fluoroscopy may be activated manually, or the ON-OFF switching process for the fluoroscopic recordings may be automated via the software utilizing optical character recognition (OCR).

In the manual portion of the software coding, a software button may be programmed and configured such that an operator starts the recording from the fluoroscope while the physician has activated the fluoroscope (generally by pressing a foot paddle). Similarly the operator stops the recording after the physician has taken the foot off the paddle.

Since this method is very inefficient and for many types of procedures it is not practical, it is highly desirable to program and configure the software such that the recording automatically starts when the physician pushes the paddle, and the fluoroscope is ON. Similarly in this methodology, the computer automatically stops recording when the physician takes the foot off the paddle. Generally, the fluoroscope is ON only when the physician has the foot on the paddle.

In one aspect of this disclosure, the method and system utilizes optical character reader (OCR) technology to trigger as an automatic ON-OFF switch for recording in the mapping system only while the fluoroscopy is ON.

5 The software is configured and programmed such that when the symbol appears on the fluoroscopy screen, it acts as a switch for the system to start recording, and when the symbol disappears the system is commanded to stop recording. The implementation of this may be done utilizing various different software's, as is known in the art.

In the implementation, the coordinates of the area where the symbol appears is regionalized and stored in the code. The software is then trained to recognize the symbol when it appears and trigger the recording mode. It will be clear to one skilled in the art that this can be done for various manufacturers of fluoroscopy equipment.

Going back to FIGS. 5 and 6, the recorded high resolution image 570 and live fluoroscope image 572 which is generally in lower resolution are displayed and adjusted in a way such that they are layered exactly on top of each other on the screen, shown as 570 and 572 in the figure. Whether the "live" or recorded image(s) appears on the top or bottom can be interchanged in the software. Further, the software is configured and programmed such that a transparency factor between the two said images can be adjusted. This is depicted in our implementation in conjunction with FIG. 6, via a slider bar 574, which can be adjusted for the transparency factor which is variable, other means of adjusting relative transparency may also be used.

The transparency factor is generally a level of transparency between the recorded image and the live image. The relative transparency level can be adjusted with a slider bar 574 in our implementation. At one extreme of transparency, only the recorded image is visible and live image is masked. At the other extreme, only the live image is visible and the recorded image is masked. At any level in-between the relative weight between or clarity between recorded or live image shifts and is adjustable.

By adjusting the transparency level, the physician can utilize the outline of the pulmonary veins highlighted with contrast medium injection, and appropriately place the catheter (for example a balloon based catheter) utilizing the combination of live fluoroscopy and recorded images. As known to one skilled in the art, this can be implemented utilizing a number of different softwares, as is well known in the art.

Based on experimentation, typically, the transparency factor is adjusted somewhere in the middle based on physician preference and choice. Advantageously, the physician gets the benefit of the recorded and stored high resolution image while being exposed to only low level of radiation of the live fluoroscopy setting.

Cryoablation using cryoballoon catheter is generally performed utilizing a freeze, thaw, freeze technique. As previously stated, the goal is to render the tissue between pulmonary veins and the left atrium (LA) to be rendered electrically inactive by the ablation procedure, for all the pulmonary veins. Generally, one pulmonary vein is done at a time.

Figure 8:
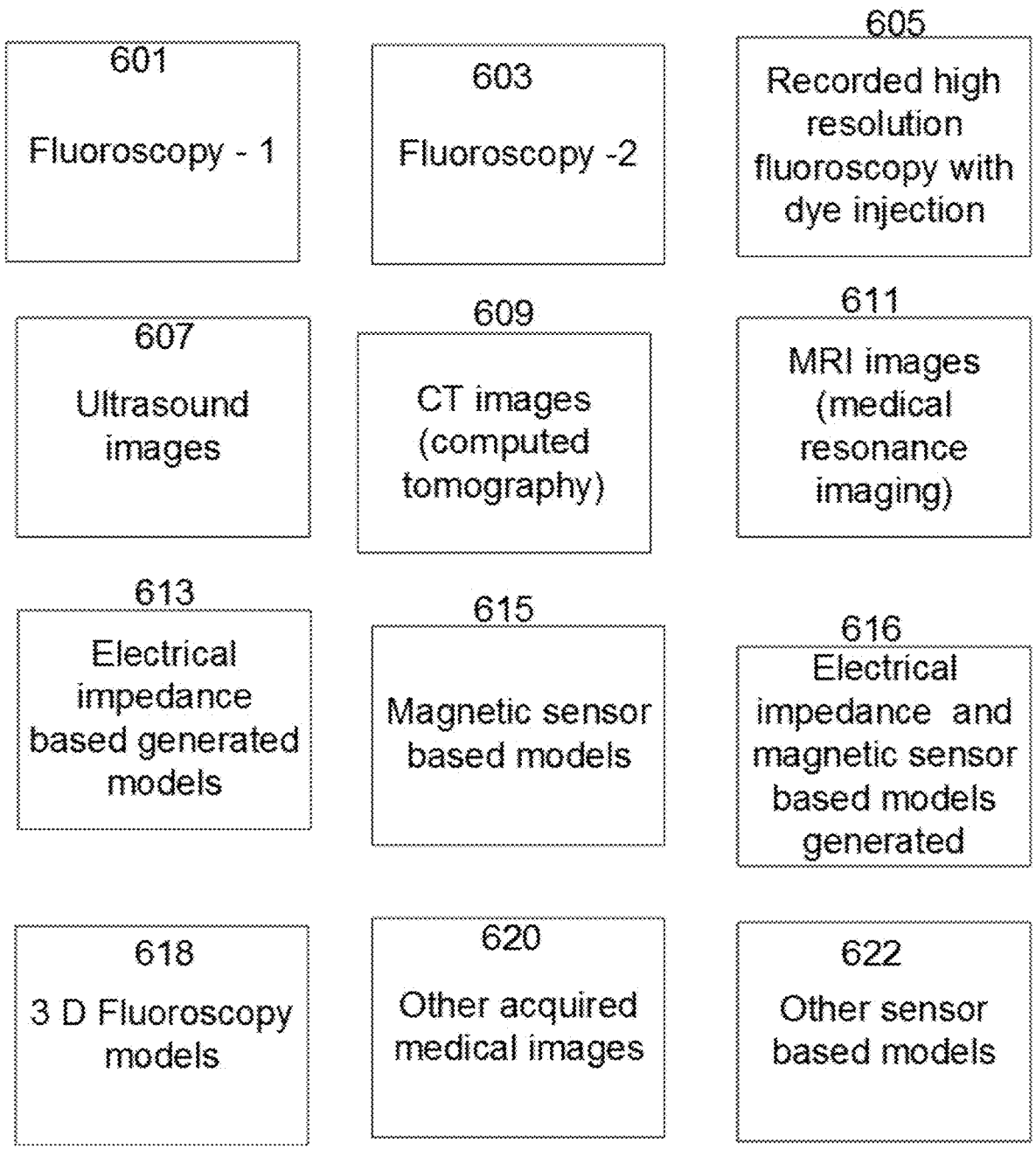
FIG. 8 is a block diagram showing different types of medical images that may be utilized or used in any combination in the mapping system of this disclosure.

Further, in the method and system of this disclosure, various different types of medical image modalities are utilized. These are shown in FIG. 8. These include fluoroscopy image(s) or various layers of fluoroscopy images 601, 603, 605. The fluoroscopy image(s) include mono-plane or bi-plane fluoroscopy, fluoroscopy rotations, fluoroscopy rotations with dye injections or fluoroscopy based 3D models. Live fluoroscopy image(s) may be superimposed or overlaid on top of (or bottom) a recorded fluoroscopic video or image which has been recorded in 'high' resolution with contrast medium (or "dye") injections.

Other images include intracardiac ultrasound (ICE) images 607, CT (computed tomography) images 609, MRI (magnetic resonance imaging) images 611, electrical impedance based generated models 613, magnetic sensor based models 615, electrical impedance and magnetic sensor based models 616, 3D fluoroscopy models 618, other acquired medical images 620, and other sensor based models 622.

In the method and system of this disclosure, any combination of image modalities shown in FIG. 8 may be used by the mapping system for Cryoballoon ablation mapping system, or any other balloon based catheter based mapping for atrial fibrillation ablations. It may also be utilized in rardiofrequency (rf) ablations and placement of a circular catheter around pulmonary veins.

Some of these combinations, without limitation are shown in FIGS. 9-16.

Figure 9:
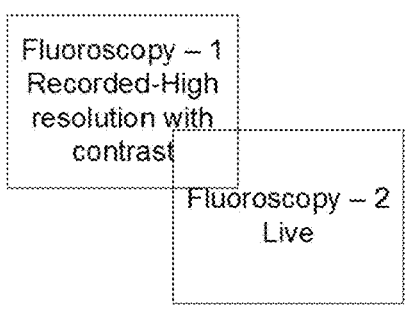
FIG. 9 is a block diagram showing two layers of fluoroscopy images overlaid/stacked on top of each other.
Figure 10:
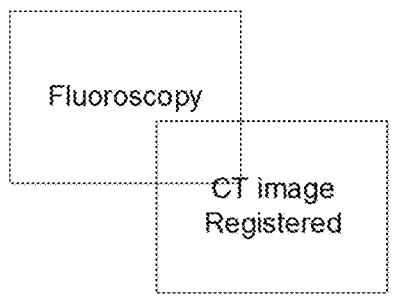
FIG. 10 is a block diagram showing CT images registered with fluoroscopy images.

In one aspect as shown with FIG. 9, live fluoroscopy may be aligned and superimposed or overlaid on top (or bottom) of a recorded high resolution fluoroscopy, which is recorded with contrast medium injection. The software is configured and programmed in a way, that a transparency factor adjusts the relative transparency between the recorded and live images. The recorded image is generally recorded in "high" resolution, with contrast medium (dye) injection. Provided the fluoroscope C-arm view and magnification factors are not changed, this technique offers the advantage that the live fluoroscopy manipulation or placement of leads or Cryoballoon catheter can take advantage of the high resolution and contrast medium (dye) injection.

In applicant's clinical testing, this has shown to be of significant help in placing of the Cryoballoon catheter in each of the four pulmonary veins. The same methodology also applies to any balloon based catheter as an aid for the proper placement of the catheter in the left atrium or around pulmonary veins.

One implementation is shown with FIGS. 20-22. In the first part of the implementation shown with FIGS. 20 and 21, a recording is made with contrast medium (dye) injection. FIG. 20 shows contrast medium in the superior pulmonary vein 636. A lumen catheter 634 is inserted in the left atrium close to left superior pulmonary vein 636, and the dye (or contrast medium) is injected. A recording is made of the dye injection. Other balloon based catheters are placed in the same way.

Following that, as is shown in FIG. 21 in our implementation, the recorded image (with dye injection) 640 is placed underneath the live fluoroscopy image 642. A transparency factor bar 644 is adjusted by an operator to have the right ratio of recorded image vs live fluoroscopy image. Utilizing this methodology, the physician is able to place the Cryoballoon catheter in appropriate pulmonary vein for the ablation procedure.

Figure 23:
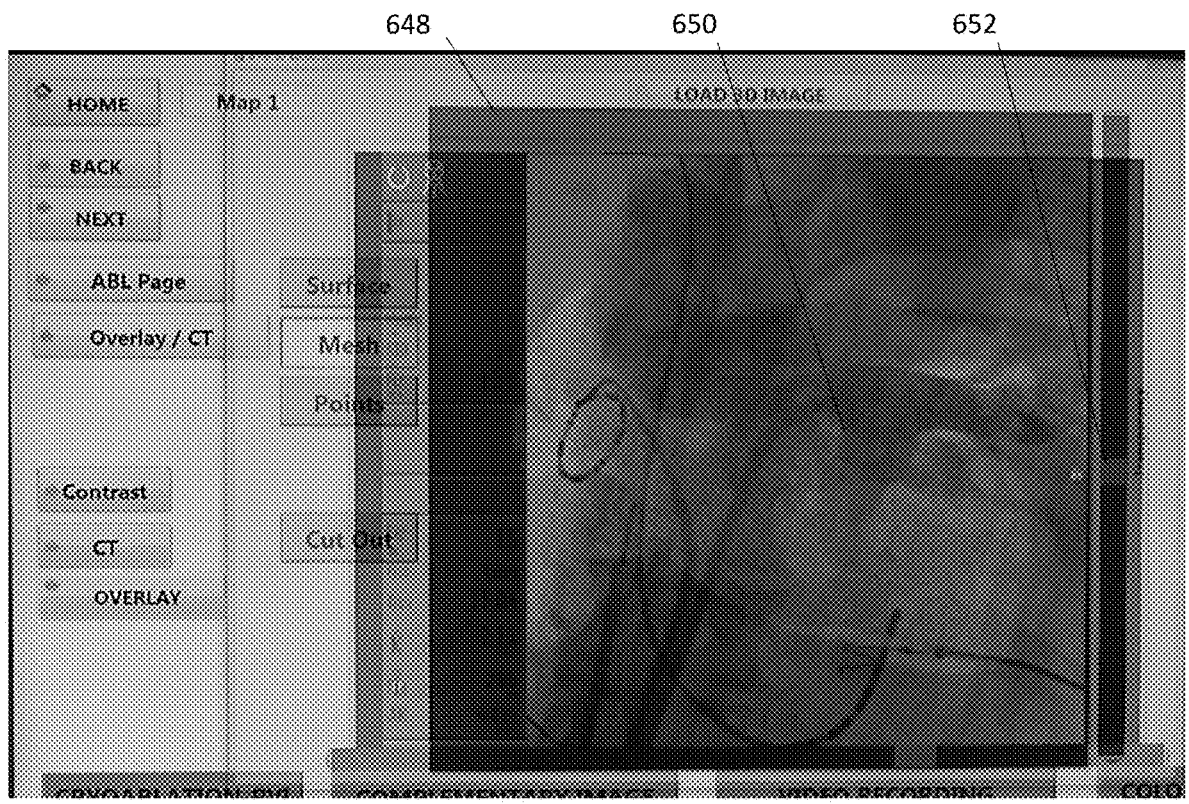
FIG. 23 is a diagram showing one implementation where a CT image is overlaid on a recorded fluoroscopy image with contrast medium ("dye") injection, and the structures are matched.

In another aspect, as shown with FIGS. 22 and 23, computed tomography (CT) images may be combined with fluoroscopy. It will be clear to one of ordinary skill in the art, that the CT image(s) may be registered or just overlaid on the fluoroscopic image(s). Registering the images involves some extra steps such as matching known anatomical points on both of the images. This is shown with FIG. 22. FIG. 22 shows an embodiment, where the CT images are combined or matched and overlaid on fluoroscopy, but are not registered. In Applicant's clinical testing this is still very useful. In this aspect, an operator visually matches the structures of the CT image with the structures on the fluoroscope. This is aided by the contrast medium (dye) injection.

Transparency

When a picture-1 (image or video) is placed on top of another picture-2 (image or video), the picture on the bottom (picture-2) is normally completely hidden. By utilizing software, a transparency factor (which can be gradual and continuous) can be configured and programmed. At one extreme of the transparency factor, the picture-2 at the bottom is completely hidden, and picture-1 is at full view. At the other extreme, picture-1 on top can be completely masked and picture-2 on bottom is in full view. This would be similar or equivalent to the top picture becoming transparent like clear glass. Utilizing software, the relative transparency between the two pictures can be easily adjusted such that the picture on the bottom is visible enough to show and take advantage of, while the picture on top (picture-1) can be used for any purposes.

In one application of this disclosure, the picture-1 can be live fluoroscopy image or video and the other (picture-2) can be a recorded fluoroscopy image of video, which was recorded with contrast medium injection ("dye") preferably in the highest resolution. By placing the live fluoroscopy on the recorded image or video with contrast, and adjusting the relative transparency between the live and recorded images, both can be utilized in a meaningful way. That is, live fluoroscopy can be used for catheter manipulation and placement, utilizing the recorded detailed anatomy and structure boundaries that are available from the contrast medium injection and which is placed underneath. The live and recorded images can also be interchanged, i.e. the recorded image can be placed on top and live fluoroscopy can be on bottom.

Similarly in another application, a CT model can be placed on top of, with structures aligned and matched with a recorded dye injected fluoroscopy, then in turn live fluoroscopy can be placed on top of these two images. By adjusting the transparency factor between the three images, all the images can be utilized. For example, the catheter can be manipulated and placed utilizing live fluoroscopy, while using the anatomic details of recorded "dye" injection, and the detailed anatomy of the CT scan.

The same methodology can be applied to different types of images shown in FIGS. 17 to 24.

Figure 24:
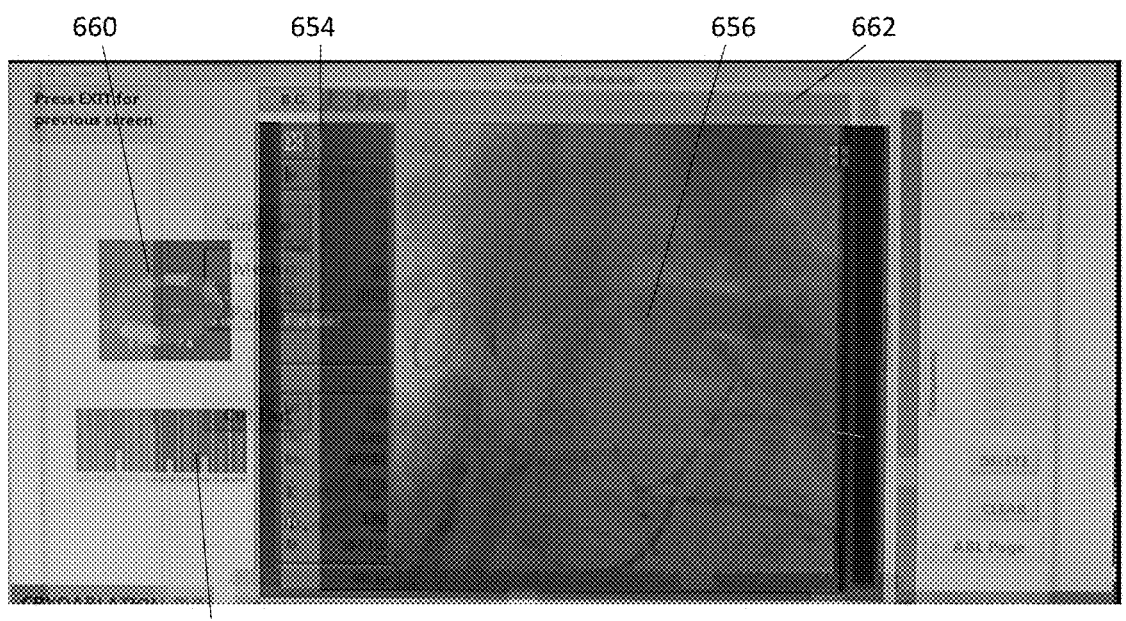
FIG. 24 is an implementation of the concept shown in FIG. 28, i.e where CT image is overlaid on a recorded fluoroscopy image and live fluoroscopy is overlaid on top of that. Further, electrical signals are also displayed on top fluoroscopy layer.

An implementation of this is shown with FIGS. 23 and 24. In the first step shown in FIG. 22, a volume rendering is done of the CT image 646. This volume rendering may be done on the mapping system via an appropriate software, or may be done on separate computer. The volume rendered 3D CT image 646 is then brought into the mapping system workstation. In the next step shown in FIG. 23 the volume rendered 3D CT image is superimposed on the recorded fluoroscopy image. As previously mentioned, this superimposition may be performed by registering the CT image on the fluoroscopy image or via the operator aligning the CT image with the recorded or live fluoroscopy image. Of course, for performing the registration process, points or tags will have to be specified on the both the fluoroscopy image and the CT image.

A transparency factor bar is generally adjusted by the operator, to show the relative weight of the fluoroscopy image vs the CT image.

In another aspect, two layers of fluoroscopy may be combined with the CT image. This is shown in conjunction with FIG. 24. In this aspect, high resolution fluoroscopy with contrast (dye) medium injection is recorded and stored in the computer (of the mapping system). In the next step, the appropriate images are brought on the monitor screen. Following that, the CT image which is 3-D is overlaid or registered on the recorded or high resolution with dye image.

It will be clear to one skilled in the art, that for the CT image to be registered approximately three common points on the each structure will need to be identified and tagged. Then via known algorithms, the images are registered when the algorithms are executed.

As an alternative, the images are matched by an operator. By utilizing the outline of the contrast medium, the CT image is matched to the outline of the fluoroscopy structures by the operator manually. This can be done, as the operator is manually able to pan, zoom and rotate the CT model on the monitor manually using a mouse. Since the placement of the Cryoballoon catheter (or other balloon based catheter) is done only one vein at a time, the operator only needs to match only one vein at a time. The advantage is that this can be done quickly and is relatively simply.

Applicant's implementation and testing of this aspect is shown in conjunction with FIG. 24. In this figure, the first (bottom) image on the screen is a high resolution recorded fluoroscopy segment with dye injection, which has a nice outline of the left atrium and at least one of the pulmonary veins. The CT image 656, is placed and aligned by the operator on the outline of the heart, which is aided by the "dye" or contrast medium injection. On top of these two layers (recorded fluoroscope and CT image) is a live fluoroscopy layer. This gives a physician the advantage of the contrast medium (dye) injection and the detailed anatomy from the CT scan.

This aids the physician in the proper placement of the Cryoballoon catheter and/or the electrode catheter in and/around the pulmonary vein. After placing the Cryoballoon catheter, and appropriate placement of the balloon, the ablation or freezing is performed. In some cases, the physician may inject a small amount of dye from the Cryoballoon catheter to check the seal of balloon with the pulmonary vein ostium (os).

The above procedure will be repeated at least four times to isolate all four pulmonary veins, as is generally done to complete the procedure.

In one implementation, the software is configured and programmed such that visual indicator of voltage levels from each pulmonary vein are shown as bar graphs indicating peak-to-peak voltage levels from different areas of the pulmonary vein. Actual signals are also shown below the bar graph.

In one embodiment, the bar colors are color coded to display the voltage levels. In this embodiment, the color coding guide is shown above the fluoroscopy image.

As is known to one skilled in the art, far-field signals from the left atrium (LA) are frequently recorded from electrodes placed in the pulmonary vein. To separate the far-field signals from the pulmonary vein recordings, physicians may perform pacing from the coronary sinus (CS) level. Alternatively, the signals may be displayed in the frequency domain. As the frequency content of the pulmonary vein potentials is different than the frequency content of left atrial signals.

Figure 13:
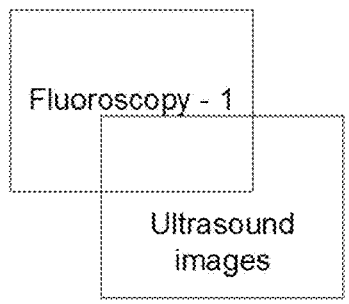
FIG. 13 is a block diagram showing combining ultrasound imaging with fluoroscopy for the purposes of the current mapping system.

In one embodiment, the ultrasound images are combined and superimposed on fluoroscopy. This is depicted in FIG. 13. Generally, ultrasound images have many advantages, and are routinely utilized during atrial fibrillation procedures performed in the United States. The ultrasound technology utilized is generally in the form of Intracardiac echocardiography (ICE). The advantages of ICE includes features where the images actually show the anatomic structures and unlike fluoroscopy or x-ray, ultrasound does not emit ionizing radiation.

Figure 15:
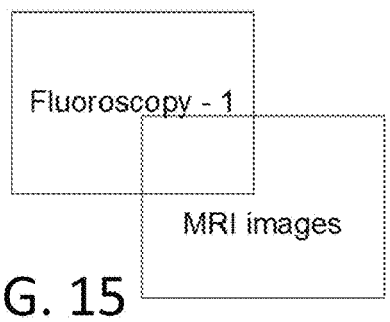
FIG. 15 is a block diagram depicting combining MRI images with fluoroscopy imaging.

In one embodiment, depicted in FIG. 15 fluoroscopy and MRI images are combined together. MRI images may be either registered or overlaid on fluoroscopy images. The MRI images also provide detailed 3D imaging, much like the CT images. As was mentioned previously, if the MRI images are registered then several tags will be placed on both the structures that are being registered. Alternatively, the MRI images may be placed or overlaid on fluoroscopy as a guide to place the Cryoballoon catheter in the proper vein.

Figure 16:
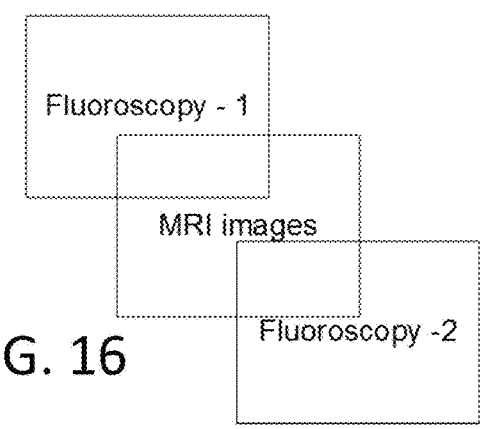

In one embodiment, two layers of fluoroscopy and MRI images may also be displayed on the monitor to guide the physician, this is shown with FIG. 16. In one aspect, high resolution fluoroscopy with contrast medium (dye) injection is recorded and used as an outline for the chamber geometry and for pulmonary vein(s). Based on the outline of the recorded images, the MRI images are positioned to the appropriate location. As with the case of CT, the MRI images may be registered with fluoroscopy based on placing common landmark tags on the recorded high resolution fluoroscopic images and the MRI. Alternatively, the MRI images may be placed by an operator (or overlaid) on the outline of the heart and/or pulmonary veins utilizing tools such as pan, zoom and rotate. Following that, a live fluoroscopy image layer is placed on the first two layers. The physician then positions the Cryoballoon catheter based on the real-time fluoroscopy layer, taking advantage of the recorded fluoroscopy and the high resolution anatomy of the 3D MRI images which are in the background.

Figure 14:
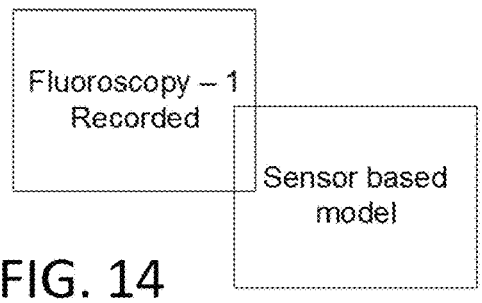
FIG. 14 is a block diagram depicting a sensor based model imaging combined with fluoroscopy imaging for the purposes of the current mapping system.

In one aspect shown with FIG. 14, a sensor based model of the heart geometry is created and registered or overlaid on fluoroscopy. The rationale for doing this is that since the Cryoballoon catheter does not communicate with sensor based mapping systems, fluoroscopy will be utilized for the placement of the Cryoballoon catheter. It will be clear to one skilled in the art that many different types of sensor based catheters are available for creating geometry. The most popular ones are electrical impedance based sensors, magnetic sensors or combination of electrical impedance and magnetic based sensors. The left atrial chamber geometry may also be made utilizing an ultrasound based catheter.

In one aspect, while recording a contrast medium ("dye") injection, a rotation of fluoroscope C-arm may be recorded. If a complete rotation is recorded, the software is programmed and configured such that any angle of fluoroscopy is available and may be used.

Figure 17:
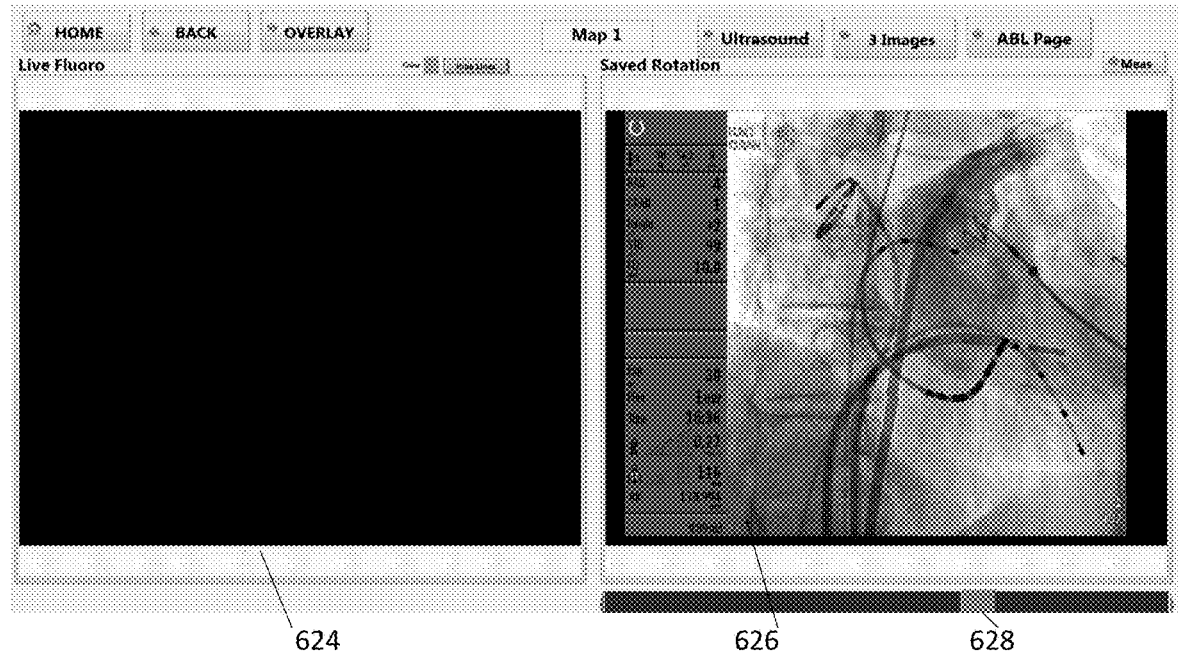
FIG. 17 is a diagram showing one implementation where live fluoroscopy and recorded fluoroscopy are displayed side-by-side.

One example of implementation is shown with FIG. 17. As shown in FIG. 17, a live fluoroscopy and a saved fluoroscopy rotation is displayed side-by-side. The saved rotation 626 is on the right side of the figure and the live fluoroscopy 624 is on the left side. Since the whole rotation is saved with contrast medium (dye) injection, as the live fluoroscopy angle is changed by the physician, the recorded "dye" injection fluoroscope image can be changed to the same angle as the live (or real-time) fluoroscope angle. In this implementation, a slider bar 628 is used to adjust the angle of the fluoroscope to match the angle of the live fluoroscope (shown on the left side of the figure).

Figure 18:
FIG. 18 is a diagram showing one implementation where live fluoroscopy and recorded fluoroscopy are displayed side-by-side and outline of the chamber and pulmonary veins are outlined on live fluoroscopy.

In one aspect, as is shown with FIG. 18 the recorded contrast medium ("dye") injection image may be used to mark the outline of the atrium and pulmonary veins on the live fluoroscopy. This is then used by the physician to guide a catheter, such as a cryoballoon catheter or any other catheter into the pulmonary veins or the os of the pulmonary veins.

Figure 11:
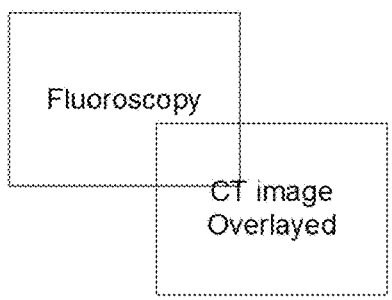
FIG. 11 is a block diagram depicting CT images overlaid/stacked on top of fluoroscopy images.
Figure 12:
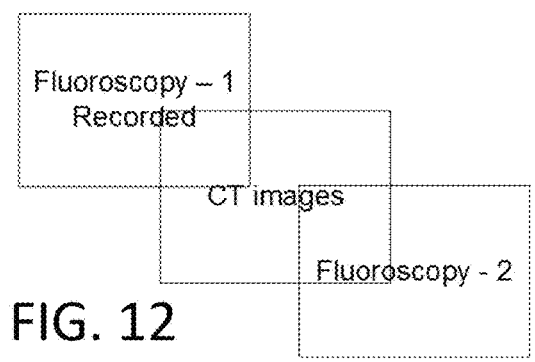

Of course, the physician has control over the amount of contrast medium ("dye") to inject and where to inject the contrast medium ("dye"). Generally, one of two methods are used. In one method, the contrast medium ("dye") is injected with a power injector in the right side of the heart. In this case the contrast medium ("dye") will go through the lungs and return to the pulmonary veins and the left atrium. At the point the "dye" starts to show up in the pulmonary veins (in approximately 5-8 seconds), a recording is generally made. An example of the image obtained with this method is shown in FIG. 11. The second method is to inject the "dye" straight into the left atrium and/or pulmonary veins, with or without a power injector.

In our implementation, FIG. 19 shows an example of "dye" injected into the left atrial chamber 632 via a lumen catheter 630. This is also substantiated with the "dye" being above the coronary sinus (CS) catheter 629 shown in the picture. Anatomically, the coronary sinus (CS) runs between the left atrium and left ventricle.

Also, for our implementation FIG. 20 shows an example of "dye" injection, this time in the left superior vein 636 via a lumen catheter 634 close to the os of the pulmonary veins.

FIG. 21 shows our testing of the concept shown in FIG. 9, where two fluoroscopy images are overlaid on top of each other. Once the two layers of fluoroscopy, high resolution images with contrast medium ("dye") and live fluoroscopy are overlaid on top of each other, one of the images may be manually moved to align the structures such that they are overlaid on top of each other and aligned and adjusted appropriately. The software is configured and programmed such that the transparency between the recorded and stored image(s) and live images can be adjusted by the operator. This is implemented with the aid of transparency bar 644, as shown in the figure. At one extreme of the transparency bar, only the recorded image(s) are visible. At the other extreme, only the live fluoroscope is visible. The transparency is adjusted by the operator such that the physician can manipulate the catheter on the live image, but at the same time have the benefit of the clear anatomic details from high resolution images with contrast medium ("dye") injection.

Further, as the catheter is placed in the appropriate pulmonary vein, the electrical signals are also recorded. The software and hardware is configured such that each pair of electrode picks up the peak-to-peak voltage signals, color codes the signals according to the size of the voltage levels and display's them in the form of a real-time bar graph 641 or ring graph 643. The ring graph 643 is configured and programmed such that the ring 643 is a 3D structure which can be rotated or moved in any angle.

In one aspect, a volume rendered 3D image if available can also be utilized in the placement of the catheter for atrial fibrillation ablation. A patient's CT scan is processed and a 3D volume rendering of the region of interest is obtained using software and techniques well known in the art. An example of this is shown in FIG. 22. The 3D volume rendering of the image 646 is done either using the mapping system computer, or is done on a separate computer and brought into the mapping system computer. The CT image 646 (in FIG. 18) can be panned, zoomed, moved or rotated such that it can be properly aligned with other images such as the fluoroscope image for example.

In one aspect, as was mentioned earlier and shown with FIG. 22, the CT image may be used with recorded fluoroscopy image (high resolution with contrast medium or "dye" injection) and live fluoroscopy for aiding the placement of the catheter such as balloon catheter or any other catheter which needs to be placed around the pulmonary veins.

In our implementation, shown in FIG. 23, in the first part the CT image 646 is aligned with recorded fluoroscopy image which may be in high resolution along with contrast medium injection or "dye" injection. The purpose of this is to show the details of the appropriate anatomy and to match the structures of the CT image with the fluoroscopy image.

In one aspect, the CT image may be registered with the fluoroscopy image. For the registration process several points (at least three) need to be defined that are common to both structures.

In one aspect, instead of registering the CT image with fluoroscopy, the CT image is overlaid on the fluoroscopy. The size, orientation and position of the CT image to match fluoroscopy structures are manually performed by the operator. This involves approximation and operator judgment, but for the current application, it works well.

Shown in FIG. 23, is one implementation which we have tested and found to work well. The operator adjusts and overlays the CT image on the fluoroscope after it has been properly resized and properly oriented. Further, the transparency is adjusted such that when live fluoroscopy is overlaid on top of the CT image such that it will be useful.

FIG. 24 shows, the final layer of live fluoroscopy which is placed at the top layer for visualization and placement of a cryoballoon catheter or any other catheter. Once the catheter is placed in the proper position, the signals may also be recorded as is shown in bargraph 658 or in the form of a 3D ring 660 as is shown in the figure.

As the Cryoballoon catheter is placed in the appropriate pulmonary vein, an electrode catheter with multiple electrodes is generally advanced and placed in the pulmonary vein more distal to the balloon.

Referring again to FIG. 24, as the Cryoballoon catheter is placed in each of the pulmonary veins and the multiple electrode catheter is placed in the pulmonary veins, the signals recorded from the electrodes are displayed on the monitor along with the fluoroscope image. In the method and system of this disclosure, the underlying signals from each electrode are recorded and displayed on the monitor screen. This is shown in the form of a bar graph 658, which are the peak-to-peak voltage signals. In one aspect the software is configured and programmed such that the bars are color coded based on the underlying peak-to-peak voltage. Additionally, in one implementation the underlying signal measurements are converted to color based on a color coding scheme and are displayed in the form of a ring 660 which adds a three dimensional element, as the ring can be manipulated in 3D.

In the method and system of this disclosure, after the balloon is inflated and the catheter is appropriately placed in the pulmonary vein, ablation is performed by freezing the tissue. The length or duration of freezing is determined by the physician. In one aspect of the disclosure, the ablation (freezing) areas' are marked or "tagged" for aiding the procedure and also stored for documentation purposes. In the method and system of this disclosure, various ways are disclosed for this and are shown with FIGS. 25-27.

The software is configured and programmed in a way such that every time there is an ablation, the area representative of the ablation contact area of freezing is marked ("tagged"). Generally, in RF ablation the ablation area is relatively small because the ablation is point by point ablation. With Cryoballoon ablation, the whole pulmonary vein is typically freeze ablated in a single shot. Therefore, the ablation tagging ideally needs to be such that it captures that.

Figure 25:
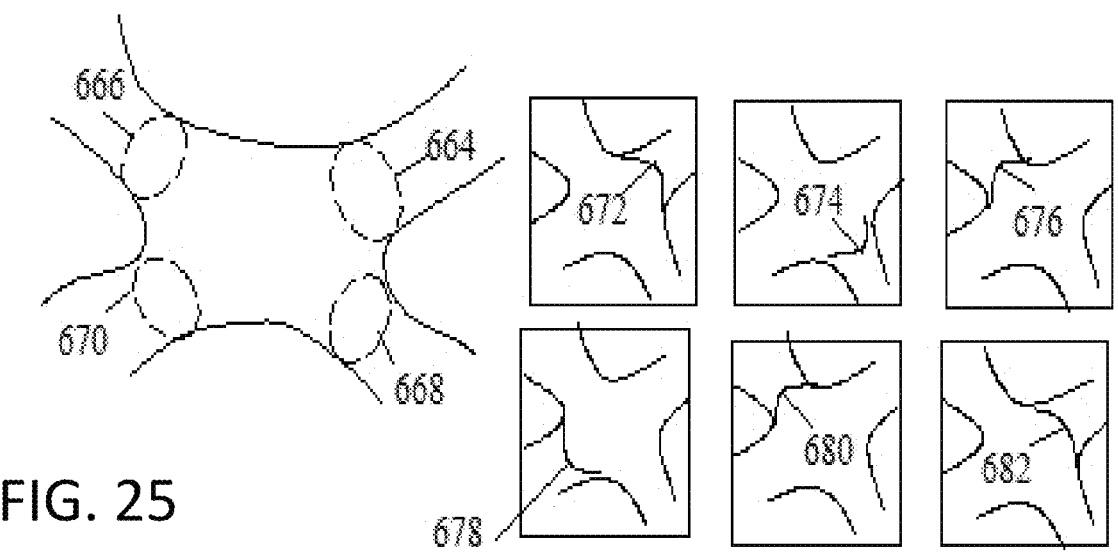
FIG. 25 is a diagrammatical representation showing marked sites of individual cryoballoon catheter freezes or cryo-ablations.

In one aspect, shown in conjunction with FIG. 25 the software is configured and programmed such that the ablation contact area is marked with the aid of a computer mouse by drawing a series of lines or circles or other markings. In one embodiment, each freeze is saved as separate picture or frame. Therefore, if there are six freezes (ablations) for example, then six pictures are saved. In the review screen, all of the screens are shown next to each other, for the physician to visualize where ablations have occurred.

As shown in FIG. 25, in the planning of the Cryoballoon ablation procedure at the level of left superior pulmonary vein os 664, left inferior pulmonary vein os 668, right superior pulmonary vein os 666, right inferior pulmonary vein os 670 are shown in the top portion of the figure. The bottom portion of the figure shows ablation markings or ablation "tags" 672, 674, 676, 678, 680, and 682 at various ablation sites. When the operator retrieves the review tag screen, the physician is able to visualize where the ablations have been performed.

Figure 26:
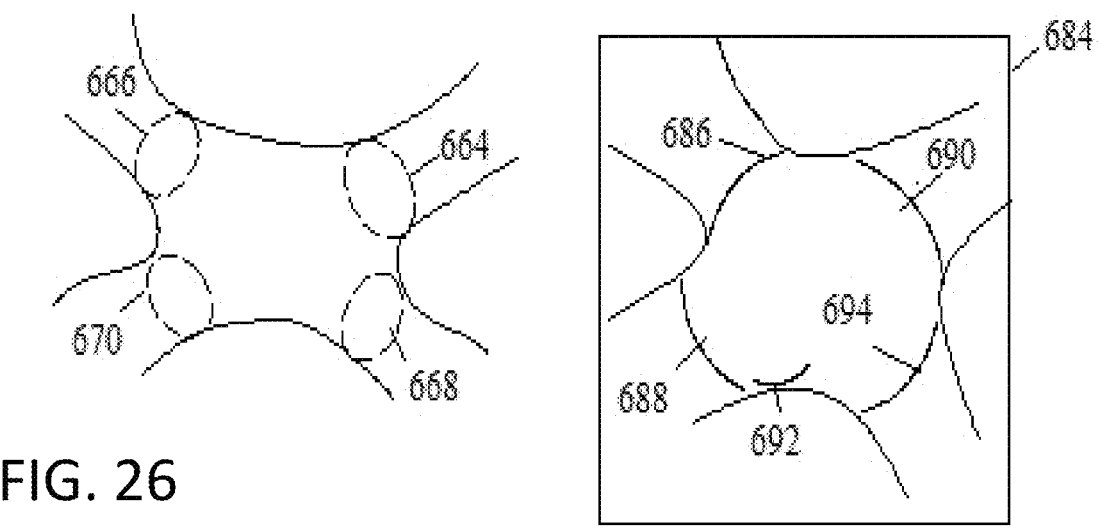
FIG. 26 is a diagram showing various cryo-ablations in one picture.

In another aspect, the various images comprising the ablation tags are merged together utilizing software coding and manipulation and are displayed in one figure. This is depicted in FIG. 26, where ablation tags 686, 688, 690, 694 and 692 are merged into one figure. As is well known to one skilled in the art, various software packages are available for this purpose. One such software for example is Photoshop, available from Adobe. MATLAB is another package which has built-in function libraries specifically for this. Many other software packages are also available and may be used. This may also utilize the process of registration in 2D.

Figure 27:
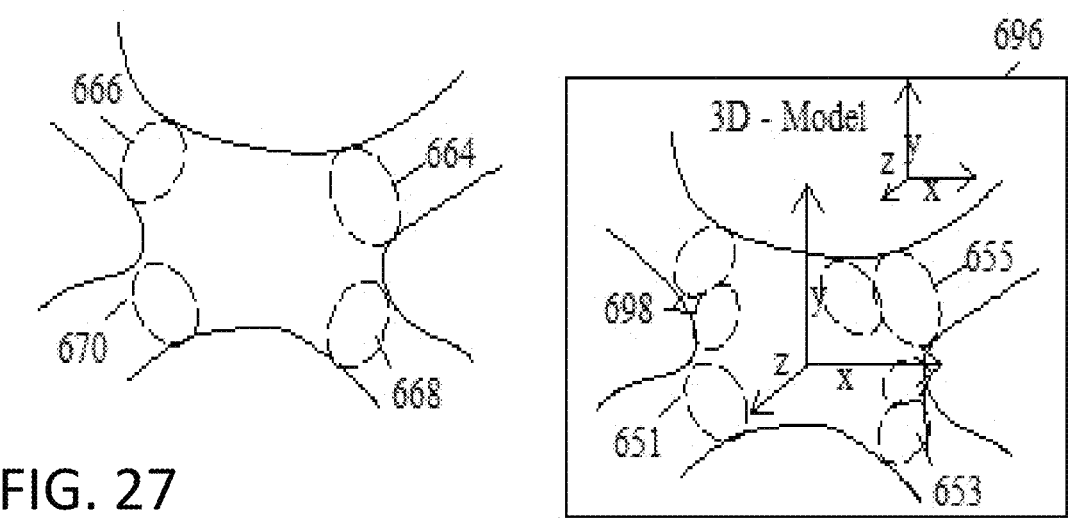
FIG. 27 is a diagram depicting various cryo-ablation lesions on a three dimensional (3-D) image, such as a CT image which can be rotated in 3-D (3 dimensions).

In another aspect, various ablation tags are placed on a 3D model, such as a 3D CT model or a 3D MRI model which is registered or overlaid on the fluoroscopy image, as described earlier in this disclosure. This embodiment is depicted in FIG. 27, where tags 651, 653, 655,696 and 698 are marked on a 3D model which can be rotated in 3D.

It will be clear to one skilled in the art that the 3D model may be one that is created using a sensor such as impedance, magnetic or any other type of sensor.

In one aspect, the ablation markings or "tags" may also be correlated with the length of the ablation freeze. For example, the ablation "tags" or markings may be color coded depending on the length of the freeze. In another example the "tag" markings may be larger or more dense depending on the length of the freezing time.

In this disclosure, in one aspect, both endoscopy based images, and CT (or MR) images or CT (or MR) images which are overlaid on fluoroscopy are displayed for navigation and guidance for atrial fibrillation ablation procedure. It is advantageous for navigation and guidance, to correlate the image view from inside the pulmonary veins (as via an endoscopy through the balloon catheter), and the outside or inside image view for placement via a CT or MR image(s). The CT or MR image(s) may be overlaid or superimposed on a fluoroscopy image(s). If the CT or MR image(s) is overlaid on the fluoroscopy image(s), a transparency factor between the fluoroscopy and CT images may be adjusted such that both the fluoroscopy and CT/MR images are visible for navigation and guidance. This is further explained in conjunction with block diagrams 47B and 47C.

Figure 28:
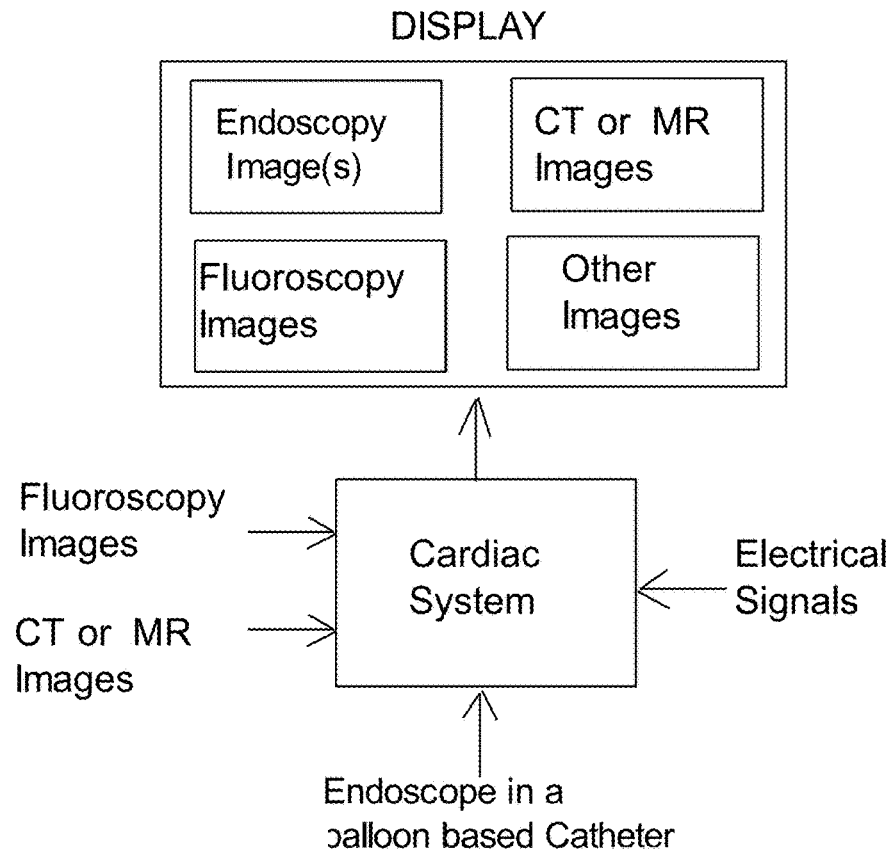
FIG. 28 is a block diagram depicting displaying images from endoscopy and CT (or MR) images, physicians to correlate inside and outside view of pulmonary vein region.

As shown in conjunction with FIG. 28, the Cardiac System is connected to one or more display device(s). The Cardiac System of this disclosure has interface electronics for acquiring patient's electrical signals. The patient's electrical signals are any combination of surface EKG (generally 12-Lead) and/or intracardiac signals. The Cardiac System also comprises interface electronics for acquiring patient's fluoroscopy images. This may be in the form of a specialized board. Additionally, the Cardiac System also comprises means for acquiring patient's CT or MR images. The patient's CT or MRI may be 3D volume rendered on the Cardiac System via volume rendering software installed in the Cardiac System. Alternatively, the volume rendering may be performed on a separate computer or workstation, and the digital files stored in an appropriate format on an external storage medium, and this external storage device is then connected to the Cardiac System for transferring the digital files.

Typically, the endoscope is coupled to the balloon based ablation catheter. Depending on the manufacturer, the endoscopy catheter or fiber is threaded into the balloon catheter, or may go thru the balloon catheter. With some manufacturer's, when the endoscope is placed in the pulmonary vein for visualization, only blood is visible. But, once the balloon is inflated, the blood flow to that particular pulmonary vein is occluded, and visualization inside the pulmonary vein is generally very good. It generally gives a clear visualization of the pulmonary vein from inside. As the endoscopy is pulled back towards the left atrium, the os of the pulmonary vein is generally visualized, as well as, the branches. The branches (or the same region) is/are also visualized from the outside on the CT or MR images, or CT/MR images overlaid on fluoroscopy.

In the method of this disclosure, for the purpose of navigation and guidance for atrial fibrillation ablation, the physician is able to correlate the internal view via endoscopy and the external view via CT/MRI for the purpose of placing the balloon or for the purpose of directing the ablation energy, whether it's RF or laser energy, or any other form of energy.

The software and hardware of the Cardiac System is configured and programmed for displaying the endoscopic images, and CT (or MRI), or CT (or MRI) overlaid on fluoroscopy (images) on a display monitor. It will be clear to one in the art, that the display is on the same monitor, or the display may be on separate monitors where the physician can observe both monitors during the procedure.

The implementation for this is well known to one of ordinary skill in the art.

Figure 29:
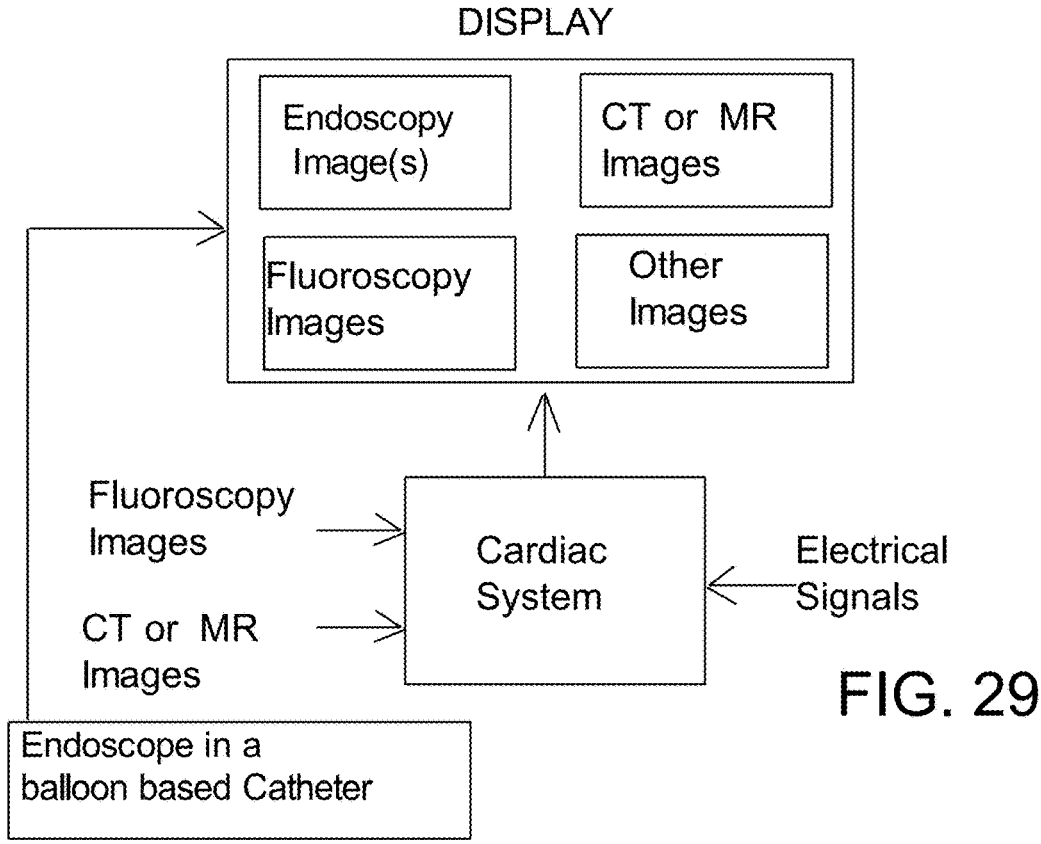
FIG. 29 is an alternative block diagram depicting displaying images from endoscopy and CT (or MR) images, physicians to correlate inside and outside view of pulmonary vein region.

As shown in conjunction with FIG. 29, in an alternative embodiment the endoscopic images are not brought into the Cardiac System, but are displayed directly from the balloon catheter or endoscopic manufacturer's equipment directly on to a display monitor. And, CT or MR images are displayed from the Cardiac System on to the same display monitor or a separate display monitor close to each other, where the physician can observe both monitors.

Saving and Utilizing 3D Anatomical Structures in Separate Digital Files

In this disclosure, various anatomical segments are overlaid on images of live fluoroscopy. Anatomical segment(s) in this disclosure are one or more region(s) or an organ or part thereof on a patient's CT/MRI image identified as an area of interest, wherein each such area is 3D volume rendered and is stored in a separate digital file.

Figure 30:
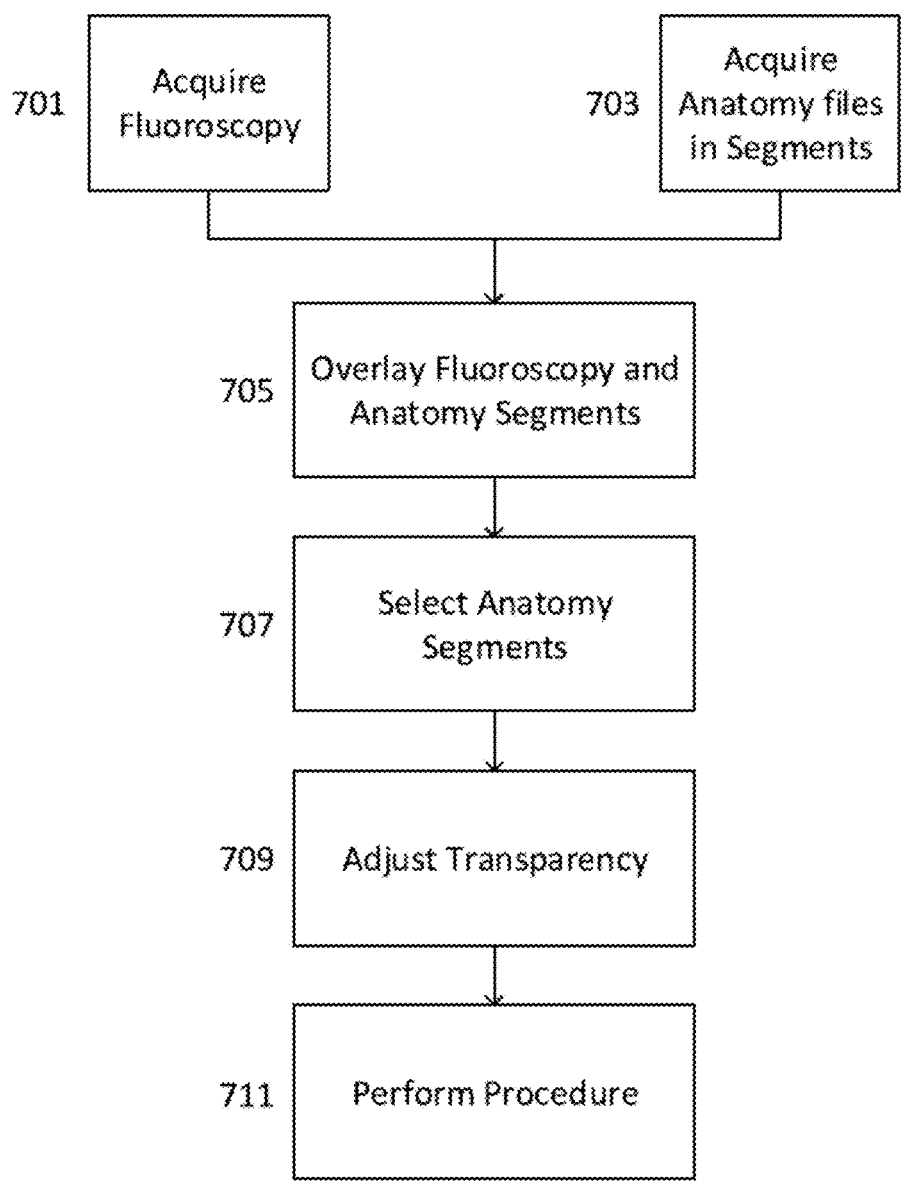
FIG. 30 is a simplified block diagram showing overlaying CT or MR image in segments on fluoroscopy.

FIG. 30, depicts the general concept of an overlay of anatomy in various CT (computed tomography) or MRI image segments and fluoroscopy, of one preferred embodiment utilizing a simplified block diagram. As depicted in the block diagram, live fluoroscopy images 701 are acquired into the system, utilizing an "image acquisition" board(s) which have been installed in the workstation. Additionally, CT (computed tomography) or MRI (magnetic resonance imaging) segmented files of various anatomical structures which have been volume rendered and segmented in 3D (3-dimensions) and saved as separate digital files, are also acquired into the workstation (block 703). In this disclosure, patient's CT (computed tomography) is analyzed, and various parts of the anatomy (described later) are 3D volume rendered and saved as separate digital files. Also, generally, an .stl file format is used, but other file formats may also be used. Any suitable file format for 3D structures may be used. For example, 3D PDF file format may also be used. It will be clear to one in the art, that MRI images are done essentially the same way. Thus, for the purposes of this disclosure any mention of images or CT segments also include MR images or MR image segments.

In one aspect, the 3D volume rendering is performed on the Mapping system workstation. In another aspect, the 3D volume rendering is performed on a different computer medium (including laptops or other computer devices), and the digital files may be saved on an external drive or some other storage media for transfer to the cardiac mapping system workstation.

In the disclosure of this invention, the various anatomy segments are combined together on the display, as they are synchronized spatially, and are overlaid or superimposed on live fluoroscopy images (block 705) (in this disclosure fluoroscopy implies fluoroscopy images). Advantageously, for aiding in the procedure, selected relevant anatomy segments are displayed. Importantly, the anatomy segments displayed are dependent on which part of the procedure is being performed, and this will generally change as the procedure progresses. Once the relevant segments are selected, (block 707), a transparency factor is adjusted, such that both the 3D volume rendered CT structures (in segments) and underlying live fluoroscopy images are conveniently visible, (block 709). The procedure is commenced with proper placement of the catheter (or balloon) block 711.

A more detailed workflow is explained further below with the aid of flow diagrams. As explained before, in the method and system of this disclosure, 3D (3-dimensional) volume rendered anatomical segments are prepared using a 3D volume rendering software. It will be clear to one in the art, that the 3D volume rendered digital structures can be from CT (computed tomography) or from MR (magnetic resonance) imaging. Both CT and MRI are highly detailed imaging modalities. For the purposes of this disclosure, either can be used, and anything explained with CT will apply equally to MRI imaging also, as the methodology is pretty much the same.

Utilizing a volume rendering software the CT or MRI segment files are stored. The storing media can be within the cardiac mapping system workstation or an external medium. It is noted that the data is stored in a way, such that different anatomical structures are stored in different corresponding digital files. The anatomical structures can be any anatomical structures of the body, which may be small or large. Some examples of anatomical structures without limitation are, left atrium (LA), pulmonary veins (PV), appendage, coronary sinus, right atrium, esophagus, and spine. One advantage of storing different anatomical structures in separate digital files is that they can be selectively turned ON and turned OFF. This is advantageous because during different parts of procedure, different structures are required or preferred. Further, any group of structures (or files) can be selectively turned OFF and any given structure (or files) can be selectively turned ON. This can be done in any combination.

Figure 31:
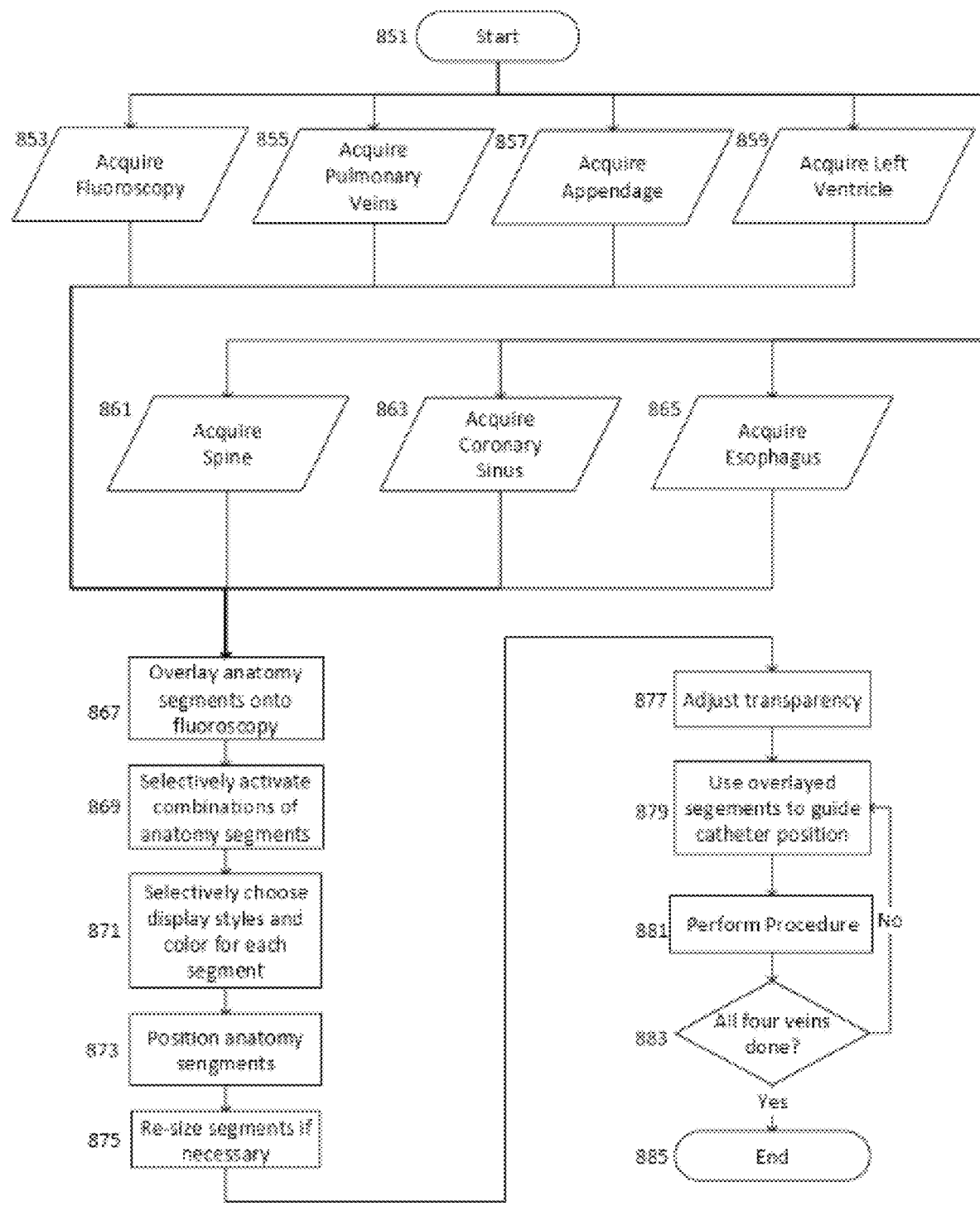
FIG. 31 is a flow diagram showing the steps of overlaying CT or MR images which are in anatomy segments, and overlaying them on live fluoroscopy for balloon based catheter ablations.

As shown in the flow diagram in FIG. 31, at the start of the procedure 851, live fluoroscopy 853 is acquired into the workstation of the mapping system, using specialized boards. Additionally, other anatomical structures are acquired in segments as separate digital files such as pulmonary veins 855, appendage 857, left ventricle 859, spine 861, coronary sinus 863 and esophagus 865. Other digital files of anatomical structures which are not shown in the diagram may also be acquired. Some of these files corresponding to anatomical structures are used as anatomical landmarks, for proper positioning when overlaying the CT (or MRI) on live fluoroscopy images. For example, spine 861, coronary sinus 863 or esophagus 865 may be used for this purpose. After all the digital files corresponding to various anatomical segments are acquired, utilizing software which is configured and programmed for this purpose, the selective combinations are activated (step 869) corresponding to selective anatomical segments. The methodology for implementing this is well known to one of ordinary skill in the art.

For the anatomical segments that are turned ON, display styles and color are adjusted, shown in step 871. These segments are overlaid in the proper position on fluoroscopy, step 873. For the purposes of this disclosure, the proper overlay can be manual which is visually guided by the operator, or may be registered automatically using algorithms. Of course, if automatic registration is performed, generally at least three fiducial points would need to be defined. In many cases some resizing will be performed step 875. A transparency factor between live fluoroscopy images, and CT (or MRI) segments is adjusted, step 877 in such a fashion that both live fluoroscopy and recorded CT (or MRI) segments are both visualized. The weight of the recorded and live images may be adjusted as needed depending on the operator or physician preference. Once the transparency is adjusted, the overlaid anatomical segments are used for navigation and guidance for performing the procedure, and for proper placement of the balloon for the balloon catheter (step 881). After completion of the first vein, all the other pulmonary veins are done steps (883,885). Typically, there are four pulmonary veins, but there may be more or less depending on the individual patient's anatomy.

Figure 32:
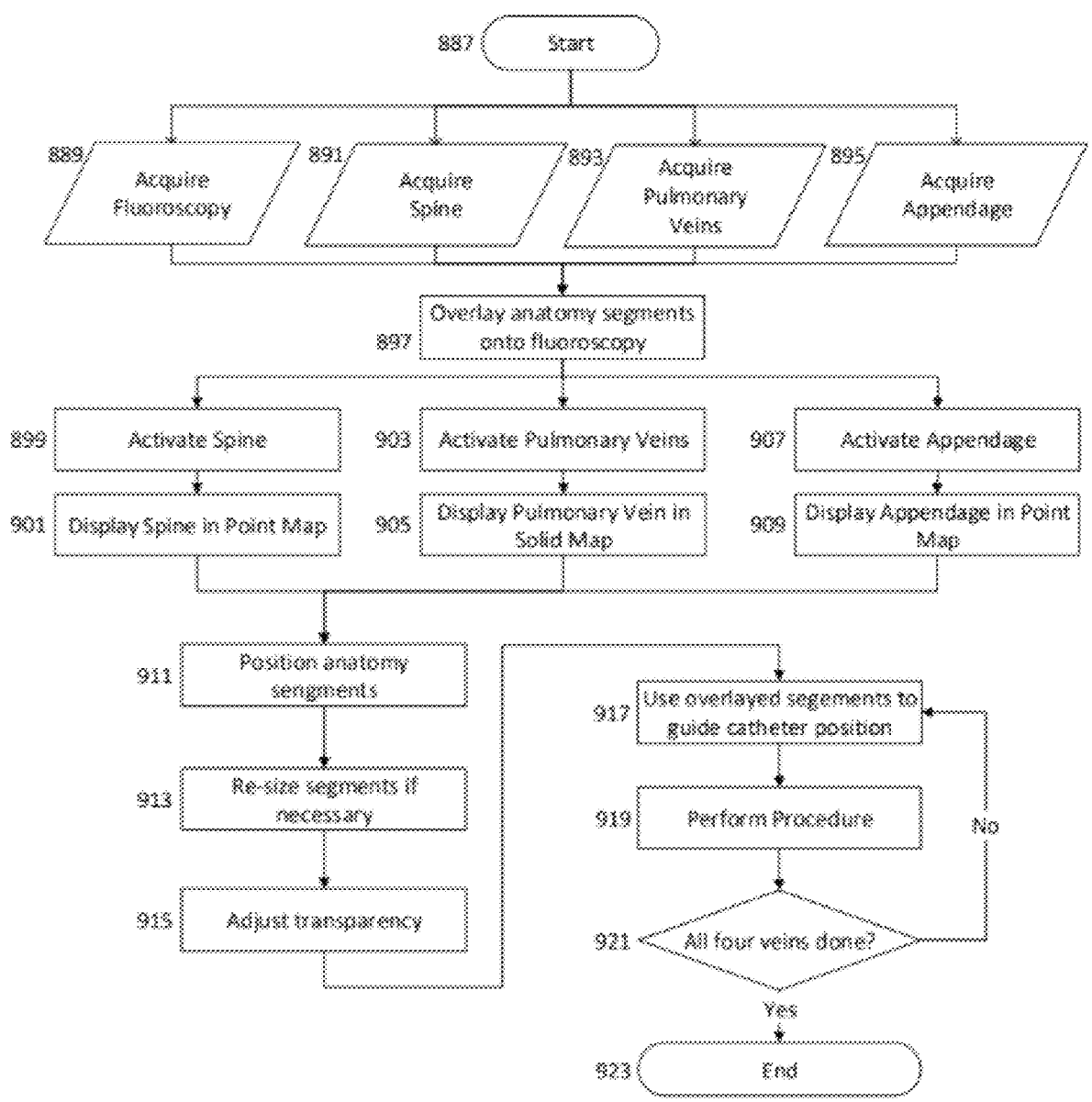
FIG. 32 is a flow diagram showing the steps of overlaying CT or MR images which are in anatomy segments, and overlaying them on live fluoroscopy for balloon based catheter ablations.

Workflow for the implementation of this disclosure can be flexible and varied depending on the institution, the physician and different operators. One of the important aspects is that the different anatomical segment are stored as separate digital files so that individual anatomical segment(s) can be turned ON and turned OFF independently from each other. Further, of the many anatomical segments (and corresponding digital files) any combination of segments can be turned ON and turned OFF. An alternative workflow is shown with the flow diagram in FIG. 32. At the start of the procedure, step 887 live fluoroscopy 889 and various anatomical segments 891, 893, 895 in separate digital files are acquired into the workstation. The various anatomical segments are overlaid on fluoroscopy, shown in step 897. Of the various anatomic segments (such as spine, pulmonary veins, appendage etc.), selected segments are turned ON and selected segments are turned OFF. Thus, any combination of segments may be turned ON and any combination may be turned OFF.

Further, the combination of segments that are turned ON and turned OFF may change during the course of the procedure. The turned ON images and CT segments are positioned on the live fluoroscopy, step 911. Some level of re-sizing, if required is performed step 913. Once all the appropriate segments are turned ON and matched to fluoroscopy, the transparency between live fluoroscopy and CT (or MRI) segments is adjusted (step 915) such that both the live fluoroscopy and CT images can be visualized and are utilized for performing the procedure by placing the balloon catheter (917, 919) at the proper position. Using this methodology of steps, all four veins are done (921) with the ablation process.

When all the pulmonary veins are finished (923) with ablation, the system may be used for checking quality or effectiveness of the ablations performed. A spiral or some other form of multi-electrode catheter may be placed in the pulmonary veins to see if any of the veins are still "active" after the ablation procedure. Depending on the "electrical activity" level of the pulmonary veins, further ablations may be performed utilizing the steps described above.

Figure 33:
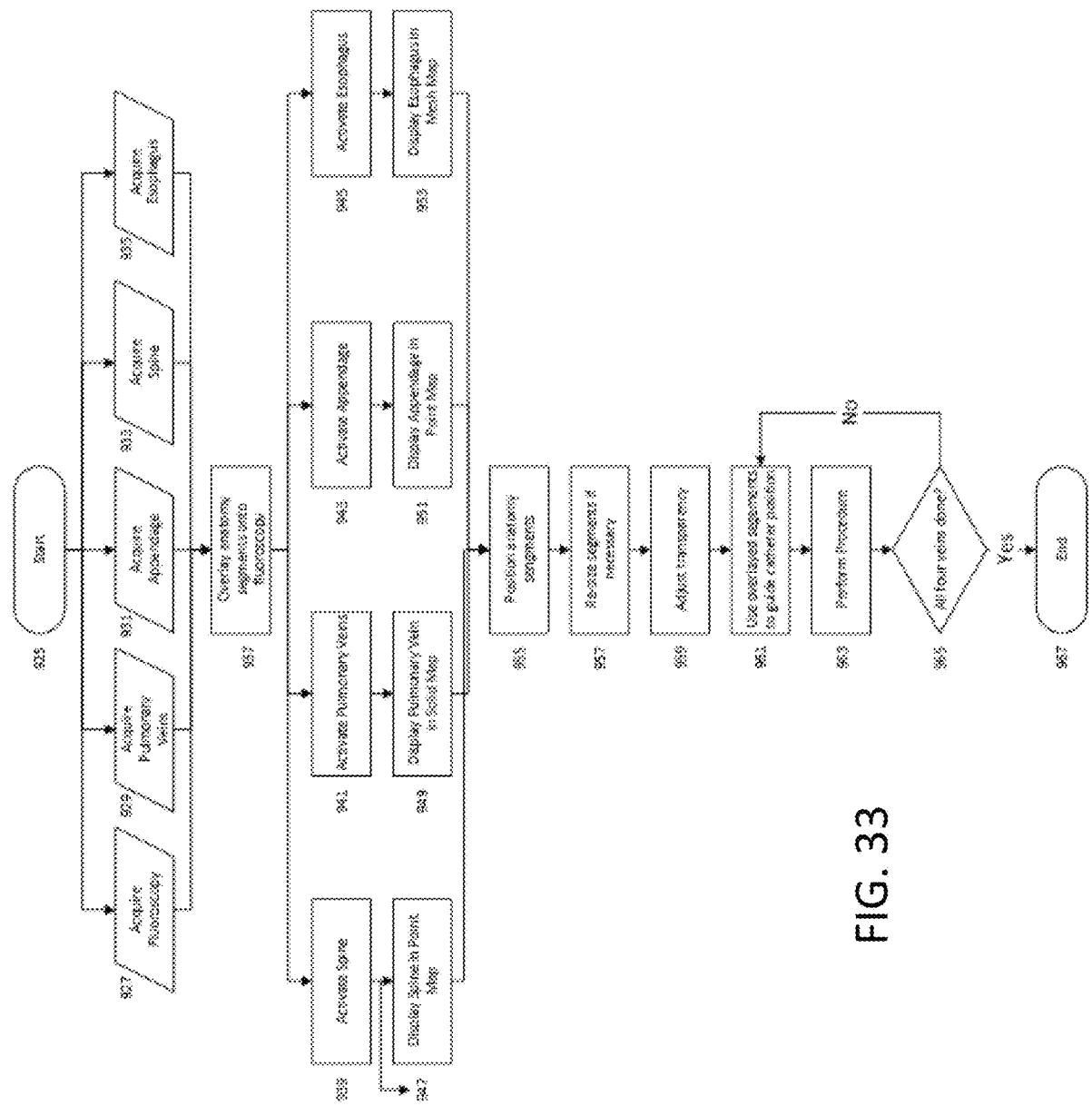
FIG. 33 is a flow diagram showing the steps of overlaying CT or MR images which are in anatomy segments, and overlaying them on live fluoroscopy for balloon based catheter ablations.

As previously mentioned, alternative work flows may be utilized for placing the CT or MR images for doing atrial fibrillation ablations with balloon based catheters. A similar but alternative workflow is shown in conjunction with FIG. 33. At the start 925 of the procedure, live fluoroscopy is acquired 927, as well as, different combination segments of CT or MRI (in digital files) are acquired such as without limitation, pulmonary veins 929, appendage 931, spine 933 and esophagus 935 etc. The acquired anatomy segments are overlaid on fluoroscopy (step 937) images. A unique combination of segments are turned ON and turned OFF. Further, there are options for displaying the anatomy segments in different ways, such as a solid structure, mesh structure or point structure without limitation, as other options are also available for displaying. Of the anatomical segments that are activated, for each segment solid, mesh or point display is chosen, shown in steps 939 to 953. Then, similarly as before, the anatomy segments are positioned or overlaid (or registered) on fluoroscopy images, step 955. Some re-sizing may be necessary if done manually, as shown in step 957. Once the combination of anatomical structures are overlaid, a transparency is adjusted between live fluoroscopy and the CT or MR image segments 959. The overlay of the CT or MR image segments is used to guide the balloon based or circular catheter positioning and performing the procedure (steps 961-963) until all four veins are done (step 965). The image overlay part is then completed 967.

Figure 34:
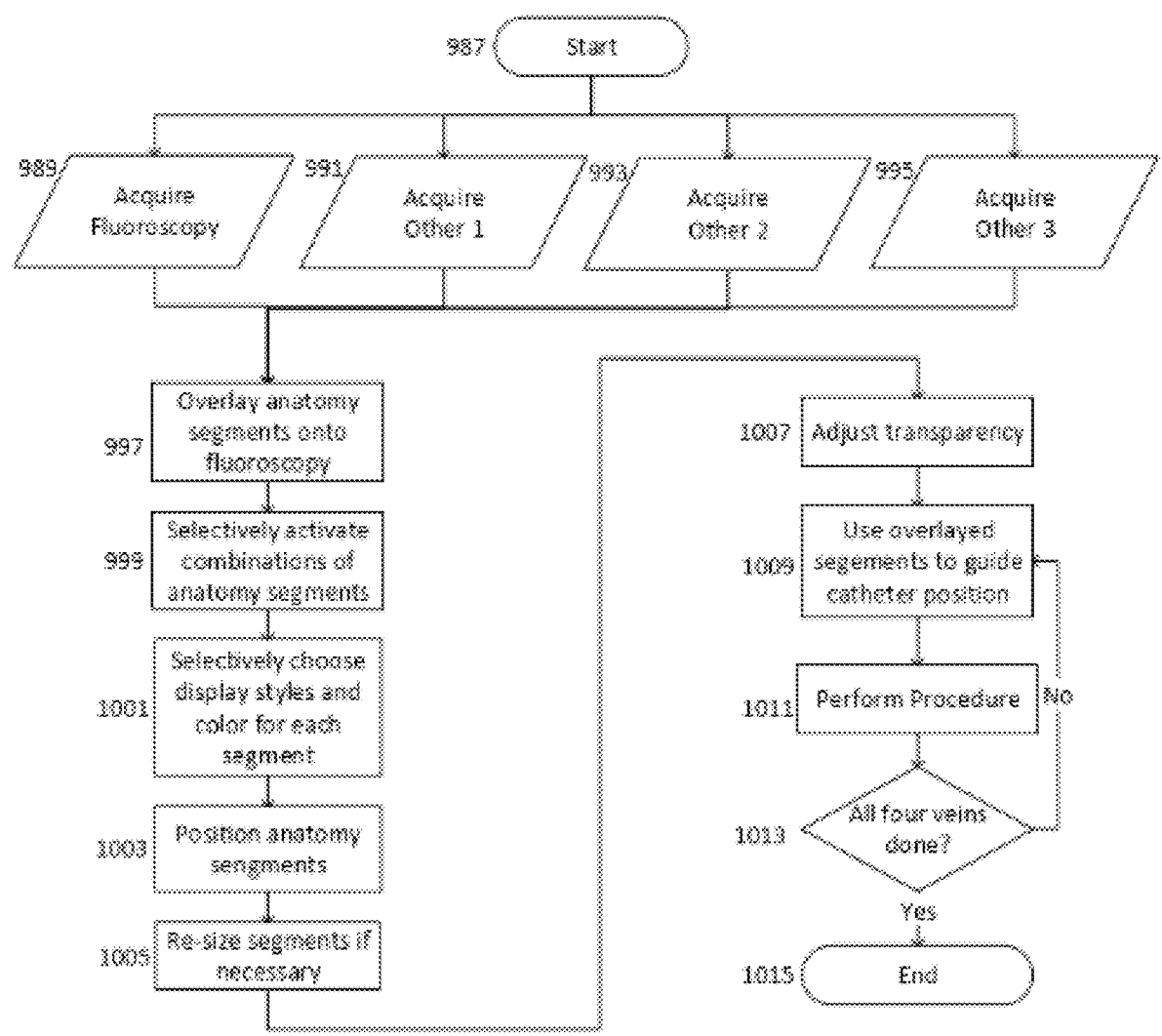
FIG. 34 is a flow diagram showing the steps of overlaying CT or MR images which are in anatomy segments, and overlaying them on live fluoroscopy for balloon based catheter ablations.

Another similar but alternative methodology is shown in conjunction with flow diagram in FIG. 34. At the start 987, live fluoroscopy is acquired 989, as well as, other relevant anatomical segments are acquired (991-995) which in this figure are labeled other 1, other 2, and other 3. These anatomical segments may be any anatomical segments. Some examples without limitation are left atrium (LA), pulmonary veins (PV) anterior part of the atrium and appendage, coronary sinus, right atrium, left ventricle, section of spine, esophagus. Other related or relevant anatomical segments may also be used. These anatomical segments are overlaid onto live fluoroscopy images, step 997. Of the different anatomical segments, selected anatomical segments are turned OFF which are not needed at the time. This way a combination of anatomical segments are turned ON and a combination of anatomical segments are turned OFF, step 999. Display styles of segments such as solid, mesh or point structures is selected, as shown in step 1001. Other styles not mentioned here may also be used. The anatomy segments are positioned 1003 and re-sized as needed 1005. As shown in the previous flow diagrams, transparency between live fluoroscopy and CT or MR image segments is adjusted 1007 to a level where both can be visualized, as an aid to guiding the procedure. These overlaid images with adjusted transparency is used to guide the catheters and perform the procedure (steps 1009, 1011). This part of the procedure is completed 1015 when all four pulmonary veins have been done (step 1013).

Implementation

Figure 35:
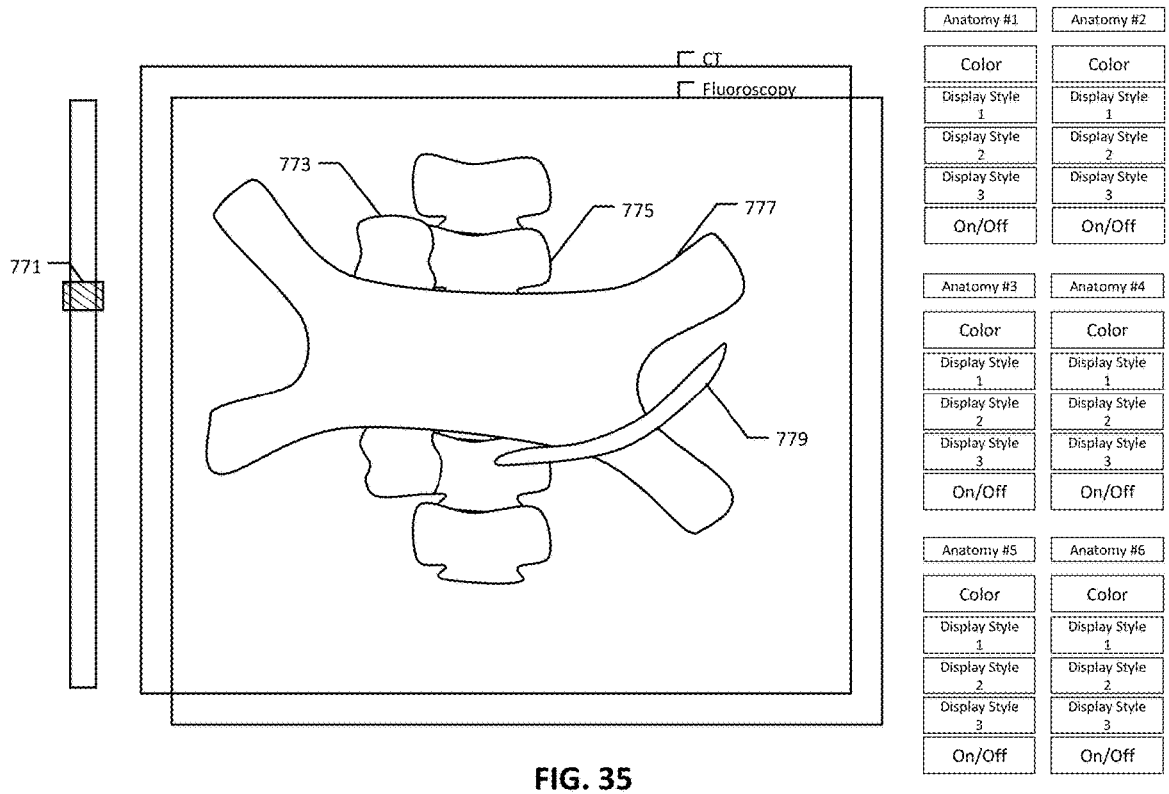
FIG. 35 is a diagram depicting implementation of CT or MRI anatomy segments showing pulmonary veins, spine, esophagus, and coronary sinus (CS) segments overlaid on live fluoroscopy.

Implementation of this can be performed utilizing various different software's. Applicant's have implemented this utilizing C++, Matlab™ and Labview™ For the purposes of doing 3D volume rendering of anatomy segments, various software's from different vendors are available. Some examples of vendor's are Ziosoft, Fuji Film, Siemens, and GE healthcare. The DICOM viewer software, will give 3D volume rendering of various structures of the body from the patient's CT files. These structures can be further analyzed and segmented. Once the different anatomical segments are segmented, they are stored in separate digital files FIG. 35 shows the display of the system in our implementation when computed tomography (CT) images are overlaid on fluoroscopy. In the implementation system allows for the CT image to be segmented, then selectively display in several ways, as shown in the next few figures. This iteration shows the CT segments for the esophagus (773), the spine (775), the pulmonary veins (777), and the coronary sinus (779). Some of these segments are of interest during the procedure, while others are used primarily for alignment (e.g. spine)—to ensure that the CT images overlay on the fluoroscopy correctly. The scroll bar (771) shown in the figure, allows the user to adjust transparency between the live fluoroscopy and the CT images. The display options are shown as well. For each segment of anatomy, the user can select a color, display style, or toggle the segment altogether. The color of each anatomy, for example, can be selected to be different colors to differentiate between them. The display styles, for example, could show a solid anatomy, a mesh map, or point map, among other possibilities. The On/Off button allows the user to toggle the display of the individual anatomies.

Figure 36:
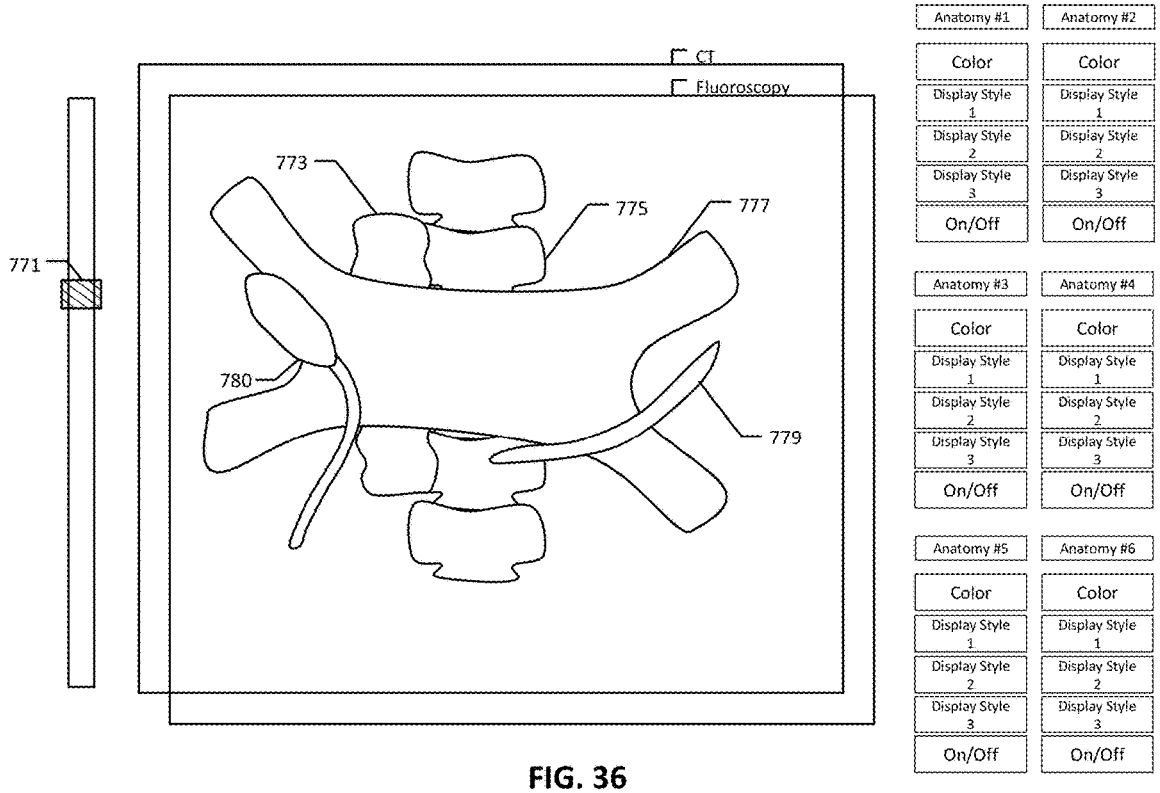
FIG. 36 is a diagram depicting implementation of CT or MRI anatomy segments showing pulmonary veins, spine, esophagus, and coronary sinus (CS) segments overlaid on live fluoroscopy, also showing a balloon catheter placement.

FIG. 36 shows another example of display in application of the system. A balloon catheter has been inserted into one of the pulmonary veins for an atrial fibrillation ablation procedure. The balloon (780) can be seen on the fluoroscopy window. Because vascular structures such as the pulmonary veins do not offer much contrast to surrounding tissue, the pulmonary veins (777) are seen on the CT window. Other anatomy, such as the spine (775) would be seen in both windows, therefore allowing the user to scale and rotate the CT images to align them to the fluoroscopy. This allows the physician to view both the balloon catheter and the placement of the catheter in relation to other structures within the body. The esophagus (773), for example, is monitored to ensure that the ablation procedure is not ablating cells outside the intended area.

Figure 37:
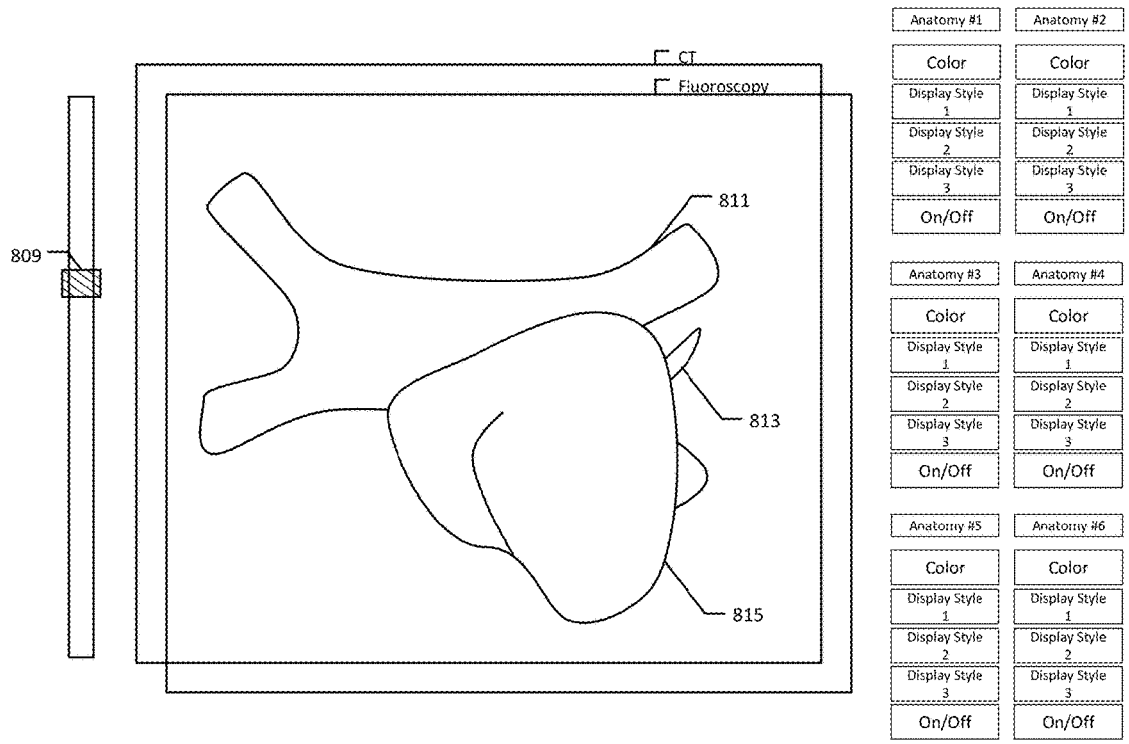
FIG. 37 is a diagram depicting implementation of CT or MRI anatomy segments showing pulmonary veins and left ventricular segments overlaid on live fluoroscopy.

FIG. 37 shows another example of the display of the system when computed tomography (CT) images are overlaid with fluoroscopy. The system allows for the CT image to be segmented, then selectively display in several ways. This iteration shows the CT segments for the pulmonary veins (811), the coronary sinus (813), and the left ventricle (815). The scroll bar (809) allows the user to adjust transparency between the live fluoroscopy images and the CT images. The display options are shown as well. For each segment of anatomy, the user can select a color, display style, or toggle the segment altogether. The color of each anatomy, for example, can be selected to be different colors to differentiate between them. The display styles, for example, could show a solid anatomy, a mesh map, or point map, among other possibilities. The On/Off button allows the user to toggle the display of the individual anatomy segments.

Figure 38:
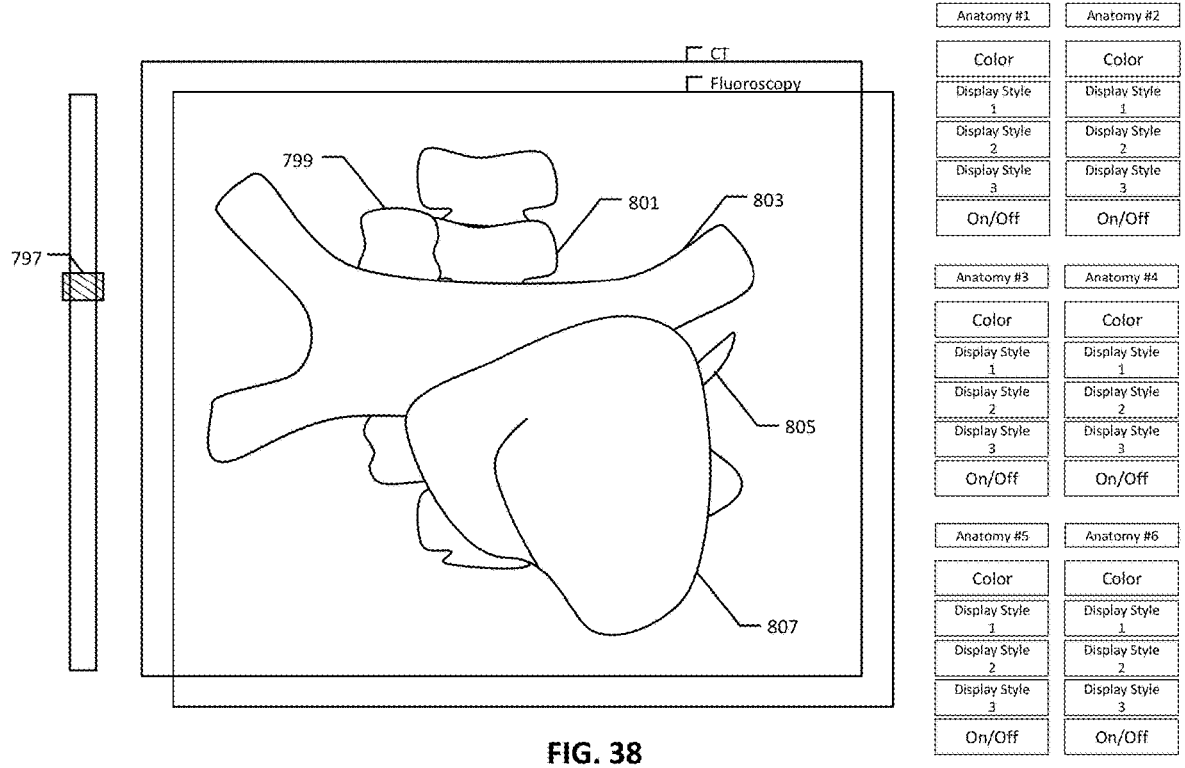
FIG. 38 is a diagram depicting implementation of CT or MRI anatomy segments showing pulmonary veins, spine, esophagus, coronary sinus (CS) and left ventricular segments overlaid on live fluoroscopy.

FIG. 38 shows another display of the implementation in a system when computed tomography (CT or MR) image segments are overlaid with fluoroscopy. The system allows for the CT (or MR) image to be segmented, then selectively display in several ways. This iteration shows the CT segments for the esophagus (799), the spine (801), the pulmonary veins (803), the coronary sinus (805), and the left ventricle (807) in an AP (anterior-posterior) view. The scroll bar (797) allows the user to adjust transparency between the live fluoroscopy images and the CT images. The display options are also shown. For each segment of anatomy, the user can also select a color, display style, or toggle the segment altogether. The color of each anatomy, for example, can be selected to be different colors to differentiate between them. The display styles, for example, could show a solid anatomy, a mesh map, or point map, among other possibilities. The On/Off button would allow the user to toggle the display of the individual anatomies.

Figure 39:
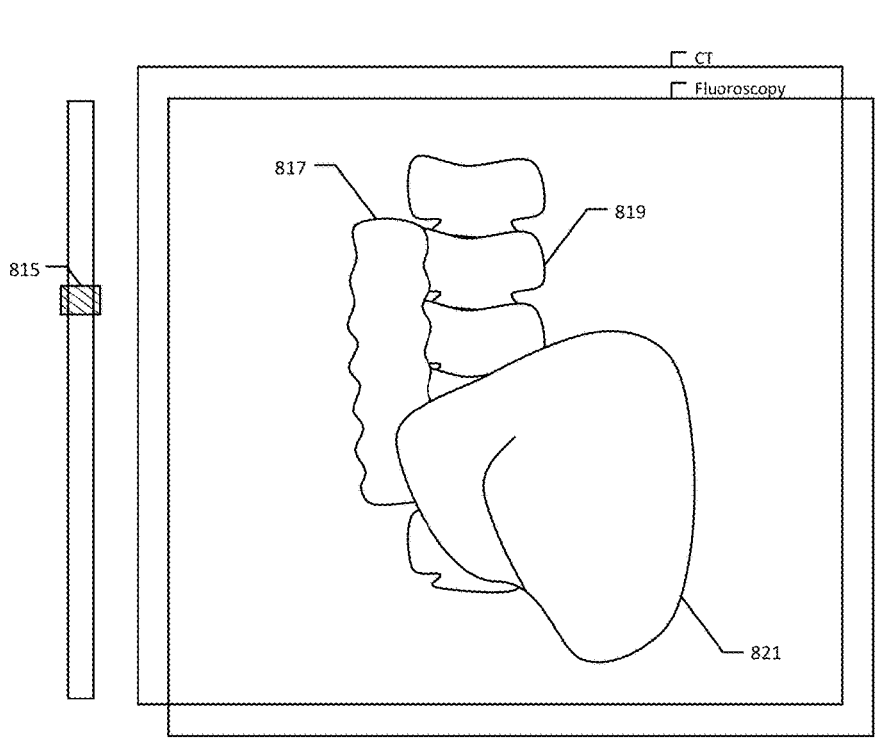
FIG. 39 is a diagram depicting implementation of CT or MRI anatomy segments showing spine, esophagus, and left ventricular segments overlaid on live fluoroscopy.

FIG. 39 shows another example of display of the system when computed tomography (CT or MRI) images are overlaid on fluoroscopy images. In this example, the pulmonary veins are selectively removed from the previous figure. The system allows for the CT image to be segmented, then selectively display in several ways. This iteration shows the CT segments for the esophagus (817), the spine (819), and the left ventricle (821). The scroll bar (815) allows the user to adjust transparency between the live fluoroscopy and the CT images. The display options are shown as well. For each segment of anatomy, the user can select a color, display style, or toggle the segment altogether. The color of each anatomy, for example, can be selected to be different colors to differentiate between them. The display styles, for example, could show a solid anatomy, a mesh map, or point map, among other possibilities. The On/Off button would allow the user to toggle the display of the individual anatomies.

Figure 40:
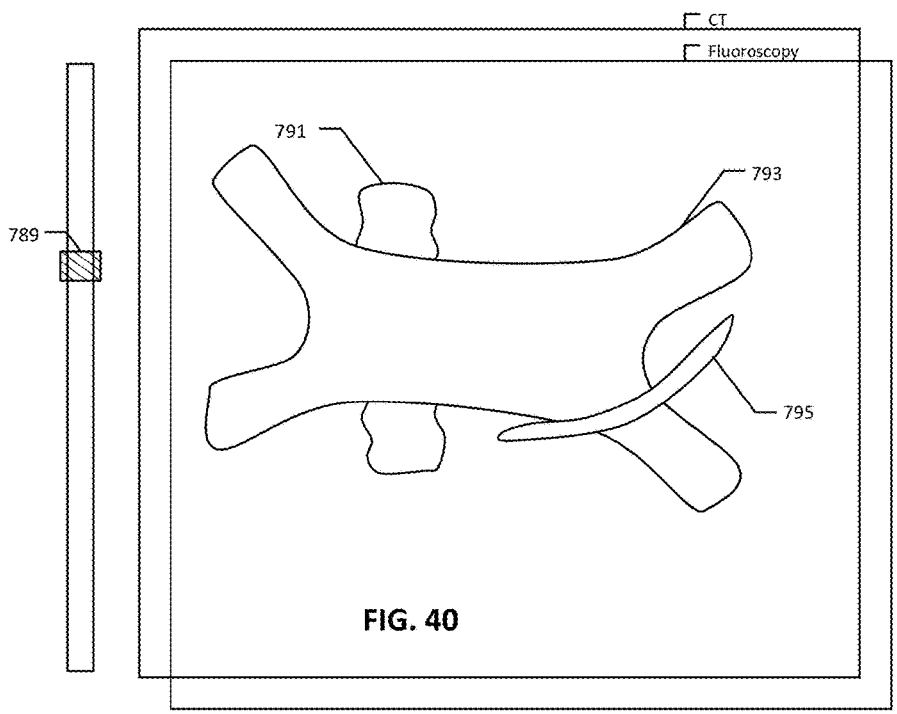
FIG. 40 is a diagram depicting implementation of CT or MRI anatomy segments showing pulmonary veins, esophagus, and coronary sinus (CS) segments overlaid on live fluoroscopy.

FIG. 40 shows another display of the system when computed tomography (CT or MRI) images are overlaid with fluoroscopy as before. As before, the system allows for the CT image to be segmented, then selectively display in several ways. This iteration shows the CT segments for the esophagus (791), the pulmonary veins (793), and the coronary sinus (795). The scroll bar (789) allows the user to adjust transparency between the live fluoroscopy and the CT images. The display options are also shown as well. For each segment of anatomy, the user can select a color, display style, or toggle the segment altogether. The color of each anatomy, for example, can be selected to be different colors to differentiate between them. The display styles, for example, could show a solid anatomy, a mesh map, or point map, or a combination among other possibilities. The On/Off button allows the user to toggle the display of the individual anatomies.

In our implementation and clinical testing of the system, this view is used a significant amount. The advantage of this view is that generally some sort of (AP) anterior-posterior view is typically used on fluoroscopy. When the atrium in the CT view is used, the anterior or front part of the atrium, which includes structures like the left atrial appendage get in the way of visualizing the left superior and left inferior veins. Advantageously, in the method of this disclosure, the front part of atrium which includes appendage is selectively removed, showing only the pulmonary veins overlaid or registered to the fluoroscopy images. This aids the physician in placing the balloon in an unobstructed view of the posterior (or back) structure is provided.

Figure 41:
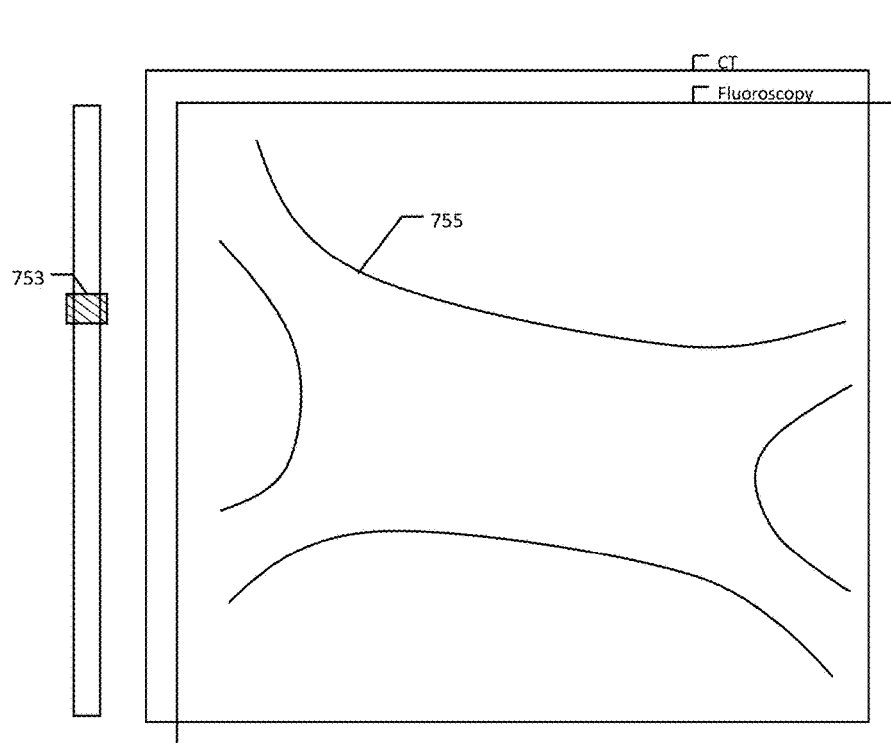
FIG. 41 is a diagram depicting implementation of CT or MRI anatomy segments showing pulmonary veins segment overlaid on live fluoroscopy.

FIG. 41 shows another display of the system when computed tomography (CT) images are overlaid with fluoroscopy. This iteration shows the CT segment for the pulmonary veins (755). An advantage of this view is that it provides an unobstructed view of the region of interest for the physician to place the balloon catheter around the left atrium or pulmonary veins. The scroll bar (753) allows the user to adjust transparency between the live fluoroscopy and the CT images. The display options are shown as well. For each segment of anatomy, the user can select a color, display style, or toggle the segment altogether. The color of each anatomy, for example, can be selected to be different colors to differentiate between them. The display styles, for example, could show a solid anatomy, a mesh map, or point map, among other possibilities. The On/Off button allows the user to toggle the display of the individual anatomies.

Figure 42:
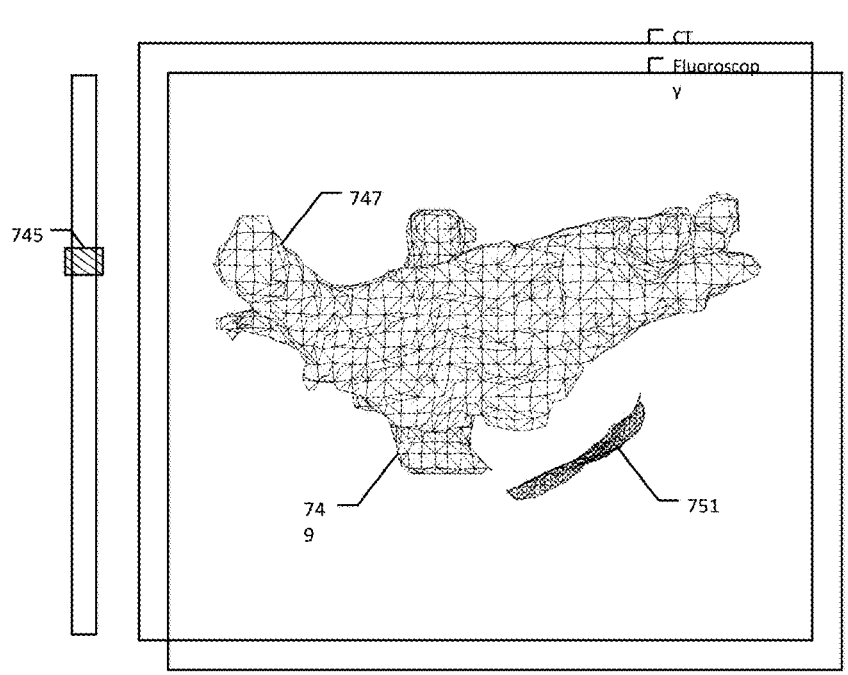
FIG. 42 is a diagram depicting implementation of CT or MRI anatomy segments showing pulmonary veins, spine, and coronary sinus (CS) segments in a mesh map overlaid on live fluoroscopy.

FIG. 42 shows another example of display of the system in mesh map, when computed tomography (CT) images are overlaid with fluoroscopy. The system allows for the CT image to be segmented, then selectively display in several ways. This iteration shows the CT segments for the pulmonary veins (747), the esophagus (749), and the coronary sinus (751). The scroll bar (745) allows the user to adjust transparency between the live fluoroscopy and the CT images. The display options are shown as well. For each segment of anatomy, the user can select a color, display style, or toggle the segment altogether. The color of each anatomy, for example, can be selected to be different colors to differentiate between them. The display styles, for example, could show a solid anatomy, a mesh map, or point map, among other possibilities. This figure shows the anatomies in a mesh map. The On/Off button allows the user to toggle the display of the individual anatomies.

Figure 43:
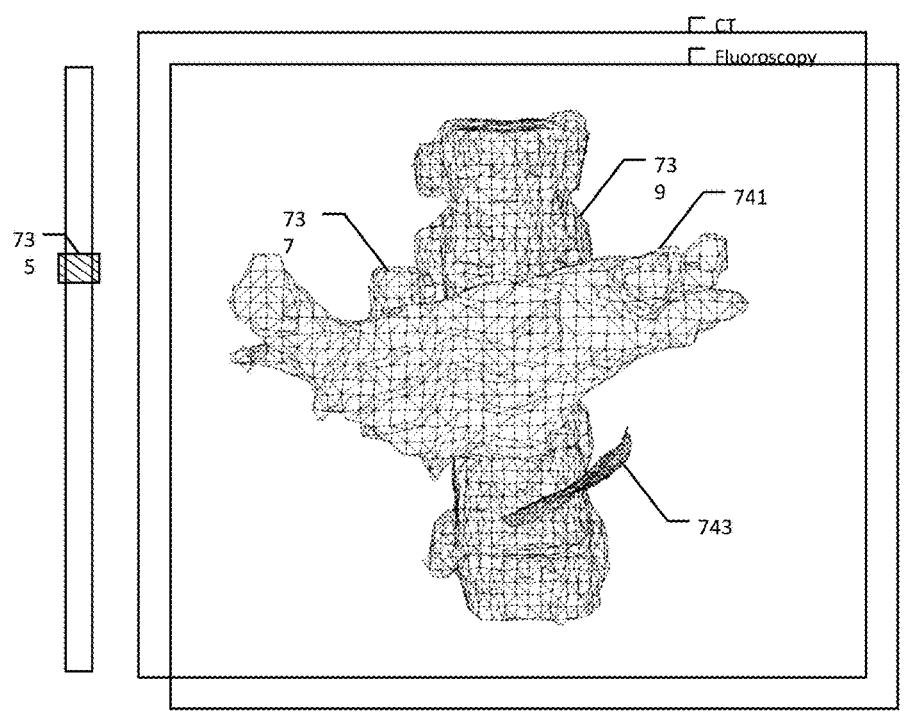
FIG. 43 is a diagram depicting implementation of CT or MRI anatomy segments showing pulmonary veins, spine, esophagus, and coronary sinus (CS) segments overlaid on live fluoroscopy.

FIG. 43 shows a display of the system when computed tomography (CT) images are overlaid with fluoroscopy. This figure shows the anatomies in a mesh map. The CT image is segmented, then selectively displayed in several ways. This iteration shows the CT segments for the esophagus (737), the pulmonary veins (741), the spine (739), and the coronary sinus (743). The scroll bar (735) allows the user to adjust transparency between the live fluoroscopy and the CT images. The display options are shown as well. For each segment of anatomy, the user can select a color, display style, or toggle the segment altogether. The color of each anatomy, for example, can be selected to be different colors to differentiate between them. The display styles, for example, could show a solid anatomy, a mesh map, or point map, among other possibilities. The On/Off button would allow the user to toggle the display of the individual anatomies.

Figure 44:
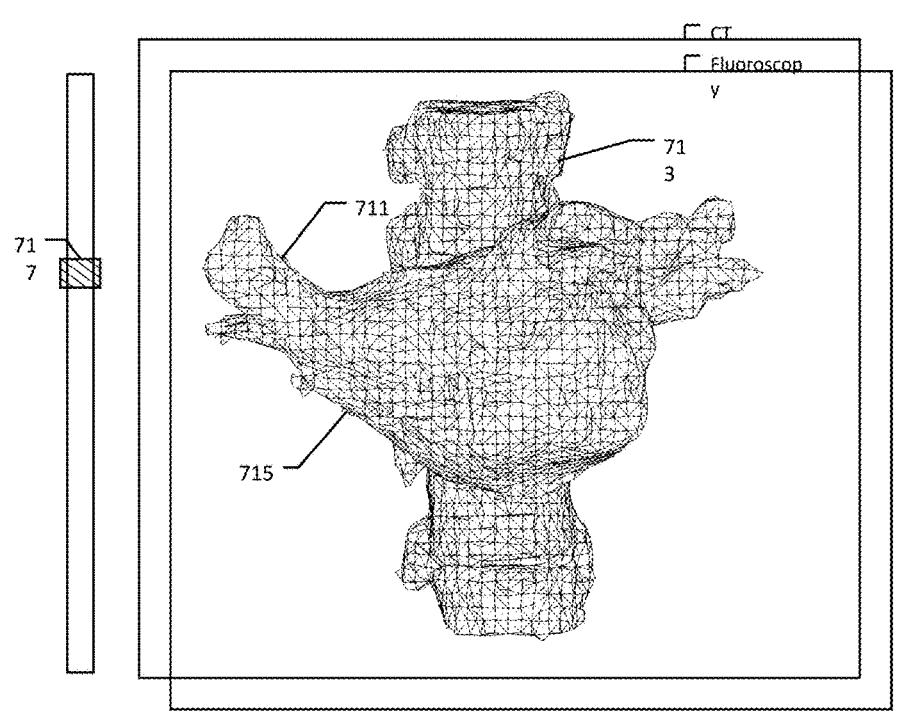
FIG. 44 is a diagram depicting implementation of CT or MRI anatomy segments showing pulmonary veins, and spine segments in mesh format overlaid on live fluoroscopy.
Figure 45:
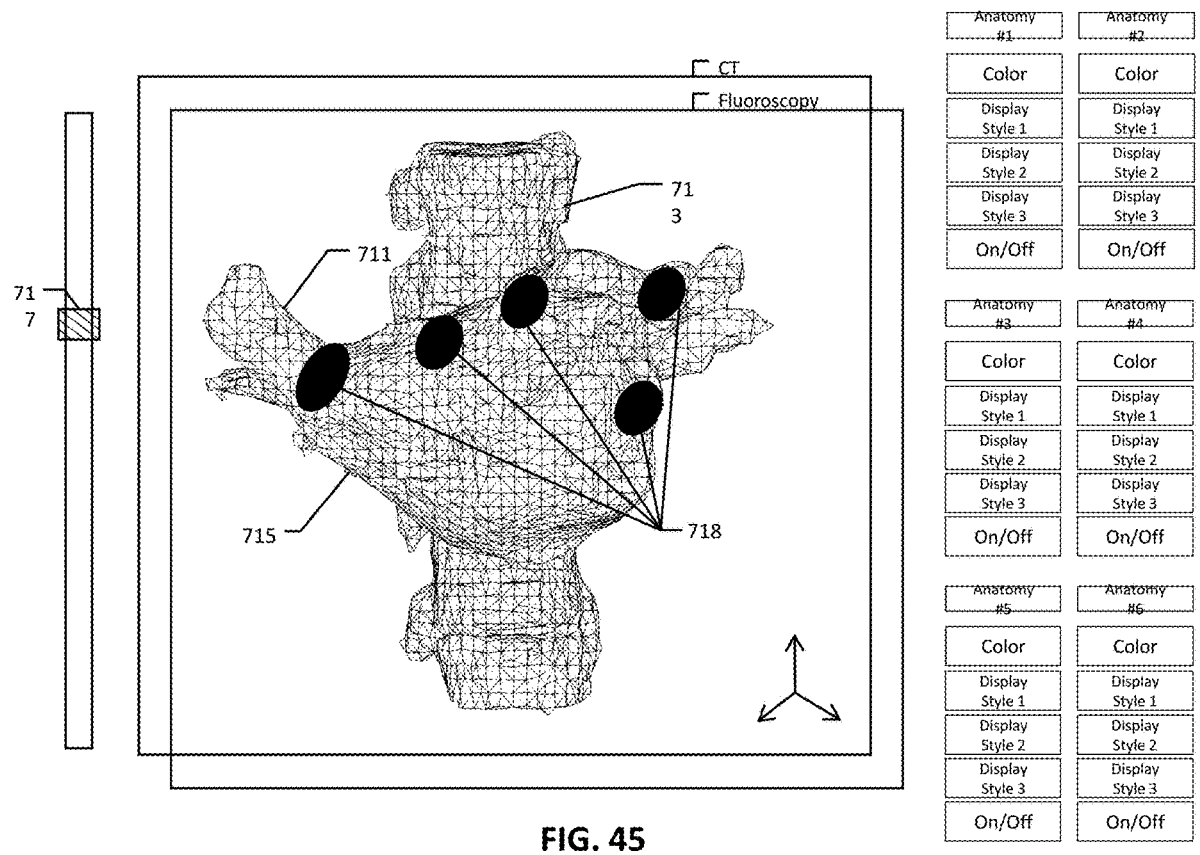
FIG. 45 is a diagram depicting implementation of CT or MRI anatomy segments showing pulmonary veins and spine segments in mesh format overlaid on live fluoroscopy, additionally depicting several 3D volume tags indicative of ablation sites with balloon catheter.

FIG. 44 shows the display of the system when computed tomography (CT) images are overlaid with fluoroscopy. The system allows for the CT image to be segmented, then selectively display in several ways. This iteration shows the CT segments for the pulmonary veins (711), the spine (713), and the esophagus (715). The scroll bar (717) allows the user to adjust transparency between the live fluoroscopy and the CT images. The display options are shown as well. For each segment of anatomy, the user can select a color, display style, or toggle the segment altogether. The color of each anatomy, for example, can be selected to be different colors to differentiate between them. The display styles, for example, could show a solid anatomy, a mesh map, or point map, among other possibilities. This figure shows the anatomies in a mesh map. The On/Off button allows the user to toggle the display of the individual anatomies.

Figure 46:
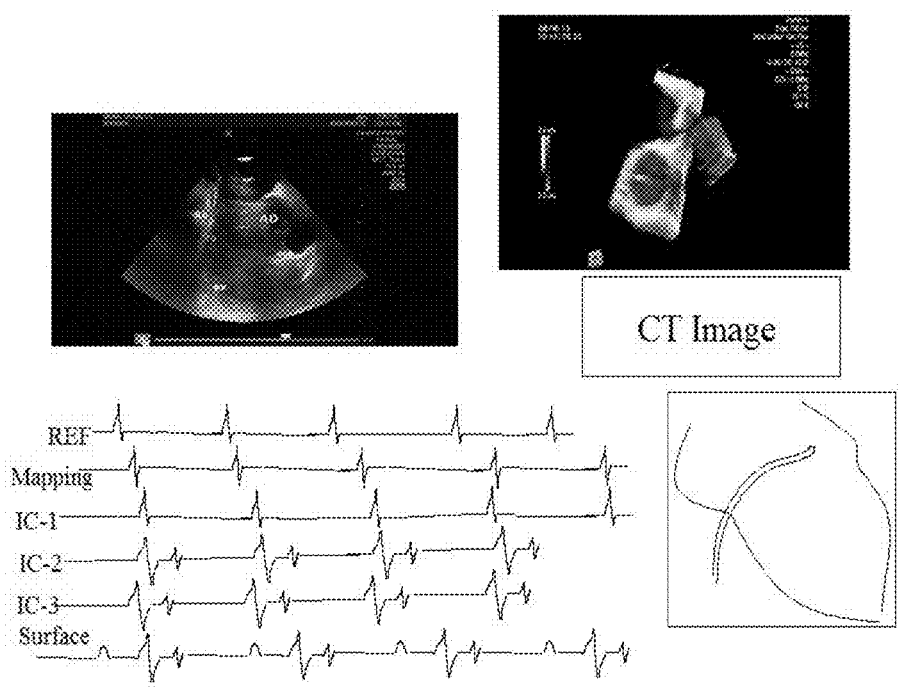
FIG. 46 depict using 2D and 3D ICE in cardiac mapping in our implementation of the cardiac mapping system, along with several channels of intracardiac and surface signals.
Figure 47:
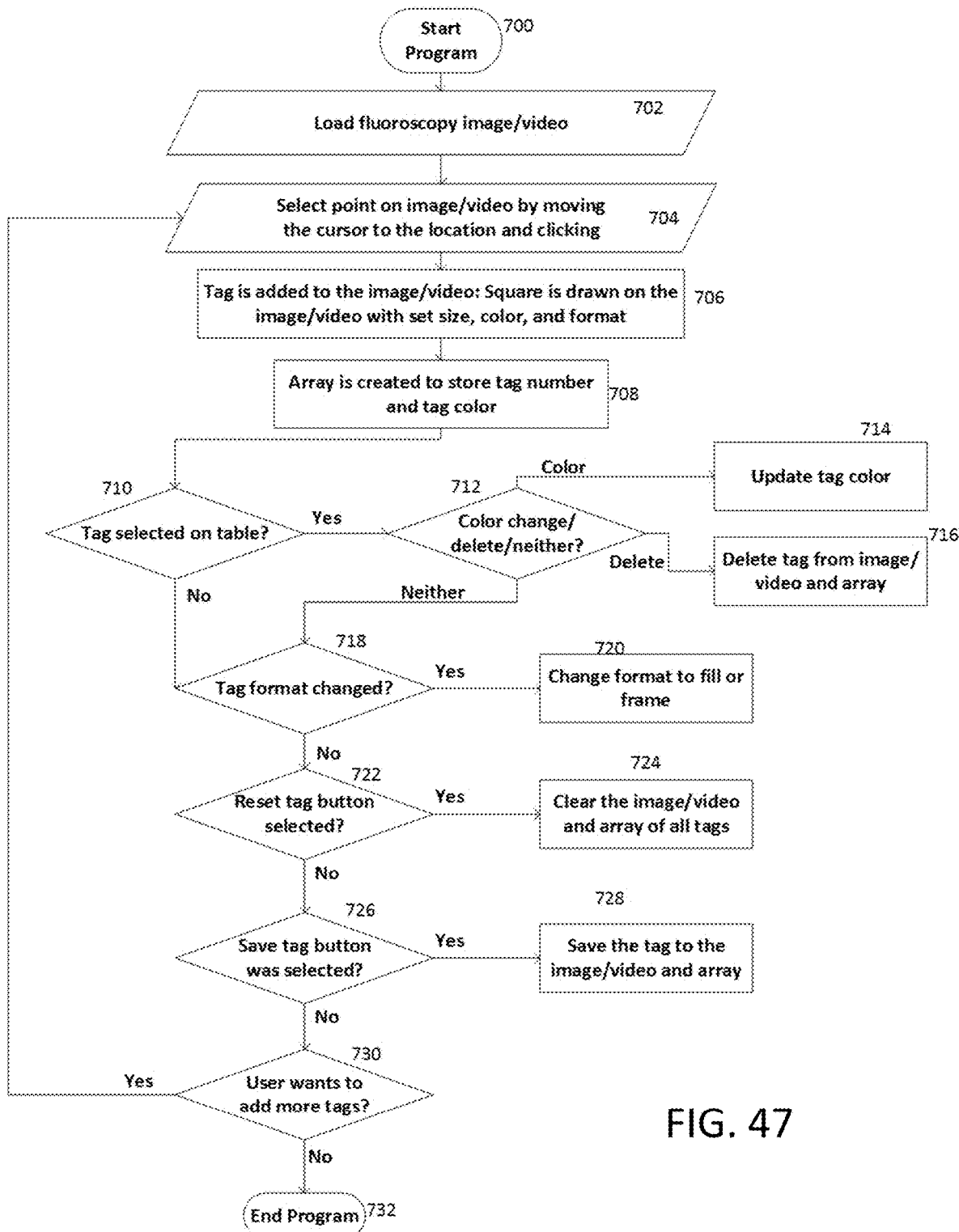
FIG. 47 is a flow diagram showing placement of tags on fluoroscopy images.
Figure 48:
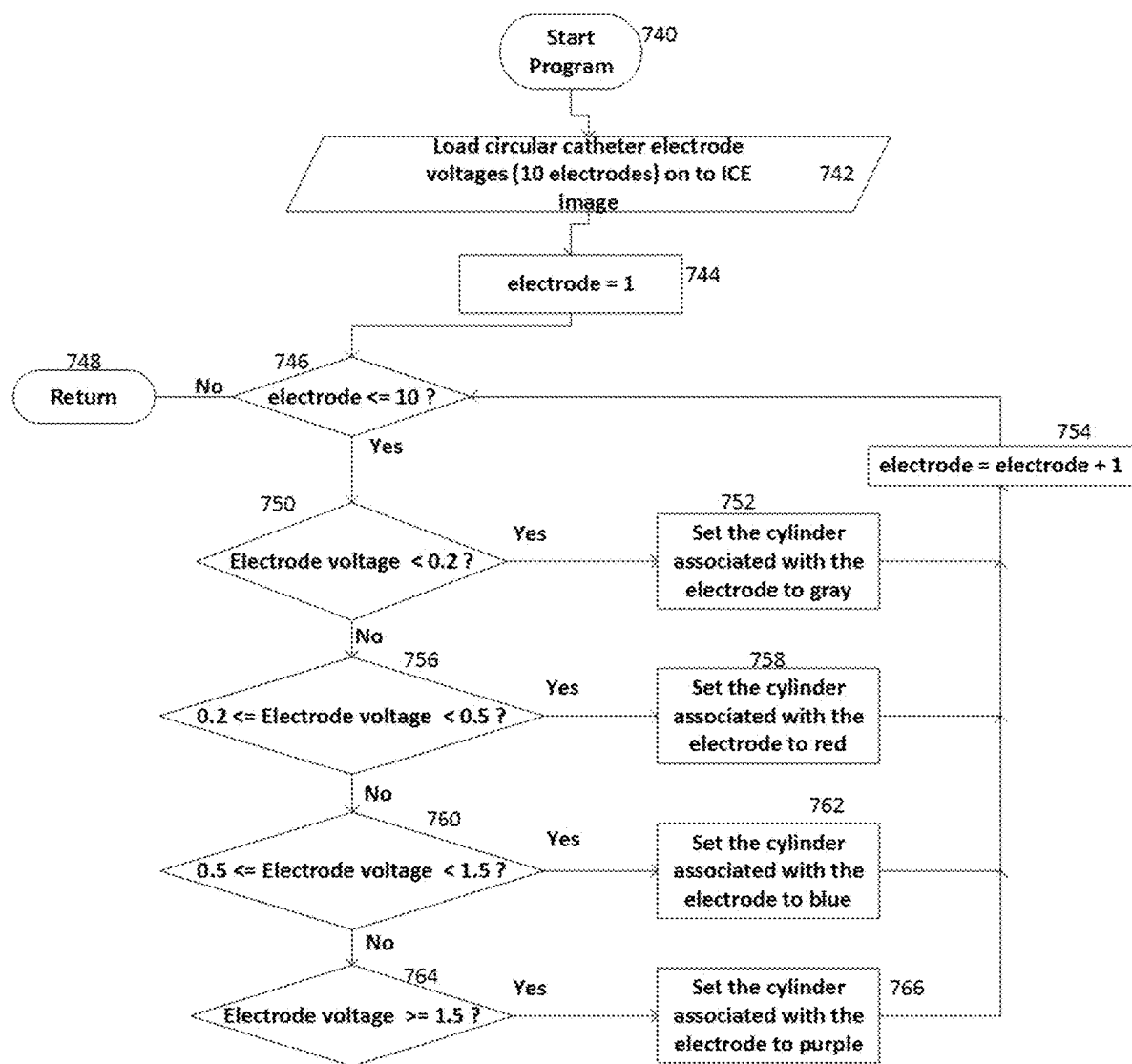
FIG. 48 is a flow diagram for depicting voltages on a circular catheter.

FIG. 46 shows the display of the system when computed tomography (CT) images are overlaid with fluoroscopy. The system allows for the CT image to be segmented, then selectively display in several ways. This iteration shows the CT segments for the pulmonary veins (711), the spine (713), and the esophagus (715). The scroll bar (717) allows the user to adjust transparency between the live fluoroscopy and the CT images. The 3D tags (718) are utilized to display the areas where ablations are performed. With each placement of the balloon catheter, the location would be recorded, and a new 3D tag would be created. The display options are shown as well. For each segment of anatomy, the user can select a color, display style, or toggle the segment altogether. The color of each anatomy, for example, can be selected to be different colors to differentiate between them. The display styles, for example, could show a solid anatomy, a mesh map, or point map, among other possibilities. This figure shows the anatomies in a mesh map. The On/Off button would allow the user to toggle the display of the individual anatomies.

ICE imaging has the advantage, that ionizing radiation is not utilized. Generally, fluoroscopy and ICE are both used for visualization of the movement of the catheter in the chamber of the heart. Fluoroscopy utilizes ionization radiation whereas ICE utilizes sound waves which are not harmful to the body.

Implementation for Creating 2D Tags on 2D Images

Creating 2D tags on 2D images depends on the coding environment you are working within. Some environments offer you functions that make the 2D tag generations easy, while others rely on you to create your own functions from scratch. Below are examples of how you could code 2D tags on 2D images in different coding environments. LabVIEW is a visual coding environment with wires connecting the flow from each process, whereas MATLAB is a more traditional line based coding environment.

LabVIEW: After the image data is loaded into LabVIEW, it is displayed using the IMAQ create VI which creates a 2D scene to display the loaded image data. In order to add the 2D tag to the image data, the IMAQ Overlay Rectangle VI is used. The IMAQ Rectangle VI draws a rectangle the over the image data at a specific location with a specific color, size, and fill.

MATLAB: After the image data is loaded into MATLAB, it is displayed using the image function which creates a 2D figure window that displays the loaded image data. In order to add the 2D tag to the image data, a small image mask can be created in a 2D matrix that represents the shape and size of the tag. The location of the tag can be manipulated by shifting the mask around the image and the color of the tag can be changed by altering the red, green, and blue pixel values.

Creating 3D Scenes with 3D Objects

Creating 3D scenes with 3D objects depends on what coding environment you are working within. Some environments offer you functions that make the 3D scene and object generations easy, while others rely on you to create your own functions from scratch. Below are examples of how you could code 3D scenes and objects in different coding environments. LabVIEW is a visual coding environment with wires connecting the flow from each process, whereas MATLAB is a more traditional line based coding environment.

LabVIEW: In order to create a 3D scene, the Create Object VI is used without any input. Once the empty scene is generated, the Add Object VI can be used in conjunction with the Create Cylinder VI, Create Sphere VI, etc. to generate a shape within the scene. Each shape's VI accepts information about the color, size, location, and rotation of the object. In order to overlay 3D tags on 3D medical image data, the Medical Image Extract Isosurface VI and the Medical Image Draw Isosurface VI would be used to project the medical image data in a 3D scene and then the same process as before would be done to add tags (3D objects).

MATLAB: In order to create a 3D scene, a 3D object must first be generated using the sphere function, cylinder function, etc. and then plotted using the surf function. Each shape's function accepts information about the size, location, and rotation of the object. In order to overlay 3D tags on 3D medical image data, the isosurface function and the patch function would be used to project the medical image data in a 3D scene and then the shape functions would be used to create the 3D tags. The color of the medical image data and the tags can be altered by manipulating the red, green, and blue voxel values.

It will be clear to one skilled in the art, that that the newly developed 3D or 4D ice are also used in cardiology and cardiac electrophysiology. In the 4D ICE, the fourth dimension is time. Since 2D ICE still has the advantage that it can visualize through the structures. The 3D and 4D imaging have the advantage that full and moving structures are visualized.

In one aspect of this disclosure, both 2D and 4D ICE imaging is utilized in the same procedure. One example of our implementation is shown in FIG. 46, where 2D and 4D ICE images are both shown, and signals are shown below. The ablation and/or anatomical tags may be marked separately on the different figures or the 2D and 4D ICE images may be registered with each other. Of course, for registration fiducial points would have to be labeled, and the registration process would have to be run through the software.

As was shown in FIG. 4, other images such as fluoroscopy and CT may also be brought into the mapping system for cardiac mapping and guiding ablation for cardiac arrhythmias.

Figure 49:
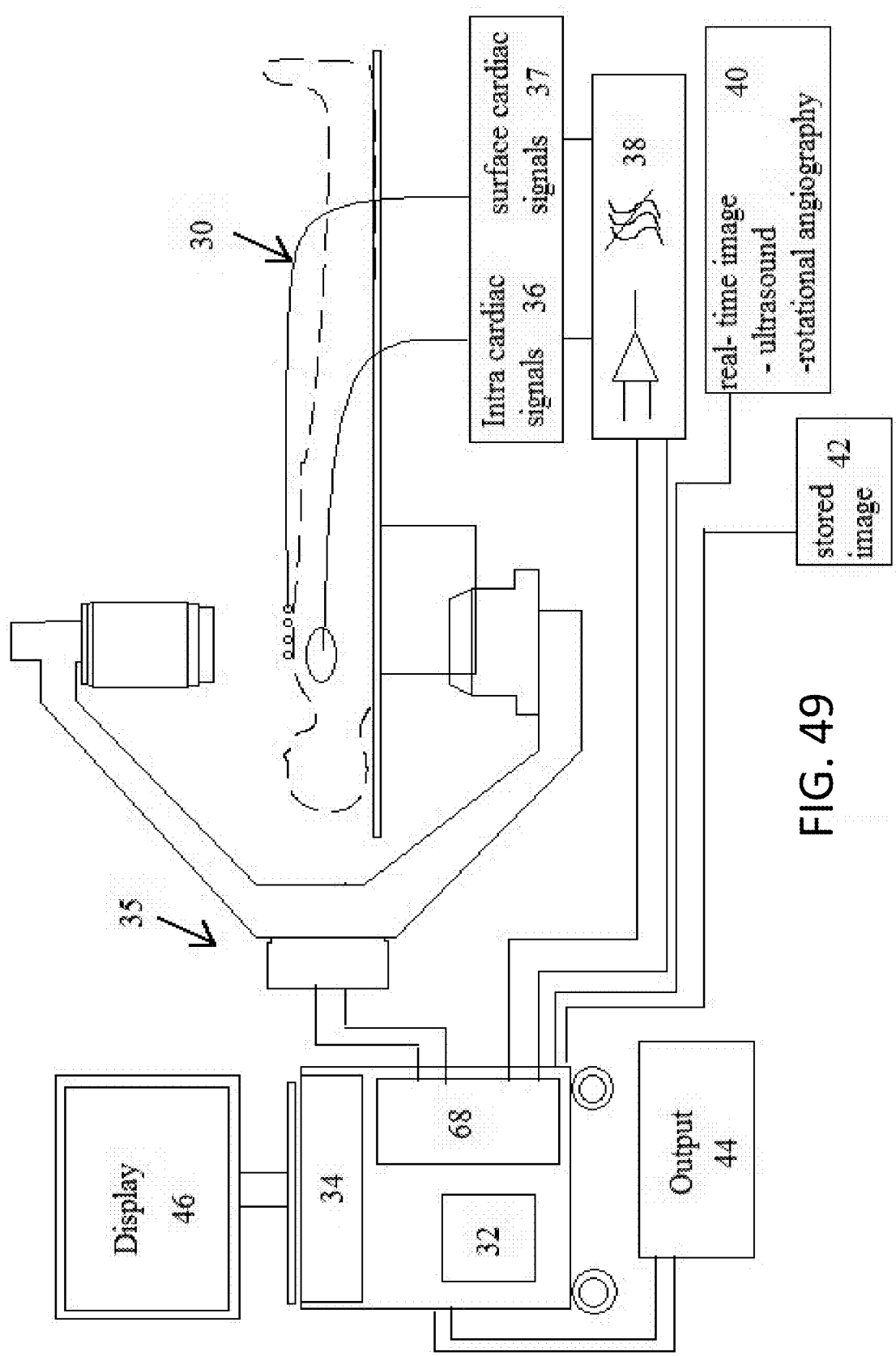
FIG. 49 depicts utilizing fluoroscopy based mapping system where other type of images can also be brought into the mapping system.

The concept of fluoroscopy based cardiac mapping system is shown in conjunction with FIG. 49. Both fluoroscopy images and electrical signals (both surface and intracardiac) of the patient are brought into the cardiac mapping system. In the method and system of this disclosure, fluoroscopy includes single plane fluoroscopy, bi-plane fluoroscopy, rotational angiography, and overlay of regular fluoroscopy and stored high resolution angiograms. In rotational angiography, the heart chamber is temporarily stopped from beating by extremely fast pacing or injection of adenosine. A bolus of contrast medium or "dye" is injected either into the left atrium or on the right side of the heart which passes thru the lungs and is move through the left atrium, and the fluoroscopy is rotated around the patient, and with computing a 3D model is generated similar to volume rendering of the left atrium (LA) of a CT scan.

Figure 50:
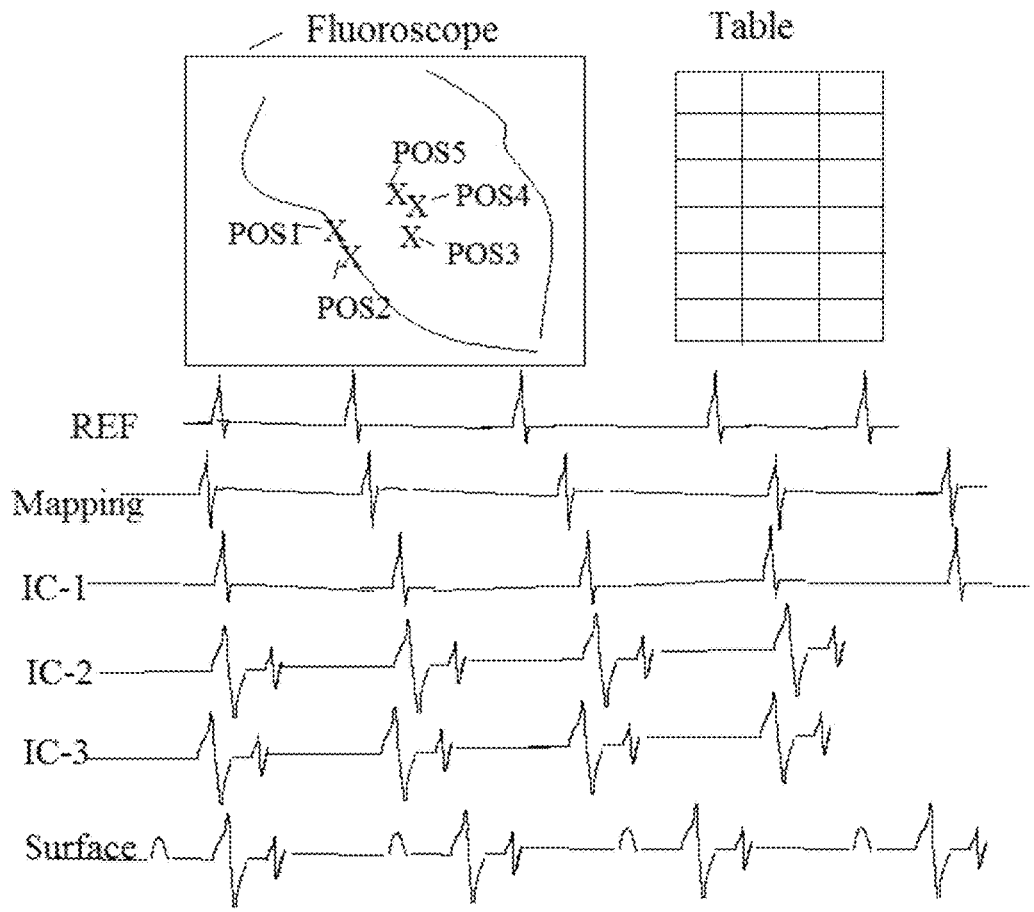
FIG. 50 depicts a fluoroscopy based mapping system where a table is generated for collecting points for mapping.

In the method and system of this disclosure, fluoroscopy based cardiac mapping is performed in one of several ways. In one aspect, as explained in conjunction with FIG. 50 a catheter is manipulated by the physician utilizing fluoroscopy. At various locations, inside the heart chamber, the positions are tagged. These location tags, have a corresponding electrical timing which can be measured relative to a reference catheter such as a coronary sinus (CS) catheter for atrial arrhythmias and right ventricular (RV) catheter or a body surface lead for ventricular mapping. These values can be stored in a table. This is also shown in FIG. 50. The timing from various mapped positions is displayed on the fluoroscopy image. In order to further organize the information, the information displayed on the fluoroscopy image may also be color coded, similar to a heat map.

The information stored in the table and displayed on the fluoroscopy map, may include relative timing information, voltage information, dipole density information, charge density information, conduction velocity, slew rate, and/or one of various other measured or derived parameters.

Figure 51:
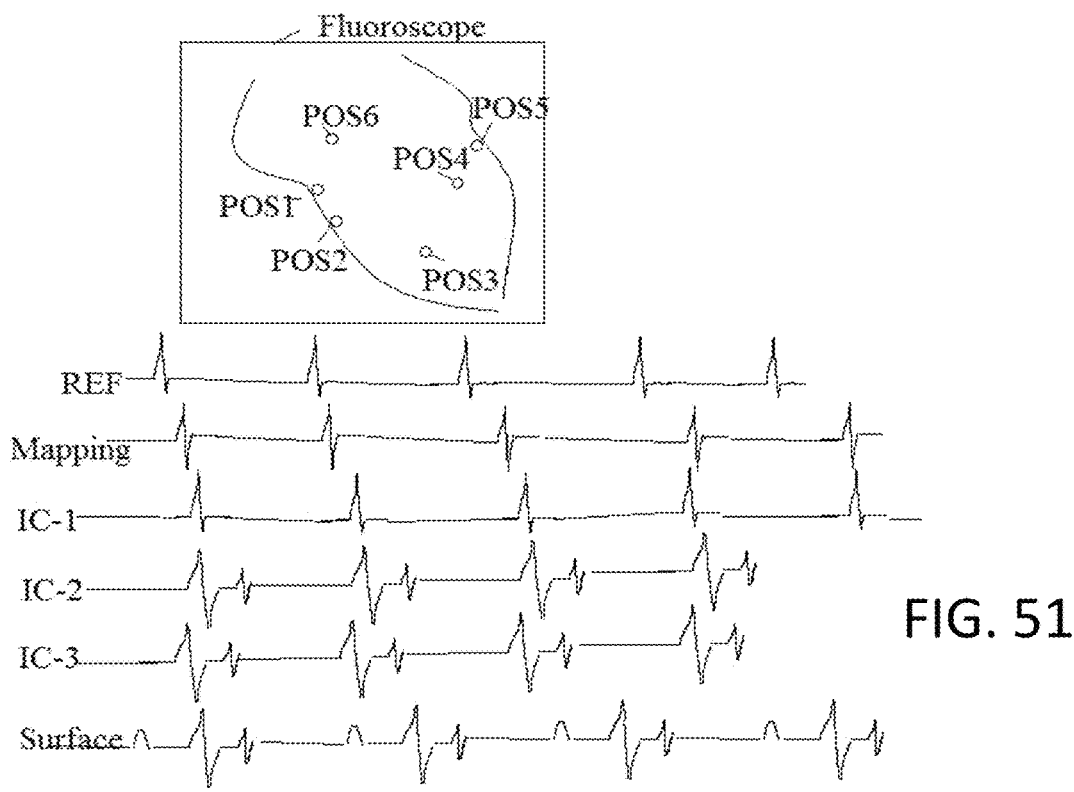
FIG. 51 depicts a fluoroscopy based mapping system where real-time information is provided.

One form of fluoroscopy based mapping may be performed without using a reference catheter (shown in FIG. 51). In this embodiment, visual indicators may be placed on the fluoroscopy image (with a computer mouse) as the catheter is manipulated, and these visual indicators are linked to sensing the electrical activity as it reaches across the respective electrode (unipolar) or electrode pair (for bipolar) sensing. Information about propagation or activation sequence may then be displayed without using a reference catheter for timing.

In yet another embodiment for fluoroscopy mapping, 3D information may be computed from fluoroscopy and overlaid on live fluoroscopy. The 3D computing from fluoroscopy may be performed in one of various ways, which may include rotation or 3D information may be computed from single views.

Figure 52:
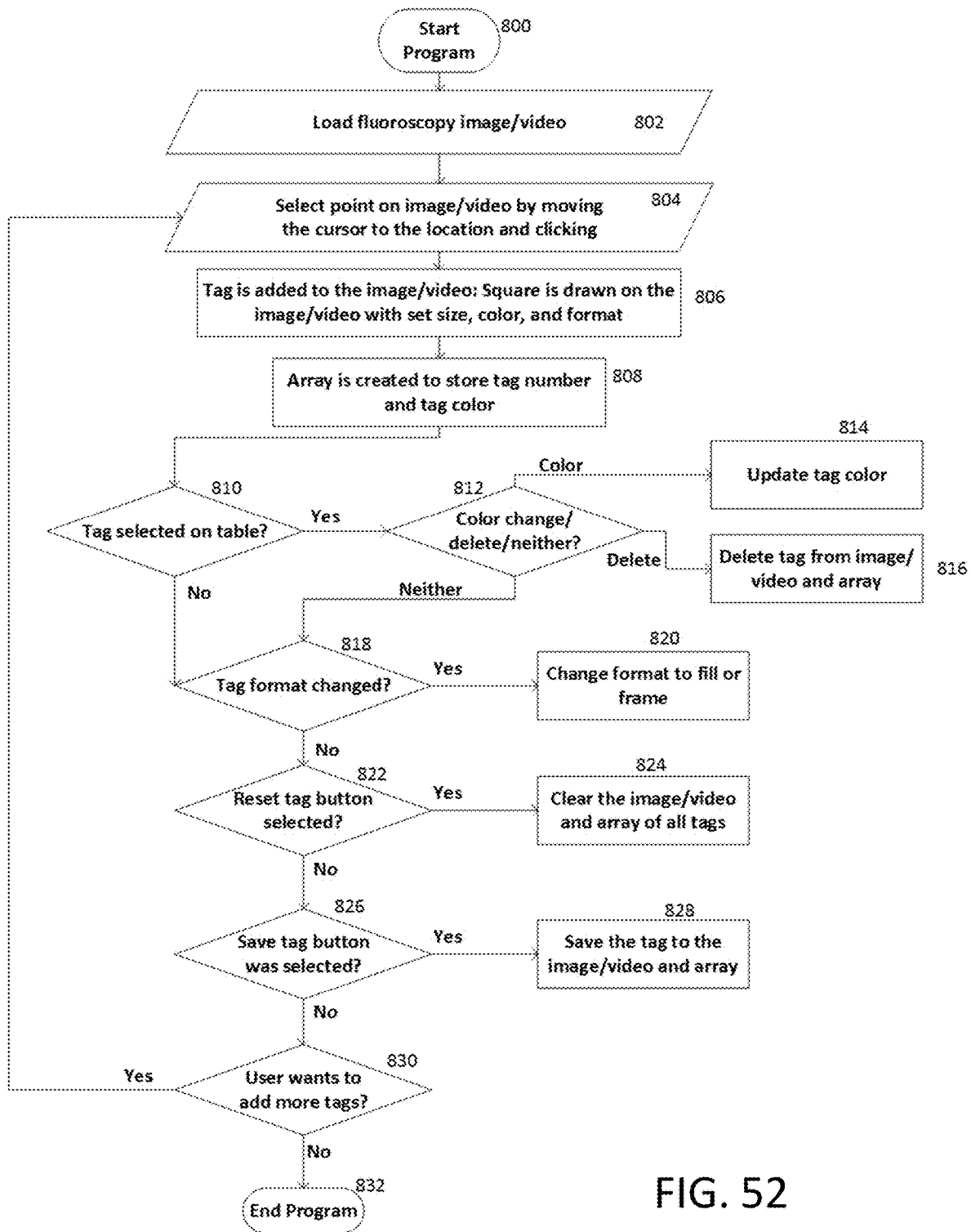
FIG. 52 is a flow diagram showing the placement of color tags on fluoroscopy images.

During the cardiac ablation procedures in addition to mapping, ablation tags are also marked on the images. In this embodiment, the ablation tags are marked on fluoroscopy image. One implementation of adding ablation tags fluoroscopy images is shown in FIG. 52. The implementation shows loading a fluoroscopy image or video in (step 802). A point is then selected on the image or video by moving the cursor to the desired location (step 804). The tag produces a square on the image with a pre-set color, format, and size (step 806), and the tag information is also stored in an array (step 808). Afterwards, condition statements are called upon a selected tag (step 810) that modify the tag color (step 812), format (step 818), resets the tag properties to the presets (step 822), deletes the selected tag (step 816), or saves it (step 826). A final condition statement allows the user to create a new tag (step 830), which then prompts the user to select the location on the image or video shown in step 804.

In one aspect, fluoroscopy images may be overlaid on top of each other. In this aspect, high resolution image/images are obtained generally with contrast medium injection. High resolution images can also be obtained without contrast medium "dye" injection, but it is preferred that they are obtained with "dye" injection.

Figure 53:
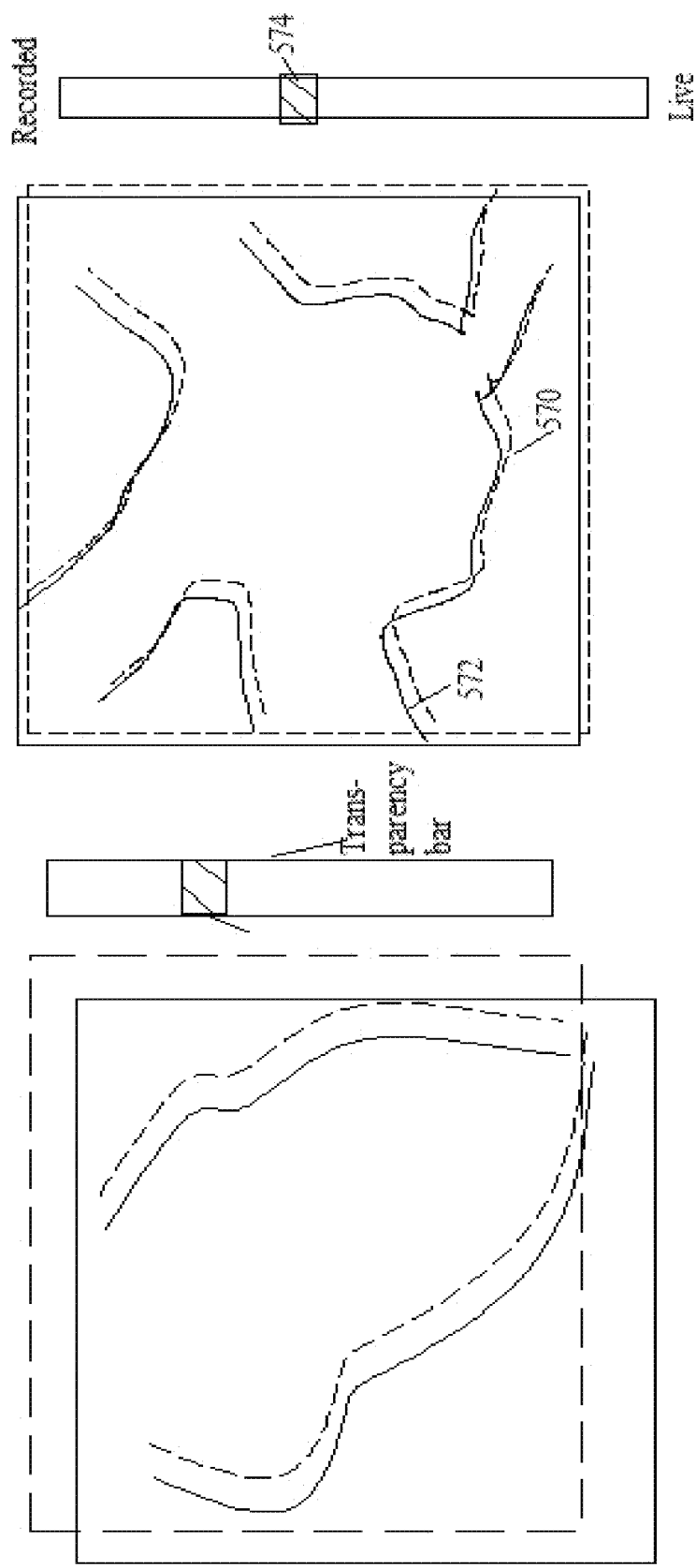
FIG. 53 depicts an aspect of mapping where real-time and recorded images are overlaid on top of each other and the transparency between the images can be adjusted at various levels.

The appropriate recorded and stored high resolution images are then brought on the screen and live fluoroscopy images are then placed on top of the stored high resolution images. A transparency factor is then adjusted between the recorded images and live images. The transparency factor is generally adjusted to a level such that advantage can be taken of the recorded "dye" injection in the background, while at the same time a live catheter can be manipulated on the live fluoroscopy. This is also shown in FIG. 53, where two images are superimposed on top of each other. The left figure shows an example where the "dye" was injected in the right atrium (RA). This is generally useful for right atrial arrhythmias, such as accessary pathways, focal atrial tachycardias, and typical flutter etc.

The figure to the right shows an example where the "dye" was injected in the left atrium (LA and pulmonary veins) to show the outline of the typical four pulmonary veins, which is generally useful when performing pulmonary vein isolations (PVIs).

An implementation of this is shown in FIG. 54, where the two images are overlaid on top of each other and live fluoroscopy is shown on top of the figure and various signals are shown in bottom part of the figure.

This methodology could be particularly useful in placing balloon based catheters for performing atrial fibrillation ablations, such as Arctic Front™ catheter available from Medtronic Corporation. Other balloon based catheters include, laser ablation balloon catheter available from CardioFocus corporation. Other balloon based catheters for pulmonary vein isolation (PVI) also include hot balloon catheters.

These balloon based catheters are generally advanced to the left atrial chamber, where the balloon is typically inflated. The balloon is then advanced to the OS of the pulmonary vein, and each pulmonary vein is ablated in a "single shot" method, until the desired effect is obtained.

Figure 56:
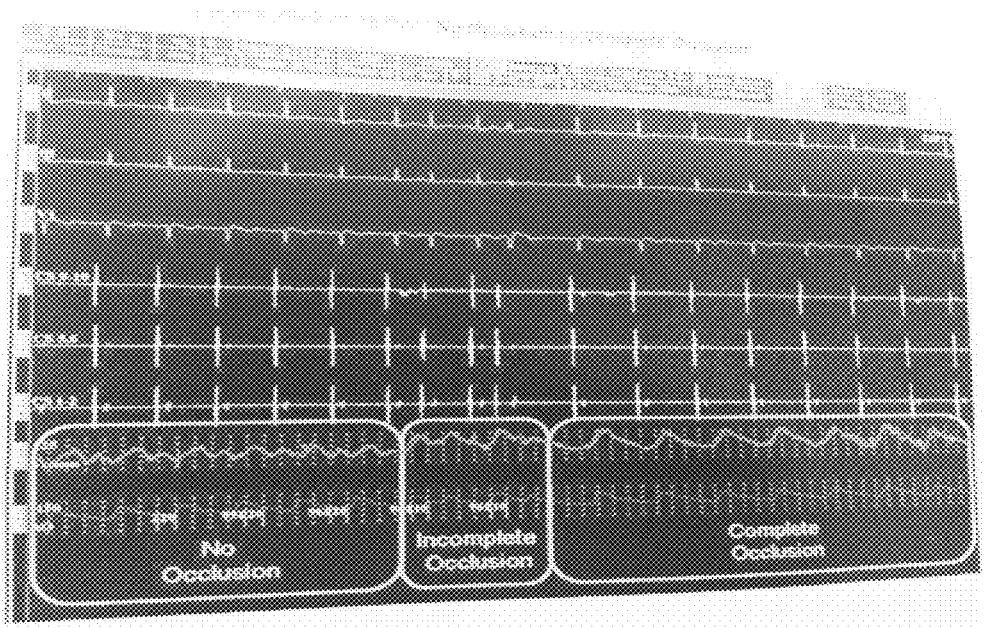
FIG. 56 shows pressure tracing used in the proper placement of cryoballon catheter showing no occlusion, incomplete occlusion and complete occlusion.
Figure 64:
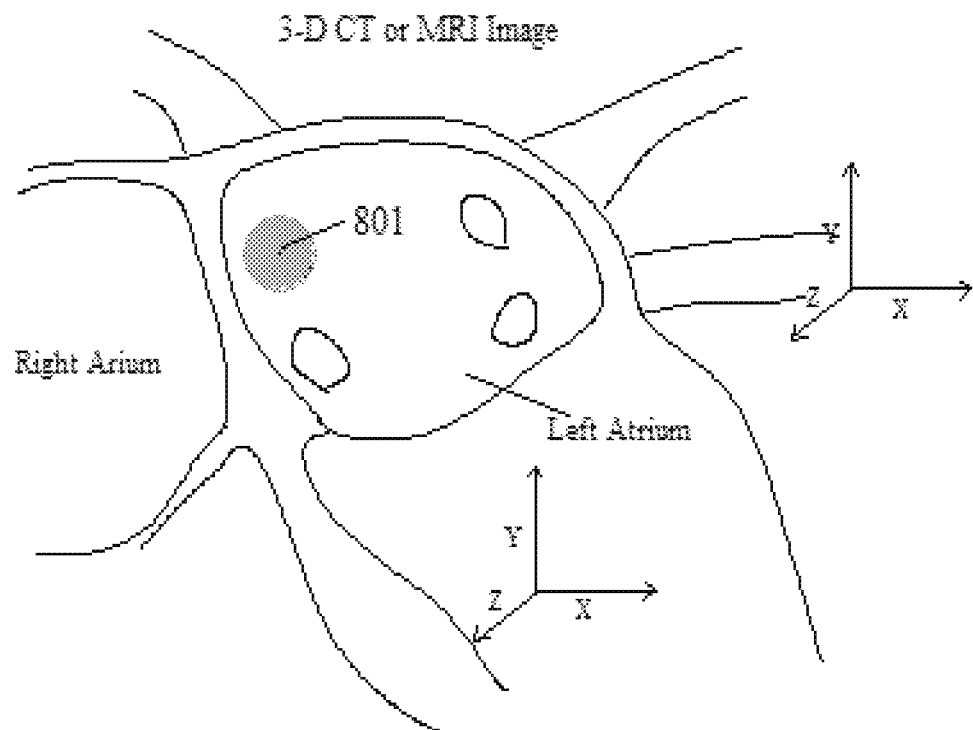
FIG. 64 is a schematic diagram showing posterior side of the left atrium with a tag on the on the right superior pulmonary vein.

In the case of Cryoballoon catheters, many physicians will inject a small amount to contrast medium "puff" to verify that there is a good seal between the balloon and os of the pulmonary veins. In one aspect, physicians may also utilize, pressure tracings to verify that that the balloon is against the tissue and is making good contact. Examples of pressure tracings are shown in FIGS. 55 and 64. As shown in FIG. 55, before there is occlusion the A waves are larger than the V waves, but with occlusion V waves are larger than A waves. Further, FIG. 56 shows an example where there is incomplete occlusion. In the bottom part of FIG. 56, shows the progression from no occlusion to incomplete occlusion, to complete occlusion.

Figure 57:
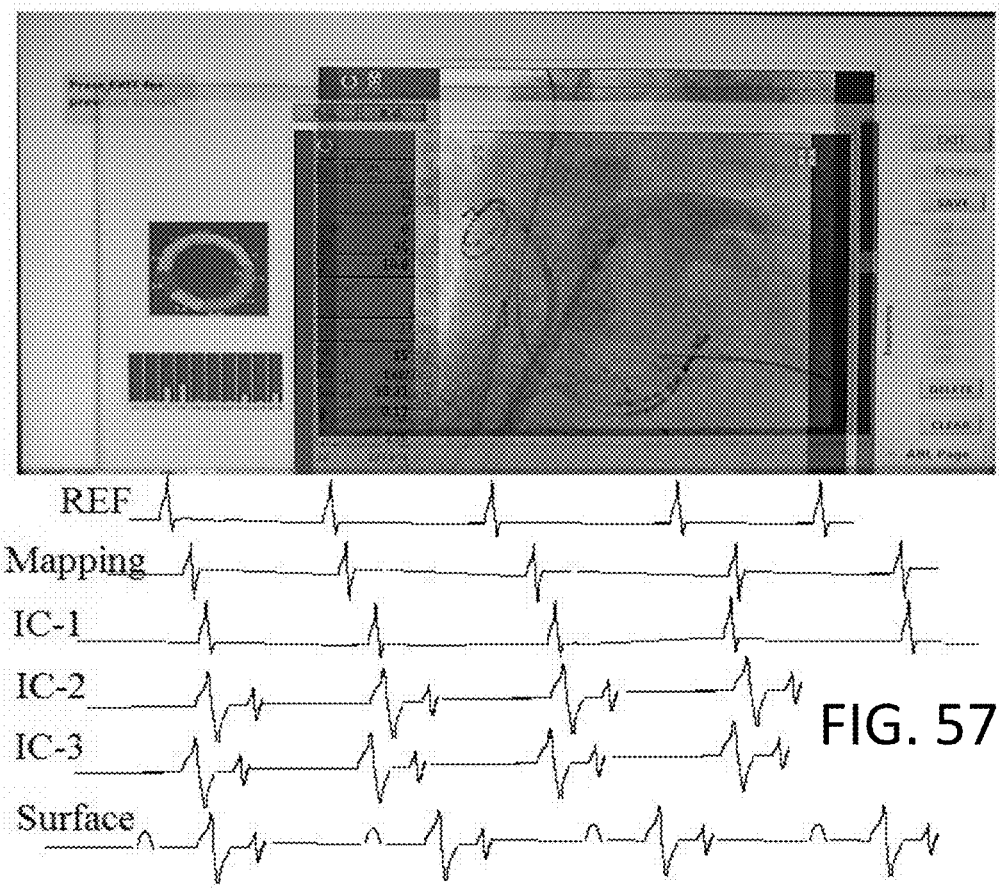
FIG. 57 shows two layers of fluoroscopy along with electrical signals both in graphical form and analog signals from multiple channels.

In one embodiment as shown with FIG. 57, as a high resolution image and live fluoroscopy are overlaid on top of each other, electrical signals from a circular catheter are displayed on the fluoroscopy screen. In one aspect the electrical signals are displayed on a ring which can be rotated in 3D. In another aspect, these electrical signals are color coded based on the underlying size of the peak-to-peak voltages. In one implementation, a real time bar graph of the peak-to-peak voltages is also displayed.

Placement of a 3-Dimensional (3D) Color Coded Ring on or Around Fluoroscopy Images or Intracardiac Echo (ICE) Images In one aspect of the disclosure a 3-dimensional (3D) ring is placed on or around fluoroscopy images or intracardiac echo (ICE) images. The 3D circular ring corresponds to a circular catheter such as a Lasso® catheter available from Biosense Webster, which has multiple electrodes or electrode pairs. Circular catheters for placement around pulmonary veins are also available from other manufacturers.

In the methodology of this disclosure a 3-dimensional (3D) ring is designed on the computer utilizing software. The computer designed ring is further subdivided into multiple segments. The number of segments on the ring corresponds to the number of electrodes or electrode pairs of the circular catheter, depending on whether the recordings are unipolar or bipolar. The recordings from the electrodes (or electrode pairs) are numbered and correspond to the amplitude of the voltage signal picked up from those electrodes, which is generally dependent on tissue contact, tissue viability and health of the underlying tissue.

Various segments of the computer generated 3D ring is also numbered. Coding of the software is configured and programmed to link the electrode (or electrode pair) of the circular catheter to the corresponding segment of the software generated 3D ring. The electrode number of the circular catheter corresponds to the same number on the computer generated ring. Therefore the underlying signals are accurately represented on the color of the segments on the ring.

Signal amplitude from the electrodes or electrode pairs are measured. A color coding scheme is assigned. Based on the color coding scheme, as the voltage signals are generated depending on the placement of the circular catheter, they are measured and constantly updated on the 3D ring displayed on the monitor.

Further, as the physician moves the circular catheter around the left atrium and pulmonary veins, a graphical color coded representation on the ring is constantly updated based on the underlying signals.

In one aspect a pre-ablation and post ablation ring may be generated, displayed and stored.

As previously mentioned, various software packages may be utilized for the implementation of the program. On implementation is shown in conjunction with FIG. 58. In the step 842 circular catheter electrode voltages are loaded. These circular catheters may have 8 or 10 electrodes, however the implementation in FIG. 58 shows 10 electrodes. The flow diagram details the implementation of putting color on the elements of the circular catheter. The algorithm iterates through the number of electrodes (step 844), color-codes the electrodes based on voltage measurements, increments the iterator (step 854), and ends the iteration when the total number of electrodes has been reached (step 854). Electrode voltages that are less than 0.2 volts are color-coded gray (step 852). Electrodes with a voltage greater than or equal to 0.2 and less than 0.5 are color-coded red (step 858). Electrodes with a voltage greater than or equal to 0.5 and less than 1.5 are color-coded blue (step 862). Electrodes with a voltage greater than or equal to 1.5 are color-coded purple shown in step 866.

An implementation which the applicant has tested is shown in FIG. 21 and FIG. 24. Shown in conjunction with FIG. 21, the 3D ring 643 is displayed next to fluoroscopy image. The circular catheter is shown in the fluoroscopy and is positioned in the right superior pulmonary vein. As previously mentioned the number of electrodes on the circular catheter correspond to the number of segments of the 3D ring. The segments are also numbered on the 3D and are visible in the figure. In FIG. 24 the 3D ring is also displayed next to the fluoroscopy image.

In one aspect of the methodology, once the balloon catheter is placed in position for ablation, and the position of occlusion is verified with such techniques as dye injection or pressure tracings, during ablation a different menu or screen may be observed during ablation or freezing. Generally, it is of interest to be watching electrical signals, especially from a circular catheter in or around the pulmonary veins. This is also shown in FIG. 59 as time domain signals. It is also of interest to be watching the signals get smaller and the appropriate signals to disappear as a result of the energy delivery to the tissue. Of Course, the energy delivery may be in one of various forms, such as Cryoenergy, laser energy, RF energy or ultrasound energy.

In one aspect of the disclosure, computed tomography (CT) images are also utilized. Computed tomography has the advantage that a highly detailed geometry is delineated in the CT images. It was shown in FIG. 8 that various images are brought into the current mapping system computer. As was depicted in FIG. 8, the CT images are brought into the mapping system. Generally, a patient's CT are stored in on a compact disc (CD) or a DVD, which can be used to do the volume rendering of the region of interest, which is the left atrium (LA) and all the pulmonary veins and the left atrial appendage (LAA). Alternatively, the patients CT data may retrieved from the hospital network and volume rendering performed. Once the volume rendering is performed the new digital file is brought into the mapping system computer as a digital file.

As is known in the art, the advantage of CT is that it provides detailed 3 dimensional (3D) information about the region of interest. For atrial fibrillation ablations, the region of interest being left atrium (LA) and left atrial appendage (LAA), and the details of the pulmonary veins. In the method and system of the current disclosure, the volume rendered CT image is brought into the mapping system computer. The software is configured and programmed such that the volume rendered CT image can be placed and overlaid in the dye injected fluoroscopy image. The structures can be manually lined up to match the anatomy. This aids the physician in the physical placement of the ablation or balloon based catheter at the os of the pulmonary veins. Of course, once the catheters are placed, they are checked for proper placement before ablation is commenced. For example, with the Cryoballoon catheters proper placement can be verified utilizing dye injection to see "leakage" or the placement may performed utilizing pressure tracings.

The electrodes of the circular catheter are broken into segments. Each segment corresponds to an electrode (for unipolar) and an electrode pair (for bipolar) recordings. The same can also be represented with a real-time bar graph, as is also shown in FIG. 58. Each electrode or electrode pairs is connected to the A/D converter of the amplifiers. Once the signals are obtained by the mapping system computer, the peak-to-peak voltage signals are measured and used for the color coding scheme and representation.

A volume rendered CT image is shown in FIG. 60 as one example. In one embodiment, a volume rendered CT image is appropriately overlaid on a recorded high resolution fluoroscopy image which may be with dye or contrast medium injection. This helps in the proper placement or proper overlaying of the CT image on recorded fluoroscopy. Once that is done, live fluoroscopy may be overlaid on top of that, and the relative transparency adjusted to the point where the catheter is manipulated and the recorded fluoroscopy is an anatomical guide for positioning the catheter. Further, the signals from the catheter are also displayed on the overlaid fluoroscopy (shown in FIG. 61).

This embodiment is particularly useful for atrial fibrillation ablations utilizing balloon based catheters, an example of which is the Cryoballoon catheter available from Medtronic corporation. Another example is a laser balloon catheter available from Cardio Focus. Various other balloon based catheter technologies are also currently under development. One advantage of balloon based catheters is that it can provide "single shot" approach vs a point-by-point approach which is typically used in radiofrequency (RF) ablations.

One example of an implementation is shown in FIG. 61. Where the image screen is actually 3 layers of imaging which are, recorded fluoroscopy, CT image an live fluoroscopy. The signals on the left are a color coded graphical version of the signals which are linked to the underlying electrodes or electrode pairs.

Placing 3D Volumetric Tags on Existing CT or MRI Images

In one aspect, 3D volumetric tags are placed on a volume rendered CT or MRI image. Even though the example disclosed here is with CT the same process is applied to MRI images as both are true 3D images.

Utilizing medical images disclosed above, the balloon based catheter is placed at the appropriate location for ablation, whether its cryo ablation or laser ablation or any other type of balloon based catheter ablation. In the methodology of this disclosure, a volume rendered computed tomography (CT) image is positioned on the medical image which is used to position the balloon, for example a fluoroscopy image. Once the layer of CT image is placed on top (or bottom) of the fluoroscopy image where the balloon is visualized, the transparency between images is adjusted by an operator such that both images can be visualized. Additionally, the volume rendered CT is adjusted in both size and orientation. A 3D volumetric tag is added to the appropriate location on the CT image. Minor adjustments may have to be made to position the volumetric tag to just the right position using tools such as the mouse or other built-in tools in the program such as slider bars to move the location of the volumetric tag in the x, y and z axis. Once the tag is adjusted to the appropriate location in x, y and z axis, the tag is fixed to that location and is generally saved to memory and displayed in a convenient manner.

As the procedure progresses, same steps are repeated until the procedure is completed. As the second pulmonary vein is ablated tags are cumulatively added to the second vein, third vein and fourth vein progressively. Advantageously, as the procedure progress the physician can monitor the progress of where the ablation lesions have been delivered on a 3D CT model. Another advantage is that the front (or anterior portion) of the CT can be sliced away and the 3D volumetric tags can be visualized from inside showing in the 3D volume structure areas indicative of where ablation has been already performed. Mesh maps and point maps may also be utilized to visualize inside the CT model.

As will be clear to one skilled in the art, the 3D volume tags may be ring shaped, sphere shaped, "pear" shaped or any other shape based on design preference. Several of these pre-defined shapes are created and stored in the program.

Figure 62:
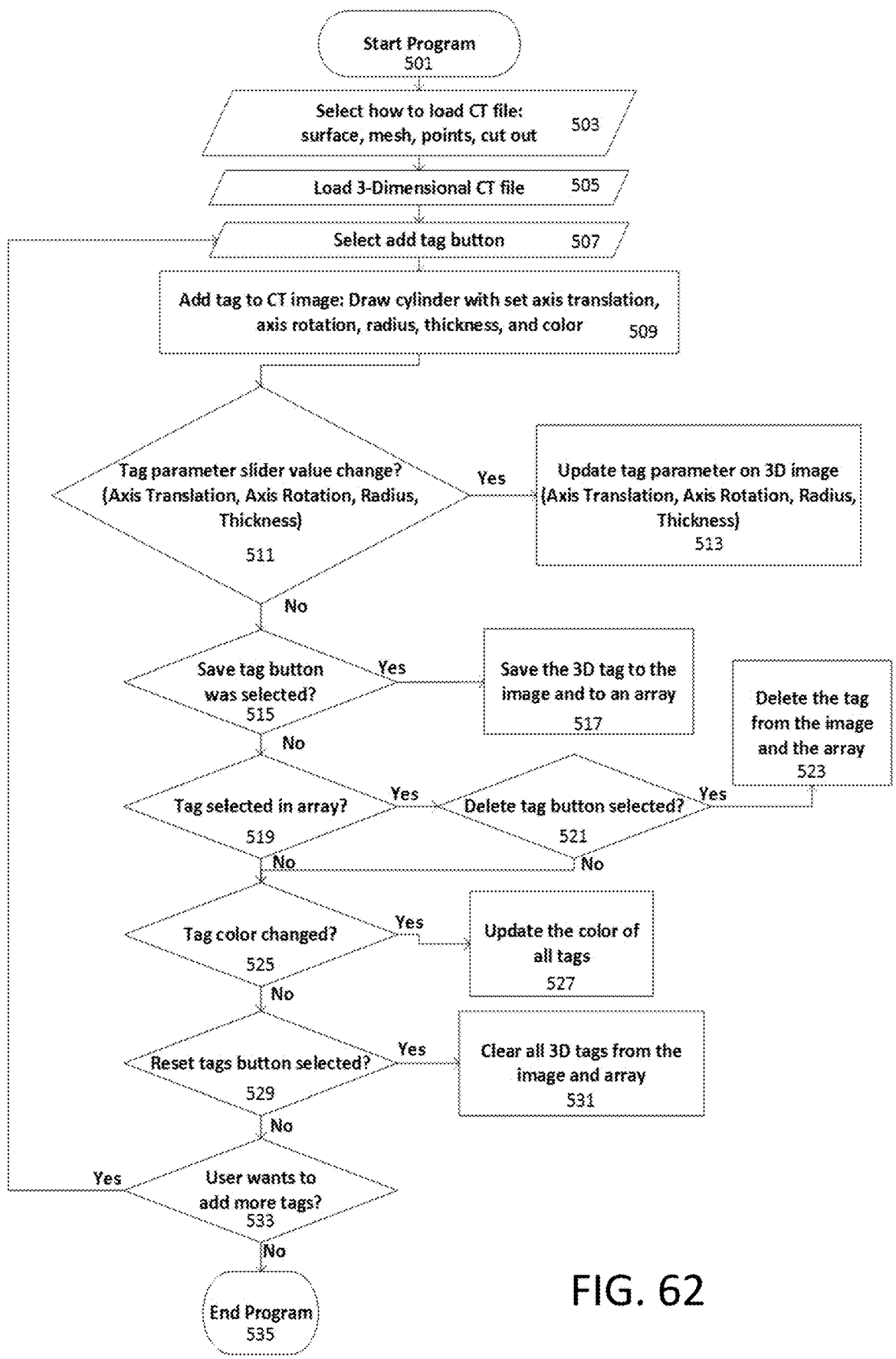
FIG. 62 is a flow diagram for adding volume tags to an existing volume rendered 3D CT images.
Figure 63:
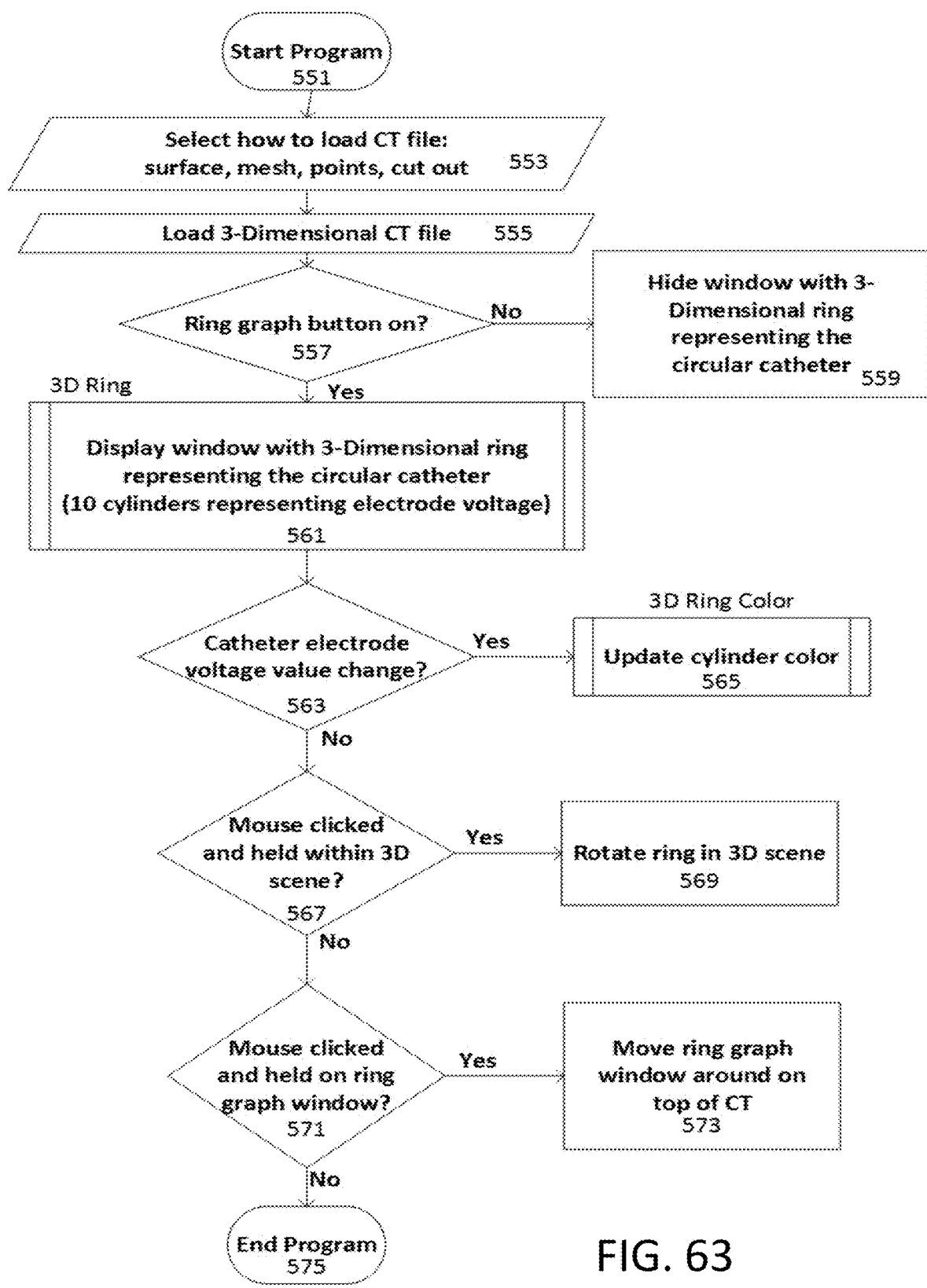
FIG. 63 is a flow diagram for adding 3D ring tags to an existing volume rendered 3D CT images.
Figure 84:
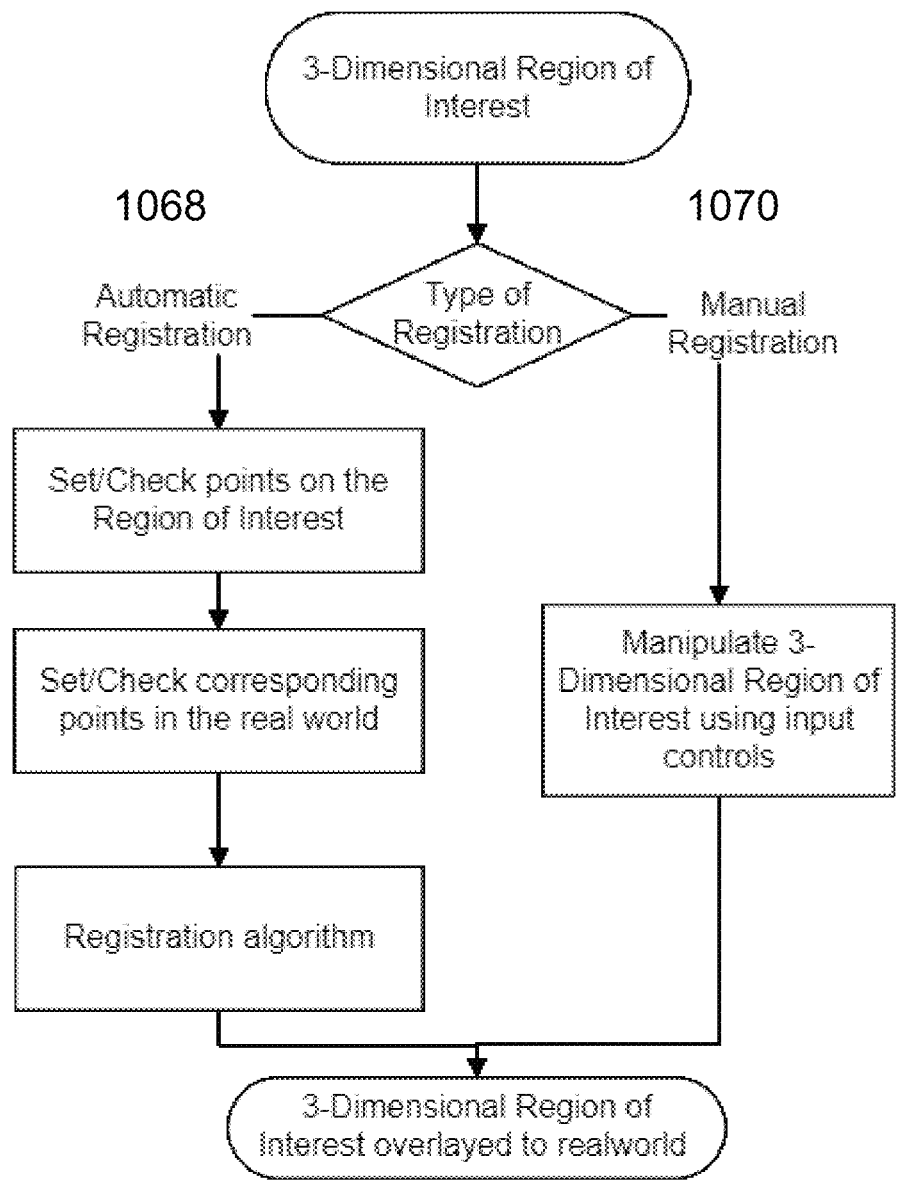
FIG. 84 is a flow diagram depicting the 2 types of registration for the 3-Dimensional region of interest.
Figure 85:
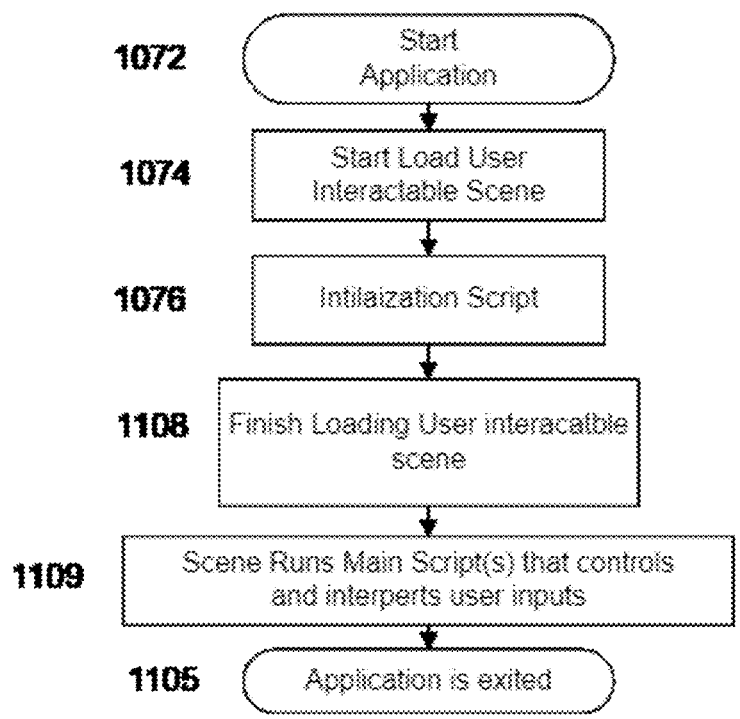
FIG. 85 is a flow diagram that is the overview of the application process for the pre-procedural systems.

Software implementation is also shown with flow diagrams in FIGS. 62 and 63. One implementation of adding tags to a 3D CT during cardiac ablation is shown in FIG. 84 where at the start of the program 501 may prompt the user to load the CT file as a surface, mesh, points, or cut-out 503, which will then load the 3D CT file 505. The user can select the "add tag" button 507 which places a tag on the screen with a specified radius, rotation, position, thickness and color 509. If the tag parameter slider value changes, which modifies the tag axis' translation, rotation, radius 511, then the tag's properties are updated on the 3D image 513. If the user decides to save the tag 515, then the 3D CT tag is saved 517. If the tag is selected within a list of tags 519, the user has an option to delete the tag 521, change the color 525, or reset the selected tag 529, prompting the program to delete the tag 523, update the color 527, or clear the selected 3D tags from the array list 531, respectively. If the user decides to add more tags 533, then step 507 is repeated.

One implementation of adding a ring on a 3D CT to simulate a circular catheter is shown in FIG. 63. The user is prompted to load a CT file as a surface, mesh, points, or a cut-out 555. If the ring graph button is off 557 then the window showing the 3 dimensional ring representing the circular catheter is hidden 559. If the button is on, then a program displays a window, showing the 3 dimensional ring representing the circular catheter. Here, cylinders represent electrode voltage, 561. If the catheter electrode voltage value changes 563, then a program updates the cylinder color 565. If the computer mouse that communicates with the computer is clocked and held within the 3D scene 567, then the mouse's manipulations result in rotating the ring in the 3D scene 569. If the mouse is clocked and held on the ring graph window 571, then the mouse's manipulations result in moving the ring graph window around on top of the CT 573.

Shown in conjunction with FIG. 64 is a schematic of the heart depicting right atrium and left atrium. Once the balloon is positioned at the right superior pulmonary vein and ablation is performed, a 3D volumetric tag is positioned as shown in FIG. 64 as tag 801. In the CT model the front (or anterior) portion is cut away in one embodiment to visualize the tag inside the chamber. Alternatively, a mesh map or a point map may be utilized for visualization inside the chamber.

Figure 65:
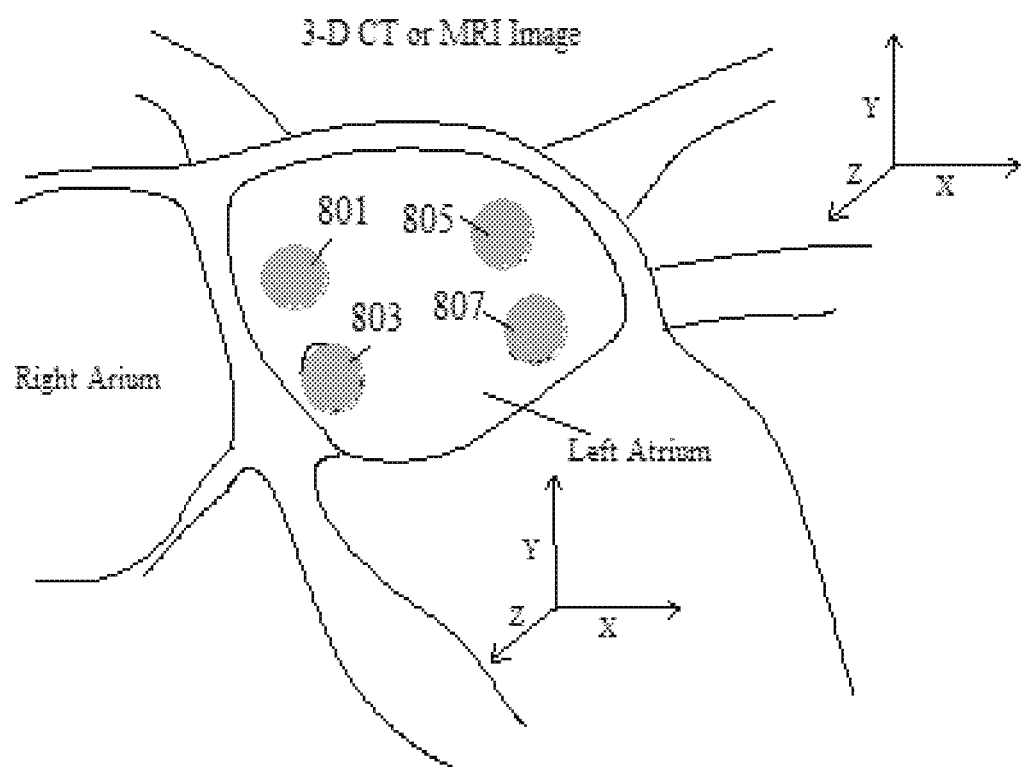
FIG. 65 is a schematic diagram showing posterior side of the left atrium depicting tags on all four pulmonary veins.

As the procedure progresses, tags around the other pulmonary veins are also placed. As shown in FIG. 65, tag 803 depicting area around the right inferior pulmonary vein indicative of ablation around right inferior pulmonary vein, tag 807 around left inferior pulmonary vein, and tag 805 around left superior pulmonary vein is also depicted in FIG. 65.

It will also be clear that the volumetric shape of the tag is pre-defined which is built and stored in the computer. The orientation and size is adjusted by the operator. The placement of the shape tag is performed by an operator.

Figure 66:
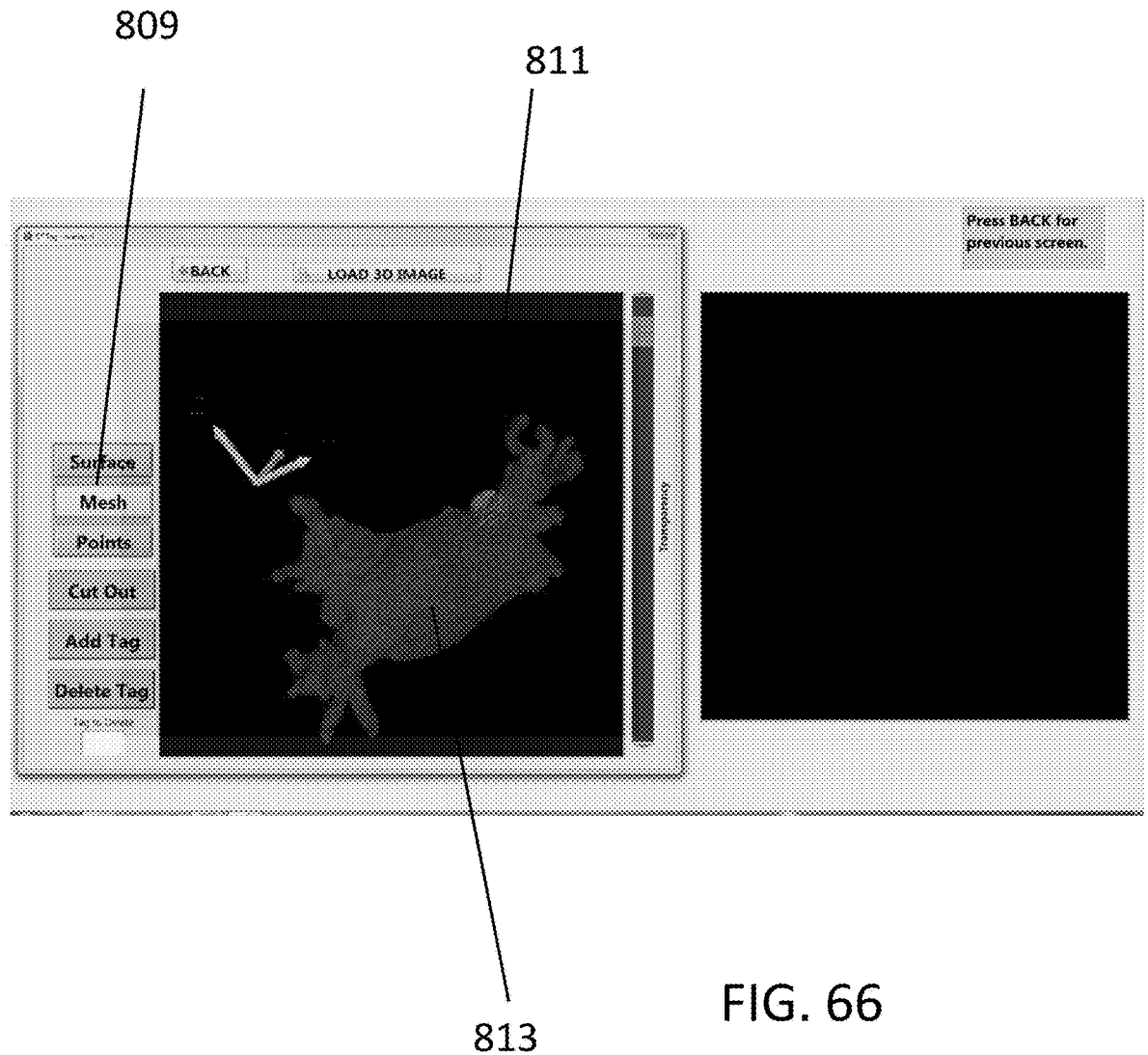
FIG. 66 shows one implementation where 3D volume tags is placed on a CT mesh structure, indicative of where the ablation has been performed.
Figure 67:
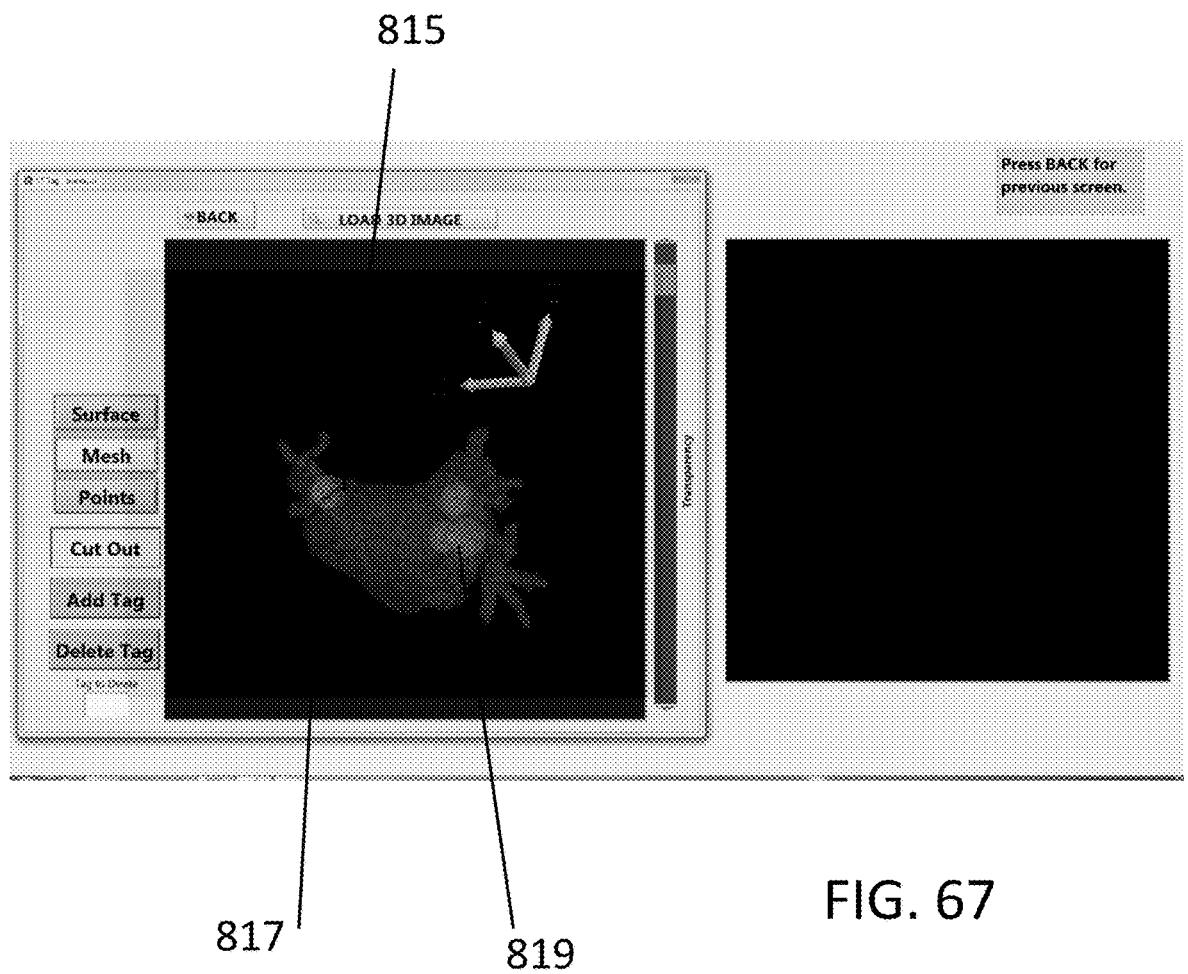
FIG. 67 shows one implementation where multiple 3D volume tags are shown placed around pulmonary veins showing areas indicative of where ablations has been performed.
Figure 68:
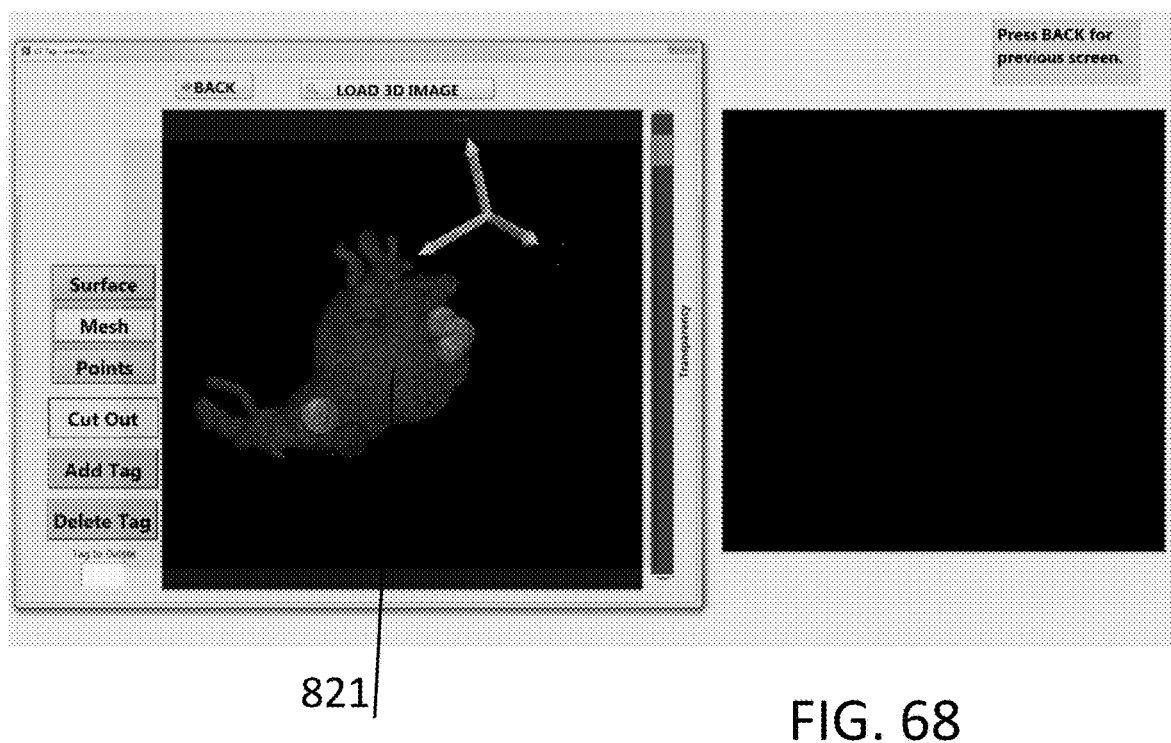
FIG. 68 shows the same tags as in FIG. 89 in a different orientation.
Figure 89:
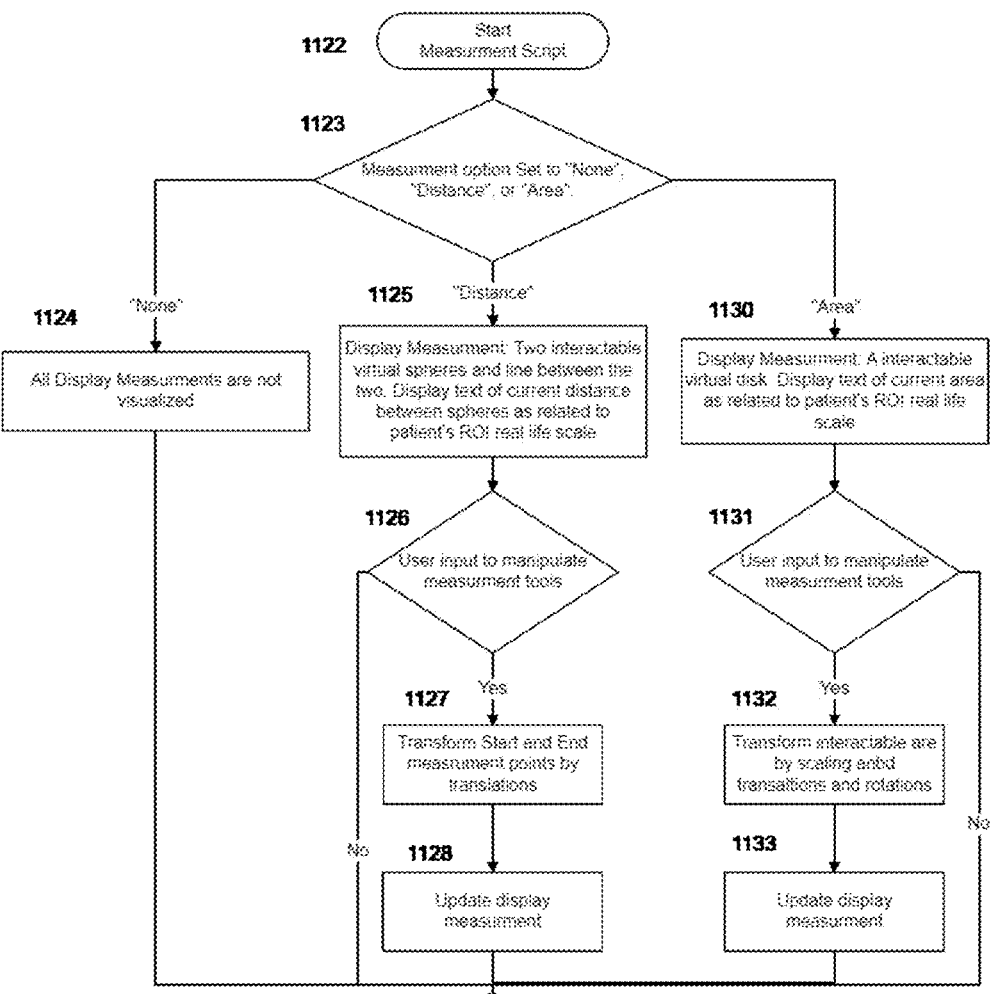
FIG. 89 is a flow diagram for the measurement script called by the main script that controls and interprets user inputs as in FIG. 87 used by the pre-procedural application as in FIG. 85.

One implementation of this, developed and used by us in clinical studies is shown in conjunction with FIGS. 66, 67 and 68. Shown in FIG. 89 is a CT of the left atrium 813 and pulmonary vein shown as a mesh. A 3D spherical tag 811 is shown around the right superior pulmonary vein corresponding to the tissue indicative of the tissue area where the ablation has been performed with a balloon catheter.

The 3D volumetric tag is placed by positioning the volume rendered CT image on the balloon, which has been positioned by the physician utilizing a medical image, typically fluoroscopy or ICE but may be any other imaging modality. Once the balloon is placed in the position for ablating, say using fluoroscopy for example the CT image is placed on the fluoroscopy image. A transparency factor between the two images is adjusted such that the balloon is visible and the CT image is visible. The CT image is resized, reoriented and repositioned such that the anatomy of the fluoroscopy and CT closely matches. Based on that, a predefined volume tag (e.g. a sphere) is placed on the CT image. The volume tag, which is indicative of the area which is ablated is adjusted in the x, y and z axis to precisely represent the area indicative of where the ablation has occurred. The tag is then saved on the image.

As further ablations are performed, the same series of steps are repeated to add additional 3D volume tags. This is also shown in FIGS. 67 and 68. In FIG. 67 3D volumetric tags 817, 819 are shown. In FIG. 68 shows the same tags are shown in a different orientation. The advantage of multiple tags is that when the ablation procedure is ongoing the physician can appreciate where the ablation have been performed to carry the procedure to the finish.

In one aspect of the disclosure, real-time MRI (magnetic resonance imaging) may be used. Because of the strong magnetic fields of MRI technology, of course the catheters need to be MRI safe.

There are several advantages of MRI technology. One advantage is that MRI provides highly detailed 3D images of the cardiac structures. Another major advantage is that the patients and medical staff is not exposed to the ionizing radiation.

Virtual Reality (VR), Augmented Reality (AR) or Mixed Reality Part of the System Exemplary embodiments of the invention as described herein generally include systems and methods for use of visualization devices for procedural planning and use during LAA, TAVR, or atrial fibrillation (AFib) procedure implementation, wherein these visualization devices include virtual reality (VR), augmented reality (AR), and mixed reality (MR) devices. In the interest of clarity, not all features of an actual implementation which are well known to those of skill in the art are described in detail herein. It is to be understood that the resultant invention may be implemented in various forms of hardware, software, firmware, special purpose processors, or combination thereof. With respect to the embodiments employed by the use of the virtual reality device, preferably the invention is implemented as a combination of hardware and software, moreover the application is run in conjunction with such. With respect to the embodiments employed by the use of an augmented or mixed reality device, preferably the invention is implemented by the application which is preferably uploaded and executed by a machine comprising the suitable architecture from the device.

An exemplary, non-limiting example of preprocedural planning using a visualization device is using a virtual reality head mounted display for atrial fibrillation, or TAVR, or LAA procedures. In addition to viewing the MRI or CT scans of the patient's anatomy in 3D on a 2D screen (specifically the ROI), visualization of such in an immersive head mounted display allows perspective of the entire structure in depth in an immersive environment. The user can manipulate the patient's 3D anatomy (specifically the ROI) with external controls, for this example remotes, to rotate, translate and scale to even peer inside the structure. This allows the user to fully explore the structure of the patient's anatomy to garner understanding as to best practices to approach and plan the procedure. Further features of this application can include the ability to take measurements with the controllers of the virtual anatomy that correspond with the patient's anatomical measures, and even use virtual models, such as cryo-balloon, in conjunction with the patient's anatomy to assess its use.

The process of setting up and starting the program is shown in conjunction with FIGS. 69A-69C. For the LAA device closure system (FIG. 69A), in the VR system the patient's LAA region of interest (ROI) is loaded into the proper directory where the path is defined to utilize the patient's anatomy. The VR program is turned on and activated, the proper patient is selected and visualization and pre-procedure planning is begun. For the atrial fibrillation ablation procedure (FIG. 69B) in the VR system the patient's LA and pulmonary vein region of interest (ROI) is loaded into the proper directory where the path is defined to utilized the patient's anatomy. The VR program is turned on and activated, the proper patient is selected and visualization and pre-procedure planning is begun. For the TAVR procedure (FIG. 69C), in the VR system patient's aortic root which is the region of interest (ROI) is loaded into the proper directory where the path is defined to utilize the patient's anatomy. The VR program is turned on and activated, the proper patient is selected and visualization and pre-procedure planning is begun.

The corresponding process for the MR system is also shown in conjunction with FIGS. 69A-69C. For the LAA procedure, the program is loaded into HOLOLENS™, the particular patient's anatomy where the region of interest (ROI) is the left atrium and the left atrial appendage (LAA) region can be loaded via any computer utilizing WiFi, or any other internet connection (FIG. 69A). For the atrial fibrillation ablation procedure, the program is loaded into HOLOLENS™, the particular patient's anatomy where the region of interest (ROI) is the left atrium and the pulmonary vein region can be loaded via any computer utilizing WiFi, or any other internet connection (FIG. 69B). For the TAVR procedure, the program is loaded in to HOLOLENS™, the particular patient's anatomy where the region of interest (ROI) is the aortic root region, can be loaded via any computer utilizing WiFi, or any other internet connection (FIG. 69C).

Figures 70, 71:
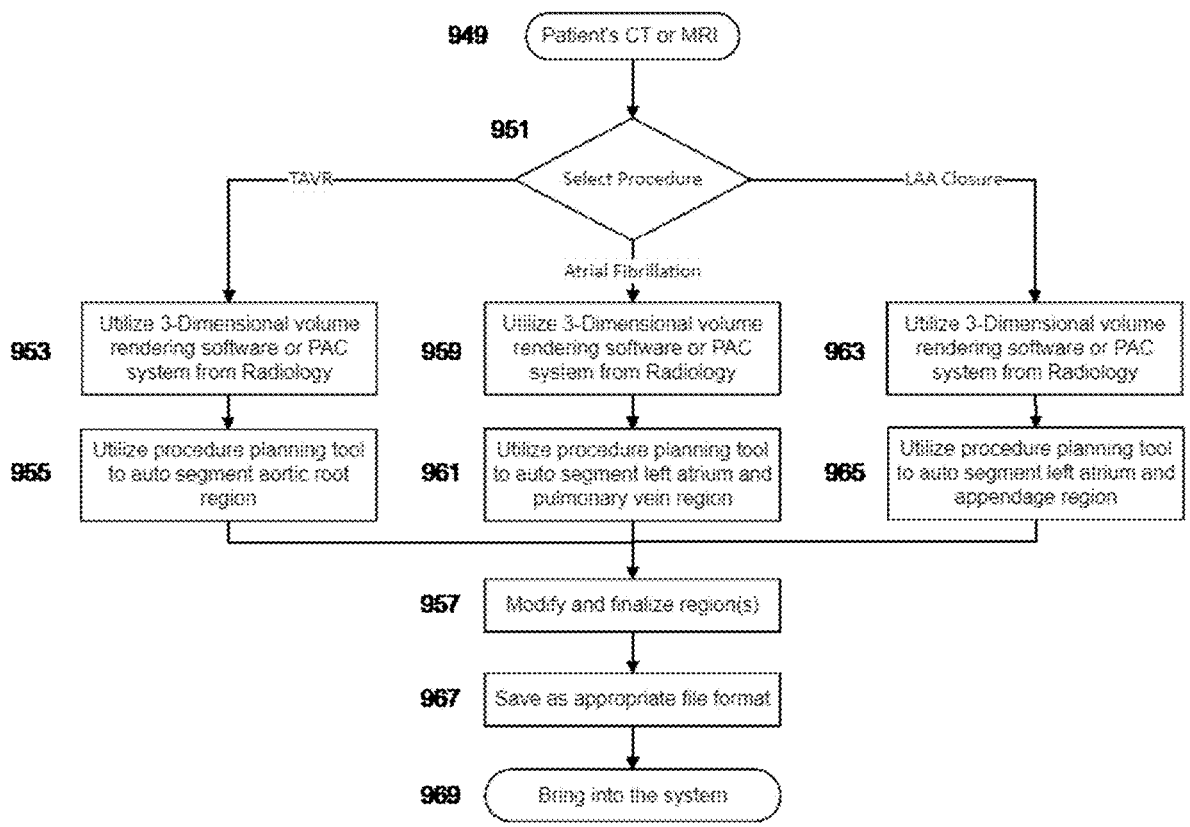
FIG. 70 depicts a flow diagram for the process of taking MRI/CT images and creating a usable 3-Dimensional region of interest.
FIG. 71 is a table with a nonexclusive list of possible file formats usable/readable by the VR, MR, or AR device.

The process of taking the patient's CT or MRI image and bringing it into the system for visualization is demonstrated in FIG. 70. First, the process starts with the patient's CT or MRI (step 949). Next the specific procedure the image will be used for is determined (step 951). If the procedure is for a TAVR procedure, 3D volume rendering software or PAC system for radiology is utilized (step 955). Next, a procedure planning tool is utilized to auto segment the aortic root region (step 955). The process then proceeds to step 957. If the selected procedure is for atrial fibrillation, 3D volume rendering software or PAC system for radiology is utilized (step 959). Next, a procedure planning tool is utilized to auto segment the left atrium and pulmonary vein region (step 961). The process then proceeds to step 957. If the selected procedure is for LAA closure, 3D volume rendering software or PAC system for radiology is utilized (step 963). Next, a procedure planning tool is utilized to auto segment the left atrium and appendage region (step 965). The process then proceeds to step 957, in which it is modified, and the region is finalized. Next it is saved as an appropriate file format (step 967). A nonexclusive list of example file formats readable by the visualization device are shown in FIG. 71. Finally, it is brought into the system (step 969).

For preprocedural planning using an immersive visualization device, virtual reality is the preferable medium. FIGS. 72i-iii depict user, top and side views respectively of a generic stereoscopic virtual reality device. The head mounted display 1016, including optical input to the user via lenses 1018, and sensors for user transformation collection 1020. Head mounted displays track the users own head transformations to display accurate visual imagery and to mitigate simulator sickness. This may be accomplished in many ways, such as video cameras attached to devices to recognize spatial information, infrared signals in conjunction with receiver and/or transmitter devices that communicate with the head mounted display, or internal tracking systems such as accelerometers. A nonexclusive list of possible examples are provide in FIG. 73.

Figure 74:
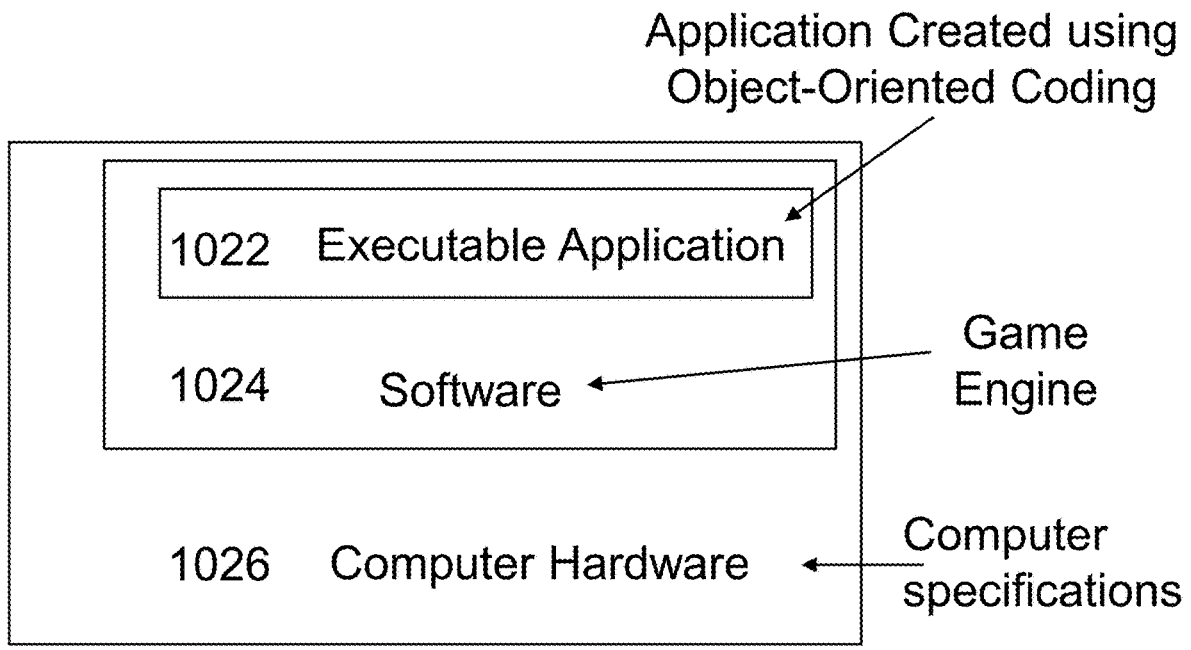
FIG. 74 shows the overall architecture and nesting of the application, software, and hardware.
Figure 75:
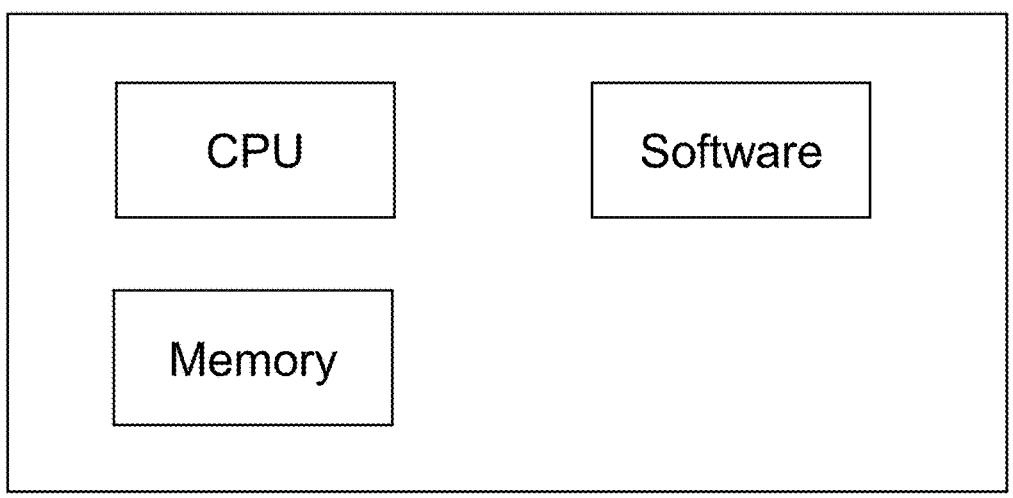
FIG. 75 demonstrates the architectures of the different components of the computer hardware.

For virtual reality head mounted displays, a computer hardware and a software are needed to run the device and update the graphics, in which an application is programmed that dictates and controls what visual input the user receives and controls the effects of the inputs and outputs of the user. FIG. 74 depicts the nesting of the relationship between the computer hardware 1026, software 1024 and the executable application 1022 that is applied to the virtual reality device. The computer system's hierarchical structure is demonstrated in FIG. 75. The use of the software, hardware, and the application are preferably used in conjunction with each other. Possible examples of such are demonstrated in FIG. 76. In one preferred embodiment, the device is a virtual reality head mounted display that is connected to a computer, running software through steam with an application written with C#coding language with the unity game engine.

Figure 77:
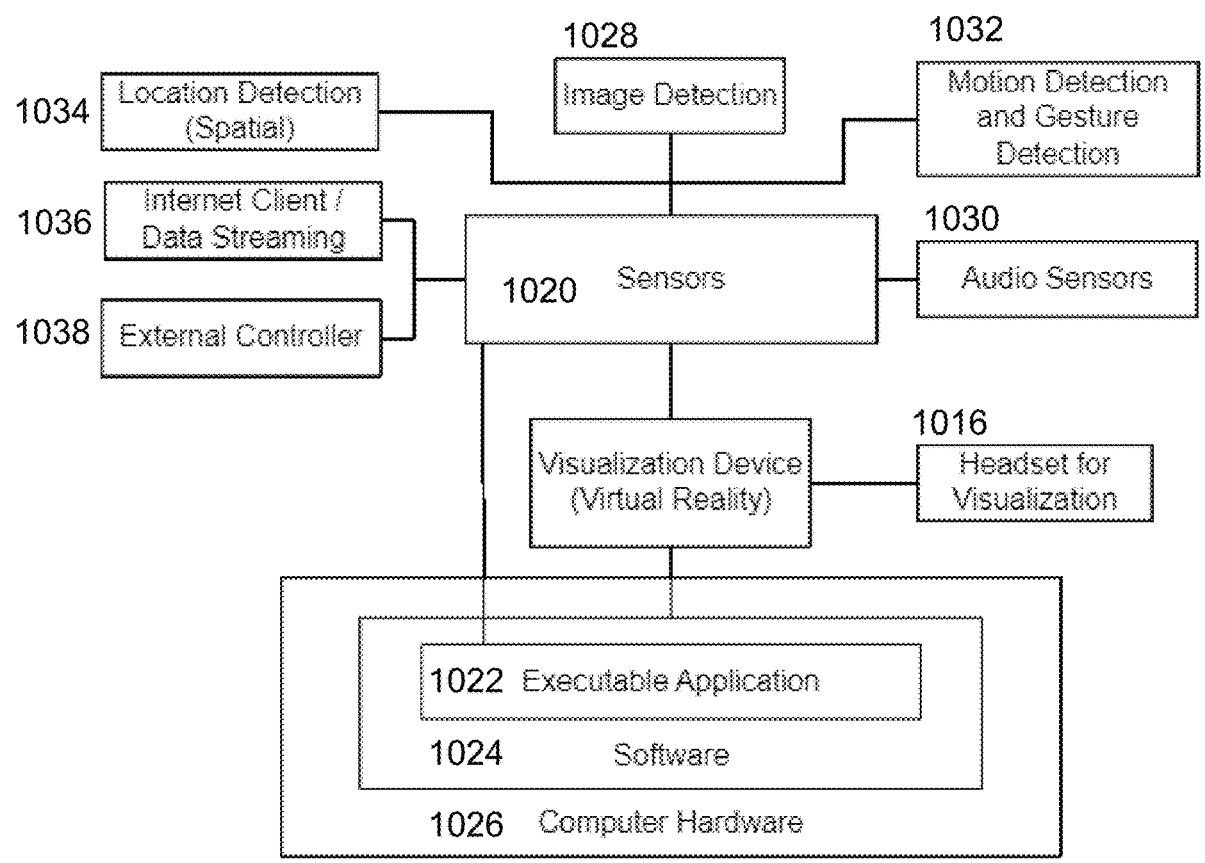
FIG. 77 is a diagram of the different components and architecture of the virtual reality device and related sensors.

The application is what controls and ultimately executes the interface between the experience the user views and their interaction within the virtual world. FIG. 77 demonstrates the implementation of the application 1022 to the virtual reality. Sensors 1020, such as those for image 1028, audio 1030, motion and gesture 1032, spatial 1034, data streaming 1036, and external input 1038 detection may communicate with both the virtual reality device and the application 1022 itself. The headset 1016 as part of the virtual reality is what is used for the visualization by the user.

Figures 78, 79:
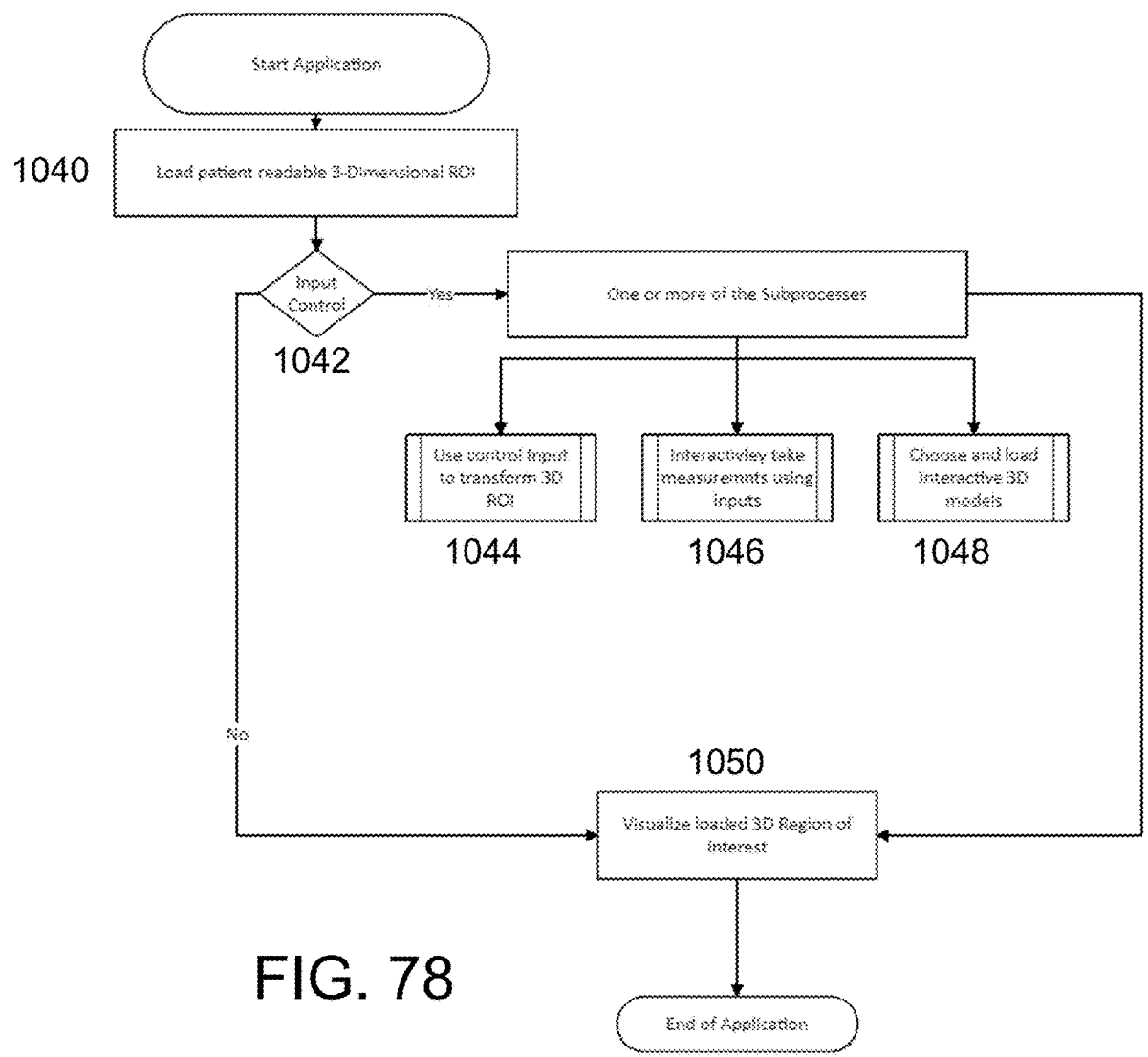
FIG. 78 is a flow diagram of the overview of the application for virtual reality preprocedural system.
FIG. 79 is a table with a nonexclusive list of possible virtual models of devices used in LAA closure device, TAVR, and atrial fibrillation procedures.

In order to have the ability to use the application for preprocedural planning, a user interface and framework is used. Referring to FIG. 78, the application loads the created file of the 3D version of the patient's region of interest 1040. The selection of this file is done by the user, in which it can be uploaded from an internet service or through the hardware. If the embodiment of the application does not include the feature to allow user input control 1042 through sensors 1020, the remainder of the applications comprises visualization of the 3D region of interest with the virtual environment (step 1050). If the embodiment includes the feature 1042, the user may be able to manipulate the virtual environment and the 3D region of interest 1044. Manipulations may include transformations of its rotation, scaling, and position, as well as those of the viewers. If the embodiment includes the feature 1046 have users take virtual measurements through sensors 1020, the user may be able to take virtual measurements through sensors 1020. Measurements may include the ability measure distances of anatomical structures via use of differing virtual objects. If the embodiment allows the feature for the user to interact with models associated with LAA, TAVR, and/or Afib procedures 1048, the user may interact with 3D virtual models associated with devices of LAA, TAVR, and/or Afib procedures. This includes choosing and loading the model and interacting with it through sensors 1020 and with the 3D region of interest. The visualization of the ROI is updated 1050. FIG. 79 displays a nonexclusive list of exemplary models.

Figure 80:
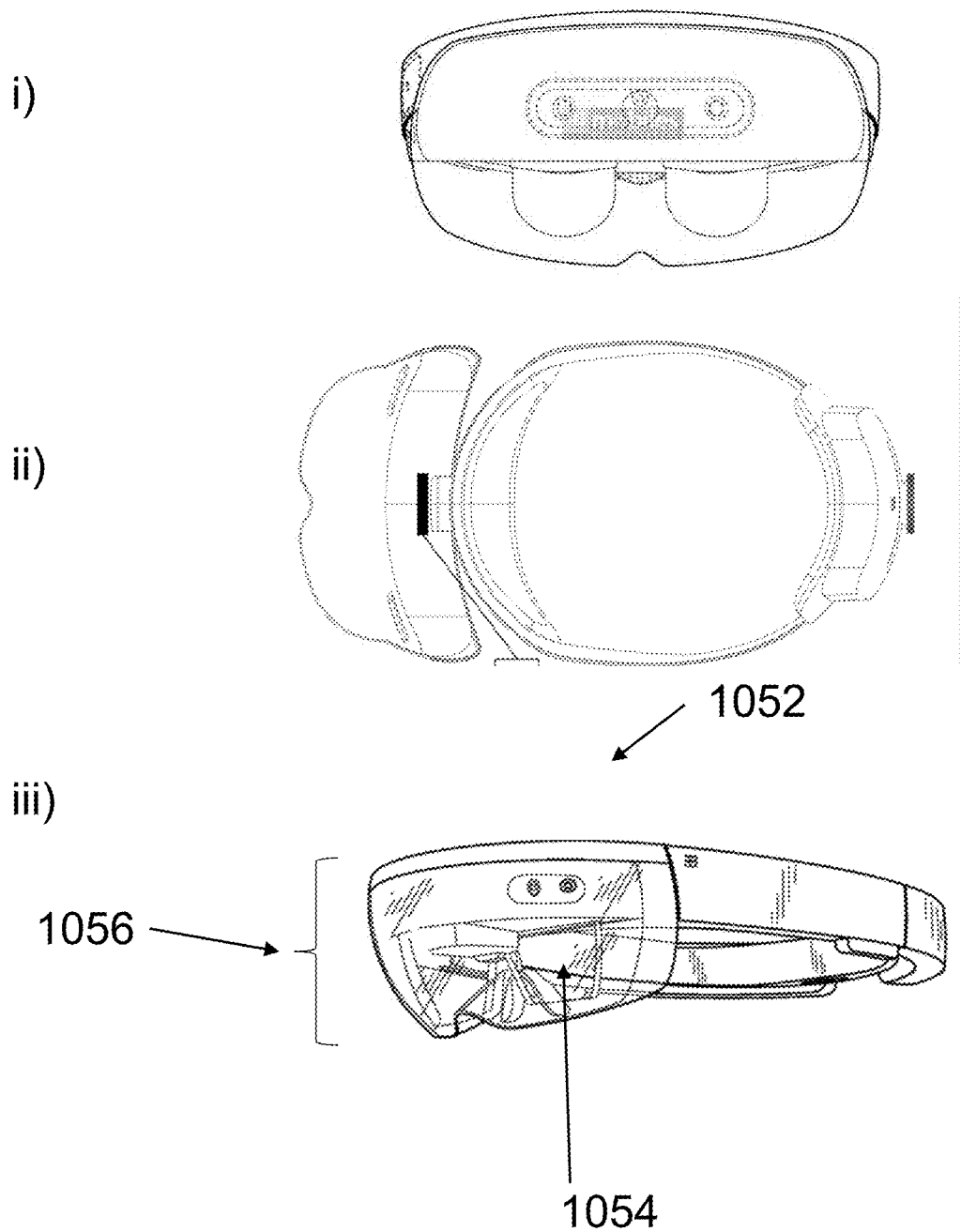
FIG. 80 demonstrates a generic augmented/mixed reality device from different views.

Another embodiment of the invention is for use during LAA, TAVR, or afib procedures. For use during a procedure using an immersive visualization device, augmented and or mixed reality devices are the preferable medium, even though these can used pre-procedure also. FIGS. 80*i-iii* depict user, top and side views respectively of a generic augmented or mixed reality device. The head set 1052, including optical input to the user via lenses 1054, and sensors for user transformation collection 1056. Augmented and mixed reality devices augment an observer's view of the real world by superimposing computer generated graphical information. The observer may observe a real scene directly with his or her eyes, with the additional graphical information being blended there with via a semi-transparent display located between the observer and the real scene. Such a display device can be, for example, a see-through head mounted display. The display can also be opaque, like a computer screen or a non-see-through head mounted display. Such a display then presents to the observer the complete augmented view, i.e., a combination of the real-world view and the graphics overlay. A video camera may take the place of the real-world observer to capture the real worldview. These devices often have sensors to distinguish the spatial representation of the real world about the users, sensors to record a user's position, rotation, and translation.

Figure 81:
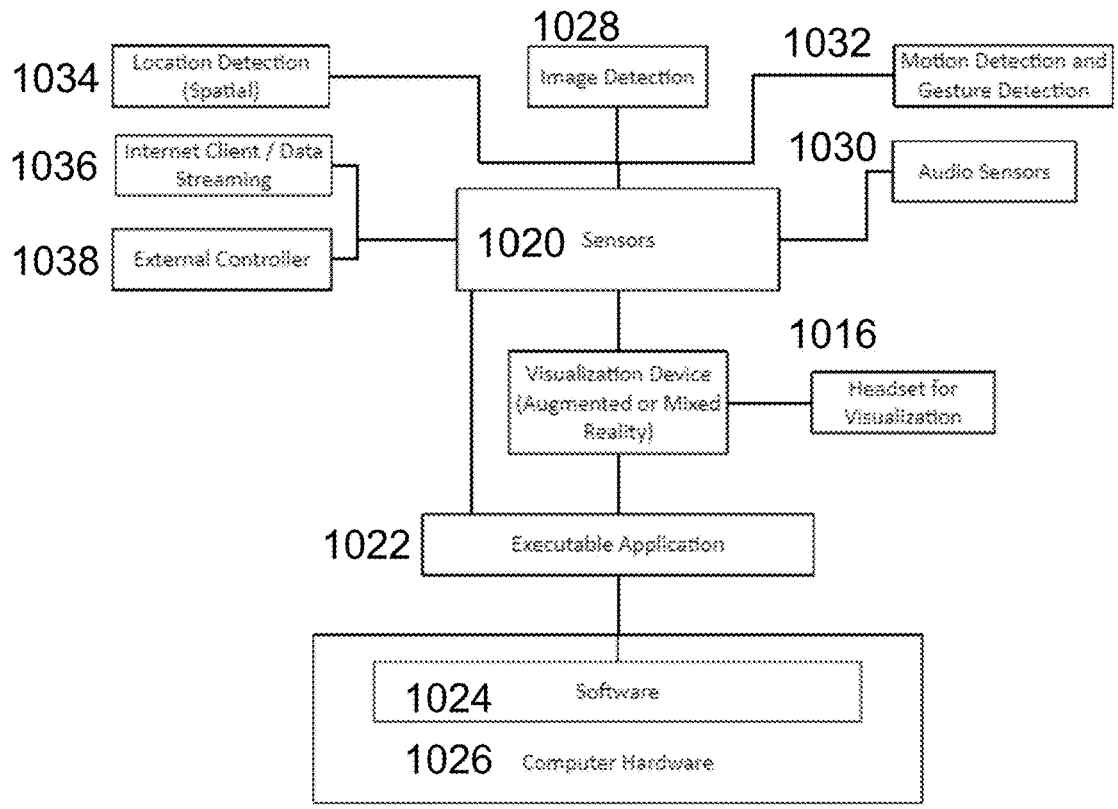
FIG. 81 is a diagram of the different components and architecture of the augmented/mixed reality device and related sensors.
Figure 82:
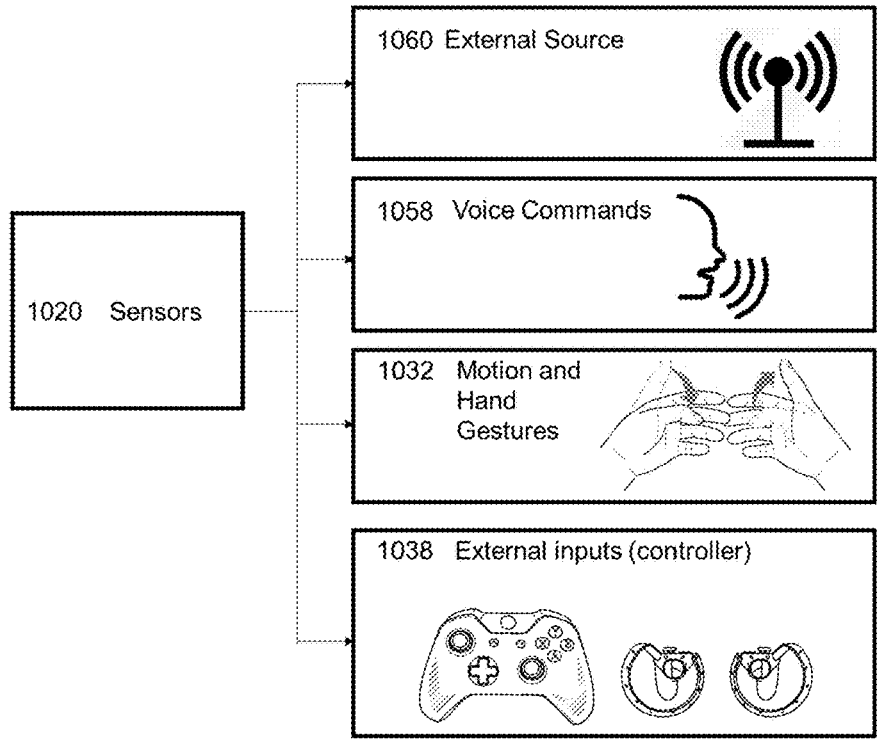
FIG. 82 a diagram of device sensors and example possible sensors.

For most augmented and mixed reality devices, they may run applications without the use of computer hardware and software during the execution, in which an application is programmed that dictates and controls what visual input the user receives and controls the effects of the inputs and outputs of the user. FIG. 81 depicts the relationship between the computer hardware 1026, software 1024 and the executable application 1022 that is applied to the augmented of mixed reality device. The application is created and implemented using the computer hardware 1026 and software 1024, in which the application is deployed from prior to its use with the augmented or mixed reality device. For visualization, the resultant holograms and visual user interface in conjunction with the view of the real world will be through the headset 1016. Sensors 1020, such as those for image 1028, audio 1030, motion and gesture 1032, spatial 1034, data streaming 1036, and external input 1038 detection may communicate with both the augmented or mixed reality device and the application 1022 itself. FIG. 82 further depicts examples of sensors used to gather user inputs, including motion and hand gestures 1032, external inputs (controller) 1038, voice commands 1058, or external sources (data streaming) 1060.

Figure 83:
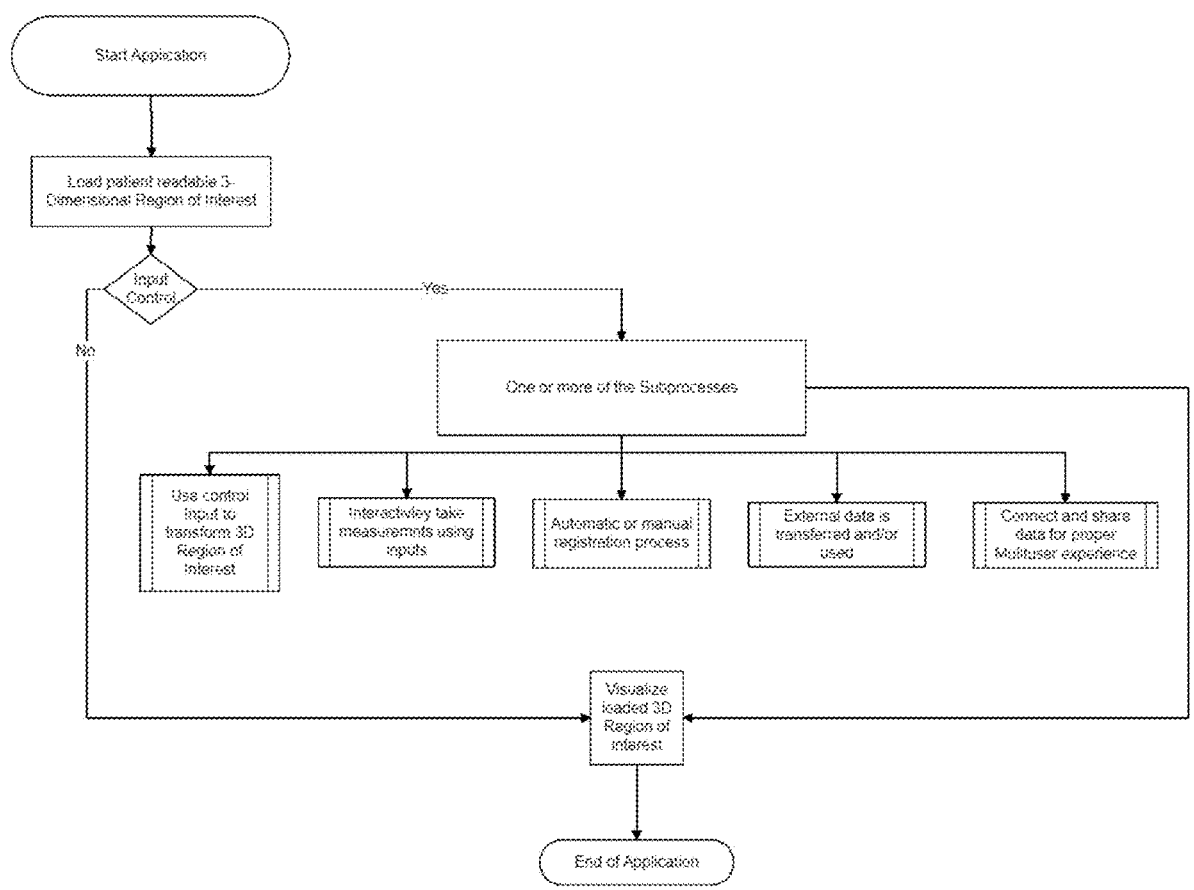
FIG. 83 is a flow diagram of the overview of the application for augmented/mixed reality intra-procedural system.

For use of the application during the procedure, a user interface and framework is used. Referring to FIG. 83, the application loads the created file of the 3D version of the patient's region of interest 1040 as a hologram. The selection of this file is done by the user, in which it can be uploaded from an internet service or through the hardware. If the embodiment of the application does not include the feature to allow user input control 1042 through sensors 1020, the remainder of the applications comprises visualization of the 3D region of interest as a hologram with the augmented or mixed reality device (step 1050). If the embodiment allows the feature 1042, the user may carry out the following capabilities through sensors 1020. The user may be capable to manipulate the 3D region of interest 1044. Manipulations may include transformations of its rotation, scaling, and position and texture. If the embodiment allows the feature to take measurements 1046, the user may be able to take virtual measurements through sensors 1020. Measurements 1046 may include the ability to measure distances of anatomical structures via use of differing holographic objects. The user may also connect and external sources to send data through Wi-Fi to the application 1064. If the embodiment allows the feature to allow multiuser capability 1066, the user may positionally interact and share the 3D region(s) of interest holographic properties in real time between multiple users via the internet 1066. If the embodiment has the ability to register the 3D region of interest 1062, the user will be able to register the 3d region of interest to real world features 1062. This process is further characterized by FIG. 84. Registration can be either manual 1070, or automatic 1068. Automatic registration comprises the steps of setting or checking set points on the 3D hologram of the region of interest, setting or checking corresponding point in the real world, and a registration algorithm that transforms the 3D region of interest so that the corresponding points of 3D region of interest and real world overlap with minimum error. Manual registration comprises the step of manipulating the 3D region of interest using the sensors 1020 to visualize in with the real world.

Figure 86:
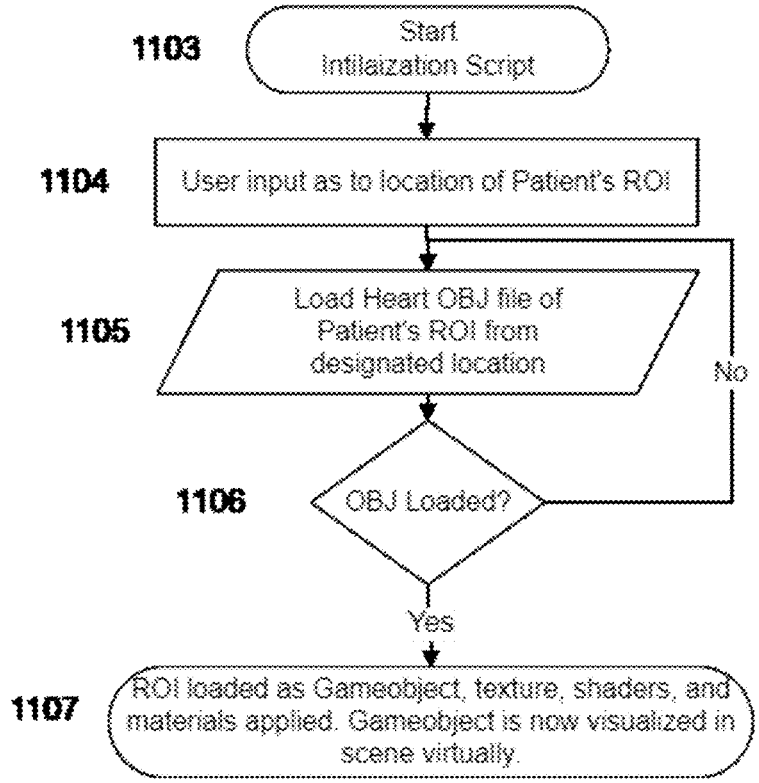
FIG. 86 is a flow diagram for the initialization script used by the pre-procedural application as in FIG. 85.

One implementation of the application for utilizing virtual reality for visualization or pre-procedure planning for left atrial appendage (LAA) closure device procedure, TAVR, or atrial fibrillation ablation procedure is shown in FIGS. 85-93. The implementation in FIG. 85 highlights the organizational architecture of the application among separate scripts. The application is started in step 1072, in which the application loads the user interactable scene (step 1074). Within the scene the initialization script is ran (step 1076), this workflow is shown in FIG. 86.

In FIG. 86 the initialization script starts (step 1103). Next the user inputs where the location of the patient's ROI OBJ file (or readable file format) location on the device running the application (step 1104). Next the heart OBJ file of patient's ROI from designated location (step 1105) from step 1104. If the OBJ wasn't loaded (step 1106), step 1105 is repeated. If the OBJ was loaded (step 1106) the ROI is loaded as a game object and texture, shaders, and materials are applied to the game object and it is visualized as a virtual game object in the scene (step 1107). Gameobject(s) (or sometimes referred to as "game objects"), is the term used in respect to what the 3 dimensional ROI is referred to within the application/scripts.

Returning to FIG. 85, after completion of the initialization script (step 1076), the application finishes loading user interactable scene (step 1108), this includes the process of finalizing the ability to interact with the virtual scene and all scripts. Next the scene runs the main script that control and interprets user inputs (step 1109). This workflow is shown in FIG. 87.

Figure 87A:
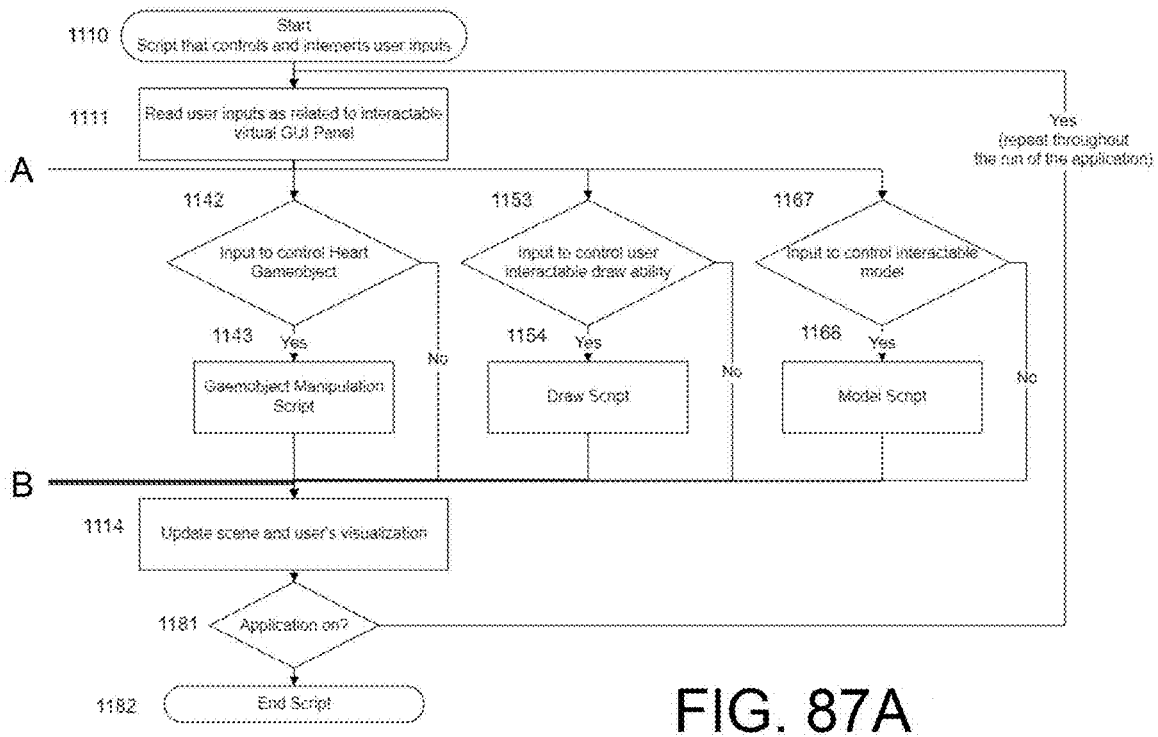
FIG. 87 is a flow diagram for the main script that controls and interprets user inputs used by the pre-procedural application as in FIG. 85.
Figure 87:
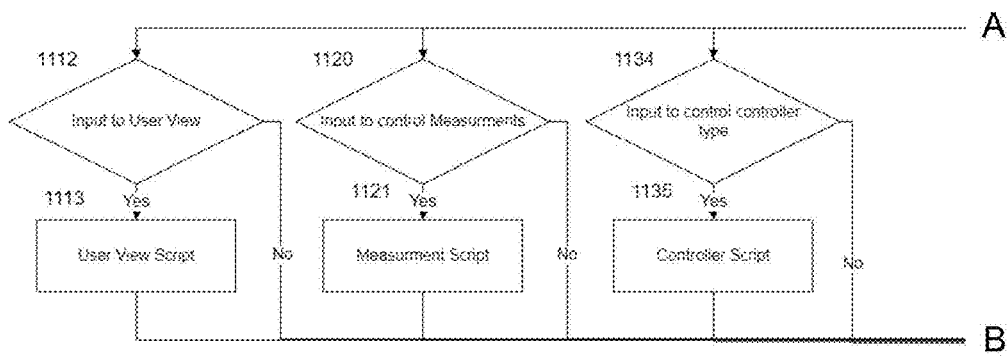

In FIG. 87, the script that controls and interprets user inputs starts (step 1110). Next, the script reads the inputs as related to interactable virtual graphical user interface (GUI) panel within the application's scene (step 1111). In this sense, the "scene" refers to all the gameobjects that are visualized and/or are interactable. In parallel, the inputs are read, and determination of the inputs are made. If the user input is to control the user view (step 1112), the user view script is ran (step 1113). The workflow for the user view script is demonstrated in FIG. 88.

Figure 88:
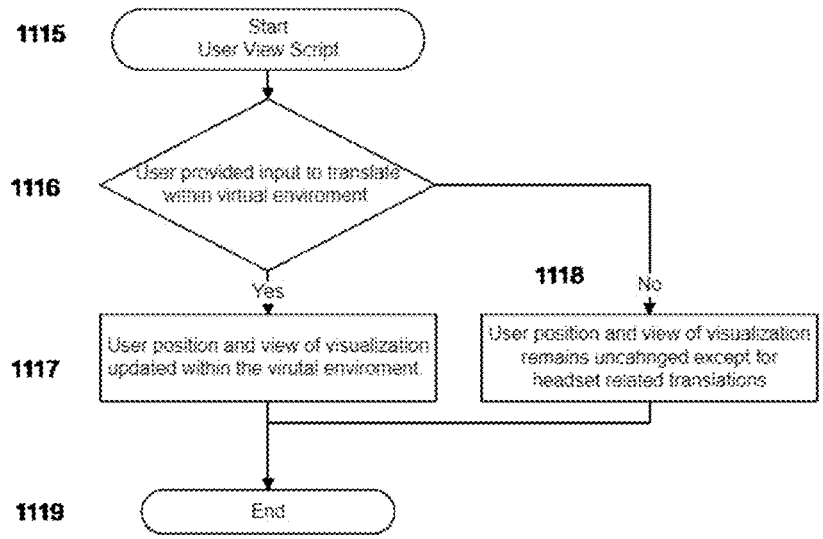
FIG. 88 is a flow diagram for the user view script called by the main script that controls and interprets user inputs as in FIG. 87 used by the pre-procedural application as in FIG. 85.

In FIG. 88 the user view script starts (step 1115). If user input provided input to translate within the virtual environment (step 1116), then the user position and view of visualization is updated within the virtual environment (step 1117) and the script ends (step 1119). If the user didn't provide inputs to translate within virtual environment (step 1116) the user position and view of the visualization remains unchanged (step 1118) and the script ends (step 1119). Independent of user input the visualization within the application is updated automatically with user head movement of the headset.

Returning to FIG. 87, after step 1113, the visualization and virtual scene are updated (step 1114). If the input was not for the user view (step 1112), the script proceeds to step 1114. If the user input is to control measurements (step 1120), the measurement script was run (step 1121). The workflow for the user view script is demonstrated in FIG. 89.

In FIG. 89 the measurement script starts (step 1122). Next the detection of which measurement option was selected is found (step 1123). If the option selected was "None", all display measurements are no longer visualized (step 1124) and the script ends (step 1129). If the option selected was "Distance" the display measurement is two interactable virtual spheres with a line between the two with text displaying the current distance between the two virtual spheres as related to the patient's ROI scale (step 1125). Next if the user input to manipulate measurement tools (step 1126) the start and end measurements points are transformed (step 1127) and the displayed measurement is updated (step 1128), if not the script ends (step 1129). If the option selected was "area" the display measurement is an interactable virtual disk that displays a text of the current are as related to the patient's ROI real life scale (step 1130). If the user input to manipulate measurement tools is present (step 1131), the interactable virtual disk is transformed (step 1132) and the displayed measurement is updated (step 1133). If not the script ends (step 1129).

Returning to FIG. 87, after step 1121, the visualization and virtual scene are updated (step 1114). If the input was not for the measurement control (step 1120), the script proceeds to step 1114. If the user input is to control controller type (step 1134), the controller script was run (step 1135). The workflow for the controller script is demonstrated in FIG. 90.

Figure 90:
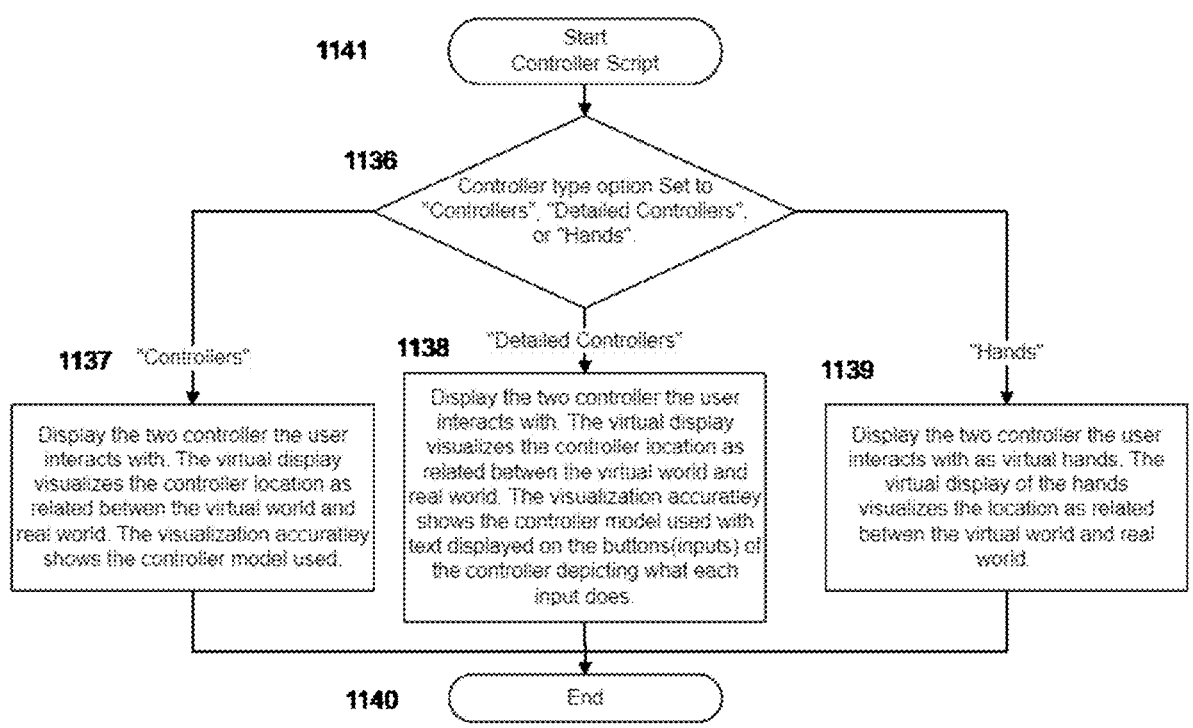
FIG. 90 is a flow diagram for the controller input script called by the main script that controls and interprets user inputs as in FIG. 87 used by the pre-procedural application as in FIG. 85.

In FIG. 90 the controller script starts (step 1141). Next the detection of which controller option was selected is found (Step 1136). If the option selected was "Controllers", the virtual display of the controller the user interacts with is the realistic virtual model of the controllers used. The visualization's transformation is accurately shown in the virtual environment (step 1137). If the option selected was "distance", the virtual display of the controller the user interacts with is the realistic virtual model of the controllers used. The visualizations position is accurately shown in the virtual environment. Virtual text is displayed on each of the controllers' inputs briefly depicting what each input does with respect to the application (step 1138). If the option selected was "Hands", the virtual display of the controller the user interacts with are virtual hand models, the visualization's transformation is accurately shown in the virtual environment (step 1139). After steps 1137-1139, the script ends (step 1140).

Returning to FIG. 87, after step 1135, the visualization and virtual scene are updated (step 1114). If the input was not for the measurement control (step 1134), the script proceeds to step 1114. If the user input is to control Heart (ROI) game object (step 1142), the game object manipulation script was run (step 1143). The workflow for the game object manipulation script is demonstrated in FIG. 91.

Figure 91:
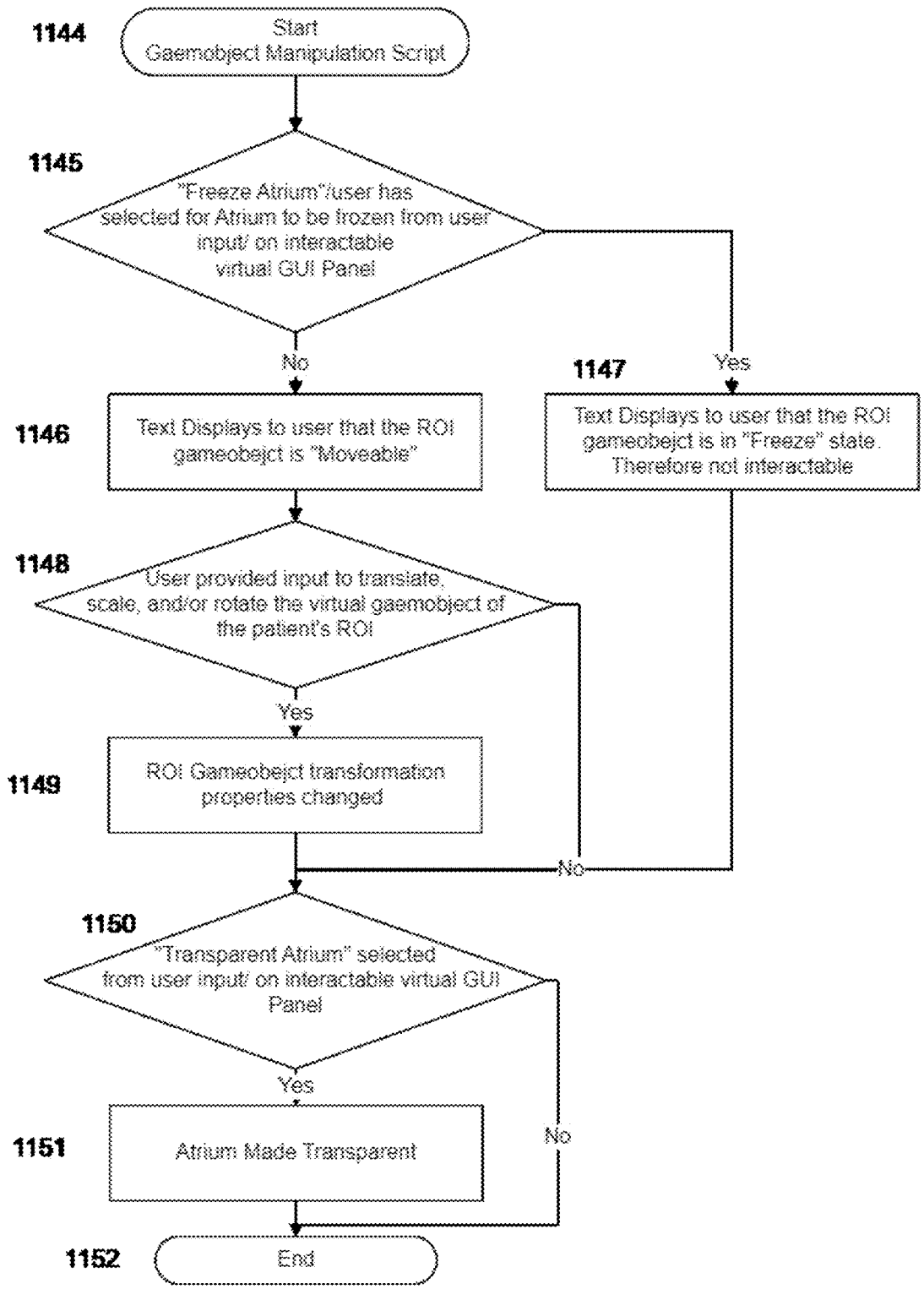
FIG. 91 is a flow diagram for the game object manipulation script called by the main script that controls and interprets user inputs as in FIG. 87 used by the pre-procedural application as in FIG. 85.

In FIG. 91 the game object manipulation script starts (step 1144). Next the detection of whether the option for the atrium to be in "freeze atrium mode" from user input (such as in the interactable virtual GUI interface) is found (Step 1145). If it is, a virtual text displays to the user that the ROI virtual game object is in freeze state and therefore not interactable (step 1146) and the script proceeds to step 1150. If the heart isn't in freeze mode, a text displays to the user that the ROI is moveable and is interactable with user input (1146). Next, if the user provided inputs to transform the ROI game object (scale, translate, rotate) (step 1148), the ROI game objects transformation and visualization changes based on inputs (step 1149). If not, it proceeds to step 1150. At step 1150, a detection of whether "transparent atrium" option was inputted or selected from interactable virtual, GUI panel. If it was, the atrium is made transparent virtual (step 1151) and the script ends (step 1152), otherwise the script ends.

Returning to FIG. 87, after step 1143, the visualization and virtual scene are updated (step 1114). If the input was not for the game object manipulation control (step 1134), the script proceeds to step 1114. If the user input is to control user interactable draw ability (step 1153), the draw script was run (step 1154). The workflow for the draw script is demonstrated in FIG. 92.

Figure 92:
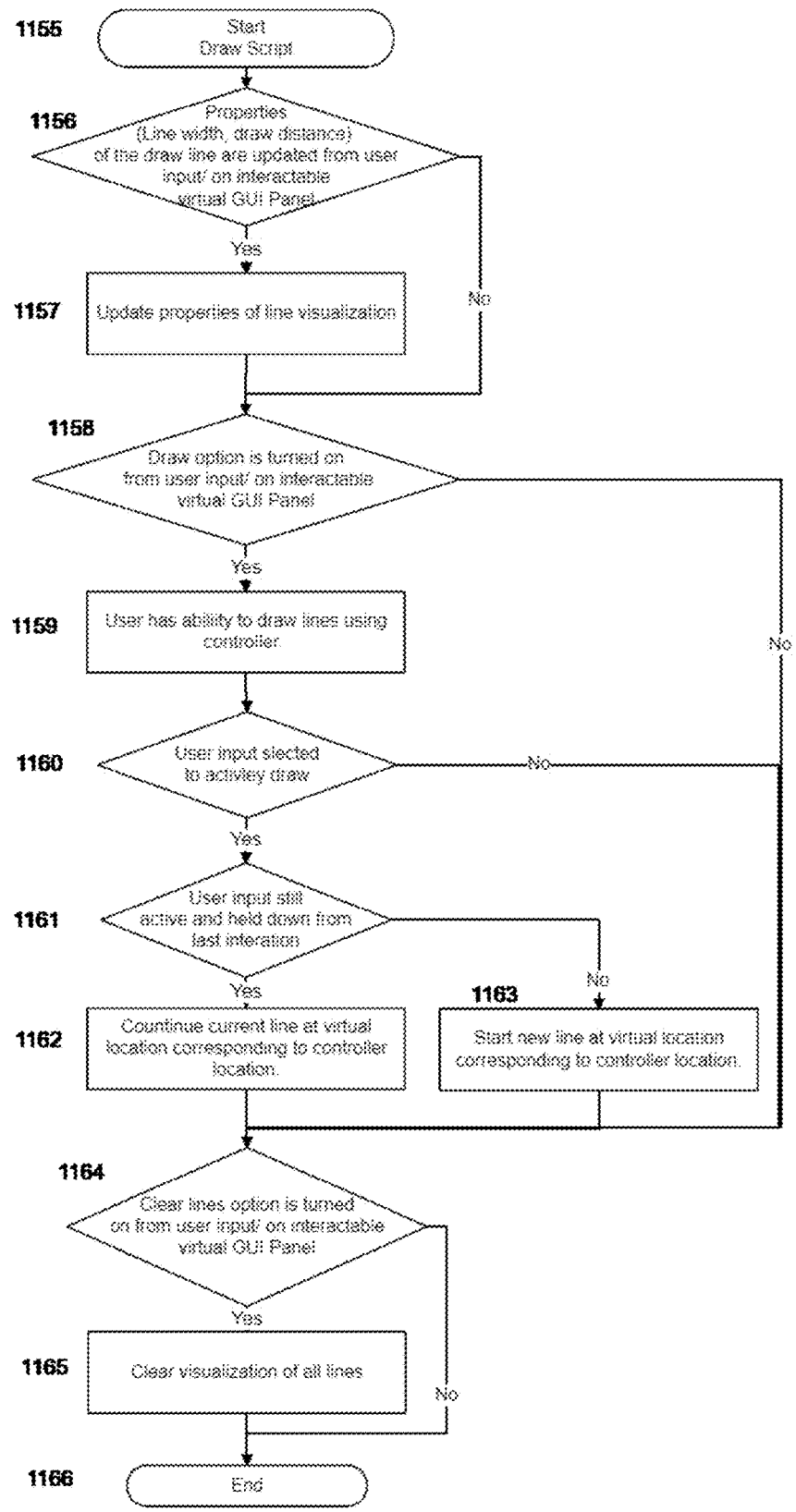
FIG. 92 is a flow diagram for the draw script called by the main script that controls and interprets user inputs as in FIG. 87 used by the pre-procedural application as in FIG. 85.

In FIG. 92 the draw script starts (step 1155). First the script checks if the properties of the visualized line are updated by the user input, possibly from the interactable GUI (step 1156). If they were, the properties of the line for visualization are updated (step 1157) and proceed to step 1158. If not the script proceeds to step 1158. At step 1158, the script detects whether the draw option from user input/interactable GUI is turned on. If it isn't, the script proceeds to step 1164. If it is, the user has ability to draw virtual lines with the controllers or user input (step 1159). Next, if the user input is not selected to actively draw (step 1160), the script proceeds to step 1164. If it is, the script detects if the input is still active and held down from last scripts run (step 1161). If it is, the visualization of the line is continued at the current location of the controller's location (step 1162), if not, the visualization starts new line at the virtual location corresponding to controller location (step 1163). From step 1162 and 1163, the script then proceeds to step 1164. At step 1164, the script checks if the clear lines option is turned on from user input or interactable virtual GUI. If so the visualization of all lines is cleared (step 1165) and then the script ends (step 1166), if not, the script ends.

Returning to FIG. 87, after step 1154, the visualization and virtual scene are updated (step 1114). If the input was not for the draw control (step 1134), the script proceeds to step 1114. If the user input is to control user interactable model (step 1167), the model script was run (step 1168). The workflow for the model script is demonstrated in FIG. 93.

Figure 93:
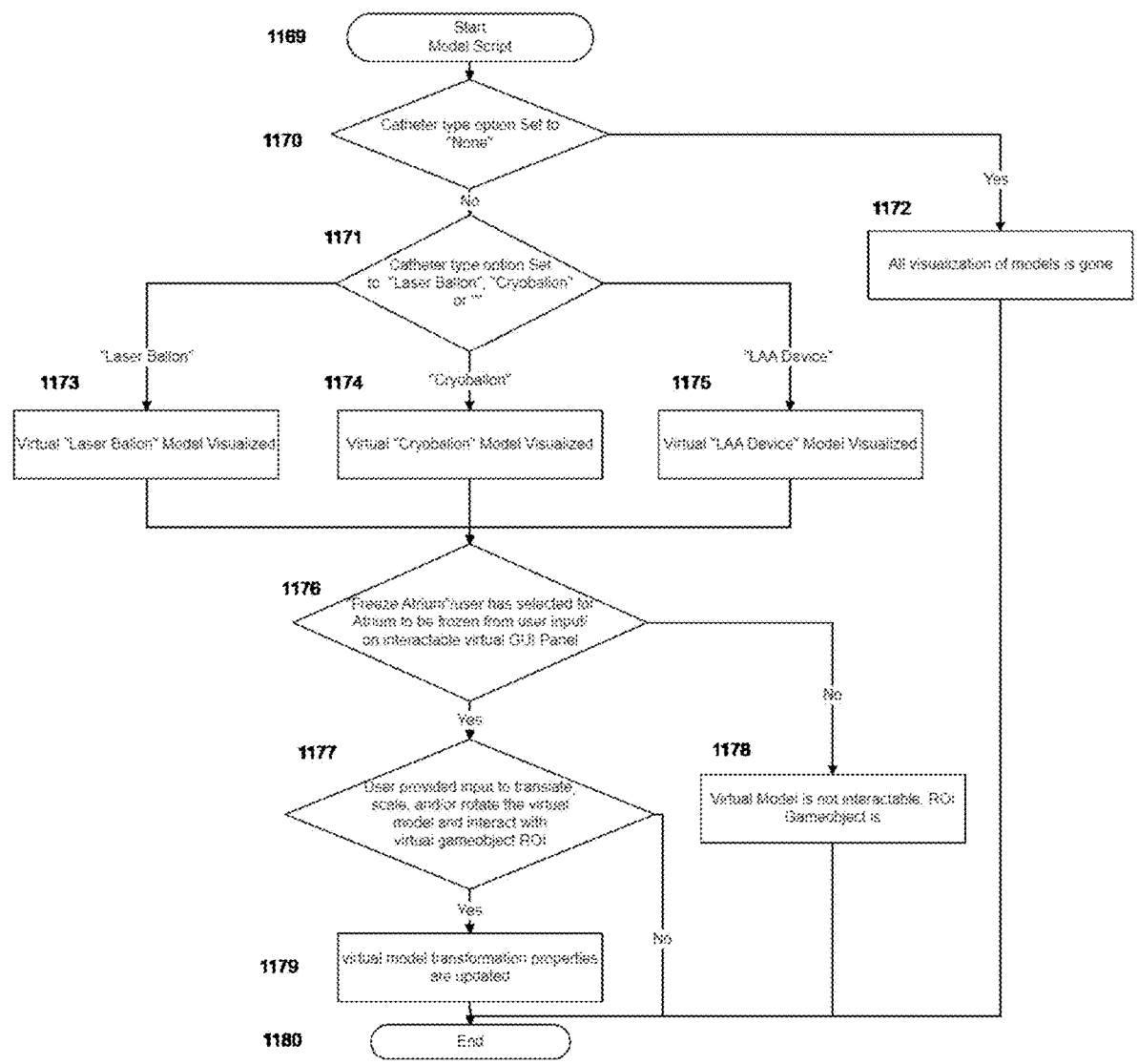
FIG. 93 is a flow diagram for the model script called by the main script that controls and interprets user inputs as in FIG. 87 used by the pre-procedural application as in FIG. 85.
Figure 94:
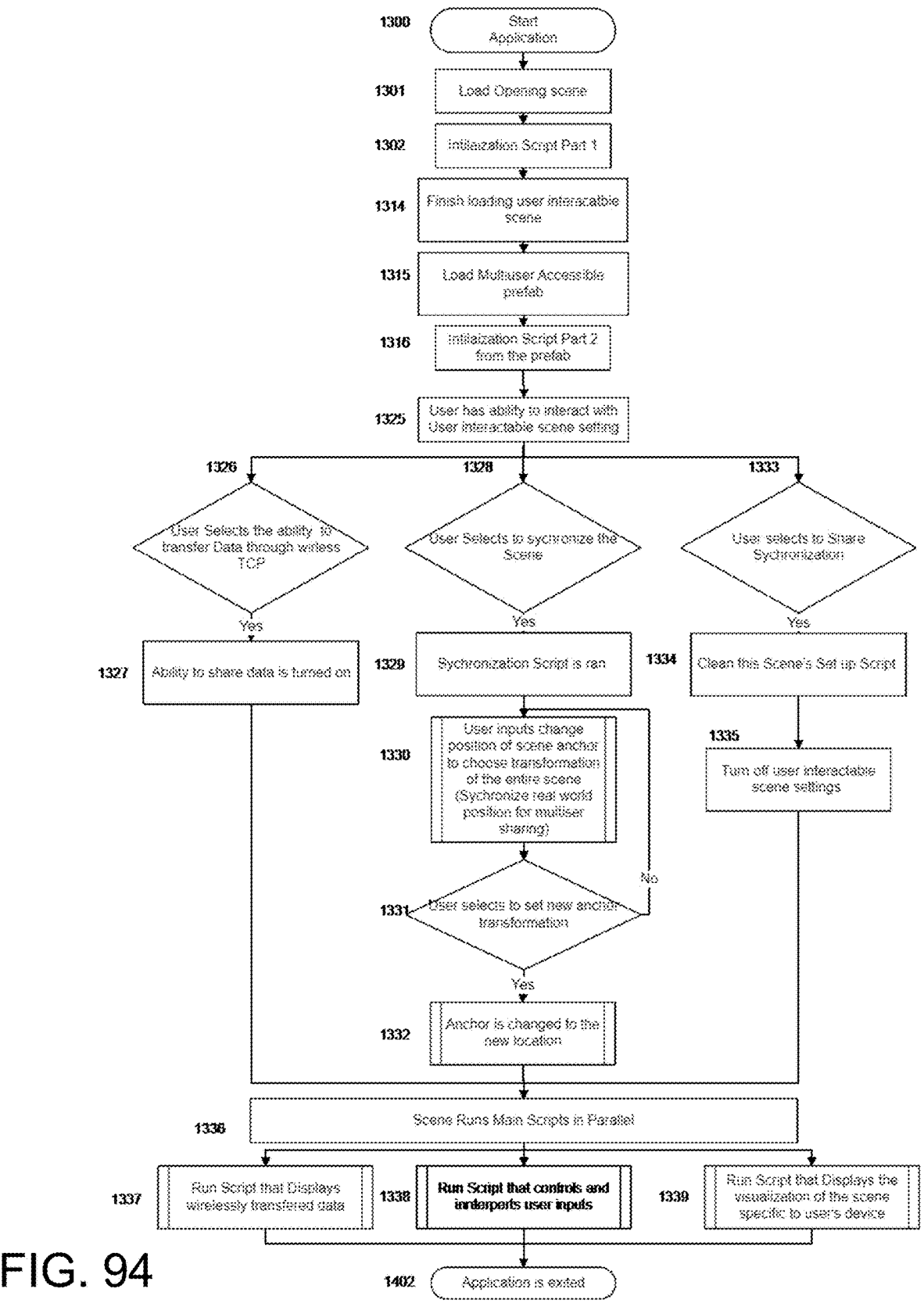
FIG. 94 is a flow diagram that generalizes the application process for the intra-procedural systems.

In FIG. 93 the model script starts (step 1169). Next the script determines if the user input/interactable GUI is set to a catheter type of none (step 1170). If it is, the script ends (step 1180). If not, the type of model selected by user input/interactable GUI is detected (step 1171). If the virtual model chosen is a laser balloon, the laser balloon model is virtually visualized (step 1173), if the virtual model chosen is a cryoballon, the cryoballon is virtually visualized (step 1174), and if the virtual model chosen is a model used for LAA closure, the model used for LAA closure is virtually visualized (step 1175). In this context, the model used for LAA closure can be a variety of different models used for LAA closure procedures. Steps 1173-1175 proceed to step 1176. In step 1176 the script detects whether the freeze atrium option was selected as a user input or interactable virtual GUI panel (step 1176). If it was not, the virtual model is not interactable, the ROI game object ROI is (step 1178), and the script ends (step 1180). If step 1176 is true, the script determines if user input was provided to transform the virtual model (step 1177). If there is, the virtual model's transformation properties are updated, and the script ends (step 1180), otherwise the script ends (step 1180).

Returning to FIG. 87, after step 1168 the visualization and virtual scene are updated (step 1114). If the input was not for the control of an interactable model (step 1167), the script proceeds to step 1114. From step 1114, if the application is still running, the application restarts to step 1111 (reading user inputs). If the application is no longer on, the script ends (step 1182).

Figure 95:
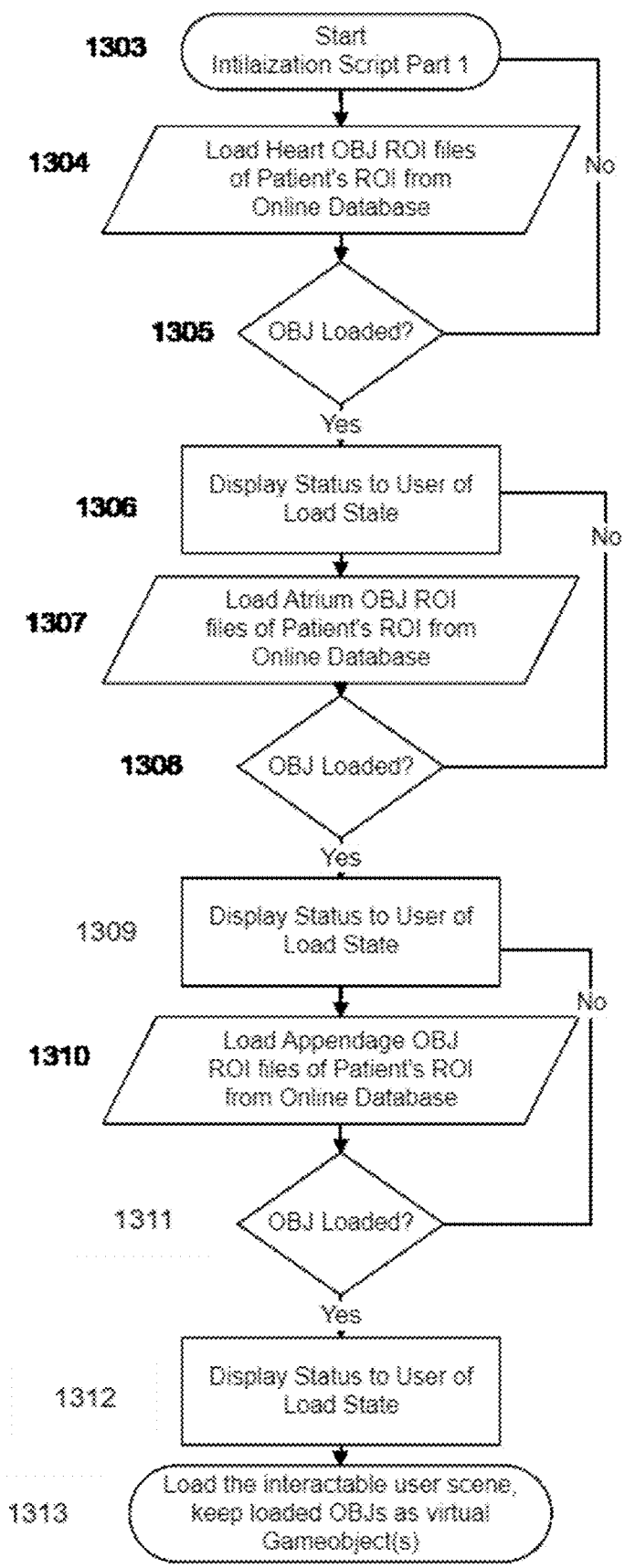
FIG. 95 is a flow diagram for the initialization script part 1 used by the intra-procedural application as in FIG. 94.

One implementation of the application for utilizing augmented reality (AR) or mixed reality (MR) for left atrial appendage (LAA) closure device procedure, or TAVR procedure, or atrial fibrillation ablation procedure is shown in FIGS. 94-101(A-C). The implementation in FIG. 94 highlights the organizational architecture of the application among separate scripts. The application is started in step 1300, in which the application loads the opening "scene" (step 1301). The scene in this term relates to the virtual environment interface and all resulting scripts that are updated each framerate of the application's refresh to the devices output. Within the opening scene the initialization script Part 1 is ran (step 1302), this workflow is shown in FIG. 95.

In FIG. 95, the initiation script part 1 is started (step 1303). The script then attempts to load the "heart" OBJ (or any readable format or model) file from an online database that the script is programmed to access (step 1304). Determination of whether the OBJ was successfully loaded is made (step 1305). If it was not, the script returns to step 1304, if it was, the current success status of the heart OBJ load is displayed to the user (step 1306). Steps 1304-1306 are repeated in steps 1307-1309 for the atrium OBJ and 1310-1312 for the appendage OBJ respectively (or any collection of OBJ ROI). Finally, the script loads the next scene, which is the interactable user scene while saving and keeping the loaded OBJs as a virtual game object usable by the application and carried over to the new scene (step 1313) as the virtual ROI(s).

Returning to FIG. 94, after the initialization script part 1 is completed, the user interactable scene finishes loading (step 1314), in which the multiuser accessible prefab is loaded (step 1315). The multiuser accessible prefab is a collection of virtual game objects and scripts that are loaded within the scene that may communicate properties of those virtual game objects and scripts via the internet to any other device currently loaded with the same prefab (or in this case running this application). The initialization script part 2 is then ran from the loaded prefab (step 1316), this workflow is shown in FIG. 96.

Figure 96:
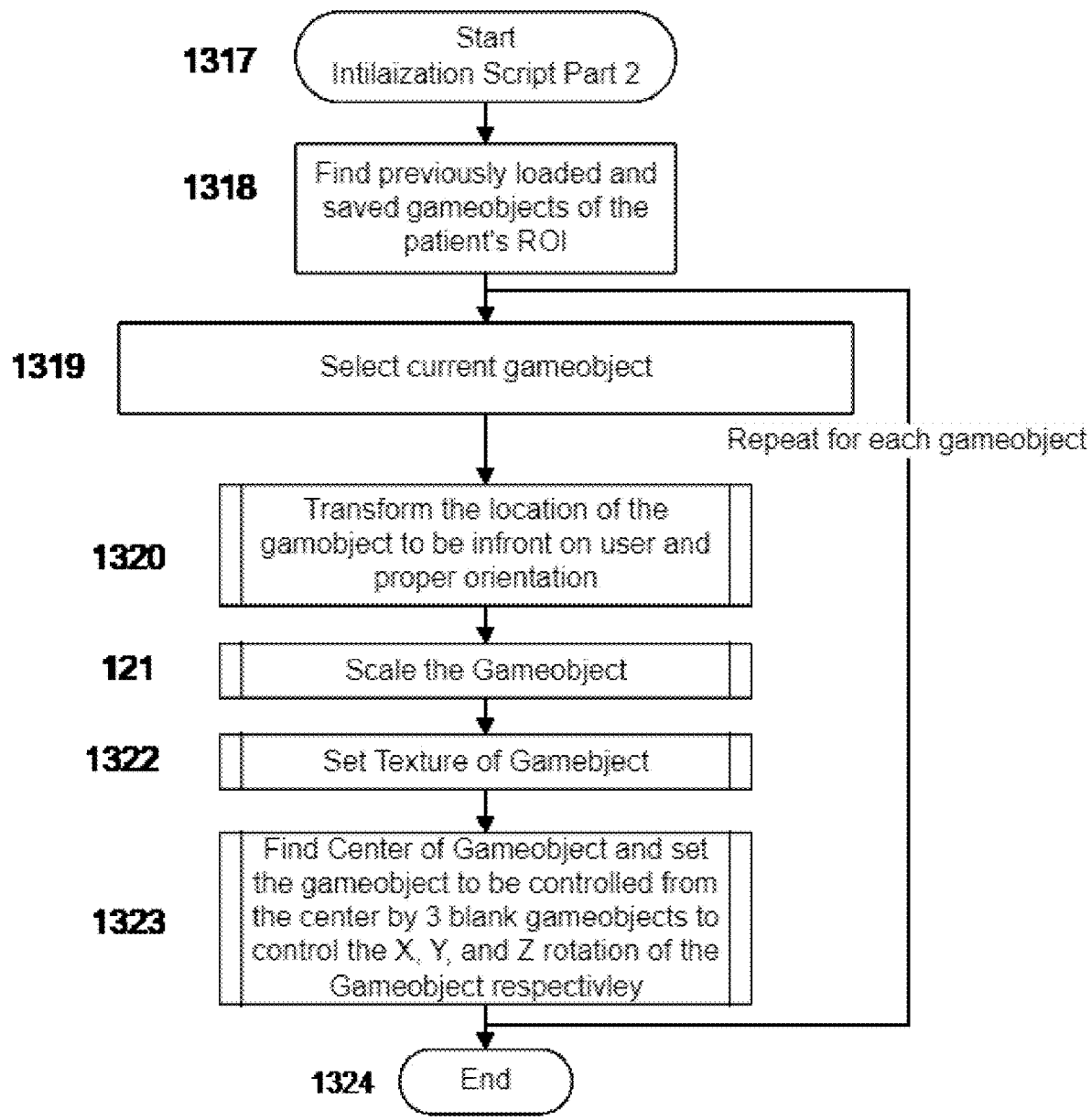
FIG. 96 is a flow diagram for the initialization script part 2 used by the intra-procedural application as in FIG. 94.

In FIG. 96, the initiation script part 2 is started (step 1317). The script then finds/locates the previously loaded and saved game objects of the patient's ROI (step 1318). The script then selects one of the game objects of the patient's ROI (step 1319), transforms the location of the selected game object to be in front of the user and of a proper orientation (step 1320), scales the selected game object (step 1321), sets the texture of the game object to a default material (step 1322), and finds the center of the selected game object so that the game object is now nested in three blank game objects that act to control the X, Y, and Z rotation of the game object respectively about the center (step 1323). Steps 1319-1323 are repeated for each of the loaded and saved game objects (therefore for the heart, atrium, and appendage game object ROI) in which the script ends (step 1324).

Returning to FIG. 94, after the initialization script part 2 is completed, the user has the ability to interact with user interactable scene settings (step 1325). During this stage the scene is updating, and the user has the ability to select the ability to transfer data through a wireless TCP communication protocol (step 1326). If this option is selected the ability to share data is turned on (step 1327) and the application returns to step 1325. If the user selects the ability to synchronize scene (step 1328) the synchronization script is ran (step 1329). This script includes the steps of using user inputs to change the transformation of a virtual visualized anchor about the visualized space (step 1330, this is useful to set the virtual anchor to a real-world anchor for resultant multiuser sharing and streaming). It includes allowing the option for the user to set the current position of the visualized anchor as the new anchor position (step 1331), which if chosen will reset all game objects transformations to be oriented with respect to the new anchor position as the anchor changes to the new position (step 1332) and returns to step 1325, or if not selected allows for the user to continue manipulating the anchor (step 1330). If the user selects the ability to share the synchronization (step 1333), the clean this scene's set up script is ran (step 1334) which cleans up scene variables and game objects in preparation of the next stage. Next the ability to interact with the user interactable scene settings is turned off (step 1335). Next the main scripts are run in parallel (step 1336). During this step, the script that displays the wirelessly transferred data (1337, workflow in FIG. 97), script that controls and interprets user inputs (1338, workflow in FIG. 98), and script that displays the visualization of the scene specific to user's device (1339, workflow in FIG. 99) all run and update with the application refresh rate. The application ends when the user exits it (step 1402).

Figure 97:
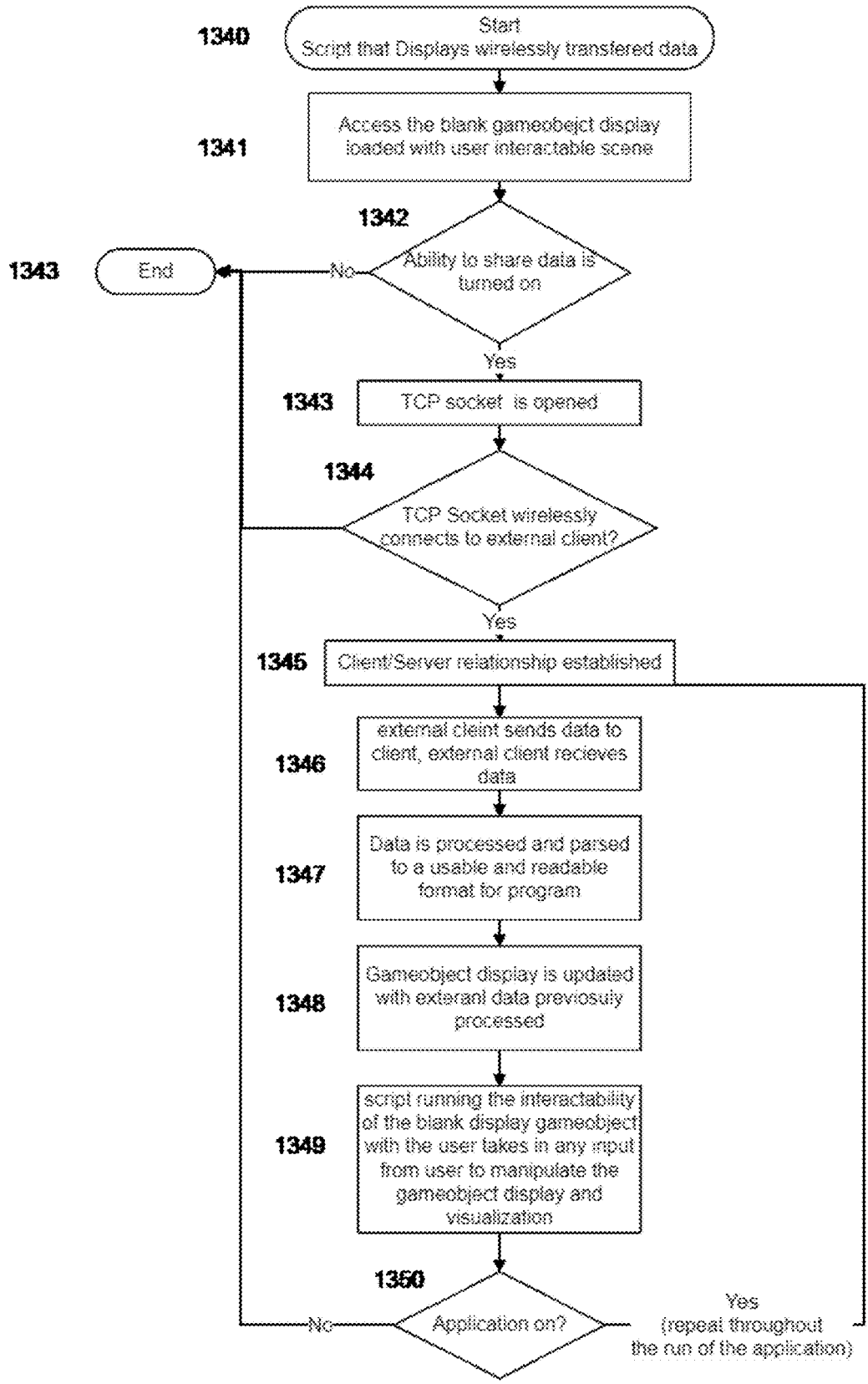
FIG. 97 is a flow diagram for the script that displays wirelessly transferred data used by the intra-procedural application as in FIG. 94.

In FIG. 97, the script that displays wirelessly transferred data starts (step 1340). Next the script accesses a blank display game object that was loaded with the user interactable scene (step 1341). The blank display game object is a virtual game object that displays the external data being received as a graph. Next, if the ability to share data was turned on (step 1342) in previous step 1327, the TCP socket is opened (step 1343a), if not the script ends (step 1343). After the TCP socket is opened, the TCP socket attempts to wirelessly connect to the external client (step 1344). If it doesn't, the script ends (step 1343), if it does, a client/server relationship is established (1345). The external client then sends and receives data to the script (and therefore the device used to run the application) (step 1346). The data is processed by converting to a usable format and parsed (step 1347). The blank display game object is updated to display the processed and parsed data (step 1348). The script running the ability to interact with the blank display game object from possible user input to manipulate the game object display and visualization (step 1349) runs. If application is still running (step 1350), the script repeats steps 1346-1350 throughout the run of the application. If not, the script ends (step 1343).

In FIG. 98, the script that controls and interprets user inputs starts (step 1351). The script reads user inputs (step 1352). In parallel, the inputs are read, and determination of the inputs are made. If the user input is to change the ROI game object transparency (step 1353), the transparency value of the visualization of the ROI game object increases or decreases depending on input (step 1354) and the properties are recorded and saved wirelessly as part of the script being housed within the prefab (step 1373). If the user input is not changed in step 1353, the script proceeds to step 1373. If the user input is to toggle between the ROI game objects (such as between the ability to visualize the heart, atrium, or appendage game object) (step 1355), the script toggles between which the ROI game object will be visualized (step 1356), and proceeds to step 1373. If the user input is not changed in step 1355, the script proceeds to step 1373. If the user input is to toggle between the ability to see game objects that are used for the registration points (step 1357), and the user completed the registration function (step 1358), the ability to see the registration points is toggled (1359) and proceeds to step 1373. If the answer is now the step 1357 or 1358, the script proceeds to step 1373. If the user input is to change the sensitivity of the user inputs (step 1360), the script increases or decreases the sensitivity of the user inputs (step 1361) and proceeds to step 1373, if not the programs proceeds to step 1373. If the user input is to toggle between the material of the ROI game object present (step 1362), the script toggles between the texture that will shown on the game object ROI (step 1363) and proceeds to step 1373, if not the programs proceeds to step 1373. If the user input is to change the sensitivity of the ROI game objects point cloud density (1364), the value of the point cloud density will increase of decrease depending on user input (step 1366) and proceeds to step 1373, if not the programs proceeds to step 1373. If the user input is to transformation of the ROI game object (1367), the properties of the rotation, translation and scale of the game objects ROI are updated (step 1368) and proceeds to step 1373, if not the programs proceeds to step 1373. If the user input is in response to the registration process/function (1369), and the input is not held down for more than a set time (step 1370), the input is sent to the registration function (step 1371). The registration function workflow is shown in FIG. 100.

Figure 100:
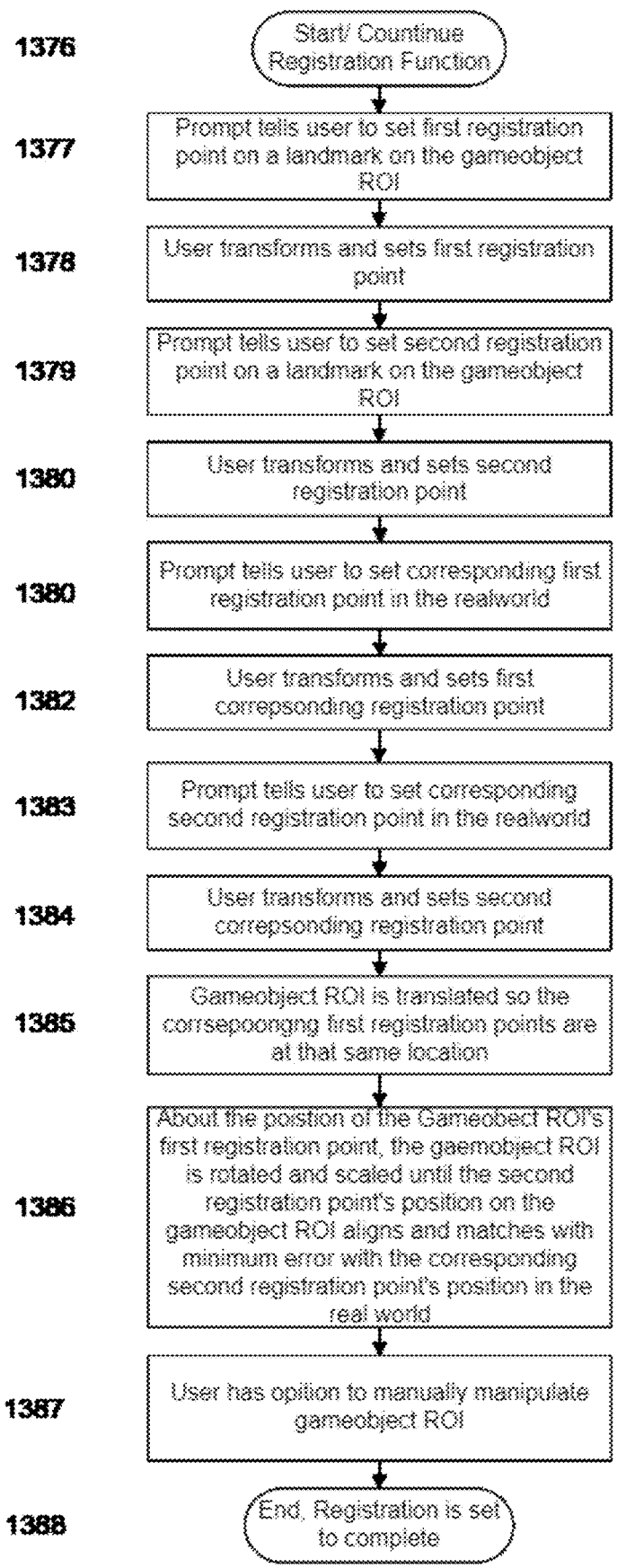
FIG. 100 is a flow diagram for the registration function used by the intra-procedural application as in FIG. 94.

In FIG. 100, the registration function starts (step 1376). The function run sand updates with the script that controls and interprets user inputs. The prompt informs the user to set first registration point on a landmark on the game object ROI (step 1377). Next, the user transforms and sets first registration point (step 1378). The prompt informs the user to set second registration point on a landmark on the game object ROI (step 1379). Next, the user transforms and sets second registration point (step 1380). Prompt tells user to set corresponding first registration point in the real world (step 1381). User transforms and sets first corresponding registration point (step 1382). Prompt tells user to set corresponding second registration point in the real world (step 1383). User transforms and sets second corresponding registration point (step 1384). Game object ROI is translated so the corresponding first registration points are at that same location (step 1385). About the position of the Game object ROI's first registration point, the game object ROI is rotated and scaled until the second registration point's position on the game object ROI aligns and matches with minimum error with the corresponding second registration point's position in the real world (step 1386). User has option to manually manipulate game object ROI transformation (step 1387). Registration process ends in step 1388.

Returning to FIG. 98, If the input is held down for more than the set time (step 1370), the registration is reset to null (including the registration function) (step 1372) and proceeds to step 1373. If application is still running (step 1374), the script restarts at step 1352. If not, the script ends (step 1375).

Figure 99:
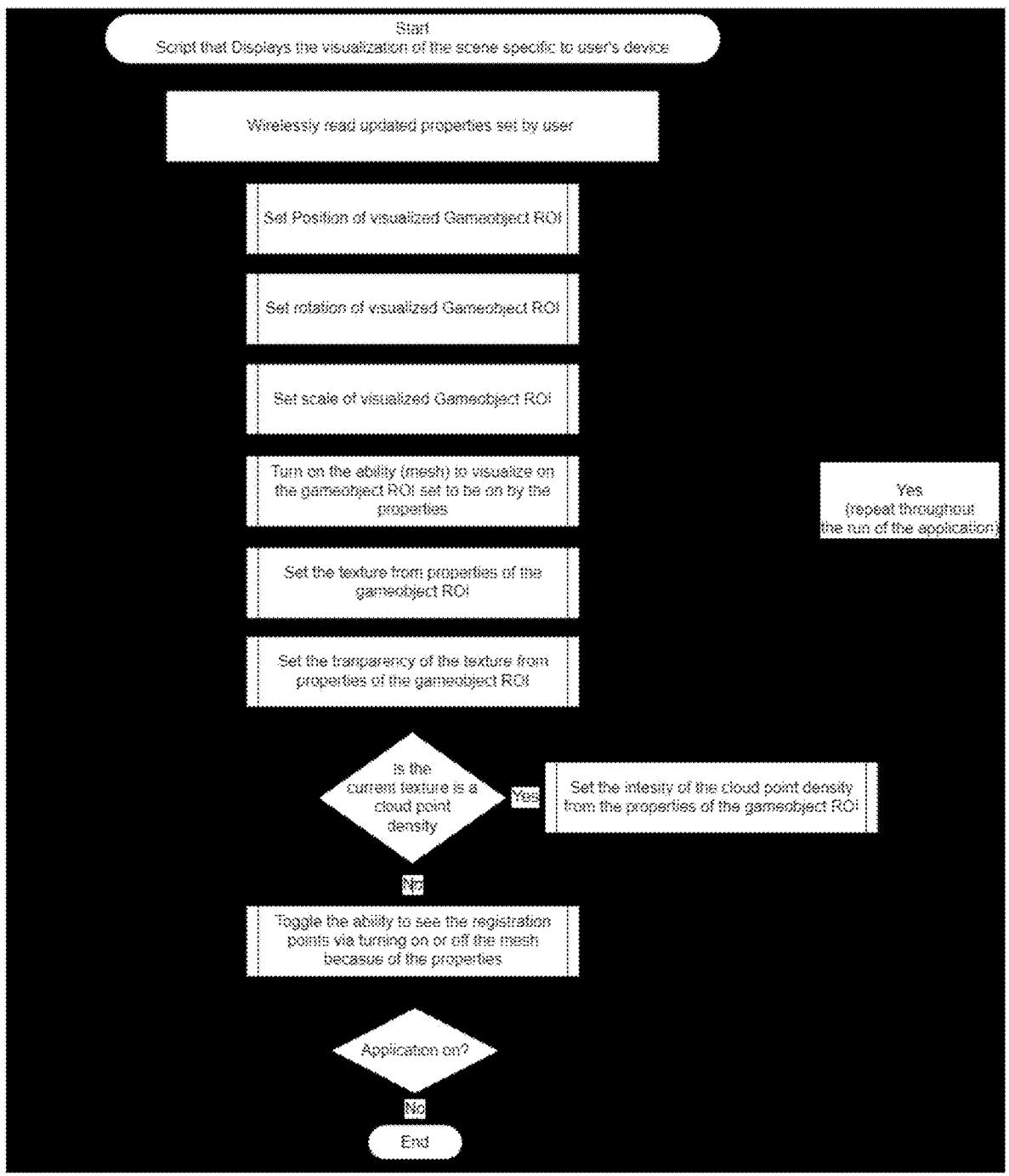
FIG. 99 is a flow diagram for the script that displays the visualization of the scene specific to user's device used by the intra-procedural application as in FIG. 94.

In FIG. 99, the script that displays the visualization of the scene specific to user's device starts (step 1389). The script wirelessly reads and updates the properties (step 1390) that are accessible to any user running the prefab and application such as those updated in step 1373. Using these properties, the position (step 1391), rotation (step 1392) and scale (step 1393) of the visualized game object ROI. The ability to visualize the game object ROI specifically set by user to visualize is set by the properties (step 1394). The texture/material visualized on the game object ROI are updated by the properties. The transparency of the texture of the game object ROI was updated using the properties (step 1396). If the current texture set by the properties is the cloud point density (step 1397), the intensity of the cloud point density from the properties are changed (step 1398), after and if 1397 is not true the ability to visualization the registration points are set by the properties (step 1399). Next, if the application is on (step 1400), the script restarts at step 1390, if not the script ends (step 1401).

Figure 101A:
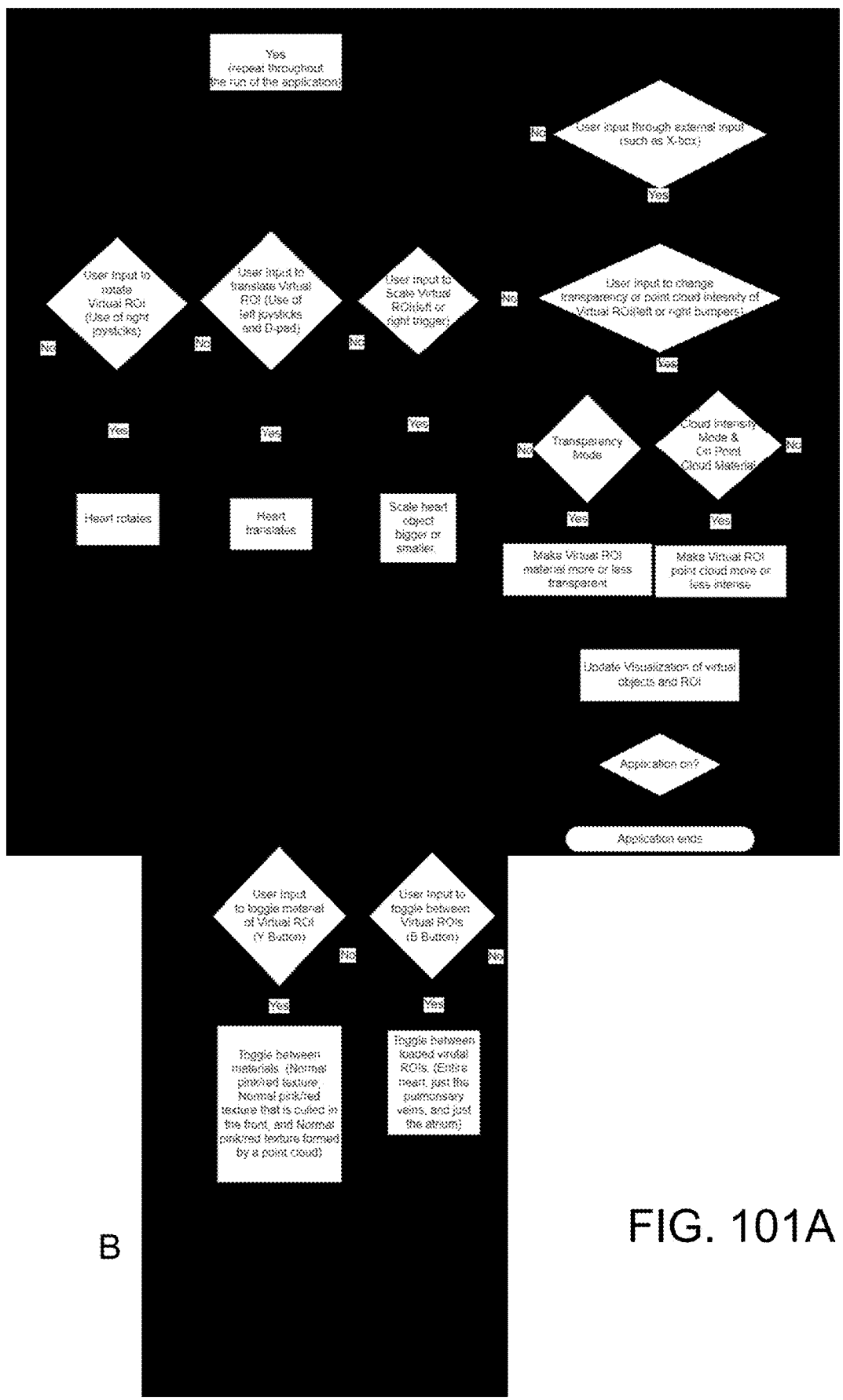
FIG. 101A-101C is a flow diagram for the functions and features of the main scripts used by the intra-procedural application as in FIG. 94.
Figure 101B:
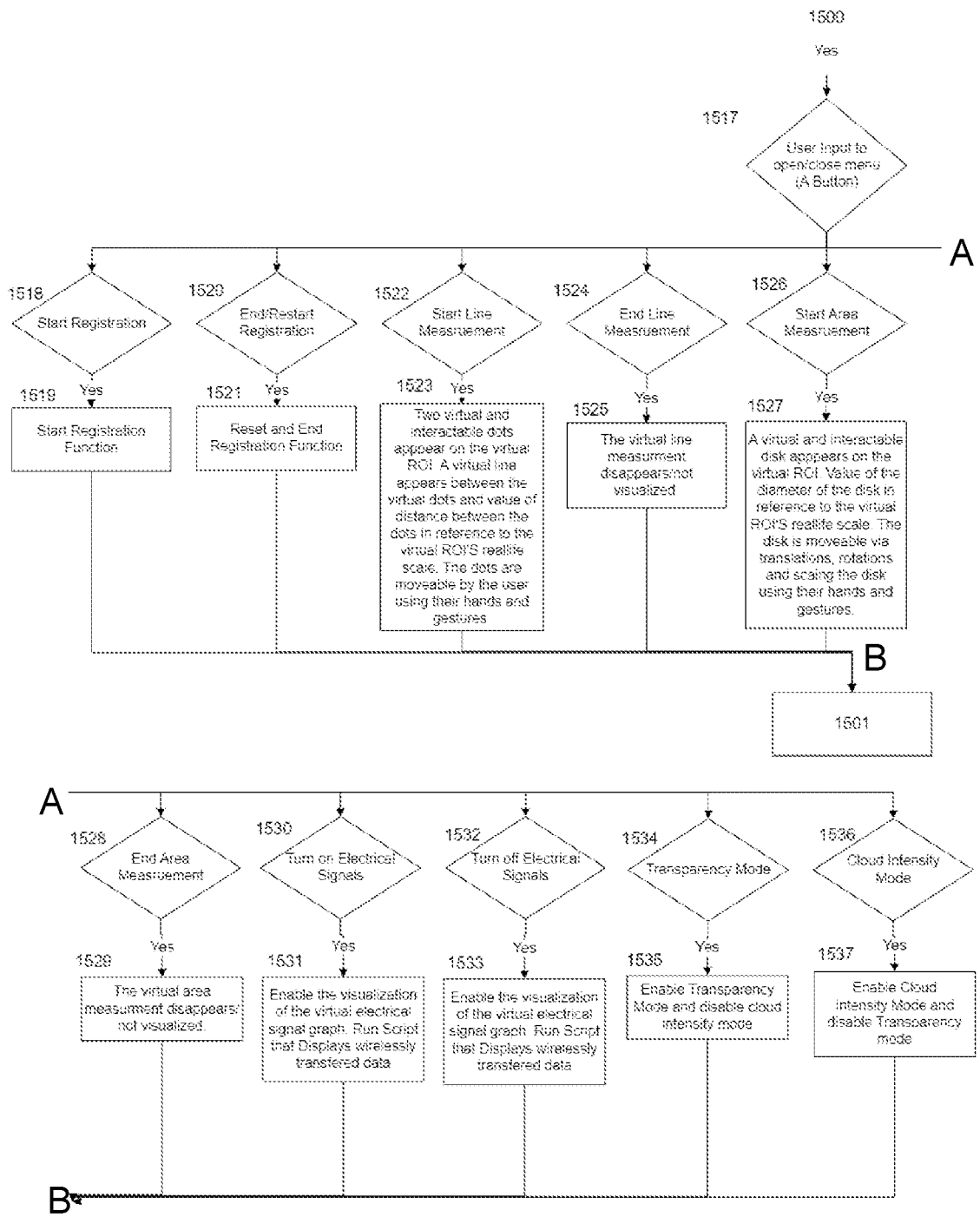
Figure 101C:
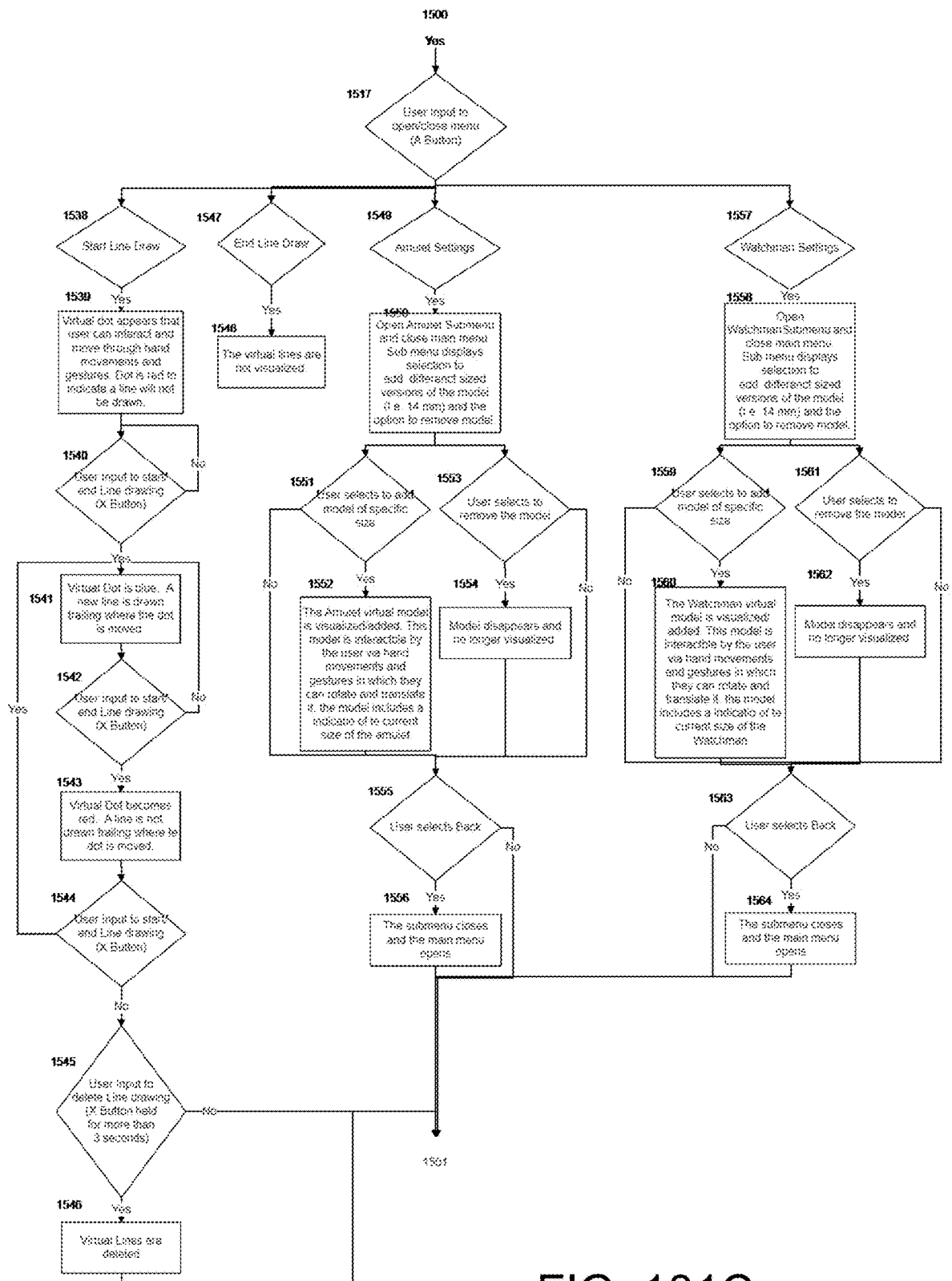

In FIG. 101A-C, another version of the applications implementation is demonstrated. Starting from step 1336 in FIG. 94, from where the initialization is complete and the scripts are running, the application determines if an external input was entered (step 1500) using for an example an X-BOX™ controller. If it was, depending on the type of input the script will update the visualization. If not, the visualization is updated as is (step 1501). If the user input is to rotate the virtual ROI (step 1502), the ROI rotates (step 1503) and the visualization is updated (step 1501). If the user input is to translate the virtual ROI (step 1504), the ROI translates (step 1505) and the visualization is updated (step 1501). If the user input is to scale the virtual ROI (step 1506), the ROI scales (step 1507) and the visualization is updated (step 1501). If the user input is to change the transparency or intensity of the virtual ROI material (step 1508), and it is in transparency mode (step 1509), the virtual ROI material is made more of less transparent (step 1510). If it is in cloud intensity mode and also on point cloud material (step 1511), the virtual ROI point cloud is made less or more intense (step 1512). Subsequently, the visualization is updated (step 1501). If the user input is to toggle the material of the virtual ROI (step 1513), the ROI's material is changed (step 1514) and the visualization is updated (step 1501). If the user input is to toggle between loaded virtual ROIs (step 1515), the ROI objects change (step 1516) and the visualization is updated (step 1501). If the user input opens or closes the main menu (step 1517), they may select from the main menu features. If they select start registration (step 1518), the registration function starts as in FIG. 100 (step 1519) and the visualization is updated (step 1501). If they select end/restart registration (step 1520), the registration function is reset and is turned off (step 1521) and the visualization is updated (step 1501). If they select start line measurement (step 1522), two virtual and interactable dots appear on the virtual ROI. A virtual line appears between the virtual dots and value of distance between the dots in reference to the virtual ROI'S real-life scale. The dots are moveable by the user using their hands and gestures (step 1523), and the visualization is updated (step 1501). If they select end/restart registration (step 1520), the registration function is reset and is turned off (step 1521) and the visualization is updated (step 1501). If they select end line measurement (step 1524), the virtual line measurement feature ends and is not visualized (step 1524) and the visualization is updated (step 1501). If they select start area measurement (step 1526), a virtual and interactable disk appears on the virtual ROI. Value of the diameter of the disk in reference to the virtual ROI'S real-life scale. The disk is moveable via translations, rotations and scaling the disk using their hands and gestures (step 1527), the visualization is updated (step 1501). If they select end area measurement (step 1528), the virtual area measurement feature ends and is not visualized (step 1529) and the visualization is updated (step 1501). If they select turn on electrical signals (step 1530), the virtual signal graph is initiated and the process of data transfer as in FIG. 97 is completed (step 1531) and the visualization is updated (step 1501). If they select turn off electrical signals (step 1532), the virtual signal graph is turned off and no longer visualized (step 1533) and the visualization is updated (step 1501). If they select transparency mode (step 1534), the transparency mode is set (step 1535) and the visualization is updated (step 1501). If they select point cloud intensity mode (step 1536), the point cloud intensity mode is set (step 1537) and the visualization is updated (step 1501). If they select start line draw (step 1538), a virtual dot appears that user can interact and move through hand movements and gestures (step 1539). Dot is red to indicate a line will not be drawn. If input is initiated to start the line (step 1540), the virtual dot turns blue and a virtual line is drawn following where the dot is moved (step 1541). If the user hits select again (step 1542), the dot turns red and the line stops being created (step 1543). If the select is hit gain (step 1544), a new line is created repeating steps 1541-1544. If the select is held down for longer time (step 1545), the virtual lines are deleted. The visualization is updated (step 1501). If the user selects end line draw (step 1547), the virtual lines are not visualized (step 1548) and the visualization is updated (step 1501). If the user selects the amulet settings (step 1550), the submenu is opened (step 1550). If the user selects a model of a specific size (step 1551), the Amulet virtual model is visualized/added. This model is intractable by the user via hand movements and gestures in which they can rotate and translate it. The amulet is just an example, it could be any virtually modeled device used in TAVR, LAA closure, or AFib procedures. The model includes an indication of the current size of the amulet (step 1552). If the user selects to remove the model (step 1553), the model disappears and is no longer visualized (step 1554). If the user selects back (step 1555), the submenu closes and the main menu returns (step 1556). The visualization is updated (step 1501). If the watchman settings are selected (step 1557), the same process as the amulet setting are applied from steps 1550-1556 to the watchman model in steps 1558-1564 and the visualization is updated (step 1501). If the application is still on (step 1565), the process is restarted at step 1500, else the application ends.

While this disclosure has been described with reference to preferred embodiments, it will be understood by those skilled in the art that various changes may be made without departing from the scope of the invention. In addition, many modifications may be made to adapt a particular situation or material to the teaching of the invention with departing from the essential scope thereof. Therefore, it is intended that the disclosure not be limited to the particular embodiments disclosed for carrying out this invention, but that the invention will include all embodiments falling within the scope of the appended claims.

The invention claimed is:

1. A method for visualization or pre-procedure planning utilizing virtual reality (VR) for transcutaneous aortic valve replacement (TAVR) procedure, or left atrial appendage (LAA) closure device procedure, or atrial fibrillation ablation procedure, comprising the steps of:

providing a computer-based hardware and a software configured with a virtual reality headset and sensors, wherein said software adapted to be used with a gaming engine and object-oriented programming in said virtual reality headset display environment;

providing a patient's computed tomography (CT) or magnetic resonance imaging (MRI) images for the procedure;

segmenting and volume rendering said patient's computed tomography (CT) or medical resonance imaging (MRI) to create an appropriate anatomic 3-dimensional (3D) region of interest (ROI);

programing said computer based hardware and software with an application configured and programmed with pre-created virtual device models with the ability to interact with said 3-dimensional (3D) region of interest (ROI) for aiding in transcutaneous aortic valve replacement (TAVR) procedure, or left atrial appendage (LAA) closure device procedures, or atrial fibrillation ablation procedures; and utilizing said hardware and software configured with a virtual reality headset and sensors for visualization or pre-procedure planning in said virtual reality headset display environment for transcutaneous aortic valve replacement (TAVR) procedure, or left atrial appendage (LAA) closure device procedure, or atrial fibrillation ablation procedure, utilizing said virtual reality (VR) headset and sensors.

2. The method of claim 1, wherein said virtual reality headset and sensor(s) utilized is independent of the manufacturer of the device.

3. The method of claim 1, wherein said created virtual device models can be resized and/or placed within virtual anatomic models of the region of interest for the procedure, utilizing sensors.

4. The method of claim 1, wherein measurements or markings are displayed within virtual anatomic structure, which is the region of interest.

5. A method of utilizing augmented reality (AR) or mixed reality (MR) for transcutaneous aortic valve replacement (TAVR) procedure, or left atrial appendage (LAA) closure device procedure, or atrial fibrillation ablation procedure, comprising the steps of:
  providing an augmented reality (AR) or mixed reality (MR) device comprising, an augmented reality (AR) or mixed reality (MR) headset, an application programmed to said augmented reality (AR) or mixed reality (MR) device, and a means to control;
  providing a patient's computed tomography (CT) or magnetic resonance imaging (MRI) images for the procedure;
  performing volume rendering to create a 3D region of interest from said patient's CT or MRI, and adapted to be readable by said application utilized on said augmented reality (AR) or mixed reality (MR) device;
  loading at least one said 3D region of interest into said augmented reality (AR) or mixed reality (MR) device with said application, wherein said application is configured and programmed with gaming engine and object oriented programming and adapted for utilizing for transcutaneous aortic valve replacement (TAVR) procedure, or left atrial appendage (LAA) closure device procedure, or atrial fibrillation ablation procedure; and
  displaying said 3D volume rendered images as a hologram(s) wherein said 3D volume rendered images have been pre-selected and said pre-selected hologram(s) are displayed next to real-time imaging when said augmented reality (AR) or mixed reality (MR) device is worn by an operator, and further wherein said operator can manipulate said hologram(s) while wearing said (AR) or mixed reality (MR) device to be utilized intra-procedure for utilizing during a transcutaneous aortic valve replacement (TAVR) procedure, or left atrial appendage (LAA) closure device procedure, or atrial fibrillation ablation procedure.

6. The method of claim 5, wherein said augmented reality (AR) or mixed reality (MR) device utilized is independent of the manufacturer.

7. The method of claim 5, wherein said holograms are controlled via hand gestures and/or an X-BOX™ controller.

8. The method of claim 5, wherein said hologram(s) is/are displayed next to fluoroscopy images and/or ultrasound images.

9. The method of claim 5, wherein said hologram(s) is overlayed or registered to fluoroscopy images and/or ultrasound images.

10. The method of claim 5, wherein said application is configured and programmed such that measurements are displayed in the hologram or around the hologram.

11. The method of claim 5, wherein previously created device models and 3-dimensional (3D) anatomic models are loaded into the said augmented reality (AR) or mixed reality (MR) device for displaying as holograms via use of this application.

12. A system for visualization or pre-procedure planning utilizing virtual reality (VR) for transcutaneous aortic valve replacement (TAVR) procedure, or left atrial appendage (LAA) closure device procedure, or atrial fibrillation ablation procedure, comprises:
  a computer-based system with hardware and a software adapted to work with a virtual reality headset and sensors, wherein said software adapted to be used with a gaming engine and object oriented programming within said virtual reality (VR) headset display environment;
  a patient's computed tomography (CT) or magnetic resonance imaging (MRI) images for the procedure that has capability for 3D volume rendering a region of interest (ROI) for transcutaneous aortic valve replacement (TAVR) procedure, or left atrial appendage (LAA) closure device procedure, or atrial fibrillation ablation procedure; and
  said computer based hardware and said software configured with an application with the ability to create a virtual device models and/or interact with said region of interest (ROI) utilizing gaming engine and object oriented programming, wherein said application further configured and programmed such that said created virtual device models are pre-created and interact with said region of interest (ROI) in ways which is programmed for aiding in transcutaneous aortic valve replacement (TAVR) procedure, or left atrial appendage (LAA) closure device procedures, or atrial fibrillation ablation procedures, utilizing said virtual realty headset display environment and sensors.

13. The system of claim 12, wherein said created virtual device models can be resized and/or placed within virtual anatomic models of the region of interest for the procedure.

14. The system of claim 12, wherein measurements or markings are displayed within virtual anatomic structure, which is the region of interest, utilizing sensors.

15. A system for utilizing augmented reality (AR) or mixed reality (MR) for transcutaneous aortic valve replacement (TAVR) procedure, left atrial appendage (LAA) closure device procedure or atrial fibrillation ablation procedure, comprises:
  an augmented reality (AR) or mixed reality (MR) device comprising, an augmented reality (AR) or mixed reality (MR) headset, an application programmed to said augmented reality (AR) or mixed reality (MR) device, and a means to control;
  a patient's computed tomography (CT) or magnetic resonance imaging (MRI) images for the procedure that has capability for 3D volume rendering a region of interest (ROI) for transcutaneous aortic valve replacement (TAVR) procedure, or left atrial appendage (LAA) closure device procedure, or atrial fibrillation ablation procedure;
  said application configured with the capability to loading said region of interest (ROI) into said augmented reality (AR) or mixed reality (MR) device, wherein said application is configured and programmed for aiding in transcutaneous aortic valve replacement (TAVR) procedure, or left atrial appendage (LAA) closure device procedure, or atrial fibrillation ablation procedure; and said augmented reality (AR) or mixed reality (MR) device capable of displaying holograms of at least one 3-dimensional (3D) anatomical segments during a procedure wherein said 3-dimensional (3D) anatomical segments have been pre-selected and said pre-selected hologram(s) are displayed next to real-time imaging when said augmented reality (AR) or mixed reality (MR) device is worn by an operator, and further wherein said operator can manipulate said hologram(s) while wearing said (AR) or mixed reality (MR) device, further wherein said holograms of said regions of interest(s) (ROI) capable of being free floating or capable of being used in conjunction with a fluoroscopy image(s) or ultrasound image(s).

16. The system of claim 15, wherein said holograms are controlled via hand gestures and/or an X-BOX™ controller.

17. The system of claim 15, wherein said hologram(s) is/are displayed next to fluoroscopy images and/or ultrasound images.

18. The system of claim 15, wherein said hologram is overlayed or registered to fluoroscopy images and/or ultrasound images.

19. The system of claim 15, wherein said application is configured and programmed such that measurements are displayed in the hologram or around the hologram.

20. The system of claim 15, wherein previously created models are placed with the hologram, or within the hologram.

21. The system of claim 15, wherein Microsoft's Hololens-2 or a higher version of MICROSOFT™ HOLOLENS™ is utilized for said augmented reality (AR) or mixed reality (MR) device.

22. The method of claim 15, wherein said augmented reality (AR) or mixed reality (MR) device is independent of the manufacturer.

* * * * *